US006864235B1

(12) United States Patent
Turley et al.

(10) Patent No.: US 6,864,235 B1
(45) Date of Patent: Mar. 8, 2005

(54) COMPOSITIONS AND METHODS FOR TREATING CELLULAR RESPONSE TO INJURY AND OTHER PROLIFERATING CELL DISORDERS REGULATED BY HYALADHERIN AND HYALURONANS

(76) Inventors: Eva A. Turley, 235 St. Clair Avenue West, Toronto (CA), M4V 1R4; Tony F. Cruz, 72 Thorncrest Road, Etobicoke (CA), M9A 1S9

( * ) Notice: Subject to any disclaimer, the term of this patent is extended or adjusted under 35 U.S.C. 154(b) by 134 days.

(21) Appl. No.: 09/685,010

(22) Filed: Oct. 5, 2000

Related U.S. Application Data

(63) Continuation-in-part of application No. 09/541,522, filed on Apr. 3, 2000, now abandoned.
(60) Provisional application No. 60/127,457, filed on Apr. 1, 1999.

(51) Int. Cl.[7] .............................................. C07K 14/705
(52) U.S. Cl. ......................... 514/12; 530/300; 530/350; 530/324; 530/395; 435/69.1
(58) Field of Search ....................... 514/12, 2; 530/300, 530/350, 324, 395, 387.1; 435/69.1, 7.1, 320.1, 325; 436/86

(56) References Cited

U.S. PATENT DOCUMENTS

| | | | |
|---|---|---|---|
| 4,018,884 A | 4/1977 | Cleeland, Jr. et al. | 424/7 |
| 4,359,535 A | 11/1982 | Pieczenik | 435/317 |
| 4,376,110 A | 3/1983 | David et al. | 436/513 |
| 4,411,993 A | 10/1983 | Gillis | 435/68 |
| 4,486,530 A | 12/1984 | David et al. | 435/7 |
| 4,528,266 A | 7/1985 | Pieczenik | 435/6 |
| 4,543,439 A | 9/1985 | Frackelton, Jr. et al. | 935/92 |
| RE32,011 E | 10/1985 | Zimmerman et al. | 260/112 B |
| 4,551,433 A | 11/1985 | DeBoer | 435/253 |
| 4,603,112 A | 7/1986 | Paoletti et al. | 435/235 |
| 4,736,866 A | 4/1988 | Leder et al. | 800/1 |
| 4,744,981 A | 5/1988 | Pavanasasivam | 424/85 |
| 4,745,051 A | 5/1988 | Smith et al. | 435/68 |
| 4,769,330 A | 9/1988 | Paoletti et al. | 435/68 |
| 4,816,597 A | 3/1989 | Snyder, II et al. | 560/25 |
| 4,851,341 A | 7/1989 | Hopp et al. | 435/68 |
| 4,870,009 A | 9/1989 | Evans et al. | 435/70 |
| 4,873,191 A | 10/1989 | Wagner et al. | 435/172.3 |
| 4,897,255 A | 1/1990 | Fritzberg et al. | 424/1.1 |
| 4,902,614 A | 2/1990 | Wakabayashi et al. | 435/7 |
| 4,987,071 A | 1/1991 | Cech et al. | 435/91 |
| 4,988,496 A | 1/1991 | Srinivasan et al. | 424/1.1 |
| 5,017,487 A | 5/1991 | Stunnenberg et al. | 435/172.3 |
| 5,087,571 A | 2/1992 | Leder et al. | 435/240.2 |
| 5,091,309 A | 2/1992 | Schlesinger et al. | 435/69.1 |
| 5,106,951 A | 4/1992 | Morgan, Jr. et al. | 530/391.9 |
| 5,110,833 A | 5/1992 | Mosbach | 521/50 |
| 5,162,215 A | 11/1992 | Bosselman et al. | 435/172.3 |
| 5,166,057 A | 11/1992 | Palese et al. | 435/69.1 |
| 5,169,784 A | 12/1992 | Summers et al. | 435/320.1 |
| 5,175,383 A | 12/1992 | Leder et al. | 800/2 |
| 5,175,384 A | 12/1992 | Krimpenfort et al. | 800/2 |
| 5,204,244 A | 4/1993 | Fell et al. | 435/69.6 |
| 5,217,879 A | 6/1993 | Huang et al. | 435/69.1 |
| 5,219,740 A | 6/1993 | Miller et al. | 435/69.6 |
| 5,221,778 A | 6/1993 | Byrne et al. | 800/2 |
| 5,225,539 A | 7/1993 | Winter | 530/387.3 |
| 5,242,687 A | 9/1993 | Tykocinski et al. | 424/93 |
| 5,243,041 A | 9/1993 | Fernandez-Pol | 536/23.5 |
| 5,254,678 A | 10/1993 | Haseloff et al. | 536/23.2 |
| 5,266,317 A | 11/1993 | Tomalski et al. | 424/93 T |
| 5,288,514 A | 2/1994 | Ellman | 427/2 |
| 5,288,641 A | 2/1994 | Roizman | 435/320.1 |
| 5,328,834 A | 7/1994 | Ngo et al. | 435/68.1 |
| 5,347,075 A | 9/1994 | Sorge | 800/2 |
| 5,359,051 A | 10/1994 | Cook et al. | 536/26.7 |
| 5,387,742 A | 2/1995 | Cordell | 800/2 |
| 5,395,750 A | 3/1995 | Dillon et al. | 435/5 |
| 5,463,564 A | 10/1995 | Agrafiotis et al. | 364/496 |
| 5,482,856 A | 1/1996 | Fell, Jr. et al. | 435/320.1 |
| 5,506,337 A | 4/1996 | Summerton et al. | 528/391 |
| 5,545,808 A | 8/1996 | Hew et al. | 800/2 |
| 5,567,607 A | 10/1996 | Zhao et al. | 435/172.1 |
| 5,580,859 A | 12/1996 | Felgner et al. | 514/44 |
| 5,591,624 A | 1/1997 | Barber et al. | 435/240.2 |
| 5,633,076 A | 5/1997 | DeBoer et al. | 435/172.3 |
| 5,693,761 A | 12/1997 | Queen et al. | 536/23.53 |
| 5,693,762 A | 12/1997 | Queen et al. | 530/387.3 |
| 5,698,435 A | 12/1997 | Robinson et al. | 435/240.2 |
| 5,716,613 A | 2/1998 | Guber et al. | 424/93.2 |
| 5,716,826 A | 2/1998 | Gruber et al. | 435/320.1 |
| 5,716,832 A | 2/1998 | Barber et al. | 435/172.3 |
| 5,741,957 A | 4/1998 | Deboer et al. | 800/2 |

(List continued on next page.)

FOREIGN PATENT DOCUMENTS

| | | |
|---|---|---|
| EP | 0415731 A2 | 3/1991 |
| EP | 0440219 A1 | 8/1991 |

(List continued on next page.)

OTHER PUBLICATIONS

Day, A. J. (2002) Hyaluronan–binding proteins: tying up the giant. J. Biol. Chem. vol. 277, pp. 4585–4588.*

(List continued on next page.)

*Primary Examiner*—Karen Cochrane Carlson
*Assistant Examiner*—Samuel Wei Liu
(74) *Attorney, Agent, or Firm*—Fish & Richardson P.C.

(57) ABSTRACT

The present invention provides compositions and methods for treating a tissue disorder associated with a response-to-injury process or proliferating cells in a mammal. The tissue disorders include fibrosis, inflammation, degeneration and invasive disorders such as those occur in cancerous cells. The methods provided herein include administering to the mammal, an effective amount of a composition that alters the activity of transition molecules within a cell. Transition molecules are shown to be comprised of hyaladherins, hyaluronans and associated molecules that regulate the transitional phenotype.

14 Claims, 56 Drawing Sheets

U.S. PATENT DOCUMENTS

| | | | | |
|---|---|---|---|---|
| 5,770,380 A | 6/1998 | Hamilton et al. | | 435/7.1 |
| 5,780,009 A | 7/1998 | Karatzas et al. | | 424/9.1 |
| 5,780,225 A | 7/1998 | Wigler et al. | | 435/6 |
| 5,789,245 A | 8/1998 | Dubensky, Jr. et al. | | 435/320.1 |
| 5,814,482 A | 9/1998 | Dubensky, Jr. et al. | | 435/69.3 |
| 5,817,491 A | 10/1998 | Yee et al. | | 435/172.3 |
| 5,840,479 A | 11/1998 | Little et al. | | 435/5 |
| 5,843,723 A | 12/1998 | Dubensky, Jr. et al. | | 435/69.3 |
| 5,849,288 A | 12/1998 | Reisner | | 424/93.21 |
| 5,851,529 A | 12/1998 | Guber et al. | | 424/188.1 |
| 5,872,005 A | 2/1999 | Wang et al. | | 435/320.1 |
| 6,271,344 B1 | 8/2001 | Turley | | |

FOREIGN PATENT DOCUMENTS

| | | | |
|---|---|---|---|
| EP | 0612844 A2 | | 8/1994 |
| EP | 0 721 012 | | 7/1996 |
| EP | 0360257 B1 | | 11/1996 |
| EP | 0 950 708 | | 10/1999 |
| WO | Wo 89/01973 | | 3/1989 |
| WO | WO 90/02809 | | 3/1990 |
| WO | WO 90/07862 | | 7/1990 |
| WO | WO 90/07936 | | 7/1990 |
| WO | WO 91/00285 | | 1/1991 |
| WO | WO 92/15677 | | 9/1992 |
| WO | WO 92/15679 | | 9/1992 |
| WO | WO 93/10218 | | 5/1993 |
| WO | Wo 93/11230 | | 6/1993 |
| WO | WO 93/12227 | | 6/1993 |
| WO | WO 93/20242 | | 10/1993 |
| WO | WO9321312 | * | 10/1993 |
| WO | WO 93/21312 | | 10/1993 |
| WO | WO 93/25234 | | 12/1993 |
| WO | WO 93/25698 | | 12/1993 |
| WO | WO 94/03622 | | 2/1994 |
| WO | Wo 92/06693 | | 4/1994 |
| WO | WO 95/02566 | | 1/1995 |
| WO | WO 95/04277 | | 2/1995 |
| WO | WO 95/10607 | | 4/1995 |
| WO | Wo 95/12387 | | 5/1995 |
| WO | WO 95/16209 | | 6/1995 |
| WO | WO 95/16712 | | 6/1995 |
| WO | WO 95/16918 | | 6/1995 |
| WO | WO 95/24186 | | 9/1995 |
| WO | WO 95/24929 | | 9/1995 |
| WO | WO 95/30642 | | 11/1995 |
| WO | WO 96/00148 | | 1/1996 |
| WO | WO9738098 | * | 10/1997 |
| WO | WO 97/38098 | | 10/1997 |
| WO | Wo 99/01164 | | 1/1999 |
| WO | WO 00/01841 | | 1/2000 |
| WO | WO 00/29447 | | 5/2000 |
| WO | WO 00/39166 | | 7/2000 |
| WO | WO 01/80899 | | 11/2001 |
| WO | WO 02/13848 | | 2/2002 |
| WO | WO 02/28415 | | 4/2002 |

OTHER PUBLICATIONS

Assmann, V. et al. (1999) The Intracellular hyraluronan receptor RHAMM/IHABP interacts with microtubules and actin filaments J Cell Sci. vol. 112, pp. 3943–3954.*

William J. Kuhns et al., "Hyaluronic Acid–Receptor Binding Demonstrated by Synthetic Adhesive Proteoglycan Peptide Constructs and by Cell Receptors on the Marine Sponge Microciona prolifera," Reports from the MBL General Scientific Meetings; Reference: Biol. Bull. 195: 216–218 (Oct. 1998).

Savani et al., "The Role of Hyaluronan and Its Receptors in restonosis After Balloon Angioplasty: Development of a Potential Therapy", Inc. J. Tiss. Reac. XVII (4) pp. 141–151 (1995).

W.F. Cheung, "Receptor for hyaluronan–mediated motility (RHAMM), a hyaladherin that regulates call responses to growth factors", Biochemical Society Transactions, pp. 135–142 (Feb. 1999).

U.S. Patent application Ser. No. 09/544,522, Turkey et al., filed Apr. 3, 2000.

Chao, et al., "The characterization of a human RHAMM cDNA: conservation of they hyaluronan–binding domains", *Gene*, vol. 174, No. 2, (1996), pp. 299–306.

Jean, et al., "Unmasking a Hyaluronan–binding site of the BX7B type in the H3 heavy chain of the inter–alpha–Inhibitor family", *European Journal of Biochemistry*, vol. 268, No. 3, (Feb. 1, 2001), pp. 544–553.

Volker, et al., "The human hyaluron receptor RHAMM is expressed as an intracellular protein in breast cancer cells", *J. Cell Science*, vol. 111, (1998), pp. 1685–1694.

International Search Report of Aug. 22, 2001 in PCT Application No. PCT/I00/01534 (copending application).

Alting–Mees et al., "Monoclonal Antibody Expression Libraries: A Rapid Alternative to Hybridomas," *Strategies in Molecular Biology 3*: 1–9, 1990.

Bauer et al., "A genetic enrichment for mutations constructed by oligodeoxynucleotide–directed mutagenesis," *Gene 37*: 73–81, 1985.

Bird et al., "Single–Chain Antigen–Binding Proteins," *Science 242*(4877): 423–426, 1988.

Brinster et al., "Factors affecting the efficiency of introducing foreign DNA into mice by microinjecting eggs,"*PNAS 82*(13): 4438–4442, Jul. 1985.

Chothia et al., "Domain Association in Immunoglobulin Molecules. The Packing of Variable Domains," *Journal of Molecular Biology 186*(3): 651–663, 1985.

Craik et al., "Use of Oligonucleotides for Site–Specific Mutagenesis," *BioTechniques 3*(1): 12–19, 1985.

Curiel et al., "High–Efficiency Gene Transfer Mediated by Adenovirus Coupled to DNA–Polylysine Complexes," *Human Gene Therapy 3*(2):147–154, 1992.

Drinkwater and Klinedinst,"Chemically induced mutagenesis in a shuttle vector with a low–background mutant frequency," *PNAS 83*(10):3402–3406, May, 1986.

Fisher–Hoch et al., "Protection of rhesus monkeys from fatal Lassa fever by vaccination with a recombinant vaccinia virus containing the Lassa virus glycoprotein gene," *PNAS 86*(1): 317–321, Jan. 1989.

Flexner et al., "Attenuation and immunogenicity in primates of vaccinia virus recombinants expressing human interleukin–2," *Vaccine 8*(1):17–21, Feb., 1990.

Forster and Symons, "Self–Cleavage of Plus and Minus RNAs of a Virusoid and a Structural Model for the Active Sites," *Cell 49*(2):211–220, Apr. 24, 1987.

Gerlach et al., "Construction of a plant disease resistance gene from the satellite RNA of tobacco ringspot virus," *Nature 328*(6133): 802–805, Aug., 1987.

Hammer et al., "Production of transgenic rabbits, sheep and pigs by microinjection," *Nature 315*: 680–683, Jun. 20, 1985.

Haseloff and Gerlach, "Simple RNA enzymes with new and highly specific endoribonuclease activities," *Nature 334*(6183): 585–591, Aug. 18, 1988.

Heijne, Gunner von, "Signal Sequences, The Limits of Variation," *Journal of Molecular Biology 184*(1): 99–105, 1985.
Hirashima et al., *Molecular Biology of RNA*: New Perspectives, Academic Press, Inc., San Diego, CA, 1987, Chapter 26, "A New Immune System against Viral Infection Using Antisense RNA: micRNA–Immune System," pp. 401–413.
Hopp et al., "A Short Polypeptide Marker Sequence Useful For Recombinant Protein Identification and Purification," *BioTechnology 6*(10): 1204–1210, Oct., 1988.
Horwitz et al., "Selection of new biological activities from random nucleotide sequences: evolutionary and practical considerations," *Genome 3*: 112–117, 1989.
Huse et al., "Generation of a Large Combinatorial Library of the Immunoglobulin Repertoire in Phage Lambda," *Science 246*(4935): 1275–1281, Dec., 1989.
Inman, "Covalent Linkage of Functional Groups, Ligands, and Proteins of Polyacrylamide Beads," *Methods in Enzymology*, vol. 34, Affinity Techniques, Enzyme Purification: Part B, Jakoby and Wilchek (eds.), Academic Press, New York, 1974, pp. 30–59.
Jones et al., "Replacing the complementarity–determining regions in a human antibody with those from a mouse," *Nature 321*: 522–525, May 29, 1986.
Kit, Saul, "Recombinant–Derived Modified–Live Herpesvirus Vaccines," *Adv. Exp. Med. Biol. 215*: 219–235, 1989.
Köhler and Milstein, "Continuous cultures of fused cells secreting antibody of predefined specificity," *Nature 256*(5517): 495–497, Aug. 7, 1975.
Kyte and Doolittle, "A Simple Method for Displaying the Hydropathic Character of a Protein," *Journal of Molecular Biology 157*(1): 105–132, 1982.
Look et al., "The Identification of Cyclooxygenase–1 Inhibitors From 4–Thiazolidinone Combinatorial Libraries," *Biorganic and Medicinal Chemistry Letters 6*(6):707–712, 1996.
Luytjes et al., "Amplification, Expression, and Packaging of a Foreign Gene by Influenza Virus," *Cell 59*: 1107–1113, Dec. 22, 1989.
Liao and Wise, "A Simple high–efficiency method for random mutagenesis of cloned genes using forced nucleotide misincorporation," *Gene 88*: 107–111, 1990.
McMichael et al., "Cytotoxic T–Cell Immunity To Influenza," *The New England Journal of Medicine 309*(1): 13–17, 1983.
Morrison et al., "Chimeric human antibody molecules: Mouse antigen–binding domains with human constant region domains," *PNAS 81*(21): 6851–6855, Nov. 1984.
Moss and Flexner, "Vaccinia Virus Expression Vectors," *Annals of the New York Academy of Sciences 569*:86–103, 1989.
Mulligan et al., "Synthesis of rabbit β–globin in cultured monkey kidney cells following infection with a SV40 β–globin recombinant genome," *Nature 277*: 108–114, Jan., 1979.
Novotnỳ and Haber, "Structural invariants of antigen binding: Comparison of immunoglobulin $V_L$–$V_H$ domain dimers," *PNAS 82*(14): 4592–4596, Jul., 1985.
Palmiter et al., "Metallothionein–Human GH Fusion Genes Stimulate Growth of Mice," *Science 222*(4625): 809–814, Nov., 1983.
Palmiter and Brinster, "Transgenic Mice," *Cell 41*(2): 343–345, Jun., 1985.
Phillips and Wei, "Solid Phase Synthesis of Benzimidazoles," *Tet. Letters 37*: 4887–4890, 1996.
Poznansky et al., "Gene Transfer into Human Lymphocytes by a Defective Human Immunodeficiency Virus Type 1 Vector," *Journal of Virology 65*(1): 532–536, Jan., 1991.
Presta, "Antibody engineering," *Current Op. Struct. Biol. 2*:593–596, 1992.
Riechmann et al., "Reshaping human antibodies for therapy," *Nature 332*(6162): 323–327, Mar. 24, 1988.
Ruhland et al., "Solid–Supported Combinatorial Synthesis of Structurally Diverse β–Lactams," *J. Am. Chem. Soc. 118*(1): 253–254, 1996.
Sastry et al., "Cloning of the immunological repertoire in *Escherichia coli* for generation of monoclonal catalytic antibodies: Construction of a heavy chain variable region–specific cDNA library," *PNAS 86*(15): 5728–5732, Aug., 1989.
Scatchard et al., "The Attractions of Proteins for Small Molecules and Ions," *Annals of The New York Academy of Sciences 51*(4): 660–673, 1949.
Smith and Gillam, "Constructed Mutants Using Synthetic Oligodeoxyribonucleotides as Site–Specific Mutagens," *Genetic Engineering 3*:1–32, 1981.
Stein and Cheng, "Antisense Oligonucleotides as Therapeutic Agents–Is the Bullet Really Magical?" *Science 261*(5124): 1004–1012, Aug. 20, 1993.
Walbot and Bruening, "Plant development and ribozymes for pathogens," *Nature 334*(6179): 196–197, Jul. 21, 1988.
Walder and Walder, "Oligodeoxynucleotide–directed mutagenesis using the yeast transformation system," *Gene 42*: 133–139, 1986.
Wang et al., "The Overexpression of RHAMM, a Hyaluronan–binding Protein That Regulates ras Signaling, Correlates with Overexpression of Mitogen–activated Protein Kinase and Is a Significant Parameter in Breast Cancer Progression," *Clinical Cancer Research 4*(3): 567–576, Mar., 1998.
Wilchek and Bayer, "The Avidin–Biotin Complex in Bioanalytical Applications," *Analytical Biochemistry 171*: 1–32, 1988.
Wu et al., "Targeting Genes: Delivery and Persistant Expression of a Foreign Gene Driven by Mammalian Regulatory Elements in Vivo," *The Journal of Biological Chemistry 264*(29): 16985–16987, Oct. 15, 1989.
Yap and Ada, "Transfer of specific cytotoxic T lymphocytes protects mice inoculated with influenza virus," *Nature 273*: 238–239, May 18, 1978.

* cited by examiner

-Focal Adhesions (-FA)

+Focal Adhesions (+FA)

+RHAMM

-RHAMM

+RHAMM cells make less focal contacts than their parental cells (-RHAMM)

• In most cells responding to injury, podosomes are formed and disassembled rapidly (-RHAMM, 6 vs. 24 hrs)

· Overexpression of RHAMM results in increased and sustained production of podosomes

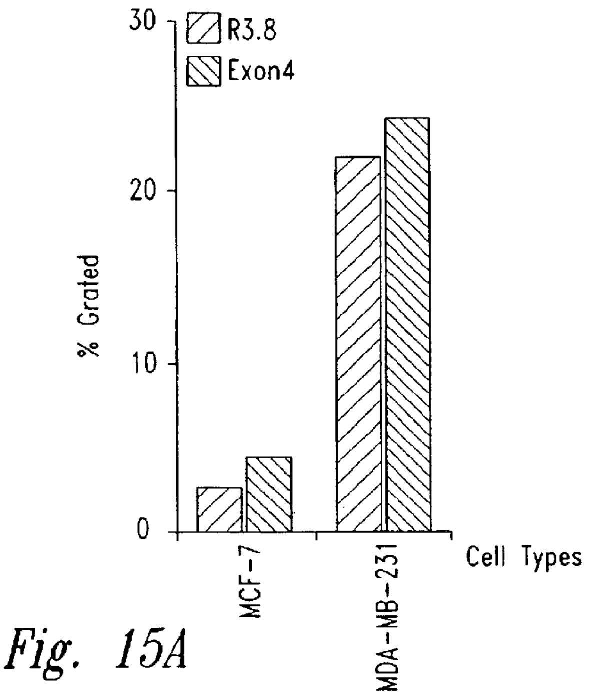

*Fig. 15A*

RHAMM Peptides

Murine Exon3 sequence:
N-terminal ---KLQATQKDLTESKGKIVQLEGKL--- 23aa SEQ ID. NO. 14

For Exon3 antibody, used the peptide sequence:
(C) KLQATQKDLTESKG SEQ ID. NO. 15

Murine Exon4 sequence:
N-terminal ---VSIEKEKIDEKCETEKLLEYIQEIS--- 25aa SEQ ID. NO. 16

For Exon4 antibody, used the peptide sequence:
(C) VSIEKEKIDEKC/S SEQ ID. NO. 17

For antibody to Human RHAMM v5, used the peptide sequence:
(C) LKSKFSENGNQKNL SEQ ID. NO. 18

Homology between three peptides from murine (M) and human (H) RHAMM (as used to raise antibody)

| | | | |
|---|---|---|---|
| 1) Exon3 | M: | KLQATQKDLTESKG | as in SEQ ID. NO. 15 |
| | H: | ---V--RS-E-Q-- | SEQ ID. NO. 19 |
| 2) Exon4 | M: | VSIEKEKIDEKC | as in SEQ ID. NO. 17 |
| | H: | -----------S | as in SEQ ID. NO. 17 |
| 3) v5 | M: | --A----D-H---M | SEQ ID. NO. 20 |
| | H: | LKSKFSENGNQKNL | as in SEQ ID. NO. 18 |

*Fig. 15B*

Effects of Exon4 Antibody and LZP on the Podosome Formation of LR21

Exon4 HA-tag Merge

Cortactin FN-TR Overlay

Anti-RHAMM (exon3) IgG control

Stromelysin I

A: RGGGRGRRR
B: RGGGRGGRR
C: RGGGRGGGR
D: RGGGGGGGR
*Fig. 26A*
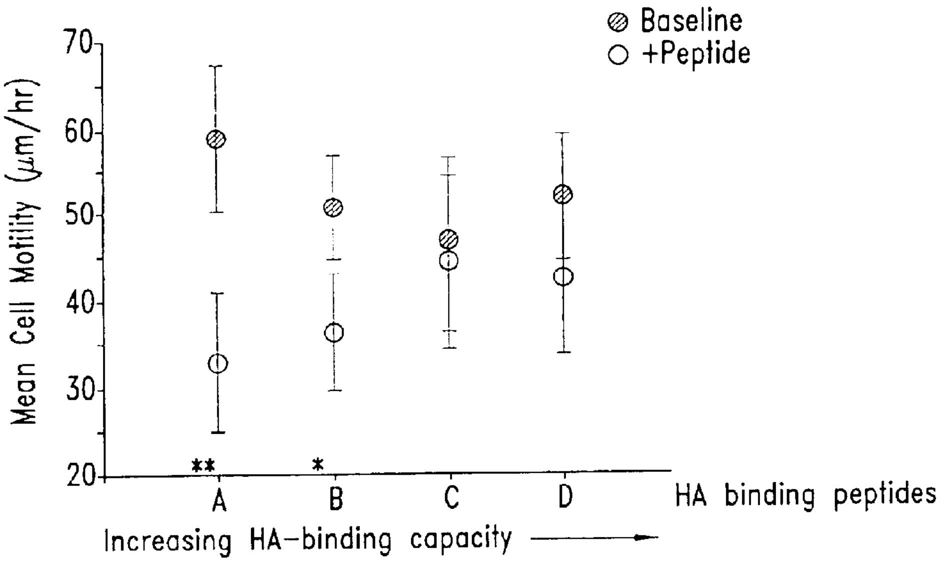
*Fig. 26B*
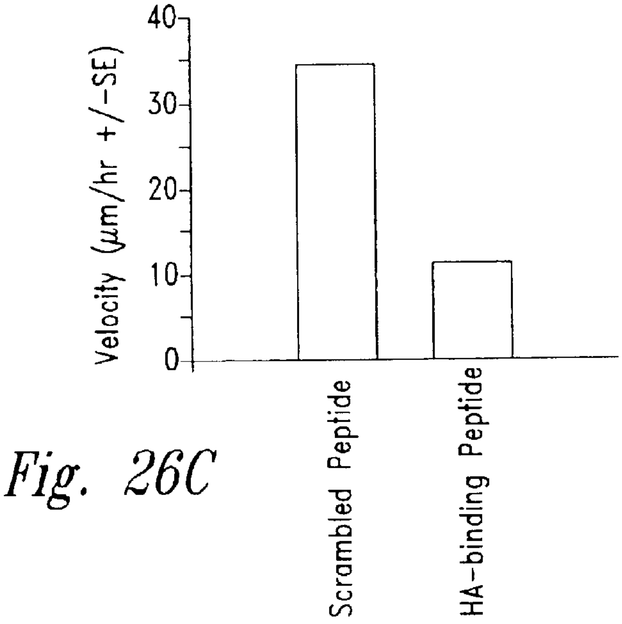
*Fig. 26C*

| Patient | % of total X4+ cells | % of total V5+ cells | *Neutrophils* % of total cells | % of X4+ cells | % of V5+ cells | *Monocytes/macrophages* % of total cells | % of X4+ cells | % of V5+ cells | *T cells* % of total cells | % of X4+ cells | % of V5+ cells |
|---|---|---|---|---|---|---|---|---|---|---|---|
| W.H. | ND | 50.7 | 70.5 | 81.2 | ND | 21.8 | 87.1 | 66.4 | 6.7 | 11.7 | 13.0 |
| M.T. | 74.6 | 20.7 | 80.7 | ND | 9.9 | 11.2 | 89.6 | ND | 9.0 | <2.0 | ND |
| L.S. | 43.9 | 34.4 | ND | ND | ND | 8.5 | ND | 53.8 | 20.4 | 5.3 | <2.0 |
| S.M. | 67.6 | 4.0 | 67.3 | 80.9 | ND | ND | ND | ND | 3.0 | 10.0 | <2.0 |
| M.M. | 19.2 | 19.6 | 25.2 | 68.3 | ND | ND | ND | ND | 2.7 | 4.5 | 8.0 |
| D.D | 35.7 | 31.2 | 40.7 | 99.3 | ND | ND | ND | ND | 6.9 | <2.0 | 9.9 |
| P.B. (r) | 77.4 | 71.8 | ND | ND | ND | 9.2 | 99.8 | 88.3 | 4.4 | 13.0 | 33.2 |
| P.B. (l) | 85.0 | 82.3 | ND | ND | ND | 12.8 | 99.4 | 58.3 | 3.4 | 11.0 | 30.2 |
| S.L. | 51.6 | 45.5 | 61.7 | 92.1 | 77.2 | 8.8 | 73.4 | 85.6 | 24.0 | 6.0 | 9.0 |
| R.C. | 10.6 | 6.7 | 54.1 | 63.8 | 13.8 | 5.6 | 50.3 | 43.9 | 6.3 | 8.5 | 11.9 |
| N.N. | 27.9 | 10.3 | 44.1 | 54.6 | 21.4 | 3.5 | 77.1 | 49.4 | 6.8 | 33.1 | 22.2 |
| M.G | 85.48 | 84.63 | 86.7 | 99.6 | 99.5 | 5.52 | 98.7 | 98.9 | 6.36 | 4.8 | 7.6 |

- ND - non-determined
- (r) - right knee
- (l) - left knee

*Fig. 37*

| Normalized Values | |
|---|---|
| U87 MG | 9.22 |
| U343MG-A | 9.19 |

RHAMM binding protein cDNA (RABP) (partial)

GAA TTC GCG GCG GCG TCG ACC AAC AAG CCC CCT GCT GTT TCC CCG GGG
E F A A A S T N K P P A V S P G
GTG GTC TCC CCA ACC TTT GAA CTT ACA AAT CTT CTA AAT CAT CCT GAC
V V S P T F E L T N L L N H P D
CAT TAT GTA GAA ACA GAG AAC ATT CAG CAT CTC ACA GAC CCG GCT CTA
H Y V E I E N I Q H L T D P A L
GCA CAT GTG GAT AGA ATA AGC GAA GCC CGG AAA CTG AGT ATG GGA TCT
A H V D R I S Q A R K L S M G S
GAT GAT GCT GCC TAC ACA CAA GCT CTG CTG GTG CAC CAG AAG GCC AGG
D D A A Y T Q A L L V H Q K A R
ATG GAA CGG CTT CAA AGA GAG CTC GAG ATG CAA AAG AAA AAG CTG GAT
M E R L Q R E L E M Q K K K L D
AAA CTC AAA TCT GAG GTC AAT GAG ATG GAA AAT AAT CTA ACT CGA AGG
K L K S E V N E M E N N L T R R
CGC CTG AAG AGA TCA AAT TCC ATT TCC CAG ATA CCG TCA CTC GAA GAA
R L K R S N S I S Q I P S L E E
ATG CAG CAG TTG AGA AGT TGT AAT AGA CAA CTC CAG ATT GAC ATT GAC
M Q Q L R S C N R Q L Q I D I D
TTT GAC TGC TTA ACC AAA GAA ATT GCA TCT TTT TCA AGC CCG AGG ACC
F D C L T K E I A S F S S P R T
ACA TTT TAA CCC CAG CGC TAT TCA TAA CTT TTA TGA CAA TAT TGG ATT
T F *
TGT AGG CCC TGT GCC ACC AAA ACC CAA AGA TCA AAG GTC CAC CAT CAA
AGG TCG ACG CGG

*Fig. 49A*

```
Human:   1 MSFPKAPLKRFNDPSGCAPSPGAYDVKTLEVLKGPVSFQKSQRFKQQKESKQNLNVDKDTTLPASARKVKSSESK

Human:  76 KESQKNDKDLKILEKEIRVLLQERGAQDRRIQDLETELEKMEARLNAALREKTSLSANNATLEKQLIELTRTNEL

Human: 151 LKSKFSENGNQKNLRILSLELMKLRNKRETKMRGMMAKQEGMEMKLQVTQRSLEESQGKIAQLEGKLVSIEKEKI
                           |+||||||||||||||| || |||||+||| ||+ | || ||||||||||||||||
Mouse:   1                 MRALSLELMKLRNKRETKMRSMMVKQEGMELKLQATQKDLTESKGKIVQLEGKLVSIEKEKI

Human: 226 DEKSETEKLLEYIEEISCASDQVEKYKLDIAQLEENLKEKNDEILSLKQSLEENIVILSKQVEDLNVKCQLLEKE
           |||+|||||||| |||||||||+|+|||||| |||| |||| |||||||| + ||| ||| ||||||| |
Mouse:  63 DEKCETEKLLEYIQEISCASDQVEKCKVDIAQLEEDLKEKDREILSLKQSLEENITF-SKQIEDLTVKCQLLETE

Human: 301 KEDHVNRNREHNENLNAEMQNLKQKFILEQQEHEKLQQKELQIDSLLQQEKELSSSLHQKLCSFQEEMVKEKNLF
           ++  |++ ||+ |+|+|||| | ++++||+|| |||||||| |||||||||+ | |+||||||| |||+|
Mouse: 138 RNDLVSKDRERAETLSAEMQILTERLALERQEYEKLQQKELQSQSLLQQEKELSARLQQQLCSFQEEMTSEKNVF

Human: 376 EEELKQTLDELDKLQQKEEQAERLVKQLEEEAKSRAEELKLLEEKLKGKEAELEKSSAAHTQATLLL--------
            |||| | ||| +|||||+||||||||| || ||+| |+ |+ || |||| ||| || |+
Mouse: 213 KEELKLALAELDAVQQKEEQSERLVKQLEEERKSTAEQLTRLDNLLREKEVELEKHIAAHAQAILIAQEKYNDTA

Human:     ---------------------------------------------------------------------------

Mouse: 288 QSLRDVTAQLESVQEKYNDTAQSLRDVTAQLESEQEKYNDTAQSLRDVTAQLESEQEKYNDTAQSLRDVTAQLES

Human: 443 QEKYDSMVQSLEDVTAQFESYKALTASEIEDLKLENSSLQEKAAKAGKNAEDVQHQILATESSNQEYVRMLLDLQ
           ||||+   ||| ||||| ||||+ |  |||||||| +|||| | | |+ |||| |||  ||+|||| ||+ |||
Mouse: 363 QEKYNDTAQSLRDVTAQLESYKSSTLKEIEDLKLENLTLQEKVAMAEKSVEDVQQQILTAESTNQEYARMVQDLQ

Human: 518 TKSALKETEIKEITVSFLQKITDLQNQLKQQEEDFRKQLEDEEGRKAEKENTTAELTEEINKWRLLYEELYNKTK
           +| ||| |||||| |||+|||||+|||+||+||||||||++ | |||||   ||| |||||||||||||| |||
Mouse: 438 NRSTLKEEEIKEITSSFLEKITDLKNQLRQQDEDFRKQLEEKGKRTAEKENVMTELTMEINKWRLLYEELYEKTK

Human: 593 PFQLQLDAFEVEKQALLNEHGAAQEQLNKIRDSYAKLLGHQNLKQKIKHVVKLKDENSQLKSEVSKLRCQLAKKK
           ||| |||||| |||||||||| ||||||||||||+|||||||||||||||||||||||||||||||+|| |+|
Mouse: 513 PFQQQLDAFEAEKQALLNEHGATQEQLNKIRDSYAQLLGHQNLKQKIKHVVKLKDENSQLKSEVSKLRSQLVKRK

Human: 668 QSETKLQEELNKVLGIKHFDPSKAFHHESKENFALKTPLKEGNTNCYRAPMECQESWK*
           |+|++|| ||+| |||+||||||| | |||||   ||||||| ||
Mouse: 588 QNELRLQGELDKALGIRHFDPSKAFCHASKENF---TPLKEGNPNCC*
```

*Fig. 50*

Note: normal blood glucose level = 99-140

Incidence of abnormal blood glucose level in NOD mice

Incidence of abnormal urine glucose level in NOD mice

Note: Increased H20 consumption indicative of Diabetes Insipidus, a complication of Diabetes Mellitus Effect of P-16 peptide on water consumption in NOD mice Note: 2 untreated animals died during the course of experiment Effect of P- 16 peptide on kidney weight in NOD mice

SEQUENCE LISTING

```
<160> NUMBER OF SEQ ID NOS: 72

<210> SEQ ID NO 1
<211> LENGTH: 8
<212> TYPE: PRT
<213> ORGANISM: Artificial Sequence
<220> FEATURE:
<223> OTHER INFORMATION: Peptide that binds a hyalauronan
<221> NAME/KEY: VARIANT
<222> LOCATION: (1)...(5)
<223> OTHER INFORMATION: Xaa = any amino acid
<221> NAME/KEY: HELIX
<222> LOCATION: (1)...(5)
<223> OTHER INFORMATION: Alpha-helix
<221> NAME/KEY: VARIANT
<222> LOCATION: (6)...(8)
<223> OTHER INFORMATION: Xaa = Lysine or Arginine

<400> SEQUENCE: 1

Xaa Xaa Xaa Xaa Xaa Xaa Xaa Xaa
 1               5


<210> SEQ ID NO 2
<211> LENGTH: 11
<212> TYPE: PRT
<213> ORGANISM: Artificial Sequence
<220> FEATURE:
<223> OTHER INFORMATION: Peptide that binds a hyalauronan
<221> NAME/KEY: VARIANT
<222> LOCATION: (1)...(5)
<223> OTHER INFORMATION: Xaa = any amino acid
<221> NAME/KEY: HELIX
<222> LOCATION: (1)...(5)
<223> OTHER INFORMATION: Alpha-helix
<221> NAME/KEY: VARIANT
<222> LOCATION: (6)...(6)
<223> OTHER INFORMATION: Xaa = Lysine or Arginine
<221> NAME/KEY: VARIANT
<222> LOCATION: (7)...(7)
<223> OTHER INFORMATION: Xaa = Hydrophobic or neutral amino acid
      consisting of I,L,V,Q,S
<221> NAME/KEY: VARIANT
<222> LOCATION: (8)...(9)
<223> OTHER INFORMATION: Xaa = Lysine or Arginine
<221> NAME/KEY: VARIANT
<222> LOCATION: (10)...(10)
<223> OTHER INFORMATION: Xaa = Hydrophobic or neutral amino acid
      consisting of I,L,V,Q,S
<221> NAME/KEY: VARIANT
<222> LOCATION: (11)...(11)
<223> OTHER INFORMATION: Xaa = Lysine or Arginine

<400> SEQUENCE: 2

Xaa Xaa Xaa Xaa Xaa Xaa Xaa Xaa Xaa Xaa Xaa
 1               5                   10


<210> SEQ ID NO 3
<211> LENGTH: 12
<212> TYPE: PRT
<213> ORGANISM: Artificial Sequence
<220> FEATURE:
```

-continued

```
<223> OTHER INFORMATION: Peptide that binds a hyalauronan
<221> NAME/KEY: VARIANT
<222> LOCATION: (1)...(5)
<223> OTHER INFORMATION: Xaa = any amino acid
<221> NAME/KEY: HELIX
<222> LOCATION: (1)...(5)
<223> OTHER INFORMATION: Alpha-helix
<221> NAME/KEY: VARIANT
<222> LOCATION: (6)...(6)
<223> OTHER INFORMATION: Xaa = Lysine or Arginine
<221> NAME/KEY: VARIANT
<222> LOCATION: (7)...(7)
<223> OTHER INFORMATION: Xaa = Hydrophobic or neutral amino acid
      consisting of I,L,V,Q,S
<221> NAME/KEY: VARIANT
<222> LOCATION: (8)...(8)
<223> OTHER INFORMATION: Xaa = Lysine or Arginine
<221> NAME/KEY: VARIANT
<222> LOCATION: (9)...(9)
<223> OTHER INFORMATION: Xaa = Hydrophobic or neutral amino acid
      consisting of I,L,V,Q,S
<221> NAME/KEY: VARIANT
<222> LOCATION: (10)...(12)
<223> OTHER INFORMATION: Xaa = Lysine or Arginine

<400> SEQUENCE: 3

Xaa Xaa Xaa Xaa Xaa Xaa Xaa Xaa Xaa Xaa Xaa Xaa
 1               5                  10


<210> SEQ ID NO 4
<211> LENGTH: 10
<212> TYPE: PRT
<213> ORGANISM: Artificial Sequence
<220> FEATURE:
<223> OTHER INFORMATION: Peptide that binds a hyalauronan
<221> NAME/KEY: VARIANT
<222> LOCATION: (1)...(5)
<223> OTHER INFORMATION: Xaa = any amino acid
<221> NAME/KEY: HELIX
<222> LOCATION: (1)...(5)
<223> OTHER INFORMATION: Alpha-helix
<221> NAME/KEY: VARIANT
<222> LOCATION: (6)...(6)
<223> OTHER INFORMATION: Xaa = Lysine or Arginine
<221> NAME/KEY: VARIANT
<222> LOCATION: (7)...(7)
<223> OTHER INFORMATION: Xaa = Hydrophobic or neutral amino acid
      consisting of I,L,V,Q,S
<221> NAME/KEY: VARIANT
<222> LOCATION: (8)...(10)
<223> OTHER INFORMATION: Xaa = Lysine or Arginine

<400> SEQUENCE: 4

Xaa Xaa Xaa Xaa Xaa Xaa Xaa Xaa Xaa Xaa
 1               5                  10


<210> SEQ ID NO 5
<211> LENGTH: 9
<212> TYPE: PRT
<213> ORGANISM: Artificial Sequence
<220> FEATURE:
<223> OTHER INFORMATION: Peptide that binds a hyalauronan
<221> NAME/KEY: VARIANT
<222> LOCATION: (1)...(5)
<223> OTHER INFORMATION: Xaa = Any amino acid
<221> NAME/KEY: HELIX
<222> LOCATION: (1)...(5)
<223> OTHER INFORMATION: Alpha-helix
<221> NAME/KEY: VARIANT
<222> LOCATION: (6)...(6)
<223> OTHER INFORMATION: Xaa = Lysine or Arginine
<221> NAME/KEY: VARIANT
<222> LOCATION: (7)...(7)
<223> OTHER INFORMATION: Xaa = Hydrophobic or neutral amino acid
      consisting of I,L,V,Q,S
```

-continued

```
<221> NAME/KEY: VARIANT
<222> LOCATION: (8)...(9)
<223> OTHER INFORMATION: Xaa = Lysine or Arginine

<400> SEQUENCE: 5

Xaa Xaa Xaa Xaa Xaa Xaa Xaa Xaa Xaa
 1               5


<210> SEQ ID NO 6
<211> LENGTH: 7
<212> TYPE: PRT
<213> ORGANISM: Artificial Sequence
<220> FEATURE:
<223> OTHER INFORMATION: Peptide that binds a hyalauronan
<221> NAME/KEY: HELIX
<222> LOCATION: (1)...(5)
<223> OTHER INFORMATION: Alpha-helix

<400> SEQUENCE: 6

Met Met Thr Val Leu Lys Arg
 1               5


<210> SEQ ID NO 7
<211> LENGTH: 11
<212> TYPE: PRT
<213> ORGANISM: Artificial Sequence
<220> FEATURE:
<223> OTHER INFORMATION: Peptide that binds a hyalauronan
<221> NAME/KEY: HELIX
<222> LOCATION: (1)...(5)
<223> OTHER INFORMATION: Alpha-helix

<400> SEQUENCE: 7

Met Met Thr Val Leu Lys Val Lys Arg Leu Arg
 1               5                  10


<210> SEQ ID NO 8
<211> LENGTH: 12
<212> TYPE: PRT
<213> ORGANISM: Artificial Sequence
<220> FEATURE:
<223> OTHER INFORMATION: Peptide that binds a hyalauronan
<221> NAME/KEY: HELIX
<222> LOCATION: (1)...(5)
<223> OTHER INFORMATION: Alpha-helix

<400> SEQUENCE: 8

Met Met Thr Val Leu Lys Val Lys Val Lys Arg Lys
 1               5                  10


<210> SEQ ID NO 9
<211> LENGTH: 10
<212> TYPE: PRT
<213> ORGANISM: Artificial Sequence
<220> FEATURE:
<223> OTHER INFORMATION: Peptide that binds a hyalauronan
<221> NAME/KEY: HELIX
<222> LOCATION: (1)...(5)
<223> OTHER INFORMATION: Alpha-helix

<400> SEQUENCE: 9

Met Met Thr Val Leu Lys Val Arg Lys Arg
 1               5                  10


<210> SEQ ID NO 10
<211> LENGTH: 9
<212> TYPE: PRT
<213> ORGANISM: Artificial Sequence
<220> FEATURE:
```

-continued

```
<223> OTHER INFORMATION: Peptide that binds a hyalauronan
<221> NAME/KEY: HELIX
<222> LOCATION: (1)...(5)
<223> OTHER INFORMATION: Alpha-helix

<400> SEQUENCE: 10

Met Met Thr Val Leu Lys Val Arg Lys
 1               5


<210> SEQ ID NO 11
<211> LENGTH: 13
<212> TYPE: PRT
<213> ORGANISM: Homo sapiens

<400> SEQUENCE: 11

Lys Leu Gln Ala Thr Gln Lys Pro Leu Thr Glu Ser Lys
 1               5                  10


<210> SEQ ID NO 12
<211> LENGTH: 12
<212> TYPE: PRT
<213> ORGANISM: Homo sapiens

<400> SEQUENCE: 12

Val Ser Ile Glu Lys Glu Lys Ile Asp Glu Lys Ser
 1               5                  10


<210> SEQ ID NO 13
<211> LENGTH: 6
<212> TYPE: PRT
<213> ORGANISM: Artificial Sequence
<220> FEATURE:
<223> OTHER INFORMATION: Peptide developed based upon the TAM domain
      (Transient Activator of MAP kinases)
<221> NAME/KEY: VARIANT
<222> LOCATION: (3)...(3)
<223> OTHER INFORMATION: Xaa = Any amino acid

<400> SEQUENCE: 13

Val Ser Xaa Lys Glu Lys
 1               5


<210> SEQ ID NO 14
<211> LENGTH: 23
<212> TYPE: PRT
<213> ORGANISM: Mus musculus

<400> SEQUENCE: 14

Lys Leu Gln Ala Thr Gln Lys Asp Leu Thr Glu Ser Lys Gly Lys Ile
 1               5                  10                  15

Val Gln Leu Glu Gly Lys Leu
            20


<210> SEQ ID NO 15
<211> LENGTH: 14
<212> TYPE: PRT
<213> ORGANISM: Mus musculus

<400> SEQUENCE: 15

Lys Leu Gln Ala Thr Gln Lys Asp Leu Thr Glu Ser Lys Gly
 1               5                  10


<210> SEQ ID NO 16
<211> LENGTH: 25
<212> TYPE: PRT
<213> ORGANISM: Mus musculus
```

-continued

<400> SEQUENCE: 16

Val Ser Ile Glu Lys Glu Lys Ile Asp Glu Lys Cys Glu Thr Glu Lys
1 5 10 15

Leu Leu Glu Tyr Ile Gln Glu Ile Ser
20 25

<210> SEQ ID NO 17
<211> LENGTH: 12
<212> TYPE: PRT
<213> ORGANISM: Mus musculus

<400> SEQUENCE: 17

Val Ser Ile Glu Lys Glu Lys Ile Asp Glu Lys Cys
1 5 10

<210> SEQ ID NO 18
<211> LENGTH: 14
<212> TYPE: PRT
<213> ORGANISM: Homo sapien

<400> SEQUENCE: 18

Leu Lys Ser Lys Phe Ser Glu Asn Gly Asn Gln Lys Asn Leu
1 5 10

<210> SEQ ID NO 19
<211> LENGTH: 14
<212> TYPE: PRT
<213> ORGANISM: Homo Sapiens

<400> SEQUENCE: 19

Lys Leu Gln Val Thr Gln Arg Ser Leu Glu Glu Gln Lys Gly
1 5 10

<210> SEQ ID NO 20
<211> LENGTH: 14
<212> TYPE: PRT
<213> ORGANISM: Mus musculus

<400> SEQUENCE: 20

Leu Lys Ala Lys Phe Ser Glu Asp Gly His Gln Lys Asn Met
1 5 10

<210> SEQ ID NO 21
<211> LENGTH: 14
<212> TYPE: PRT
<213> ORGANISM: Mus musculus

<400> SEQUENCE: 21

Gln Glu Arg Gly Thr Gln Asp Lys Arg Ile Gln Asp Met Glu
1 5 10

<210> SEQ ID NO 22
<211> LENGTH: 21
<212> TYPE: PRT
<213> ORGANISM: Homo sapien

<400> SEQUENCE: 22

Gly Thr Leu Lys Leu Asp Lys Leu Gly Ser Gln Ala Asp Thr Gly Gln
1 5 10 15

Lys Glu Leu Lys Gln
20

-continued

```
<210> SEQ ID NO 23
<211> LENGTH: 20
<212> TYPE: PRT
<213> ORGANISM: Homo sapien

<400> SEQUENCE: 23

Glu Ser Thr Asn Gln Glu Tyr Ala Arg Met Val Gln Asp Leu Gln Asn
 1               5                  10                  15

Arg Ser Thr Leu
            20


<210> SEQ ID NO 24
<211> LENGTH: 11
<212> TYPE: PRT
<213> ORGANISM: Homo sapien

<400> SEQUENCE: 24

Lys Leu Arg Ser Gln Leu Val Lys Arg Lys Gln
 1               5                  10


<210> SEQ ID NO 25
<211> LENGTH: 11
<212> TYPE: PRT
<213> ORGANISM: Artificial Sequence
<220> FEATURE:
<223> OTHER INFORMATION: Scrambled hyalauron binding peptide

<400> SEQUENCE: 25

Arg Gln Lys Val Leu Lys Arg Gln Leu Lys Ser
 1               5                  10


<210> SEQ ID NO 26
<211> LENGTH: 16
<212> TYPE: PRT
<213> ORGANISM: Artificial Sequence
<220> FEATURE:
<223> OTHER INFORMATION: Peptide that binds a hyalauronan

<400> SEQUENCE: 26

Cys Ser Thr Met Met Ser Arg Ser His Lys Thr Arg Ser His His Val
 1               5                  10                  15


<210> SEQ ID NO 27
<211> LENGTH: 9
<212> TYPE: PRT
<213> ORGANISM: Artificial Sequence
<220> FEATURE:
<223> OTHER INFORMATION: Peptide that binds a hyalauronan

<400> SEQUENCE: 27

Arg Gly Gly Gly Arg Gly Arg Arg Arg
 1               5


<210> SEQ ID NO 28
<211> LENGTH: 9
<212> TYPE: PRT
<213> ORGANISM: Artificial Sequence
<220> FEATURE:
<223> OTHER INFORMATION: Peptide composition that binds a hyalauronan
<221> NAME/KEY: VARIANT
<222> LOCATION: (1)...(1)
<223> OTHER INFORMATION: Xaa = Any basic amino acid
<221> NAME/KEY: VARIANT
<222> LOCATION: (2)...(8)
<223> OTHER INFORMATION: Xaa = Any amino acid other than an acidic amino
      acid
<221> NAME/KEY: HELIX
<222> LOCATION: (2)...(8)
```

-continued

```
<223> OTHER INFORMATION: Alpha-helix
<221> NAME/KEY: VARIANT
<222> LOCATION: (9)...(9)
<223> OTHER INFORMATION: Xaa = Any basic amino acid

<400> SEQUENCE: 28

Xaa Xaa Xaa Xaa Xaa Xaa Xaa Xaa Xaa
 1               5


<210> SEQ ID NO 29
<211> LENGTH: 11
<212> TYPE: PRT
<213> ORGANISM: Artificial Sequence
<220> FEATURE:
<223> OTHER INFORMATION: Peptide composition that binds a hyalauronan
<221> NAME/KEY: VARIANT
<222> LOCATION: (1)...(2)
<223> OTHER INFORMATION: Xaa = any basic amino acid
<221> NAME/KEY: VARIANT
<222> LOCATION: (3)...(4)
<223> OTHER INFORMATION: Xaa = any amino acid other than an acidic amino
      acid
<221> NAME/KEY: VARIANT
<222> LOCATION: (5)...(7)
<223> OTHER INFORMATION: Xaa = any basic amino acid
<221> NAME/KEY: VARIANT
<222> LOCATION: (8)...(9)
<223> OTHER INFORMATION: Xaa = any amino acid other than an acidic amino
      acid
<221> NAME/KEY: VARIANT
<222> LOCATION: (10)...(11)
<223> OTHER INFORMATION: Xaa = any basic amino acid

<400> SEQUENCE: 29

Xaa Xaa Xaa Xaa Xaa Xaa Xaa Xaa Xaa Xaa Xaa
 1               5                   10


<210> SEQ ID NO 30
<211> LENGTH: 11
<212> TYPE: PRT
<213> ORGANISM: Artificial Sequence
<220> FEATURE:
<223> OTHER INFORMATION: Peptide composition that binds a hyalauronan

<400> SEQUENCE: 30

Lys Gln Lys Ile Lys His Val Val Lys Leu Lys
 1               5                   10


<210> SEQ ID NO 31
<211> LENGTH: 10
<212> TYPE: PRT
<213> ORGANISM: Artificial Sequence
<220> FEATURE:
<223> OTHER INFORMATION: Peptide composition that binds a hyalauronan

<400> SEQUENCE: 31

Lys Leu Lys Ser Gln Leu Val Lys Arg Lys
 1               5                   10


<210> SEQ ID NO 32
<211> LENGTH: 10
<212> TYPE: PRT
<213> ORGANISM: Artificial Sequence
<220> FEATURE:
<223> OTHER INFORMATION: Peptide composition that binds a hyalauronan

<400> SEQUENCE: 32

Arg Tyr Pro Ile Ser Arg Pro Arg Lys Arg
 1               5                   10
```

-continued

<210> SEQ ID NO 33
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 33

Lys Asn Gly Arg Tyr Ser Ile Ser Arg
1 5

<210> SEQ ID NO 34
<211> LENGTH: 13
<212> TYPE: PRT
<213> ORGANISM: Artificial Sequence
<220> FEATURE:
<223> OTHER INFORMATION: Peptide composition that binds a hyalauronan

<400> SEQUENCE: 34

Arg Asp Gly Thr Arg Tyr Val Gln Lys Gly Glu Tyr Arg
1 5 10

<210> SEQ ID NO 35
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 35

Arg Arg Arg Cys Gly Gln Lys Lys Lys
1 5

<210> SEQ ID NO 36
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 36

Arg Gly Thr Arg Ser Gly Ser Thr Arg
1 5

<210> SEQ ID NO 37
<211> LENGTH: 12
<212> TYPE: PRT
<213> ORGANISM: Artificial Sequence
<220> FEATURE:
<223> OTHER INFORMATION: Peptide composition that binds a hyalauronan

<400> SEQUENCE: 37

Arg Arg Arg Lys Lys Ile Gln Gly Arg Ser Lys Arg
1 5 10

<210> SEQ ID NO 38
<211> LENGTH: 10
<212> TYPE: PRT
<213> ORGANISM: Artificial Sequence
<220> FEATURE:
<223> OTHER INFORMATION: Peptide composition that binds a hyalauronan

<400> SEQUENCE: 38

Arg Lys Ser Tyr Gly Lys Tyr Gln Gly Arg
1 5 10

-continued

<210> SEQ ID NO 39
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 39

Lys Val Gly Lys Ser Pro Pro Val Arg
1 5

<210> SEQ ID NO 40
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 40

Lys Thr Phe Gly Lys Met Lys Pro Arg
1 5

<210> SEQ ID NO 41
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 41

Arg Ile Lys Trp Ser Arg Val Ser Lys
1 5

<210> SEQ ID NO 42
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 42

Lys Arg Thr Met Arg Pro Thr Arg Arg
1 5

<210> SEQ ID NO 43
<211> LENGTH: 9
<212> TYPE: PRT
<213> ORGANISM: Artificial Sequence
<220> FEATURE:
<223> OTHER INFORMATION: Peptide composition that binds a hyalauronan

<400> SEQUENCE: 43

Lys Val Gly Lys Ser Pro Pro Val Arg
1 5

<210> SEQ ID NO 44
<211> LENGTH: 10
<212> TYPE: PRT
<213> ORGANISM: Artificial Sequence
<220> FEATURE:
<223> OTHER INFORMATION: Peptide composition that binds a hyalauronan

<400> SEQUENCE: 44

His Arg Glu Ala Arg Ser Gly Lys Tyr Lys
1 5 10

<210> SEQ ID NO 45

-continued

```
<211> LENGTH: 588
<212> TYPE: DNA
<213> ORGANISM: Homo sapien
<220> FEATURE:
<221> NAME/KEY: CDS
<222> LOCATION: (1)...(486)

<400> SEQUENCE: 45

gaa ttc gcg gcg gcg tcg acc aac aag ccc cct gct gtt tcc ccg ggg       48
Glu Phe Ala Ala Ala Ser Thr Asn Lys Pro Pro Ala Val Ser Pro Gly
 1               5                  10                  15

gtg gtc tcc cca acc ttt gaa ctt aca aat ctt cta aat cat cct gac       96
Val Val Ser Pro Thr Phe Glu Leu Thr Asn Leu Leu Asn His Pro Asp
            20                  25                  30

cat tat gta gaa aca gag aac att cag cat ctc aca gac ccg gct cta      144
His Tyr Val Glu Thr Glu Asn Ile Gln His Leu Thr Asp Pro Ala Leu
        35                  40                  45

gca cat gtg gat aga ata agc caa gcc cgg aaa ctg agt atg gga tct      192
Ala His Val Asp Arg Ile Ser Gln Ala Arg Lys Leu Ser Met Gly Ser
    50                  55                  60

gat gat gct gcc tac aca caa gct ctg ctg gtg cac cag aag gcc agg      240
Asp Asp Ala Ala Tyr Thr Gln Ala Leu Leu Val His Gln Lys Ala Arg
 65                 70                  75                  80

atg gaa cgg ctt caa aga gag ctc gag atg caa aag aaa aag ctg gat      288
Met Glu Arg Leu Gln Arg Glu Leu Glu Met Gln Lys Lys Lys Leu Asp
                85                  90                  95

aaa ctc aaa tct gag gtc aat gag atg gaa aat aat cta act cga agg      336
Lys Leu Lys Ser Glu Val Asn Glu Met Glu Asn Asn Leu Thr Arg Arg
            100                 105                 110

cgc ctg aag aga tca aat tcc att tcc cag ata ccg tca ctc gaa gaa      384
Arg Leu Lys Arg Ser Asn Ser Ile Ser Gln Ile Pro Ser Leu Glu Glu
        115                 120                 125

atg cag cag ttg aga agt tgt aat aga caa ctc cag att gac att gac      432
Met Gln Gln Leu Arg Ser Cys Asn Arg Gln Leu Gln Ile Asp Ile Asp
    130                 135                 140

ttt gac tgc tta acc aaa gaa att gca tct ttt tca agc ccg agg acc      480
Phe Asp Cys Leu Thr Lys Glu Ile Ala Ser Phe Ser Ser Pro Arg Thr
145                 150                 155                 160

aca ttt taaccccagc gctattcata acttttatga caatattgga tttgtaggcc      536
Thr Phe

ctgtgccacc aaaacccaaa gatcaaaggt ccaccatcaa aggtcgacgc gg            588


<210> SEQ ID NO 46
<211> LENGTH: 162
<212> TYPE: PRT
<213> ORGANISM: Homo sapien

<400> SEQUENCE: 46

Glu Phe Ala Ala Ala Ser Thr Asn Lys Pro Pro Ala Val Ser Pro Gly
 1               5                  10                  15

Val Val Ser Pro Thr Phe Glu Leu Thr Asn Leu Leu Asn His Pro Asp
            20                  25                  30

His Tyr Val Glu Thr Glu Asn Ile Gln His Leu Thr Asp Pro Ala Leu
        35                  40                  45

Ala His Val Asp Arg Ile Ser Gln Ala Arg Lys Leu Ser Met Gly Ser
    50                  55                  60

Asp Asp Ala Ala Tyr Thr Gln Ala Leu Leu Val His Gln Lys Ala Arg
65                  70                  75                  80

Met Glu Arg Leu Gln Arg Glu Leu Glu Met Gln Lys Lys Lys Leu Asp
                85                  90                  95
```

-continued

Lys Leu Lys Ser Glu Val Asn Glu Met Glu Asn Asn Leu Thr Arg Arg
100 105 110

Arg Leu Lys Arg Ser Asn Ser Ile Ser Gln Ile Pro Ser Leu Glu Glu
115 120 125

Met Gln Gln Leu Arg Ser Cys Asn Arg Gln Leu Gln Ile Asp Ile Asp
130 135 140

Phe Asp Cys Leu Thr Lys Glu Ile Ala Ser Phe Ser Ser Pro Arg Thr
145 150 155 160

Thr Phe

<210> SEQ ID NO 47
<211> LENGTH: 725
<212> TYPE: PRT
<213> ORGANISM: Homo sapiens

<400> SEQUENCE: 47

Met Ser Phe Pro Lys Ala Pro Leu Lys Arg Phe Asn Asp Pro Ser Gly
1 5 10 15

Cys Ala Pro Ser Pro Gly Ala Tyr Asp Val Lys Thr Leu Glu Val Leu
20 25 30

Lys Gly Pro Val Ser Phe Gln Lys Ser Gln Arg Phe Lys Gln Gln Lys
35 40 45

Glu Ser Lys Gln Asn Leu Asn Val Asp Lys Asp Thr Thr Leu Pro Ala
50 55 60

Ser Ala Arg Lys Val Lys Ser Ser Glu Ser Lys Lys Glu Ser Gln Lys
65 70 75 80

Asn Asp Lys Asp Leu Lys Ile Leu Glu Lys Glu Ile Arg Val Leu Leu
85 90 95

Gln Glu Arg Gly Ala Gln Asp Arg Arg Ile Gln Asp Leu Glu Thr Glu
100 105 110

Leu Glu Lys Met Glu Ala Arg Leu Asn Ala Ala Leu Arg Glu Lys Thr
115 120 125

Ser Leu Ser Ala Asn Asn Ala Thr Leu Glu Lys Gln Leu Ile Glu Leu
130 135 140

Thr Arg Thr Asn Glu Leu Leu Lys Ser Lys Phe Ser Glu Asn Gly Asn
145 150 155 160

Gln Lys Asn Leu Arg Ile Leu Ser Leu Glu Leu Met Lys Leu Arg Asn
165 170 175

Lys Arg Glu Thr Lys Met Arg Gly Met Met Ala Lys Gln Glu Gly Met
180 185 190

Glu Met Lys Leu Gln Val Thr Gln Arg Ser Leu Glu Glu Ser Gln Gly
195 200 205

Lys Ile Ala Gln Leu Glu Gly Lys Leu Val Ser Ile Glu Lys Glu Lys
210 215 220

Ile Asp Glu Lys Ser Glu Thr Glu Lys Leu Leu Glu Tyr Ile Glu Glu
225 230 235 240

Ile Ser Cys Ala Ser Asp Gln Val Glu Lys Tyr Lys Leu Asp Ile Ala
245 250 255

Gln Leu Glu Glu Asn Leu Lys Glu Lys Asn Asp Glu Ile Leu Ser Leu
260 265 270

Lys Gln Ser Leu Glu Glu Asn Ile Val Ile Leu Ser Lys Gln Val Glu
275 280 285

Asp Leu Asn Val Lys Cys Gln Leu Leu Glu Lys Glu Lys Glu Asp His
290 295 300

-continued

```
Val Asn Arg Asn Arg Glu His Asn Glu Asn Leu Asn Ala Glu Met Gln
305                 310                 315                 320

Asn Leu Lys Gln Lys Phe Ile Leu Glu Gln Gln Glu His Glu Lys Leu
                325                 330                 335

Gln Gln Lys Glu Leu Gln Ile Asp Ser Leu Leu Gln Gln Glu Lys Glu
            340                 345                 350

Leu Ser Ser Ser Leu His Gln Lys Leu Cys Ser Phe Gln Glu Glu Met
        355                 360                 365

Val Lys Glu Lys Asn Leu Phe Glu Glu Glu Leu Lys Gln Thr Leu Asp
    370                 375                 380

Glu Leu Asp Lys Leu Gln Gln Lys Glu Glu Gln Ala Glu Arg Leu Val
385                 390                 395                 400

Lys Gln Leu Glu Glu Glu Ala Lys Ser Arg Ala Glu Glu Leu Lys Leu
                405                 410                 415

Leu Glu Glu Lys Leu Lys Gly Lys Glu Ala Glu Leu Glu Lys Ser Ser
            420                 425                 430

Ala Ala His Thr Gln Ala Thr Leu Leu Leu Gln Glu Lys Tyr Asp Ser
        435                 440                 445

Met Val Gln Ser Leu Glu Asp Val Thr Ala Gln Phe Glu Ser Tyr Lys
    450                 455                 460

Ala Leu Thr Ala Ser Glu Ile Glu Asp Leu Lys Leu Glu Asn Ser Ser
465                 470                 475                 480

Leu Gln Glu Lys Ala Ala Lys Ala Gly Lys Asn Ala Glu Asp Val Gln
                485                 490                 495

His Gln Ile Leu Ala Thr Glu Ser Ser Asn Gln Glu Tyr Val Arg Met
            500                 505                 510

Leu Leu Asp Leu Gln Thr Lys Ser Ala Leu Lys Glu Thr Glu Ile Lys
        515                 520                 525

Glu Ile Thr Val Ser Phe Leu Gln Lys Ile Thr Asp Leu Gln Asn Gln
    530                 535                 540

Leu Lys Gln Gln Glu Glu Asp Phe Arg Lys Gln Leu Glu Asp Glu Glu
545                 550                 555                 560

Gly Arg Lys Ala Glu Lys Glu Asn Thr Thr Ala Glu Leu Thr Glu Glu
                565                 570                 575

Ile Asn Lys Trp Arg Leu Leu Tyr Glu Glu Leu Tyr Asn Lys Thr Lys
            580                 585                 590

Pro Phe Gln Leu Gln Leu Asp Ala Phe Glu Val Glu Lys Gln Ala Leu
        595                 600                 605

Leu Asn Glu His Gly Ala Ala Gln Glu Gln Leu Asn Lys Ile Arg Asp
    610                 615                 620

Ser Tyr Ala Lys Leu Leu Gly His Gln Asn Leu Lys Gln Lys Ile Lys
625                 630                 635                 640

His Val Val Lys Leu Lys Asp Glu Asn Ser Gln Leu Lys Ser Glu Val
                645                 650                 655

Ser Lys Leu Arg Cys Gln Leu Ala Lys Lys Lys Gln Ser Glu Thr Lys
            660                 665                 670

Leu Gln Glu Glu Leu Asn Lys Val Leu Gly Ile Lys His Phe Asp Pro
        675                 680                 685

Ser Lys Ala Phe His His Glu Ser Lys Glu Asn Phe Ala Leu Lys Thr
    690                 695                 700

Pro Leu Lys Glu Gly Asn Thr Asn Cys Tyr Arg Ala Pro Met Glu Cys
705                 710                 715                 720
```

-continued

Gln Glu Ser Trp Lys
725

<210> SEQ ID NO 48
<211> LENGTH: 631
<212> TYPE: PRT
<213> ORGANISM: Mus musculus

<400> SEQUENCE: 48

Met Arg Ala Leu Ser Leu Glu Leu Met Lys Leu Arg Asn Lys Arg Glu
1 5 10 15

Thr Lys Met Arg Ser Met Met Val Lys Gln Glu Gly Met Glu Leu Lys
20 25 30

Leu Gln Ala Thr Gln Lys Asp Leu Thr Glu Ser Lys Gly Lys Ile Val
35 40 45

Gln Leu Glu Gly Lys Leu Val Ser Ile Glu Lys Glu Lys Ile Asp Glu
50 55 60

Lys Cys Glu Thr Glu Lys Leu Leu Glu Tyr Ile Gln Glu Ile Ser Cys
65 70 75 80

Ala Ser Asp Gln Val Glu Lys Cys Lys Val Asp Ile Ala Gln Leu Glu
85 90 95

Glu Asp Leu Lys Glu Lys Asp Arg Glu Ile Leu Ser Leu Lys Gln Ser
100 105 110

Leu Glu Glu Asn Ile Thr Phe Ser Lys Gln Ile Glu Asp Leu Thr Val
115 120 125

Lys Cys Gln Leu Leu Glu Thr Glu Arg Asp Asn Leu Val Ser Lys Asp
130 135 140

Arg Glu Arg Ala Glu Thr Leu Ser Ala Glu Met Gln Ile Leu Thr Glu
145 150 155 160

Arg Leu Ala Leu Glu Arg Gln Glu Tyr Glu Lys Leu Gln Gln Lys Glu
165 170 175

Leu Gln Ser Gln Ser Leu Leu Gln Gln Glu Lys Glu Leu Ser Ala Arg
180 185 190

Leu Gln Gln Gln Leu Cys Ser Phe Gln Glu Glu Met Thr Ser Glu Lys
195 200 205

Asn Val Phe Lys Glu Glu Leu Lys Leu Ala Leu Ala Glu Leu Asp Ala
210 215 220

Val Gln Gln Lys Glu Glu Gln Ser Glu Arg Leu Val Lys Gln Leu Glu
225 230 235 240

Glu Glu Arg Lys Ser Thr Ala Glu Gln Leu Thr Arg Leu Asp Asn Leu
245 250 255

Leu Arg Glu Lys Glu Val Glu Leu Glu Lys His Ile Ala Ala His Ala
260 265 270

Gln Ala Ile Leu Ile Ala Gln Glu Lys Tyr Asn Asp Thr Ala Gln Ser
275 280 285

Leu Arg Asp Val Thr Ala Gln Leu Glu Ser Val Gln Glu Lys Tyr Asn
290 295 300

Asp Thr Ala Gln Ser Leu Arg Asp Val Thr Ala Gln Leu Glu Ser Glu
305 310 315 320

Gln Glu Lys Tyr Asn Asp Thr Ala Gln Ser Leu Arg Asp Val Thr Ala
325 330 335

Gln Leu Glu Ser Glu Gln Glu Lys Tyr Asn Asp Thr Ala Gln Ser Leu
340 345 350

Arg Asp Val Thr Ala Gln Leu Glu Ser Val Gln Glu Lys Tyr Asn Asp
355 360 365

-continued

```
Thr Ala Gln Ser Leu Arg Asp Val Ser Ala Gln Leu Glu Ser Tyr Lys
    370                 375                 380

Ser Ser Thr Leu Lys Glu Ile Glu Asp Leu Lys Leu Glu Asn Leu Thr
385                 390                 395                 400

Leu Gln Glu Lys Val Ala Met Ala Glu Lys Ser Val Glu Asp Val Gln
                405                 410                 415

Gln Gln Ile Leu Thr Ala Glu Ser Thr Asn Gln Glu Tyr Ala Arg Met
            420                 425                 430

Val Gln Asp Leu Gln Asn Arg Ser Thr Leu Lys Glu Glu Glu Ile Lys
        435                 440                 445

Glu Ile Thr Ser Ser Phe Leu Glu Lys Ile Thr Asp Leu Lys Asn Gln
    450                 455                 460

Leu Arg Gln Gln Asp Glu Asp Phe Arg Lys Gln Leu Glu Glu Lys Gly
465                 470                 475                 480

Lys Arg Thr Ala Glu Lys Glu Asn Val Met Thr Glu Leu Thr Met Glu
                485                 490                 495

Ile Asn Lys Trp Arg Leu Leu Tyr Glu Glu Leu Tyr Glu Lys Thr Lys
            500                 505                 510

Pro Phe Gln Gln Gln Leu Asp Ala Phe Glu Ala Glu Lys Gln Ala Leu
        515                 520                 525

Leu Asn Glu His Gly Ala Thr Gln Glu Gln Leu Asn Lys Ile Arg Asp
    530                 535                 540

Ser Tyr Ala Gln Leu Leu Gly His Gln Asn Leu Lys Gln Lys Ile Lys
545                 550                 555                 560

His Val Val Lys Leu Lys Asp Glu Asn Ser Gln Leu Lys Ser Glu Val
                565                 570                 575

Ser Lys Leu Arg Ser Gln Leu Val Lys Arg Lys Gln Asn Glu Leu Arg
            580                 585                 590

Leu Gln Gly Glu Leu Asp Lys Ala Leu Gly Ile Arg His Phe Asp Pro
        595                 600                 605

Ser Lys Ala Phe Cys His Ala Ser Lys Glu Asn Phe Thr Pro Leu Lys
    610                 615                 620

Glu Gly Asn Pro Asn Cys Cys
625                 630


<210> SEQ ID NO 49
<211> LENGTH: 11
<212> TYPE: PRT
<213> ORGANISM: Homo sapien

<400> SEQUENCE: 49

Val Ser Ile Glu Lys Glu Lys Ile Asp Glu Lys
 1               5                  10


<210> SEQ ID NO 50
<211> LENGTH: 21
<212> TYPE: PRT
<213> ORGANISM: Unknown
<220> FEATURE:
<223> OTHER INFORMATION: Peptide used in competition binding assay

<400> SEQUENCE: 50

Gln Glu Lys Tyr Asn Asp Thr Ala Gln Ser Leu Arg Asp Val Thr Ala
 1               5                  10                  15

Gln Leu Glu Ser Val
            20
```

-continued

<210> SEQ ID NO 51
<211> LENGTH: 32
<212> TYPE: PRT
<213> ORGANISM: Unknown
<220> FEATURE:
<223> OTHER INFORMATION: Peptide used in competition binding assay

<400> SEQUENCE: 51

```
Lys Gln Lys Ile Lys His Val Val Lys Leu Lys Asp Glu Asn Ser Gln
 1               5                  10                  15

Leu Lys Ser Glu Val Ser Lys Leu Arg Ser Gln Leu Val Lys Arg Lys
            20                  25                  30
```

<210> SEQ ID NO 52
<211> LENGTH: 20
<212> TYPE: DNA
<213> ORGANISM: Artificial Sequence
<220> FEATURE:
<223> OTHER INFORMATION: Primer for PCR amplication of collagen I

<400> SEQUENCE: 52
cgatgtcgct atccagctga 20

<210> SEQ ID NO 53
<211> LENGTH: 21
<212> TYPE: DNA
<213> ORGANISM: Artificial Sequence
<220> FEATURE:
<223> OTHER INFORMATION: Primer for PCR amplication of collagen III

<400> SEQUENCE: 53
atcagtcagc catctaccac c 21

<210> SEQ ID NO 54
<211> LENGTH: 18
<212> TYPE: DNA
<213> ORGANISM: Artificial Sequence
<220> FEATURE:
<223> OTHER INFORMATION: Primer for PCR amplication of ED-1

<400> SEQUENCE: 54
tggcaggaca gtagtcgc 18

<210> SEQ ID NO 55
<211> LENGTH: 21
<212> TYPE: DNA
<213> ORGANISM: Artificial Sequence
<220> FEATURE:
<223> OTHER INFORMATION: Primer for PCR amplication of ED-1

<400> SEQUENCE: 55
aaggctgctg ttgaaaggac g 21

<210> SEQ ID NO 56
<211> LENGTH: 9
<212> TYPE: PRT
<213> ORGANISM: Artificial Sequence
<220> FEATURE:
<223> OTHER INFORMATION: Peptide that binds a hyalauronan

<400> SEQUENCE: 56

```
Arg Gly Gly Gly Arg Gly Gly Arg Arg
 1               5
```

<210> SEQ ID NO 57

-continued

<211> LENGTH: 9
<212> TYPE: PRT
<213> ORGANISM: Artificial Sequence
<220> FEATURE:
<223> OTHER INFORMATION: Peptide that binds a hyalauronan

<400> SEQUENCE: 57

Arg Gly Gly Gly Arg Gly Gly Gly Arg
1 5

<210> SEQ ID NO 58
<211> LENGTH: 9
<212> TYPE: PRT
<213> ORGANISM: Artificial Sequence
<220> FEATURE:
<223> OTHER INFORMATION: Peptide that binds a hyalauronan

<400> SEQUENCE: 58

Arg Gly Gly Gly Gly Gly Gly Gly Arg
1 5

<210> SEQ ID NO 59
<211> LENGTH: 9
<212> TYPE: PRT
<213> ORGANISM: Homo sapien

<400> SEQUENCE: 59

Lys Leu Arg Ser Gln Leu Val Lys Arg
1 5

<210> SEQ ID NO 60
<211> LENGTH: 9
<212> TYPE: PRT
<213> ORGANISM: Homo sapien

<400> SEQUENCE: 60

Lys Gln Lys Ile Lys His Val Val Lys
1 5

<210> SEQ ID NO 61
<211> LENGTH: 9
<212> TYPE: PRT
<213> ORGANISM: Homo sapien

<400> SEQUENCE: 61

Arg Ser His Lys Thr Arg Ser His His
1 5

<210> SEQ ID NO 62
<211> LENGTH: 7
<212> TYPE: PRT
<213> ORGANISM: Homo sapien

<400> SEQUENCE: 62

Arg Pro His Phe His Lys Arg
1 5

<210> SEQ ID NO 63
<211> LENGTH: 11
<212> TYPE: PRT
<213> ORGANISM: Homo sapien

<400> SEQUENCE: 63

Arg Lys Ile Gln Lys His Lys Thr Ile Pro Lys
1 5 10

-continued

<210> SEQ ID NO 64
<211> LENGTH: 9
<212> TYPE: PRT
<213> ORGANISM: Homo sapiens

<400> SEQUENCE: 64

Lys Val Gly Arg Lys Val Phe Ser Lys
 1 5

<210> SEQ ID NO 65
<211> LENGTH: 9
<212> TYPE: PRT
<213> ORGANISM: Homo sapiens

<400> SEQUENCE: 65

Lys Cys Ser Val Gln Thr Leu Leu Arg
 1 5

<210> SEQ ID NO 66
<211> LENGTH: 9
<212> TYPE: PRT
<213> ORGANISM: Homo sapiens

<400> SEQUENCE: 66

Arg Thr His Leu Lys His Val Leu Arg
 1 5

<210> SEQ ID NO 67
<211> LENGTH: 9
<212> TYPE: PRT
<213> ORGANISM: Homo sapiens

<400> SEQUENCE: 67

Lys Asn Ala Ile Asn Asn Gly Val Arg
 1 5

<210> SEQ ID NO 68
<211> LENGTH: 9
<212> TYPE: PRT
<213> ORGANISM: Homo sapiens

<400> SEQUENCE: 68

Lys Gly Gln Ile Asn Asn Ser Ile Lys
 1 5

<210> SEQ ID NO 69
<211> LENGTH: 9
<212> TYPE: PRT
<213> ORGANISM: Homo sapiens

<400> SEQUENCE: 69

Arg Val Arg Gly Arg Ala Lys Leu Arg
 1 5

<210> SEQ ID NO 70
<211> LENGTH: 15
<212> TYPE: PRT
<213> ORGANISM: Artificial Sequence
<220> FEATURE:
<223> OTHER INFORMATION: Peptide that binds a hyalauronan

<400> SEQUENCE: 70

Ser Thr Met Met Ser Arg Ser His Lys Thr Arg Ser His His Val
 1 5 10 15

-continued

```
<210> SEQ ID NO 71
<211> LENGTH: 32
<212> TYPE: PRT
<213> ORGANISM: Artificial Sequence
<220> FEATURE:
<223> OTHER INFORMATION: Peptide that binds a hyalauronan

<400> SEQUENCE: 71

Cys Ser Thr Met Met Ser Arg Ser His Lys Thr Arg Ser His His Val
 1              5                   10                  15

Cys Ser Thr Met Met Ser Arg Ser His Lys Thr Arg Ser His His Val
            20                  25                  30


<210> SEQ ID NO 72
<211> LENGTH: 12
<212> TYPE: PRT
<213> ORGANISM: Homo sapien

<400> SEQUENCE: 72

Gly Ala His Trp Gln Phe Asn Ala Leu Thr Val Arg
 1              5                   10
```

COMPOSITIONS AND METHODS FOR TREATING CELLULAR RESPONSE TO INJURY AND OTHER PROLIFERATING CELL DISORDERS REGULATED BY HYALADHERIN AND HYALURONANS

CROSS-REFERENCE TO RELATED APPLICATIONS

This application is a continuation-in-part of U.S. patent application Ser. No. 09/541,522, filed Apr. 3, 2000 now abandoned; which application claims the priority to U.S. Provisional Patent Application No. 60/127,457, filed Apr. 1, 1999, all of which applications are incorporated by reference in their entirety.

TECHNICAL FIELD

The present invention relates generally to the understanding, diagnosis and treatment of a wide variety of diseases, and more specifically, to compositions and methods for treating cellular response to injury and/or the abnormal proliferation of cells.

BACKGROUND OF THE INVENTION

The normal cell in normal tissue is confined to a narrow range of function and structure regulated by its differentiation state, genetic program of metabolism, tissue specialization, by constraints induced by neighboring cells, the extracellular matrix and availability of exogenous factors and metabolic substrates. Cells are able to handle normal physiological demands (homeostasis) or adapt to excessive physiological stresses and pathological stimuli by altering their steady state to preserve cell viability and function. If the adaptive responses to stimuli are exceeded, then a sequence of cellular events follow that transform normal cells to injured or diseased cells in an attempt to remodel local tissue. This process can lead to a number of diseases driven by enhanced cell proliferation, migration and invasion, production of matrix metalloprotcinases, infiltration of inflammatory cells, tissue destruction and dysfunctional tissue remodeling. Regardless of the etiology, such disease processes are commonly found in inflammatory diseases (such as arthritis, multiple sclerosis, psoriasis, inflammatory bowel diseases, diabetes), proliferative diseases (such as cancer and metastases), degenerative diseases (such as osteoarthritis, osteoporosis, Alzheimer's, Parkinson's) and injuries caused by wounds or burns.

Current medical approaches to treat or prevent such diseases typically involve the use of reagents that attempt to block mechanisms affecting cell proliferation, cell migration, or the production of enzymes or growth factors. However, because such reagents are not specific to diseased cells and current practices do not yet allow targeting of these reagents specifically to sites of disease, such a therapeutic approach is typically toxic to the host if used for any length of time or at high dosages as may be required to treat or prevent the disease. This toxicity of current reagents is a severe limitation to the efficacy of current medical treatments.

The present invention discloses a sequence of cellular transition states that are involved in the transformation of normal cells to diseased cells that is characteristic to all cell types, and thus, all tissues. Transitory molecules produced during the early phases of disease which are responsible for the transition of cells from normal to diseased state are described, as well as the use of such molecules in the diagnosis, treatment and/or prevention of a wide variety of diseases is provided.

SUMMARY OF THE INVENTION

Briefly stated, the present invention provides compositions and methods for treating a tissue disorder associated with a response-to-injury process, or proliferating cells in a mammal. The methods include administering to the mammal an effective amount of a composition that alters the activity of transition molecules within a cell Transition molecules are comprised of hyaladherins, hyalauronans or molecules regulated by an amount of intracellular or extracellular hyaladherins or hyalauronans. The activity of hyaladherins and hyalauronans are shown to interact with regulatory processes associated with a response to injury and/or proliferative/invasive cell types.

Within one aspect of the present invention, methods are provided for treating a wide variety of inflammatory or proliferative diseases, comprising the step of administering to a warm-blooded animal (e.g., a human, horse, cow, sheep, dog, cat, or mouse) a compound to treat the inflammatory or proliferative disease.

A wide variety of compounds may be utilized within this regard, including for example (a) a polypeptide comprising the amino acid sequence BX7B (SEQ ID NO:28) which binds hyaluronic acid (HA); phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds any one of domains D1, D2, D3, D4, or, D5 of Receptor Hyaluronic Acid Mediated Motility (RHAMM) (e.g., an anti-TAM antibody); (c) a polypeptide fragment which encodes a D1, D2, D3, D4, or, D5 domain of RHAMM; and (d) a gene delivery vector which expresses antisense RHAMM, or delivers and expresses any one of (a), (b), or (c). In one embodiment, the polypeptide can be (a) a first peptide comprised of a hyaluronic acid-binding domain; (b) a hyaladherin polypeptide; (c) a second peptide comprised of a domain from a hyaladherin polypeptide; (d) a hyaladherin-binding polypeptide; (e) a third peptide comprised of a hyaladherin binding domain. Also provided are antibodies which binds to a peptide or polypeptide of (a)–(d); and/or vectors (e.g., gene delivery vectors described below) that expresses a gene encoding a polypeptide as described above or herein. More particular embodiments include methods where a hyaladherin is administered comprised of a RHAMM polypeptide. In a particular embodiment, a first peptide is administered comprised of a sequence selected from the group consisting of SEQ., ID NO: 1–10. In another embodiment, a second peptide is administered comprised of a sequence selected from the group consisting of SEQ. ID NO: 11–20. In another embodiment, a hyaladherin-binding polypeptide comprised of SEQ. ID NO: 21. In still other embodiments, an antibody is administered that binds to a peptide comprised of SEQ. ID NO: 11–20 or an antibody is administered that binds to a RHAMM polypeptide. In a more general embodiment, at least one hyaladherin is administered that is a RHAMM polypeptide.

Within other embodiments, the compound to be delivered is a polypeptide comprising less than an entire RHAMM polypeptide (i.e., less than 95 kDa or 73 kDa molecular weight), and containing at least a portion of RHAMM domains D1 (e.g., aa1–16 of human RHAMM), D2 (the "leucine zipper" domain, e.g., aa 195–122 of human RHAMM), D3 (the "TAM domain", e.g., aa 219–240 of human RHAMM), D4 (the repeat or "R" domain—e.g., aa. 442–546 of mouse and aa. 442–463 of human RHAMM, and amino acid residues 635–645 and amino acid residues 657–666 of human RHAMM. Equivalent domains in other species may e determined by comparison with the human sequence (see, e.g., FIG. 50; SEQ ID NOs: 47 and 48). Within further embodiments, antibodies are provided which bind to any one of the above RHAMM domains (i.e., domains D1, D2, D3, D4, or D5. Examples include antibodies to SEQ ID NOs: 14, 17, 23, 24, 26 and 27.

A wide variety of inflammatory or proliferative diseases may be treated with the aforementioned compounds, including for example, inflammatory or proliferative neurological diseases such as Parkinsons or Alzheimer's disease, arthritic diseases (e.g., rheumatoid arthritis and osteoarthritis), diseases associated with demylination of the nerve sheath (e.g., multiple sclerosis), inflammatory dermatosis (e.g., psoriasis), inflammatory bowel diseases, a variety of wounds (e.g., surgical excisions adhesions, scars, and cheloids, and skin ulcers), stenosis and/or restenosis (as well as proliferative, inflammatory responses or fibrotic response associated with medical implants, such as hip implants, vascular wraps, catethers, and the like), cancer and other malignant diseases, kidney fibrosis, inflammatory lung diseases (e.g., emphysema, asthma, and cystic fibrosis), obesity and obesity-related diseases (including for example, diabetes), lupus, tissue transplantation (e.g., skin grafts) and cardiovascular diseases (e.g., atherosclerosis, and stroke).

Within the context of the present invention, it should be noted that the above-noted diseases are deemed to be "treated" if the typical disease course is altered, slowed, inhibited, or prevented in a statistically significant manner, for at least one symptom or sign of the disease.

In related embodiments, the invention provides a composition for treating a tissue disorder associated with a response-to-injury process or proliferating cells in a mammal comprising the compositions described in the aforementioned methods of treating.

In a different aspect, the invention provides cell cultures which are comprised of a transition cells, wherein the transition cells include an activated erk kinase signaling activity, a stimulated activating protein-1 (AP-1) binding activity and at least one characteristic selected from the group consisting of: (a) increased podosome formation, (b) increased flux of intracellular or extracellular hyalauronans or hyaladherins, (c) increased expression of a hyaladherin, (d) an inability to form focal adhesions, (e) increased metalloproteinase activity, and (f) increased expression of hyaladherin; wherein measurements of activity or amounts are relative to a normal quiescent cell. In more specific embodiments, the cell culture is comprised of cells transfected with a nucleic acid that overexpresses a hyaladherin. In a still more specific embodiment, the cell culture overexpresses a RHAMM polypeptide. In a related aspect, the invention provides embodiments of an animal cell culture wherein the activated erk signaling activity is less than the activated erk signaling activity displayed by normal quiescent cells in response to a growth factor stimulation, wherein the growth factor stimulation is selected from the group consisting of: IL-1 stimulation, PDGF stimulation, and NTF $\alpha$ stimulation.

In still another aspect, the invention provides methods of identifying a composition for treating a tissue disorder associated with a response-to-injury process or proliferating cells in a mammal comprising, (a) treating the cell culture as described above with a candidate composition; (b) scoring for the ability of the candidate composition to inhibit podosome formation in comparison to an untreated culture containing transition cells as described above; and (c) selecting the composition that inhibits podosome formation. One embodiment provides a method where scoring for the ability to inhibit podosome formation comprises testing the treated cell culture for a reduced ability to release a protease that degrades a cellular matrix component. In a more particular embodiment of the aforementioned method, the protease is a fibronectin degrading protease that releases a CS-1 sequence from a fibronectin matrix, and the scoring comprises testing the ability of the treated cells to bind an antibody specific for the CS-1 sequence.

In a different aspect, the invention provides peptide compositions that bind a hyalauronan comprising a peptide of the sequence BX7B (SEQ ID NO:28) wherein B is a basic amino acid and X7 is a sequence of about seven residues selected from any amino acid other than an acidic amino aid, wherein the peptide forms an alpha helix and each occurrence of B is oriented on the At same side of the alpha helix, and with the proviso that the peptide does not consist of the sequences BBXXBBBXXBB, KQKIKHVVKLK, KLKSQLVKRK, RYPISRPRKR, KNGRYSISR, RDGTRYVQKGEYR, RRRCGQKKK, RGTRSGSTR, RRRKKIQGRSKR, RKSYGKYQGR, KVGKSPPVR, KTFGKMKPR, RIKWSRVSK, KRTMRPTRR, KVGKSPPVR, or HREARSGKYK (SEQ ID NOs: 29–44 respectively).

In a related aspect, the invention provides peptide compositions that bind a hyalauronan comprising a peptide of the sequence BX7B (SEQ ID NO:28) wherein B is a basic amino acid and X7 is a sequence of seven residues selected from amino acids other than acidic amino acids, wherein the peptide satisfies one of the following sets of requirements: (a) the amino acid residue at position 4, 5 or 6 is K, H, R, A, C, G, S, or T, (e.g., P-peptide (RSHKTRSHH; SEQ ID NO:61) and R-peptide (RGGGRGRRR; SEQ ID NO:27)); (b) the amino acid residue at position 4 or 5 is K, H, R, A, C, S, or T and the amino acid residue at position 6 is A, P, F, W, M, I, V, or L; (c) the amino acid residues at positions 2 and 6 are I, L, or V, and the amino acid residue at position 5 is K, H, R, Q, or N, (e.g., fibromodulin (KVGRKVFSK; SEQ ID NO:64), CD40 receptor associated factor-1 (KCSVQTLLR; SEQ ID NO:65), probable G protein coupled receptor (RTHLKHVLR; SEQ ID NO:66), leukoctye derived chemotaxin-2 (KNAINNGVR; SEQ ID NO:67), laminin gamma-2 (KGQINNSIK; SEQ ID NO:68)); (d) the amino acid residues at position 2 and 6 are I, L, or V, the amino acid residue at position 4 is N, C, Q, O, S, or T, the amino acid residue at position 5 is R, N, C, Q, H, or K, the amino acid residue at position 8 is R, N, C, Q, G, H, K, S, or T, and the amino acid residues at positions 3 and 7 are any residue except D, E, P, W, Y, M, or F; (e) the amino acid residues at positions 2 and 6 are A, I, L, or V, the amino acid residue at position 3 is anything except D, E, P, W, Y, M, or F, the amino acid residue at position 5 is R, N, Q, H, or K, the amino acid residue at position 7 is H, R, or K, (e.g., cdc37 (RVRGRAKLR; SEQ ID NO: 69)); or (f) the amino acid residues at positions 2 and 6 are I, L, or V, the amino acid residue at position 3 is any residue except D, E, P, W, Y, M, or F, the amino acid residue at position 4 is K, R, or H, the amino acid residue at position 5 is R, N, Q, H, or K, and the amino acid residue at position 7 is H, R, or K. The invention also provides peptide compositions comprising a peptide that is a part of any peptide that meets the requirements of set (b) described above as long as the peptide has no acidic residues and also satisfies the requirements of set (b).

In yet another related aspect, peptide compositions are provided that binds a hyaluronan or block podosome formation in a cell, wherein the peptide is selected from group consisting of: (H4–5)B3 (SEQ. ID. NO: 1); (H4–5) BXBBXB (SEQ. ID. NO: 2); (H4–5)BXBXBBB (SEQ. ID. NO: 3); (H4–5)BXBBB (SEQ. ID. NO: 4); and (H4–5) BXBB (SEQ. ID. NO: 5). In these embodiments B is lysine (K) or arginine (R), X is a hydrophobic or neutral amino acid selected from the group consisting of (I, L, V, Q, S) and H4–5 is sequence of 4 to 5 amino acids selected to form an alpha helix. In more particular embodiments of this aspect, the peptide is selected from the group consisting of: MMTVLKR (SEQ. ID. NO: 6); MMTVLKVKRLR (SEQ. ID. NO: 7); MMTVLKVKVKRK (SEQ. ID. NO: 8); MMTVLKVRKR (SEQ. ID. NO: 9); and MMTVLKVRK (SEQ. ID. NO: 10).

In yet a different aspect, the invention provides methods of identifying a peptide or polypeptide composition for treating a tissue disorder associated with a response-to-injury process or proliferating cells in a mammal comprising the steps of: (a) selecting a sequence from a database screened for sequences comprising a peptide of the sequences BX7B (SEQ ID NO:28) wherein B is a basic amino acid and X7 is a sequence of about seven residues selected from any amino acid other than an acidic amino aid, wherein the peptide forms an alpha helix and each occurrence of B is oriented on the same side of the alpha helix, (b) preparing a composition comprised of the selected sequence; and (c) testing the prepared composition for the ability to inhibit podosome formation according to other methods taught by this invention, and with the proviso that the peptide in (a) does not consist of the sequences BBXXBBBXXBB, KQKIKHVVKLK, KLKSQLVKRK, RYPISRPRKR, KNORYSISR, RDGTRYVQKGEYR, RRRCGQKKK, RGTRSGSTR, RRRKKIQGRSKR, RKSYGKYQGR, KVGKSPPVR, KTFGKMKPR, RIKWSRVSK, KRTMRPTRR, KVGKSPPVR, or HREARSGKYK (SEQ ID NOs: 29–44 respectively). Within certain embodiments the peptides provided herein can be less than 250, 200, 150, 100, 75, 50, or, 25 amino acids in length.

In a related aspect, the invention provides methods of identifying a peptide or polypeptide composition for treating a tissue disorder associated with a response-to-injury process or proliferating cells in a mammal comprising the steps of: (a) forming an expression library comprised of cloned sequences expressed by a cell during a transition stage response; (b) screening the expression library for sequences encoding a peptide or polypeptide that binds a hyaladherin that is stimulated in cells during the transition stage; (c) preparing a peptide or polypeptide encoded by the hyaladherin binding sequences; and (d) testing the peptide or polypeptide for the ability to affect at least one activity associated with transition stage cells, wherein the activity is selected from the group consisting of: increased erk kinase signal activation, podosome formation, metalloproteinase expression, flux of intracellular or extracellular hyaluronans or hyaladherins, expression of a hyaladherin, and inability to form focal adhesions. In one embodiment of this method, the expression vector is a two hybrid phage display system, the hyaladherin is RHAMM and the testing is for the ability to inhibit podosome formation and inhibition of erk kinase signaling activation.

In a further aspect of the present invention polypeptides are provided which comprises or consist only of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72. When the polypeptide comprises additional sequences, the polypeptide may, in certain embodiments, be less than 50 kDa or 20 kDa of molecular weight. In other embodiments, the polypeptide may be less than 60, 50, 40, 30, or 20 amino acids in length. Also provided are such polypeptides that are purified (e.g., free of cells), sterilized, and/or suitable for pharmaceutical use.

In yet other aspects of the present invention antibodies are provided which bind to any one of the peptides provided herein, including for example a polypeptide comprising or consisting only of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72. Also provided are antibodies such as noted above, which are purified (e.g., free of cells), sterilized, and/or suitable for pharmaceutical use (e.g., for use in one of the methods described herein).

In still another aspect, the invention provides methods for detecting hyaluronic acid in a sample comprising the steps of: (a) incubating the sample with a hyaluronic acid binding peptide comprising a sequence selected from the group consisting of SEQ ID NOs: 1–10; and (b) detecting an amount of a complex formed between hyaluronic acid and the hyaluronic acid binding peptide. In one embodiment, the detecting employs an antibody that specifically binds to the hyaluronic acid binding peptide.

In a related aspect, the invention provides methods of detecting a molecule that binds to a RHAMM polypeptide in a sample comprising the steps of (a) incubating the sample with the RHAMM polypeptide and with a RHAMM-binding polypeptide comprised of SEQ. ID NO: 21; and (b) detecting an amount of a complex formed between the sample and the RHAMM polypeptide by scoring for reduced binding between the RHAMM polypeptide and the RHAMM-binding polypeptide. In one embodiment, detecting employs an antibody that specifically binds to the RHAMM-binding polypeptide.

Yet another embodiment of the invention includes compositions for treating a tissue disorder associated with a response-to-injury process or proliferating cells in a mammal, wherein the composition is-comprised of a hyaluronan that binds to a hyaladherin that regulates a transition stage cell associated with the response to injury or proliferating cell disorder. In a related aspect, the invention provides a method for treating a tissue disorder associated with a response-to-injury process or proliferating cells in a mammal comprising, administering to the mammal the aforementioned hyaluronan.

Within further aspects of the present invention, vaccinating agents are provided for preventing a tissue disorder associated with a response-to-injury process or proliferating cells in a mammal wherein the vaccinating agent includes an antigen comprised of one of the aforementioned polypeptides, peptides or hyaluronans. Generally, within this aspect, the vaccinating agent is administered in a dosage and/or therapeutic regimen sufficient to generate an immune response against the selected antigen, and to prevent the tissue disorder or proliferation of cells.

These and other aspects of the present invention will become evident upon reference to the following detailed description and attached drawings. In addition, various references are set forth herein which describe in more detail certain procedures or compositions (e.g., plasmids, etc.) and are therefore incorporated by reference in their entirety.

BRIEF DESCRIPTION OF THE DRAWINGS

FIGS. 14D, 14E, and 14F are photos which supplement this data.

FIG. 15A is a bar graph which shows a comparison of RHAMM expression at a cell surface. FIG. 15B provides the sequence of various RHAMM peptides (SEQ ID NOs: 14–20).

FIGS. 26A, 26B and 26C illustrate that HA binding peptides (SEQ ID Nos. 28, 56–58) including artificial mimics are able to block cell motility.

FIG. 37 is a table which shows the percentage of cells with various isoforms of RHAMM, from a variety of RA patients.

FIG. 50 depicts the human and murine sequence of RHAMM (SEQ ID Nos. 47 and 48 respectively).

DETAILED DESCRIPTION OF THE INVENTION

Definitions

Figure 1:
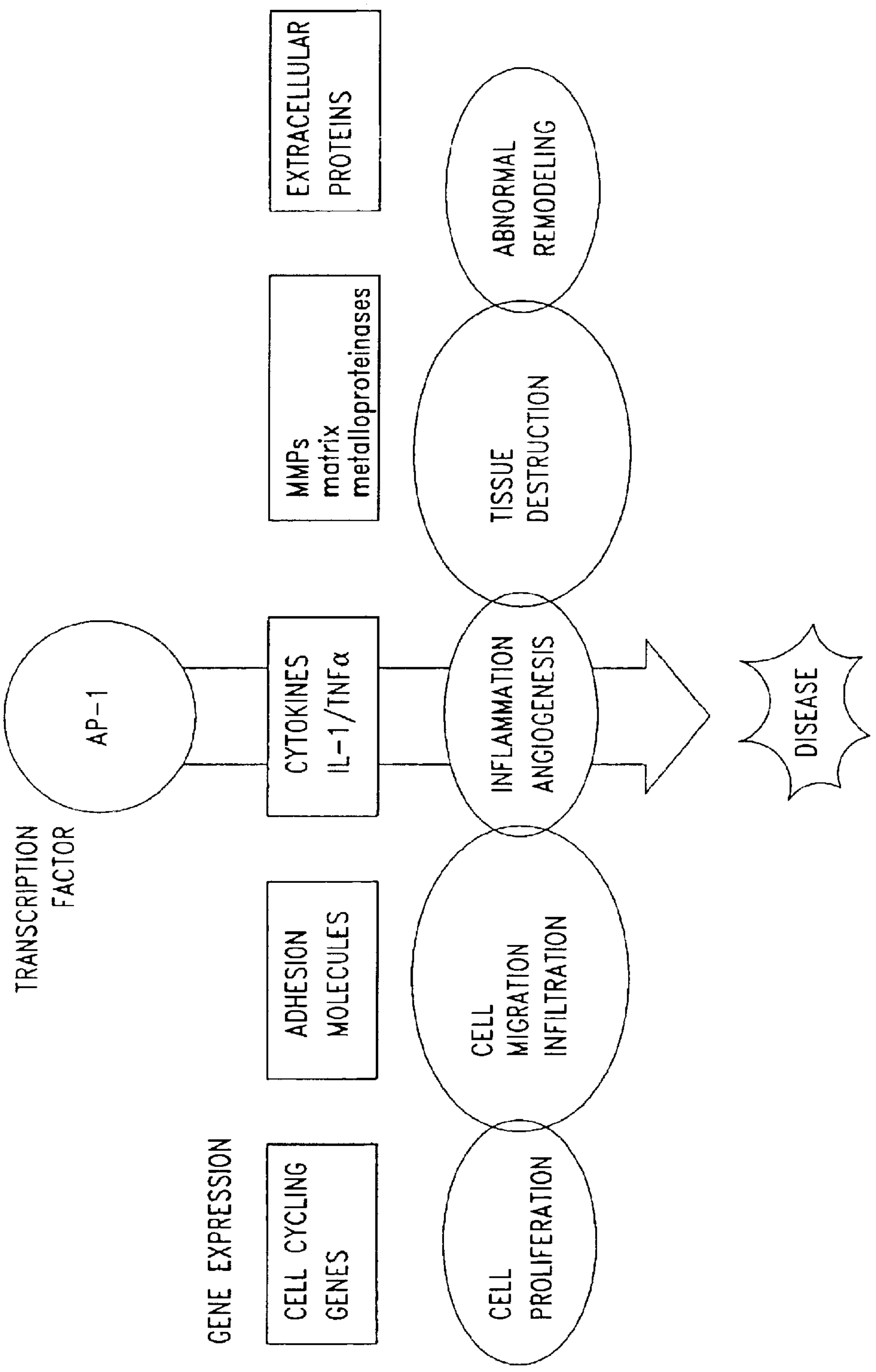
FIG. 1 is a schematic illustration of the impact of the AP-1 pathway on disease.

Prior to setting forth the invention, it may be helpful to an understanding thereof to first set forth definitions of certain terms that will be used hereinafter.

"Expression vector" and "expression cassette" refers to an assembly which is capable of directing the expression of a sequence or gene of interest. The nucleic acid expression vector must include a promoter which, when transcribed, is operably linked to the sequence(s) or gene(s) of interest, as well as a polyadenylation sequence. Within certain embodiments of the invention, the expression vectors described herein may be contained within a plasmid construct. In addition to the components of the nucleic acid expression vector, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., an SV40 or adenovirus origin of replication).

As used herein, "nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., $\alpha$-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

An "isolated nucleic acid molecule" is a nucleic acid molecule that is not integrated in the genomic DNA of an organism. For example, a DNA molecule that encodes a RHAMM binding protein that has been separated from the genomic DNA of a eukaryotic cell is an isolated DNA molecule. Another example of an isolated nucleic acid molecule is a chemically-synthesized nucleic acid molecule that is not integrated in the genome of an organism.

An "isolated polypeptide" is a polypeptide that is essentially free from contaminating cellular components, such as carbohydrate, lipid, or other proteinaceous impurities associated with the polypeptide in nature. That a particular protein preparation contains an isolated polypeptide can be shown by the appearance of a single band following sodium dodecyl sulfate (SDS)-polyacrylamide gel electrophoresis of the protein preparation and Coomassie Brilliant Blue staining of the gel.

"Gene delivery vehicle" refers to a construct which is capable of delivering, and, within preferred embodiments expressing, one or more gene(s) or sequence(s) of interest in a host cell. Representative examples of such vehicles include viral vectors, nucleic acid expression vectors, naked DNA, and certain eukaryotic cells (e.g., producer cells).

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules for which antigen specificity has not been defined. Polypeptides of the latter kind are, for example, produced at low levels by the lymph system and at increased levels by myelomas.

"Native antibodies and immunolobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V.sub.H) followed by a number of constant domains. Each light chain has a variable domain at one end (V.sub.L) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.* 186:651 (1985); Novotny and Haber, *Proc. Natl. Acad. Sci. U.S.A.* 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a .beta.-sheet configuration, connected by three CDRs, which form loops connecting, and in some cases forming part of, the .beta.-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen. "Fv" is the minimum antibody fragment which contains a complete antigen-recognition and-binding site. This region consists of a dimer of one heavy- and one light-chain variable domain in tight, non-covalent association. It is in this configuration that the three CDRs of each variable domain interact to define an antigen-binding site on the surface of the V.sub.H -V.sub.L dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H$-1) of the heavy chain. Fab' fragments differ from Fab fragments by the addition of a few residues at the carboxy terminus of the heavy chain $C_H$-1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (.kappa.) and lambda (.lambda.), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG.sub.1, IgG.sub.2, IgG.sub.3, IgG.sub.4, IgA.sub.1, and IgA.sub.2. The heavy-chain constant domains that correspond to the different classes of immunoglobulins are called .alpha., .delta., .epsilon., .gamma., and .mu., respectively. The subunit structures and three-dimensional configurations of different classes of immunoglobulins are well known.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler and Milstein, *Nature* 256:495 (1975), or can be made by recombinant DNA methods (Cabilly et al., supra).

The monoclonal antibodies herein specifically include "chimeric" antibodies I(immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from By another species or belonging to another antibody class or subclass, as well as fragments of such antibodies, so long as they exhibit the desired biological activity (Cabilly et al., supra; Morrison et al., *Proc. Natl. Acad Sci. U.S.A.* 81:6851 (1984)).

"Humanized" forms of non-human (e.g., murine) antibodies are specific chimeric immunoglobulins, immunoglobulin chains or fragments thereof (such as Fv, Fab, Fab', $F(ab')_2$, or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., *Nature* 321:522 (1986); Reichmann et al., *Nature* 332:323 (1988); and Presta, *Curr. Op. Struct. Biol.* 2:593 (1992).

As noted above, the present invention provides compositions and methods for treating a tissue disorder associated with a response-to-injury process or proliferating cells in a mammal. More specifically, based upon the pathways and progression of disease described herein, it is now understood that many diseases are related in the sense that transition molecules are involved in the initiation and progression of disease. Provided in more detail below are: (A) assays for detecting molecules suitable for use within the present invention; (B) suitable candidate molecules for use within the present invention (whether for assaying, or for therapeutic purpose); (C) antibodies (for either assaying, or for therapeutic purpose); (D) expression systems for producing and or delivering therapeutic quantities of a desired polypeptide; (E) methods of treating a wide variety of diseases; and (F) the preparation of pharmaceutical compositions, including vaccines.

A. Assays for Detecting Therapeutic Molecules

The present invention provides a number of assays suitable for detecting therapeutic molecules, which are briefly described herein, as well as in more detail below in the examples.

For example, within one aspect of the invention methods of identifying a peptide or polypeptide composition for treating a tissue disorder associated with a response-to-injury process, or, the proliferation of cells in a mammal is provided, comprising the general steps of: (a) selecting a sequence from a database screened for sequences comprising a peptide of the sequence BX7B (SEQ ID NO:28) wherein B is a basic amino acid, and X7 is a sequence of about seven residues is selected from any amino acid other than an acidic amino acid, wherein the peptide forms an alpha helix and each occurrence of B is oriented on the same side of the alpha helix, (b) preparing a composition comprised of the selected sequence; and (c) testing the prepared composition for the ability to inhibit podosome formation. Within certain embodiments, the peptide in (a) does not consist of the sequences BBXXBBBXXBB, KQKIKHVVKLK, KLKSQLVKRK, RYPISRPRKR, KNGRYSISR, RDGTRYVQKGEYR, RRRCGQKKK, RGTRSGSTR, RRRKKIQGRSKR, RKSYGKYQGR, KVGKSPPVR, KTFGKMKPR, RIKWSRVSK, KRTMRPTRR, KVGKSPPVR, or HREARSGKYK (SEQ ID NOs: 29–44 respectively).

In a related aspect, the invention provides methods of identifying a peptide or polypeptide composition for treating a tissue disorder associated with a response-to-injury process or proliferating cells in a mammal comprising the steps of: (a) forming an expression library comprised of cloned sequences expressed by a cell during a transition stage response; (b) screening the expression library for sequences encoding a peptide or polypeptide that binds a hyaladherin that is stimulated in cells during the transition stage; (c) preparing a peptide or polypeptide encoded by the hyaladherin binding sequences; and (d) testing the peptide or polypeptide for the ability to affect at least one activity associated with transition stage cells wherein the activity is selected from the group consisting of: increased erk kinase signal activation, podosome formation, metalloproteinase expression, flux of intracellular or extracellular HA or hyaladherins, expression of a hyaladherin, and inability to form focal adhesions. In one embodiment of this method, the expression vector is a two hybrid phage display system, the hyaladherin is RHAMM and the testing is for the ability to inhibit podosome formation and inhibition of erk kinase signaling activation. In a related embodiment of these methods, the library is a library of nucleic acid molecules, or organic molecules, and the library is tested in order to determine its ability to affect one of the activities set forth in (d) above. If the test is positive, the library may be deconvoluted, and screened until a single molecule is identified.

In still another aspect, the invention provides methods for detecting hyalauronic acid in a sample comprising the steps of: (a) incubating the sample with a hyalauronic acid binding peptide comprising a sequence selected from the group consisting of SEQ ID NOs: 1–10; and (b) detecting an amount of a complex formed between hyalauronic acid and the hyalauronic acid binding peptide. In one embodiment, the detecting employs an antibody that specifically binds to the hyalauronic acid binding peptide.

In a related aspect, the invention provides methods of detecting a molecule that binds to a RHAMM polypeptide in a sample comprising the steps of (a) incubating the sample with the RHAMM polypeptide and with a RHAMM-binding polypeptide comprised of SEQ. ID NO: 21; and (b) detecting an amount of a complex formed between the sample and the RHAMM polypeptide by scoring for reduced binding between the RHAMM polypeptide and the RHAMM-binding polypeptide. In one embodiment, this method includes detecting which employs an antibody that specifically binds to the RHAMM-binding polypeptide.

These as well as other methods are described in more detail below in the examples.

B. Candidate Molecules

Utilizing the assays provided herein, a wide variety of molecules may be assayed for their ability to treat or prevent a tissue disorder associated with a response-to-injury process or proliferating cells. Representative examples which are discussed in more detail below include organic molecules, proteins or peptides, and nucleic acid-molecules.

1. Organic Molecules

Numerous organic molecules may be assayed for their ability to treat or prevent a tissue disorder associated with a response-to-injury process or proliferating cells.

For example, within one embodiment of the invention suitable organic molecules may be selected from either from a chemical library, wherein chemicals are assayed individually, or from combinatorial chemical libraries where multiple compounds are assayed at once, then deconvoluted to determine and isolate the most active compounds.

Representative examples of such combinatorial chemical libraries include those described by Agrafiotis et al., "System and method of automatically generating chemical compounds with desired properties," U.S. Pat. No. 5,463,564; Armstrong, R. W., "Synthesis of combinatorial arrays of organic compounds through the use of multiple component combinatorial array syntheses," WO 95/02566; Baldwin, J. J. et al., "Sulfonamide derivatives and their use," WO 95/24186; Baldwin, J. J. et al., "Combinatorial dihydrobenzopyran library," WO 95/30642; Brenner, S., "New kit for preparing combinatorial libraries," WO 95/16918; Chenera, B. et al., "Preparation of library of resin-bound aromatic carbocyclic compounds," WO 95/16712; Ellman, J. A., "Solid phase and combinatorial synthesis of benzodiazepine compounds on a solid support," U.S. Pat. No. 5,288,514; Felder, E. et al., "Novel combinatorial compound libraries,"

WO 95/16209; Lerner, R. et al., "Encoded combinatorial chemical libraries," WO 93/20242; Pavia, M. R. et al., "A method for preparing and selecting pharmaceutically useful non-peptide compounds from a structurally diverse universal library," WO 95/04277; Summerton, J. E. and D. D. Weller, "Morpholino-subunit combinatorial library and method," U.S. Pat. No. 5,506,337; Holmes, C., "Methods for the Solid Phase Synthesis of Thiazolidinones, Metathiazanones, and Derivatives thereof," WO 96/00148; Phillips, G. B. and G. P. Wei, "Solid-phase Synthesis of Benzimidazoles," Tet. Letters 37:4887-90, 1996; Ruhland, B. et al., "Solid-supported Combinatorial Synthesis of Structurally Diverse β-Lactams," *J. Amer. Chem. Soc.* 111:253–4, 1996; Look, G. C. et al., "The Identification of Cyclooxygenase-1 Inhibitors from 4-Thiazolidinone Combinatorial Libraries," *Bioorg and Med. Chem. Letters* 6:707–12, 1996.

2. Proteins and Peptides

A wide range of proteins and peptides may likewise be assayed for their ability to treat or prevent a tissue disorder associated with a response-to-injury process or proliferating cells.

a. Combinatorial Peptide Libraries

Suitable peptide molecules may be obtained through the screening of combinatorial peptide libraries. Such libraries may either be prepared by one of skill in the art (see e.g., U.S. Pat. Nos. 4,528,266 and 4,359,535, and Patent Cooperation Treaty Publication Nos. WO 92/15679, WO 92/15677, WO 90/07862, WO 90/02809, or purchased from commercially available sources (e.g., New England Biolabs Ph.D.™ Phage Display Peptide Library Kit).

b. Peptide Mimetics

Numerous peptide mimetics may also be utilized within the present invention, including for example peptides such as:

SEQ. ID. NO:1 (H4–5)B3;

SEQ. ID. NO:2 (H4–5)BXBBXB;

SEQ. ID. NO:3 (H4–5)BXBXBBB;

SEQ. ID. NO:4 (H4-S)BXBBB; and

SEQ. ID. NO:5 (H4–5)BXBB where B is either lysine (K) or arginine (R) and X is a hydrophobic or neutral amino acid (i.e., L, V, Q, S) and H represents a series of amino acids such that an alpha helix is formed, as determined by NN-predict EMBL protein analysis. This need not be an amphipathic or coiled coil helix but such would also be suitable. Specific examples of sequences fitting these motifs that have been analyzed for effectiveness on podosome include the following:

SEQ. ID. NO: 6 MMTVLKR;

SEQ. ID. NO: 7 MMTVLKVKRLR;

SEQ. ID. NO: 8 MMTVLKVKVKRK;

SEQ. ID. NO: 9 MMTVLKVRKR; and

SEQ. ID. NO: 10 MMTVLKVRK.

In addition, the following RHAMM sequences are more highly exposed on cell surfaces and more effective at blocking podosomes, cell motility and cell invasion. These are:

SEQ ID NO: 11 KLQATQKPLTESK, and

SEQ ID NO: 12 VSIEKEKIDEKS.

Other peptides may likewise be developed based upon the TAM domain ("Transient Activator of Map kinases"). This sequence is

SEQ ID NO: 13 VS(I/L)EKE.

Since this sequence is included in those used to prepare polyclonal antibodies against RHAMM, and because such antibodies blocks cell motility and activation of erk by growth factors, TAM domains have been identified as key sites of protein-protein interaction that are required for controlling map kinase pathways. This in turn regulates the activation of the cell to migrate, proliferate and remodel extracellular matrix. Reagents to this sequence will be useful in therapeutic treatment of the diseases described above.

Antibodies, peptide mimics or antisense technology of these motifs can be used to disrupt the transient phenotype and for treatment of disease as described in more detail below.

c. Antibodies

Antibodies, as described in more detail below, may likewise be assayed for their ability to treat or prevent a tissue disorder associated with a response-to-injury process or proliferating cells.

d. Production of Proteins

Although various genes (or portions thereof) have been provided herein, it should be understood that within the context of the present invention, reference to one or more of these genes includes derivatives of the genes that are substantially similar to the genes (and, where appropriate, the proteins (including peptides and polypeptides) that are encoded by the genes and their derivatives). As used herein, a nucleotide sequence is deemed to be "substantially similar" if: (a) the nucleotide sequence is derived from the coding region of the above-described genes and includes, for example, portions of the sequence or allelic variations of the sequences discussed above, (b) the nucleotide sequence is capable of hybridization to nucleotide sequences of the present invention under moderate, high or very high stringency (see Sambrook et al., *Molecular Cloning: A Laboratory Manual*, $2^{nd}$ ed., Cold Spring Harbor Laboratory Press, NY, 1989); or (c) the DNA sequences are degenerate as a result of the genetic code to the DNA sequences defined in (a) or (b). Further, the nucleic acid molecule disclosed herein includes both complementary and non-complementary sequences, provided the sequences otherwise meet the criteria set forth herein. Within the context of the present invention, high stringency means standard hybridization conditions (e.g., (5×SSPE (SSPE comprises 0.15M NaCl. 10 mM $NaHaPo_4$, 1 mM EDTA pH 7.4) 0.5% sodium dodecyl sulfate (SDS) at 65° C., or the equivalent).

The structure of the proteins encoded by the nucleic acid molecules described herein may be predicted from the primary translation products using the hydrophobicity plot function of, for example, P/C Gene or Intelligenetics Suite (Intelligenetics, Mountain View, Calif.), or according to the methods described by Kyte and Doolittle (*J. Mol. Biol.* 157:105–132, 1982).

Proteins of the present invention may be prepared in the form of acidic or basic salts, or in neutral form. In addition, individual amino acid residues may be modified by oxidation or reduction. Furthermore, various substitutions, deletions, or additions may be made to the amino acid or nucleic acid sequences, the net effect of which is to retain or further enhance or decrease the biological activity of the mutant or wild-type protein. Moreover, due to degeneracy in the genetic code, for example, there may be considerable variation in nucleotide sequences encoding the same amino acid sequence.

Other derivatives of the proteins disclosed herein include conjugates of the proteins along with other proteins or polypeptides. This may be accomplished, for s example, by the synthesis of N-terminal or C-terminal fusion proteins which may be added to facilitate purification or identification of proteins (see U.S. Pat. No. 4,851,341, see also, Hopp et al., *Bio/Technology* 6:1204, 1988.) Alternatively, fusion proteins such as Flag/desired protein binding protein be constructed in order to assist in the identification, expression, and analysis of the protein.

Proteins of the present invention may be constructed using a wide variety of techniques described herein. Further, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site-specific (or segment specific) mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, January 1985, 12–19); Smith et al. (*Genetic Engineering: Principles and Methods*, Plenum Press, 1981); and Sambrook et al. (supra). Deletion or truncation derivatives of proteins (e.g., a soluble extracellular portion) may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al. (*Molecular Cloning: A Laboratory Manual*, 2d Ed., Cold Spring Harbor Laboratory Press, 1989).

Mutations which are made in the nucleic acid molecules of the present invention preferably preserve the reading frame of the coding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity. Alternatively, mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Nucleic acid molecules which encode proteins of the present invention may also be constructed utilizing techniques of polymerase chain reaction (PCR) mutagenesis, chemical mutagenesis (Drinkwater and Klinedinst, *PNAS* 83:3402–3406, 1986), by forced nucleotide misincorporation (e.g., Liao and Wise *Gene* 88:107–111, 1990), or by use of randomly mutagenized oligonucleotides (Horwitz et al., *Genome* 3:112–117, 1989).

The present invention also provides for the manipulation and expression of the above described genes by culturing host cells containing a vector capable of expressing the above-described genes. Such vectors or vector constructs include either synthetic or cDNA-derived nucleic acid molecules encoding the desired protein, which are operably linked to suitable transcriptional or translational regulatory elements. Suitable regulatory elements may be derived from a variety of sources, including bacterial, fungal, viral, mammalian, insect, or plant genes. Methods for expressing genes of interest are describe in more detail above.

Proteins can be isolated by, among other methods, culturing suitable host and vector systems to produce the recombinant translation products of the present invention. Supernatants from such cell lines, or protein inclusions or whole cells where the protein is not excreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art.

A protein is deemed to be "isolated" within the context of the present invention if no other (undesired) protein is detected pursuant to SDS-PAGE analysis followed by Coomassie blue staining. Within other embodiments, the desired protein can be isolated such that no other (undesired) protein is detected pursuant to SDS-PAGE analysis followed by silver staining.

3. Nucleic Acid Molecules

Within other aspects of the invention, nucleic acid molecules can be assayed for their ability to treat or prevent a tissue disorder associated with a response-to-injury process or proliferating cells. For example, within one embodiment antisense oligonucleotide molecules are provided which specifically inhibit expression of nucleic acid sequences which are associated with a response-to injury process or the proliferation of cells (see generally, Hirashima et al. in *Molecular Biology of RNA: New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012, 1993; WO 95/10607; U.S. Pat. No. 5,359,051; WO 92/06693; and EP-A2-612844). Briefly, such molecules are constructed such that they are complementary to, and able to form Watson-Crick base pairs with, a region of a transcribed mRNA sequence. The resultant double-stranded nucleic acid interferes with subsequent processing of the mRNA, thereby preventing protein synthesis.

Within other aspects of the invention, ribozymes are provided which are capable of inhibiting the expression of sequences which are associated with, or which encode proteins or polypeptides that are associated with the disorders described herein. As used herein, "ribozymes" are intended to include RNA molecules that contain anti-sense sequences for specific recognition, and an RNA-cleaving enzymatic activity. The catalytic strand cleaves a specific site in a target RNA at greater than stoichiometric concentration. A wide variety of ribozymes may be utilized within the context of the present invention, including for example, the hammerhead ribozyme (for example, as described by Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988); the hairpin ribozyme (for example, as described by Haseloffet al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

4. Labels

The gene product or any of the candidate molecules described above and below, may be labeled with a variety of compounds, including for example, fluorescent molecules, toxins, and radionuclides. Representative examples of fluorescent molecules include fluorescein, Phycobili proteins, such as phycoerythrin, rhodamine, Texas red and luciferase. Representative examples of toxins include ricin, abrin diphtheria toxin, cholera toxin, gelonin, pokeweed antiviral protein, tritin, Shigella toxin, and Pseudomonas exotoxin A. Representative examples of radionuclides include Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212 and Bi-212. In addition, the antibodies described herein may also be labeled or conjugated to one partner of a ligand binding pair. Representative examples include avidin-biotin, and riboflavin-riboflavin binding protein.

Methods for conjugating or labeling the molecules described herein with the representative labels set forth above may be readily accomplished by one of ordinary skill in the art (see Trichothecene Antibody Conjugate , U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, *Methods In Enzymology*, Vol. 34, *Affinity Techniques, Enzyme Purification: Part B*, Jakoby and Wilchek (eds.), Academic Press, New York, p. 30, 1974; see also Wilchek and Bayer, "The Avidin-Biotin Complex in Bioanalytical Applications," *Anal. Biochem.* 171:1–32, 1988).

C. Antibodies

Antibodies to the polypeptides, fragments, or peptides described herein may readily be prepared by one of skill in the art given the disclosure provided herein. Within the context of the present invention, the term "antibody" should be understood to include monoclonal antibodies, polyclonal antibodies, anti-idiotypic antibodies, antibody fragments (e.g., Fab, and $F(ab')_2$, $F_v$ variable regions, or complementarity determining regions), whether obtained from animals or humans, generated utilizing hybridoma technology, or recombinantly produced. Antibodies are generally accepted as specific against an antigen if they bind with a $K_d$ of at least $10^{-7}$ M (moles/liter), and more preferably, at least $10^{-8}$ M, $10^{-9}$ M, $10^{-10}$ M, $10^{-11}$ M, $10^{-12}$ M, $10^{-12}$ M, $10^{-14}$ M. The affinity of a monoclonal antibody or binding partner can be readily determined by one of ordinary skill in the art (see Scatchard, *Ann. N.Y. Acad. Sci.* 51:660–672, 1949). Antibodies of the present invention should also bind to the desired domain or peptide with the specificity noted above, and not against randomized peptides.

Briefly, a polyclonal antibody preparation may be readily generated in a variety of warm-blooded animals such as rabbits, mice, or rats. Typically, an animal is immunized with a desired antigen or peptide thereof, which may be conjugated to a carrier protein, such as keyhole limpet hemocyanin. Routes of administration include intraperitoneal, intramuscular, intraocular, or subcutaneous injections, usually in an adjuvant (e.g., Freund's complete or incomplete adjuvant). Particularly preferred polyclonal antisera demonstrate binding in an assay that is at least three times greater than background.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual*, Harlow and Lane (eds.), Cold Spring Harbor Laboratory Press, 1988). Briefly, within one embodiment, a subject animal such as a rat or mouse is injected with an antigen of interest or a portion thereof. The protein may be administered as an emulsion in an adjuvant such as Freund's complete or incomplete adjuvant in order to increase the immune response. Between one and three weeks after the initial immunization the animal is generally boosted and may be tested for reactivity to the protein utilizing well-known assays. The spleen and/or lymph nodes are harvested and immortalized. Various immortalization techniques, such as mediated by Epstein-Barr virus or fusion to produce a hybridoma, may be used. In a preferred embodiment, immortalization occurs by fusion with a suitable myeloma cell line (e.g., NS-1 (ATCC No. T1B 18), and P3C63—Ag 8.653 (ATCC No. CRL 1580) to create a hybridoma that secretes monoclonal antibody. The preferred fusion partners do not express endogenous antibody genes. Following fusion, the cells are cultured in medium containing a reagent that selectively allows for the growth of fused spleen and myeloma cells such as HAT (hypoxanthine, aminopterin, and thymidine) and are subsequently screened for the presence of antibodies that are reactive against the desired antigen of interest. A wide variety of assays may be utilized, including for example countercurrent immuno-electrophoresis, radioimmunoassays, radioinumunoprecipitations, enzyme-linked immunosorbent assays (ELISA), dot blot assays, western blots, immunoprecipitation, inhibition or competition assays, and sandwich assays (see U.S. Pat. Nos. 4,386,110 and 4,486,530; see also *Antibodies: A Laboratory Manual*, Harlow and Lane (eds.), Cold Spring Harbor Laboratory Press, 1988).

Other techniques may also be utilized to construct monoclonal antibodies (see Huse et al., *Science* 246:1275–1281, 1989; Sastry et al., *Proc. Natl. Acad Sci. USA* 86:5728–5732, 1989; Alting-Mees et al., *Strategies in Molecular Biology* 3:1–9, 1990; describing recombinant techniques). Briefly, RNA is isolated from a B cell population and utilized to create heavy and light chain immunoglobulin cDNA expression libraries in suitable vectors, such as λImmunoZap(H) and λImmunoZap(L). These vectors may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli*.

Similarly, portions or fragments, such as Fab and Fv fragments, of antibodies may also be constructed utilizing conventional enzymatic digestion, or recombinant DNA techniques to yield isolated variable regions of an antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources (e.g., Stratacyte, La Jolla, Calif.) Amplification products are inserted into vectors such as ImmunoZAP™ H or ImmunoZAP™ L (Stratacyte), which are then introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423–426, 1988). In addition, techniques may be utilized to change a "murine" antibody to a "human" antibody, without altering the binding specificity of the antibody. Examples of humanized antibodies include chimeric or CDR-grafted antibodies (U.S. Pat. Nos. 4,816,567 and 5,225,539), antibodies produced in genetically-altered mice (see PCT Application No. 93/12227).

One of ordinary skill in the art will appreciate that a variety of alternative techniques for generating antibodies exist. In this regard, the following U.S. patents teach a variety of these methodologies and are thus incorporated herein by reference: U.S. Pat. Nos. 5,840,479; 5,770,380; 5,204,244; 5,482,856; 5,849,288; 5,780,225; 5,395,750; 5,225,539; 5,110,833; 5,693,762; 5,693,761; 5,693,762; 5,698,435; and 5,328,834.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC (e.g. reversed phase, size exclusion, ion-exchange), purification on protein A or protein G columns, or any combination of these techniques.

D. Expression Systems

1. Vectors, Host Cells and Means of Expressing and Producing Protein

Proteins or polypeptides of the present invention may be readily expressed in a variety of host cells or organisms. For protein production and purification, proteins are preferably secreted and produced in bacteria, such as *E. coli*, for which many expression vectors have been developed and are available. Other suitable host organisms include other bacterial species (e.g., Bacillus, and eukaryotes, such as yeast (e.g., *Saccharomyces cerevisiae*), mammalian cells (e.g., Chinese hamster ovary (CHO) and COS-7), plant cells and insect cells (e.g., Sf9). Vectors for these hosts are well known.

Briefly, within one embodiment a DNA sequence encoding a desired protein or polypeptide is introduced into an expression vector appropriate for the host. The sequence is derived from an existing clone or synthesized. A preferred means of synthesis is amplification of the gene from cDNA, genomic DNA, or a recombinant clone using a set of primers that flank the coding region or the desired portion of the protein. Restriction sites are typically incorporated into the primer sequences and are chosen with regard to the cloning site of the vector. If necessary, translational initiation and termination codons can be engineered into the primer sequences. The desired sequence can be codon-optimized for expression in a particular host. For example, a secreted form of a desired protein that is expressed in a fungal host, such as yeast, can be altered in nucleotide sequence to use codons preferred in yeast. Codon-optimization may be accomplished by methods such as splice overlap extension, site-directed mutagenesis, automated synthesis, and the like.

At minimum, the vector must contain a promoter sequence. Other regulatory sequences however may also be included. Such sequences include a transcription termination signal sequence, secretion signal sequence, origin of replication, selectable marker, and the like. The regulatory sequences are operationally associated with one another to allow transcription or translation.

2. Expression in Bacteria

The plasmids used herein for expression of a desired protein or polypeptide include a promoter designed for expression of the proteins in a bacterial host. Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see e.g., U.S. Pat. Nos. 5,243,041, 5,242,687, 5,266,317, 4,745,051, and 5,169,784), mouse mammary tumor virus (MMTV), long term repeat (LTR), rous sarcoma virus (RSV) LTR, simian virus 40 (SV40), metallothionein promoter (see, e.g. U.S. Pat. No. 4,870,009) and other inducible promoters. For expression of the proteins, a promoter is inserted in operative linkage with the coding region of the desired protein or polypeptide.

The promoter controlling transcription of the desired protein may be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to the *E. coli* lacI repressor responsive to isopropl$\beta$-D-1-thiogalactoranoside (IPTG) induction, the temperature sensitive $\lambda$cI857 repressor, and the like. The *E. coli* lacI repressor is preferred.

In other preferred embodiments, the vector also includes a transcription terminator sequence. A "transcription terminator region" has either a sequence that provides a signal that terminates transcription by the polymerase that recognizes the selected promoter and/or a signal sequence for polyadenylation.

Preferably, the vector is capable of replication in bacterial cells. Thus, the vector preferably contains a bacterial origin of replication. Preferred bacterial origins of replication include the f1-ori and col E1 origins of replication, especially the ori derived from pUC plasmids.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene ($Amp^r$), tetracycline resistance gene ($Tc^r$) and the kanamnycin resistance gene ($Kan^r$). Suitable markers for eukaryotes usually require a complementary deficiency in the host (e.g., thymidine kinase (tk) in tk- hosts). However, drug markers are also available (e.g., G418 resistance and hygromycin resistance).

The sequence of nucleotides encoding the desired protein or polypeptide may also include a classical secretion signal, whereby the resulting peptide is a precursor protein processed and secreted. The resulting processed protein may be recovered from the periplasmic space or the fermentation medium. Secretion signals suitable for use are widely available and are well known in the art (von Heijne, *J. Mol. Biol.* 184:99–105, 1985). Prokaryotic and eukaryotic secretion signals that are functional in *E. coli* (or other host) may be employed. The presently preferred secretion signals include, but are not limited to pelB, mat$\alpha$, extensin and glycine-rich protein.

One skilled in the art appreciates that there are a wide variety of suitable vectors for expression in bacterial cells and which are readily obtainable. Vectors such as the pET series (Novagen, Madison, Wis.) and the tac and trc series (Pharmacia, Uppsala, Sweden) are suitable for expression of a wide variety of proteins. A suitable plasmid is ampicillin resistant, has a colEI origin of replication, $lacI^q$ gene, a lac/trp hybrid promoter in front of the lac Shine-Dalgarno sequence, a hexa-his coding sequence that joins to the 3' end of the inserted gene, and an rrnB terminator sequence.

The choice of a bacterial host for the expression of the desired protein or polypeptide is dictated in part by the vector. Commercially available vectors are paired with suitable hosts. The vector is introduced in bacterial cells by standard methodology. Typically, bacterial cells are treated to allow uptake of DNA (for protocols, see generally, Ausubel et al., supra; Sambrook et al, supra). Alternatively, the vector may be introduced by electroporation, phage infection, or another suitable method.

3. Expression in Other Organisms

A variety of other organisms are suitable for use in the present invention. For example, various fungi, including yeasts, molds, and mushrooms, insects, especially vectors for diseases and pathogens, and other animals, such as cows, mice, goats, birds, aquatic animals (e.g., shrimp, turtles, fish, lobster and other crustaceans), amphibians and reptiles and the like, may be transformed with a desired transgene.

The principles that guide vector construction for bacteria and plants, as discussed above, are applicable to vectors for these organisms. In general, vectors are well known and readily available. Briefly, the vector should have at least a promoter functional in the host in operative linkage with the desired protein or polypeptide. Usually, the vector will also have one or more selectable markers, an origin of replication, a polyadenylation signal and transcription terminator.

The sequence of nucleotides encoding the desired protein or polypeptide may also include a classical secretion signal, whereby the resulting peptide is a precursor protein processed and secreted. Suitable secretion signals may be obtained from a variety of genes, such as mat-alpha or invertase genes.

4. Transgenic Animals

Within related aspects of the present invention, proteins of the present invention may be expressed in a transgenic animal whose germ cells and somatic cells contain a gene which encodes the desired protein and which is operably linked to a promoter effective for the expression of the gene. Alternatively, in a similar manner transgenic animals may be prepared that lack the desired gene (e.g., "knockout" mice). Such trangenics may be prepared in a variet of non-human animals, including mice, rats, rabbits, sheep, dogs, goats and pigs (see Hammer et al., *Nature* 315:680–683, 1985, Palmiter et al., *Science* 222:809–814, 1983, Brinster et al., *Proc. Natl. Acad. Sci. USA* 82:4438–4442, 1985, Palmiter and Brinster, *Cell* 41:343–345, 1985, PCT Publication No. WO 99/01164, and U.S. Pat. Nos. 5,175,383, 5,087,571, 4,736,866, 5,387,742, 5,347,075, 5,221,778, 5,162,215; 5,545,808; 5,741,957; 4,873,191; 5,780,009; 4,736,866; 5,567,607; 5,633,076 and 5,175,384). Briefly, an expression vector, including a nucleic acid molecule to be expressed together with appropriately positioned expression control sequences, is introduced into pronuclei of fertilized eggs, for example, by microinjection. Integration of the injected DNA is detected by blot analysis of DNA from tissue samples. It is preferred that the introduced DNA be incorporated into the germ line of the animal so that it is passed on to the animal's progeny. Tissue-specific expression may be achieved through the use of a tissue-specific promoter, or through the use of an inducible promoter, such as the metallothionein gene promoter (Palmiter et al., 1983, ibid), which allows regulated expression of the transgene.

E. Gene Delivery Vectors

A wide variety of gene delivery vectors may be utilized to deliver and/or express a desired gene of interest in host cells. For example, within one aspect of the present invention, retroviral gene delivery vehicles may be utilized. Briefly, retroviral gene delivery vehicles of the present invention may be readily constructed from a wide variety of retroviruses, including for example, B, C, and D type retroviruses as well a spumaviruses and lentiviruses (see RNA tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Representative examples of retroviral gene delivery vectors are described in more detail in EP 0,415,731; PCT Publication NOs: WO 90/07936; WO 91/0285, WO 9311230; WO 9310218, WO 9403622; WO 9325698; WO 9325234; and U.S. Pat. Nos. 5,219,740, 5,716,613, 5,851,529, 5,591,624, 5,716,826, 5,716,832, and 5,817,491.

Other suitable gene delivery vectors can be generated from alpha viruses (see e.g., U.S. Pat. Nos. 5,091,309 and 5,217,879, 5,843,723, and 5,789,245), recombinant adenoviral vectors (see e.g., U.S. Pat. No. 5,872,005), and numerous other viruses such as pox viruses, such as canary pox virus or vaccinia virus (Fisher-Hoch et al., *PNAS* 86: 317–321, 1989; Flexner et al., *Ann. N.Y. Acad. Sci.* 569:86–103, 1989; Flexner et al, *Vaccine* 8:17–21, 1990; U.S. Pat. Nos. 4,603,112, 4,769,330 and 5,017,487; WO 89/01973); SV40 (Mulligan et al., *Nature* 277:108–114, 1979); influenza virus (Luytjes et al., *Cell* 59:1107–1113, 1989; McMichael et al., *N. Eng. J. Med.* 309:13–17, 1983; and Yap et al., *Nature* 273:238–239, 1978); herpes (Kit, *Adv. Exp. Med. Biol.* 215:219–236, 1989; U.S. Pat. No. 5,288,641); HIV (Poznansky, *J. Virol.* 65:532–536, 1991); measles (EP 0 440,219); Semliki Forest Virus, and coronavirus as well as other viral systems (e.g., EP 0,440,219; WO 92/06693; U.S. Pat. No. 5,166,057).

In addition to the above viral-based vectors, numerous non-viral gene delivery vehicles may likewise be utilized within the context of the present invention. Representative examples of such gene delivery vehicles include direct delivery of nucleic acid expression vectors or naked DNA alone (see e.g., U.S. Pat. Nos. 5,814,482 and 5,580,859), polycation condensed DNA linked or unlinked to killed adenovirus (Curiel et al., *Hum. Gene Ther.* 3:147–154, 1992), DNA ligand linked to a ligand (Wu et al., *J. of Biol. Chem* 264:16985–16987,1989), and nucleic acid containing liposomes (e.g., WO 95/24929 and WO 95/12387).

F. Compounds

As noted above, a wide variety of compounds may be utilized within this regard, including for example (a) a polypeptide comprising the amino acid sequence BX7B (SEQ ID NO:28) which binds HA; (b) an anti-TAM antibody; (c) a polypeptide fragment which encodes a D1, D2, D3, D4, or, D5 domain of RHAMM; and (d) a gene delivery vector which expresses antisense RHAMM, or, delivers and expresses any one of (a), (b), or (c).

Within one embodiment, the polypeptide BX7B (SEQ ID NO:28) comprises a polypeptide wherein B is a basic amino acid and X7 is a sequence of about seven residues selected from any amino acid other than an acidic amino acid, wherein the peptide forms an 14 alpha helix and each occurrence of B is oriented on the same side of the alpha helix, and with the proviso that the peptide does not consist of the sequences BBXXBBBXXBB, KQKIKHVVKLK, KLKSQLVKRK, RYPISRPRKR, KNGRYSISR, RDGTRYVQKGEYR, RRRCGQKKK, RGTRSGSTR, RRRKKIQGRSKR, RKSYGKYQGR, KVGKSPPVR, KTFGKMKPR, RIKWSRVSK, KRTMRPTRR, KVGKSPPVR, or HREARSGKYK (SEQ ID NOs: 29–44 respectively).

In one embodiment, the polypeptide can be (a) a first peptide comprised of a hyaluronic acid-binding domain; (b) a hyaladherin polypeptide; (c) a second peptide comprised of a domain from a hyaladherin polypeptide; (d) a hyaladherin-binding polypeptide; (e) a third peptide comprised of a hyaladherin binding domain. Also provided are antibodies which binds to a peptide or polypeptide of (a)–(d); and/or vectors (e.g., gene delivery vectors described below) that expresses a gene encoding a polypeptide as described above or herein. In a particular embodiment, peptides are provided comprised of a sequence selected from the group consisting of SEQ ID NOs: 1–20. In another embodiment, a hyaladherin-binding polypeptide comprised of SEQ ID NO: 21.

Within particularly preferred embodiments of the invention, the compound is an antibody. Representative examples of antibodies suitable for use within the present invention include antibodies to domain D1 of RHAMM amino acids 1–164 of human RHAMM (including for example: sequences recognizing the murine D1 sequence, aa. 97–111—QERGTQKRIQDME (SEQ ID NO:21); and sequences recognizing human RHAMM, aa 151–164—LKSKFSENGNQKNL (SEQ ID NO:18)); antibodies to domain D2 of RHAMM—the "leucine zipper" domain of human RHAMM from aa 195–222; antibodies which recognize the domain D3—the TAM domains of RHAMM (aa 219–240 of the human RHAMM Sequence, including antibodies which recognize the sequence VSIEKEKIDEK (SEQ ID NO:49)); domain D4 (repeat or "R" domain—aa 442–546 for mouse, and aa 442–463 for human) and domain D5 (HA binding domain, including two domains: aa 721–730 and aa 742–752 for mouse; aa 635–445 and aa 657–666 for human). In other embodiments, antibodies are provided which bind to a polypeptide comprised of SEQ ID NOs: 11–20.

As utilized herein, reference may be made to the human sequence of RHAMM for identification of the domains. However, the domains can be identified and specific antibodies generated for other species, such as for example, mouse. FIG. 50 SEQ ID NOs: 47 and 48) provides the amino acid sequence of human and mouse RHAMM (see PCT publication No. WO 97/38098 and Genbank Accession NOs: AAC52049 & Q00547). As utilized herein, it should be understood that antibodies "bind" to the above sequence if they do so with a $K_d$ of at least $10^{-7}$ M (moles/liter) (see "antibodies" above).

Also provided are polypeptides comprising a fragment of the RHAMM protein, of less than 95 or 73 kD molecular weight. Representative fragments of polypeptides contain at least all, or a portion of one of domains D1, D2, D3, D4, or D5, as set forth above. Within various embodiments, the polypeptides are less than 250, 200, 150, 100, 75, 50, or, 25 amino acids in length.

G. Methods of Treatment

As described in more detail below, a wide-variety of diseases share common disease processes such as local production of cytokines, degradative enzymes, reactive oxygen species resulting in increased cell migration and proliferation and eventual tissue destruction and cell death. These diseases may be readily treated or prevented, by administration of a composition that alters the activity of transition molecules within a cell Transition molecules are comprised of hyaladherins, hyalauronans or molecules regulated by an amount of intracellular or extracellular hyaladherins or hyalauronans. The activity of hyaladherins and hyalauronans are shown to interact with a regulatory processes associated with a response to injury and/or proliferative/invasive cell types.

In one embodiment, methods are provided comprising the general steps of administering to a mammal an effective amount of a composition comprised of any one of (a) a first peptide comprised of a hyaluronic acid-binding domain; (b) a hyaladherin polypeptide; (c) a second peptide comprised of a domain from a hyaladherin polypeptide;

(d) a hyaladherin-binding polypeptide; (e) a third peptide comprised of a hyaladherin binding domain; (f) an antibody that binds to a peptide or polypeptide of (a)–(e); and/or (g) a vector that expresses a gene encoding any of (a)–(f).

Briefly, cells in a homeostatic environment such as normally occurs within adult tissues are characterized by a differentiated state that varies with the tissue, and a low or contained rate of cell proliferation or motility. This differentiated state has typically been viewed to occur as a result of specific gene regulation. As described in more detail below, differentiated cells that are functioning within a physiological, homeostatic tissue environment are also restricted from expressing genes that regulate response-to-injury processes. These processes are regulated by master switch transcription heterodimers termed AP-1 as illustrated in FIG. 1. The three map kinase cascades identified in mammalian cells so far include erk, jnk and p38 hog pathways. These pathways collectively regulate expression of the transcription factors c-fos and c-jun. Heterodimerization of these two transcription factors results in formation of AP-1 which controls the expression of genes required for cell migration, cell proliferation, extracellular matrix remodeling and production of growth factors and cytokines that are required for amplification and maintenance of the response to injury process. It is the deregulated activation of these pathways that leads to the diseased state.

These transcription factors when activated control the expression of a plethora of molecules required for efficient repair and include proteases such as collagenases, various extracellular matrix proteins and molecules that allow the cell to respond to cytokines/growth factors by proliferating and migrating efficiently. Response-to-injury is a well-defined term referring to the ability of cells to repair and to remodel their extracellular environment to promote and ultimately re-establish the differentiated state.

As shown in more detail in the Figures, nomal cells undergo a number of intermediate changes until it becomes a diseased cell involved in chronic inflammatory diseases, proliferating diseases and degenerative diseases. In FIGS. 1, 2, 3, and 5, we show schematically a model for the key transition steps involved in the transformation of normal cell to diseased cells which is applicable to all cell types surrounded by matrix and is most likely involved in all diseases including cancers, inflammatory and degenerative diseases, wound healing and injury related diseases, inflammatory implications of host verses graft or devices. Briefly, in the normal tissue, cells are quiescent and responsible for normal and controlled tissue remodelling. Normal cells express growth factor receptors (represented by small circles) but these are not grouped together and the cell is restricted in its ability to respond to pro-inflammatory cytokines and growth factors. Rather, the cell remains in a non-proliferative state and responds to factors that regulate its state of differentiation (homeostatic responses). Upon injury, the cell rapidly releases glycosylphosphatidyl inositol linked proteins (co-receptors indicated by triangles) onto the cell surface and releases hyaluronic acid (represented by X) and other matrix molecules such as fibronectin (represented by ~) that allow the cell to initiate the beginnings of an activated state. The presence of the coreceptors permits growth factors to aggregate slightly enhancing their ability to respond to proinflammatory cytokines and growth factors yet at the same time preventing the full response that is seen in the fully diseased cell. This regulated ability to respond to growth factors as well as the production of molecules such as hyaluronic acid and fibronectin allows the formation of podosomes (represented by small triangular extensions) that facilitate the localized release of proteases and other enzymes that produce fragments of extracellular matrix. These fragments serve to recruit other cells to the site of injury including white cells that allow enhancement and stabilization of the response to injury. Furthermore, these fragments contribute to the evolution of podosomes to focal contacts. This intermediary transitional state is termed Stage C and reagents prepared against the molecules regulating podosome structure and function are predicted to prevent development of the next state, Stage D which is one that allows full responses to pro-inflammatory cytokines and growth factors. In Stage D, growth factor and cytokine receptors are aggregated into structures called focal contacts, which contain all the signaling molecules required for activation of multiple pathways. In this aggregated state, cells are able to maximally respond to growth factors and cytokines and maintenance of this state leads to disease.

Cytokines and other pro-inflammatory mediators are not capable of stimulating the expression of AP-1 dependent genes involved in cell proliferation migration, and tissue destruction. However upon injury or stress, the cells under go a series of changes which result in the transformation of normal cells to diseased cells. While not being bound by theory, it is proposed herein that cells that are initially responding to stress, whether due to heat, chemical, free radical, mechanical injury or to mutations of key proteins, react to these insults in a standard pattern. The initial stage involves the expression and secretion of matrix molecules involved in edema and inflammatory responses (for example hyaluronic acid (HA), collagen type VIII, osteopontin, tenascin, serglycin, addressin, laminin), as well as expression of transition molecules on the cell membrane and surface such as heat shock proteins and HA-binding proteins (Stage B). It is known that differentiated cells undergoing transition respond initially to injury by activating ERK kinase cascades that regulate at the least, activation of heat shock protein transcription factors and potentially other transition molecules allowing cells to remain viable as Stage B cells. These cells are characterized by enhanced production of heat shock proteins that protect the cell from aggregation of key proteins, organelle damage and ultimately apoptosis, as well as by increased presence of HA-binding molecules on the cell surface.

Once the cell has entered stage B, the presence of growth factor concentrations and other molecules at the site of injury will likely determine whether the cell now returns to its differentiated state or proceeds to Stage C. The present invention provides the unexpected discovery that closely following the initial responses, cells enter a transitional stage (defined as Stage C) which is characterized by (1) the formation of transient structures called podosomes or invadapodia; (2) disassembled actin cytoskeleton (e.g., a paucity of focal adhesion); and (3) dependence upon hyaluronan related molecules and hyaladherins for regulation of signaling cascades; and (4) altered control of growth factor initiated signaling. As illustrated in the Examples, cells plated onto plastic transiently form podosomes at 12–18 h., but this is reduced by 24 h. Plating of cells onto fibronectin enhances and stabilizes podosome formation.

Fibronectin is also necessary for the formation of focal contacts. The presence of podosomes correlates with cell surface RHAMM expression. Such cells importantly exhibit the first stage of release from the restriction of AP-1 activation exhibited by Stage A cells. Podosomes allow the cell to efficiently release proteases at lamellae tips to promote cell invasion into the matrix that will ultimately initiate controlled remodelling of its extracellular matrix detected by exposure of the CS-1 sequence in fibronectin (described in more detail hereafter). This event is believed to be required for an ability to maximally respond to growth factors/cytokines and re-establishment of tissue homeostasis. Podosomes are also ultimately the sites of focal adhesion assembly that ultimately allow a cell to proceed to Stage D. At the podosome sites, increased and persistent matrix degradation results in increased degradation fragments of matrix molecules such as collagen and CS-1 fibronectin which suppresses the expression and levels of cell surface transitions molecules. Podosomes require interactions between hyaluronan and hyaladherins as well as interactions between hyaladherins and other proteins for their structural and functional integrity. As the levels of transitions molecules such as HA-binding molecules (e.g., RHAMM, CD37) on the cell surface and cytoplasm decrease, there is an increase in the formation of focal adhesions and local accumulation of cell surface cytokine receptors, intracellular signaling molecules and cytoskeletal components (Stage D). Focal Adhesions couple integrins to growth factor/cytokine receptors and allow the cell to enter the next stage in the injury response which is characterized by heightened ability to respond to pro-inflammatory cytokines and growth factors. The formation of focal adhesions removes restriction of activation of AP-1 dependent genes by cytokines and growth factors and results in increased cell migration and proliferation, and tissue destruction.

As described in more detail below, the sustained presence of these cells, termed Stage D are largely responsible for tissue deterioration following sustained and escalated response to injury that is characteristic of many inflammatory, degenerative and proliferative type of diseases including for instance arthritis, multiple sclerosis, psoriasis, inflammatory bowel diseases, restenosis, fibronosis, atherosclerosis, diabetes. osteoarthritis, cancers, Alzheimer's, Parkinson's and wound healing.

These transitional stages (Stages B–C) are necessary for all differentiated cells in tissues to activate AP-1 dependent genes and AP-1 dependent disease processes such as cell proliferation, migration, invasion and production of matrix metalloproteinases, therefore, inflammatory, proliferative and degenerative diseases are dynamic processes that involve the continual recruitment of differentiated tissue into the pathway culminating in the stage D cells. The ability of the cell to acquire a transitional phenotype is absolutely required for it to progress to Stage D where it responds to proinflammatory cytokines/growth factors. Molecules that regulate this transient cellular phase, such as those that either disrupt hyaluronan/hyaladherin or hyaladherin/other protein interactions, make excellent therapeutic and diagnostic targets in a variety of human diseases since these molecules will not be expressed in most cells and only transiently expressed in diseased tissue. This expression pattern will provide tissue specificity and low toxicity to the human body, allowing for chronic use of reagents, a requirement for managing many diseases.

Normal cells surrounded by a normal tissues are quiescent and involved in the turnover of matrix. Furthermore, consistent with the present disclosure, cells do not possess focal adhesions in normal tissue in vivo whereas focal adhesions have been observed in diseased tissue.

Transitional stages such as that described above are evident in a wide variety of disease processes, including for example, Parkinson's, Alzheimer's, Arthritis and Osteoporosis. These, as well as other disease processes which involve transition molecules that remove AP-1 restriction from normal cells are discussed in more detail below.

1. Parkinson's

Parkinsonism is a clinical syndrome characterized by a disturbance in motor functions such as slowness of voluntary movement, diminished facial expressions, stooped posture, rigidity and tremor. The disease appears later in life. Although little is known on the cause of the disease, there is substantial evidence indicating that damage to the nigrostriatal dopaminergic system is central to the disease. The dopaminergic neurons of the substantial nigra project to the striatum in normal brain. In Parkinson's disease, the loss of these neurons results in a decrease in striatal dopamine content and this is proportional to the severity of the motor syndrome. Similar to other brain diseases, there is an increase in glisosis, which involves the recruitment and activation of glial cells. These cells are recruited as part of the repair process, however, destructive enzymes, reactive oxygen species, cytokines and pro-inflammatory mediators produced by activated glial cells contribute and acerbate the disease.

Thus, within one embodiment methods are provided for treating inflammatory neurological diseases such as Parkinsons, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

2. Alzheimer Disease

Alzheimer's disease is clinically manifested as insidious impairment of higher intellectual function with alterations in mood and behavior. Later, progressive memory loss and disorientation are observed and eventually, profound disability and death. Alzheimer's disease affects a large portion of the increasingly aging population with a prevalence as high as 47% of those over 85 years old. The total costs required for formal and informal care of AD patients was $67 million in the United States. Although there is much variability, average life expectancy is 8–10 years after dementia onset.

Alzheimer's disease is characterized by the appearance of cerebral extracellular beta-amyloid deposits as senile plaques, intraneuronal neurofibrillary tangles, granulovascular degeneration and amyloid angiopathy. Senile plaques are extracellular lesions comprised of degenerating neuronal processes and abnormal deposits of beta-amyloid protein. Senile plaques range in size from 20 to 200 $\mu$m in diameter. Microglia and reactive fibrous astrocytes are enriched in the periphery of plaques, suggesting the recruitment of cells to the diseased site. These plaques are widely distributed in the cerebral cortex and are considered a critical process in the development of the disease.

Neurofibrillary tangles are intraneuronal structures consisting of paired helical filaments in which the major constituent is a hyperphosphorylated tau protein, an axonal protein involved in microtubule assembly, and neurite regeneration and remodeling. The MAP kinase, ERK, and ubiquitin are also tightly associated with these helical filaments and may be directly involved in the stimulation of the MAP kinase pathway. The neurofibrillary tangles represent abnormal organization of cytoskeletal elements in neurons of patients with Alzheimer's disease.

Other pathological findings associated with Alzheimer's include granulovascular degeneration, Hirano bodies, neuronal and synaptic loss, and beta-amyloid deposition in the wall of small cortical blood vessels. Although some of these disease processes are found in normal aging brains, their prevalence is significantly lower than in Alzheimer's disease and correlate with the severity of dementia.

Response to neuronal injury is characterized by the activation of glial cells and the expression of a number of genes that participate in the repair of damaged neurons. Some of those products include the beta-amyloid precursor protein and neurotrophins. The glial cell recruitment and responses may compromise neuronal viability by producing cytokines, reactive oxygen species and degradative enzymes. It is generally hypothesized that in local neuronal injury, an increased beta-amyloid production results in glial cell recruitment and activation which results in the production of pro-inflammatory processes and tissue destruction. Thus, it is most likely the accumulative effects of a defective repair process that results in neuronal cell death and the formation of senile plaques. A potential therapeutic target would include the inhibition of glial cell recruitment and activation. This would prevent exacerbation of the local inflammation and tissue destruction.

Thus, within one embodiment methods are provided for treating Alzheimer disease, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

3. Arthritis and Other Inflammatory Joint Diseases

A number of inflammatory joint diseases have been characterized in humans based on analysis of signs and symptoms, including for example, rheumatoid arthritis, systemic lupus erythomatosus, Reiter's syndrome, psoriatic arthritis, ankylosing spondylitis, to name just a few. Briefly, rheumatoid arthritis (RA) is the most prevalent type of inflammatory arthritis which occurs in approximately 1.5% of the population (2). Therefore, the present characterization of human inflammatory joint disease is based on findings concerning RA. RA is characterized by synovial hyperplasia, destruction of articular cartilage and bone, infiltration of lymphocytes and macrophages into synovial tissues and accumulation of autoantibody immune complexes in synovial fluid. However, the contribution of infiltrating lymphocyte cells to the disease process is not clear. Cytokines, such as interleukin 1 (IL-1) and granulocyte-macrophage colony-stimulation factor (GM-CSF), are present in increased levels in inflamed joints and play a major role in the production of metalloproteases including MMP1 (collagenase), MMP2 (gelatinase) and MMP3 released by synovial cells which are responsible for the destruction of cartilage. IL-1, together with tumor necrosis factor (TNF), also plays a major role in accumulation of lymphocytes in the joints. Joint inflammation is mediated by plasma and lipid derived mediators, prostaglandin E2 and leukotriene B4.

Gradual destruction of articular cartilage is the most debilitating sign of the disease. Cartilage is a connective tissue which consists of chondrocytes and extracellular matrix. Collagens and proteoglycans are the major components of the matrix. Chondrocytes are responsible for preservation of the integrity of the matrix which mostly depends on the collagenous network, the majority of which consists of collagen type II. Proteolytic enzymes that degrade the cartilage components are metalloproteases, which are produced by synovial cells, chondrocytes, neutrophils, and serine proteases derived from neutrophils. Several factors can induce the expression of metalloproteases, the most potent being secretion of IL-1 by macrophages (4). Tissue inhibitor of metalloproteases (TIMP) is a ubiquitous protein and natural metalloprotease inhibitor that is present in RA synovial fluid in elevated levels. Another feature of RA is an increase in bone resorption due to activation of osteoclasts. It has been shown that monocyte derived mediators such a IL-1 and TNF, are responsible for the increase in osteoclastic activity.

In terms of treatment of RA, there are two types of drugs currently used: anti-inflammatory drugs, including non-steroid or steroid, which alleviate the inflammatory process only, and disease modifying anti-rheumatoid drugs which interfere with the disease process. However, the mechanisms of action of these drugs is mostly unknown.

Osteoarthritis (OA) is a slowly progressive degeneration of the articular cartilage that manifests in the weight-bearing joints such as the knees and hips. Osteoarthritis, described as "wear and tear" arthritis, is characterized by narrowing of the joint owing to the loss of articular cartilage and thickening of the subchondral bone. At a later stage, inflammation of the synovium may occur which plays an important role in the pathologic process by accelerating the catabolism. All these events lead to nonfunctional and painful joint. The prevalence and severity of OA increase with age, affecting 80% of the population after 55 years of age with higher frequency in women (Altman, 1987). The primary cause of OA remains unclear, joint trauma, obesity, bone microfractures and aging constitute the risk factors for OA (Altman, 1987; Hough et al., 1989).

Although the mechanisms involved in the pathogenesis of cartilage destruction in OA are not well-characterized, much evidence suggests that cytokines may play an important role. During the progression of OA, cartilage fragments in the synovial fluid elicit an inflammatory response (Loyau and Pujol, 1990; Pelletier et al., 1991 and 1993). This response results in enhanced protease and cytokine release and the production of reactive oxygen species. The cytokines, including IL-1 and TNFa, can activate MMP synthesis from chondrocytes and synoviocytes setting off a cascade leading to OA (Howell, 1986; Pelletier et al., 1983b). Apart from cytokines, growth factors also have significant effects on cartilage remodeling.

Thus, within one embodiment methods are provided for treating arthritis (e.g., rheumatoid arthritis or osteoarthritis), comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

4. Osteoporosis

Osteoporosis is a term used to define increased bone porosity of the skeleton resulting from a reduction in bone mass. This disease affects the elderly, is particularly prevalent amongst females, and is sometimes a secondary responses to other clinical conditions. Thus, osteoporosis may be primary or secondary, and depending on numerous parameters, can be localized to a certain bone region or limb, or may involve the entire skeleton. Osteoporosis normally refers to the common primary forms such as senile and postmenopausal osteoporosis, whereas secondary forms include endocrine disorders (hyperparathyroidism, hyperthyroidism, hypothyroidism, acromegaly, Cushing's syndrome, prolactinaoma, Type I diabetes), neoplasia (multiple myeloma, sarcinomatosis, mast cell disease, thyroid/parathyroid ademo), gastrointestinal disorders (malnutrition, malabsorption, hepatic insufficiency), osteoarthritis and rheumatoid arthritis, drugs (anticoagulants, chemotherapeutics, corticosteroids, lithium), and a number of other non-specific disorders (immobilization or inactivity, pulmonary disease, anemia). Regardless of the etiology, the critical loss of bone makes the skeleton vulnerable to fractures and pain. Over 15 million individuals suffer from primary osteoporosis in the United States and their direct medical costs are over $1 billion annually.

The maximum bone mass is achieved during young adulthood. In normal adults the level of bone mass is determined by genetic factors, diet, physical activity and hormonal state. During adult years and aging this bone is turned over by a continuous, controlled resorption and formation cycle. In normal individuals, a small deficit in bone mass accrues with every bone resorption and formation cycle, which can average 0.7% of the total bone mass per year. Although there is no doubt that an imbalance in the resorption and formation cycle is responsible for osteoporosis, little is known on the origins of primary osteoporosis. Most of the focus has been on age-related changes, reduced, physical activity and hormonal changes (particularly associated with menopause). It is well established that osteoblasts from the elderly, which are cells responsible for bone formation, have reduced biosynthetic potential relative to osteoblasts from young adults. In addition, peptides (bone morphogenic proteins) deposited in the mineralized matrix which stimulate osteoprogenitor cells and osteoblastic activity are less effective with aging. Thus, decreased capacity of bone formation combined with normal or elevated osteoclastic activity are largely responsible for osteoporosis associated with aging and physical inactivity.

Postmenopausal osteoporosis is characterized by a hormonal dependent accelerated bone loss. Following menopause, the yearly loss of bone mass may reach 2% of the cortical bone and 9% of the cancellous bone. Estrogen is believed to play an important role in the reduction of bone loss. The estrogen effects are thought to be mediated by cytokines, which are found elevated in osteoporotic bone. It appears that decreased estrogen levels are capable of inducing cytokines such as IL-1, which are capable stimulating bone resorption. IL-1 is the most potent stimulator of osteoclast recruitment and activity and thought to play an important role in bone resorption in post-menopausal osteoporosis. A number of genes that are induced by IL-1 (cathepsin K, matrix metalloproteinases and COX-2) are elevated in osteoporotic bone and produced by osteoblasts and osteoclasts in vitro. Inhibition of osteoclast recruitment and activation are key steps in shifting the balance from resorption to bone formation, resulting in increased bone mass.

Thus, within one embodiment methods are provided for treating osteoporosis, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

5. Multiple Sclerosis

Multiple sclerosis is the most common of the demyelinating disorders, having a prevalence of approximately 1 in 1000 persons in most of the United States and Europe. Although the etiology of multiple sclerosis (MS) is unknown, genetic, environmental and immunological factors are believed responsible for a coordinated attack on myelin. The hallmark lesion in MS is a punched-out area in which the axon is surrounded by astrocytic processes. The accompanying inflammatory reaction is characterized by infiltration of lymphocytes, monocytes and macrophages into the parenchyma of the central nervous system (CNS), analogous to the chronic inflammation in other diseases such as arthritis and psoriasis. Thus, in MS, there is increased inflammatory cell activation and infiltration, increased fibrous astrocyte activation, migration and proliferation, increased production of cytokines and matrix metalloproteinases, increased demyelination, axonal degeneration and plaque formation.

Thus, within one embodiment methods are provided for treating multiple sclerosis, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

6. Inflammatory Dermatosis

Inflammatory dermatological diseases, such as psoriasis, are very common, affecting as many as 1 to 2% of the people in the United States. It is often associated with arthritis, myopathy, spondylitic heart disease and acquired immune deficiency syndrome (AIDS). Psoriasis is a chronic inflammatory disease characterized by keratinocyte hyperproliferation and a distinct inflammatory pattern that is dependent on the type of psoriasis. The underlying pathogenesis involves three predominant and interdependent biologic processes: inflammation, epidermal hyperproliferation, and altered differentiation with parakeratosis.

The homeostasis of the epidermis depends on the balance of growth regulatory signals, which appear to be altered in psoriasis. The epidermis serves a number of important barrier functions against protein and water loss, entry of microorganisms, physiochemical trauma including ultra violet (UV). The squamous epithelium undergoes terminal differentiation resulting in an insoluble cornified envelope providing an important barrier. Keratinocyte proliferation takes place in the basal layer and migrate through the epidermis where differentiation specific proteins such as involucrin and keratins are expressed. Normal epidermis represents a normal balance between kaeratinocyte production in the basal layer and corneocyte shedding at the skin surface. Upon wounding or psoriasis, there are rapid increases in the proliferation of keratinocytes.

Thus, within one embodiment methods are provided for treating inflammatory dermatosis (e.g., psoriasis), comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

7. Inflammatory Bowel Diseases

There is overwhelming evidence that genetic and environmental factors play a role in the development of inflammatory bowel diseases (IDB), ulcerative colitis and Crohn's disease. These diseases are chronic relapsing inflammatory diseases and share many common features of unknown etiology. Crohn's disease is a granulomatous disease that may affect any portion of the gastrointestinal tract from mouth to anus, but most often involves the small intestine and colon. Ulcerative colitis is a non-granulomatosis disease limited to the colon. These diseases affect approximately 3 to 6 people per 100,000, but the incidence can vary markedly between populations.

The clinical manifestations, biochemistry and pathology of IDB demonstrate that infiltration and activation of inflammatory cells, increased local mucosal responses, overproduction of cytokines and destructive enzymes are associated with the disease process ultimately leading to tissue injury. It is not known whether the immune system infiltrates the intestine in response to luminal or mucosal antigens or that local insult or disease results in the expression of adhesion molecules and chemoattractant cytokines that induce the infiltration of inflammatory cells resulting in the immune mediated tissue injury. Regardless of the etiology, there are similarities between the disease processes in IDB and other chronic inflammatory diseases.

Similar to other inflammatory diseases, there are very high levels of pro-inflammatory cytokines (IL-1, IL-6, IL-8 and TNF), as well as anti-inflammatory cytokines (IL-4, IL-10 and IL-11) in IBD biopsies. In IBD, there is a disturbed balance between the levels of pro-inflammatory cytokines and anti-inflammatory cytokines that favors the former. The expression of IL-1, IL-6, IL-8 is increased in inflammatory lesions of patients with IDB (p382-4). These cytokines are produced by infiltrating inflammatory cells and local epithelial cells and fibroblasts. It is thought that these imbalances result in increased expression of genes such as adhesion molecules, matrix metalloproteinases and inflammatory mediators that are involved in cell migration and proliferation, and tissue destruction. Current therapeutic strategies aim at inhibiting IL-1 and TNF activity.

Thus, within one embodiment methods are provided for treating inflammatory bowel disease, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

8. Other Inflammatory Diseases

As described above, there are several classes of molecules and disease processes that are common to all chronic inflammatory diseases. These include increased expression of adhesion molecules, cytokines and matrix metalloproteinases, increased cell proliferation and migration, increased inflammatory cell activation and infiltration, increased angiogenesis, and increased tissue destruction and dysfunctional matrix remodeling. These disease processes are tightly regulated in normal differentiated cells and require the activation of AP-1 transcription factors and AP-1 dependent genes. Since the restriction of AP-1 activation in normal cells can be reversed in a controlled fashion by transition molecules (such as RHAMM), the inhibition of expression, activity and signaling of transition molecules will be useful therapeutically for not only the diseases described above, but also for other inflammatory diseases such as diabetes mellitus; restenosis; atherosclerosis; systemic lupus erythematosus; emphysema; AIDS; chronic endometriosis; pulmonary, myocardial and hepatic fibrosis; inflammatory polyradiculoneuropathy; chronic cystitis; acute mastitis; cholecystitis; gastritis; nephritis; hepatitis; bronchial asthma; vasculitis; chronic bronchitis; kidney fibrosis, pericarditis and myocarditis; pancreatitis; peritonitis; prostatitis; septic shock; periodentitis, thyroiditis; retinopathy.

Thus, within one embodiment methods are provided for treating the above described treating diseases (e.g., lupus, diabetes mellitus, or, kidney fibrosis), comprising administering to a patient a compound selected from the group consisting of (a) a polypeptide comprising the amino acid sequence BX7B (SEQ ID NO:28) which binds HA; phage display selected peptides that bind HA such as polypeptides comprising –15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

9. Wound Healing and Responses to Injury

Wound healing responses to injury involve a complex series of cellular and inflammatory processes resulting in the deposition of connective tissues and its remodeling into abnormal tissue or scarring. The underlying mechanisms of wounding or injury responses involve the induction of an acute inflammation, production of cytokines and growth factors, regeneration of parenchymal cells, migration, proliferation and differential of parenchymal and connective tissue cells, synthesis of extracellular matrix proteins, angiogenesis and fibrosis, and remodeling of connective tissues. In addition, these healing processes are common in a variety of clinical areas such as scarring from surgical incisions, wounds or various derma inflammatory diseases, restenosis following angioplasty, vascular grafts, stroke and surgical adhesions. Interference of processes that induce abnormal tissue deposition and remodeling will enhance an orderly wound or injury repair resulting in the development of normal functional tissue. Since transition molecules, such as RHAMM, regulate a number of the diseased processes in wound healing and the transformation of normal to diseased cells, it is likely that agents which inhibit the function of transition molecules would be useful therapeutically for the treatment of restenosis following angioplasty, vascular grafting, ballooning or any other type of injury to the vascular system, stroke, surgical incisions, burns, wounds, inflammatory skin diseases, and surgical adhesions.

The simplest form of wound repair or healing is observed following a clean surgical incision. The incision causes a limited amount of tissue disruption, which results in responses by epithelial cells and connective tissue cells, as well as infiltration of inflammatory cells. Immediately following the incision, the incision space is bathed with blood, containing fibrin and blood cells that clots and leads to the formation of a scab that covers the wound. The initial process involves the response of local basal cells in the production of cytokines and other pro-inflammatory mediators, and infiltration of neutrophils. The basal cells become mitotic and produce matrix, resulting in the thickening of the epidermis. This is followed by the migration of the epithelial cells along the cut margins and depositing basement membrane underneath the scab. The neutrophils are replace by macrophages and granulation tissue is progressively laid down containing collagen fibrils vertically oriented rather than oriented in fashion that would enhance bridging the incision space. Epithelial cell proliferation and migration continues, as well as tissue thickening. Neovascularization reaches maximal levels and the surface cells differentiate and produce normal epidermal architecture. The last stages of incision healing involve the disappearance of all inflammatory cells, edema and increased vascularization, as well as accumulation of normal collagen fibrils and strengthening of tissue.

In cases where there are more extensive surface wounds such as burns, abscess formation, inflammatory ulceritis, the reparative process is also more extensive. The larger tissue defects have greater cell loss, more fibrin and more inflammation, increased amounts of granulation tissue and wound contraction involving myofibroblasts. Regardless of the wound, the mechanisms of responsible for the processes of healing described above are similar. Wound healing is ultimately regulated by growth factors and cytokines that balance matrix synthesis and degradation locally. Collagen synthesis is a key component of wound healing and provides the tensile strength required closing of the incision. The type of collagen produced is dependent on the tissue repaired, and changes in the type of collagen may lead to dysfunction tissue. Collagen synthesis is stimulated early in tissue repair by factors such as platelet derived growth factor (PDGF), fibroblast growth factor (FGF), and transforming growth factor (TGF). On the other hand, degradation of collagen fibrils and other matrix molecules are also important. The degradative enzymes involved during wound healing include matrix metalloproteinases, neutrophil elastase, cathepsin G, kinins, plasmin and other enzymes. Inflammatory and local cells produce these enzymes. Degradation may aid in the remodeling of the connective tissue repair. If the inflammatory destructive processes are suppressed, then it is more likely to achieve a more rapid formation of the connective tissues and decrease the accumulation of scar tissue.

One type of wound healing occurs in surgical adhesions. Briefly, surgical adhesion formation is characterized by abnormal adherence and scar formation between two adjacent tissues that occur most often following surgery. Adhesions are a major cause of surgical therapy and can result in bowel or urethral obstruction. Surgical adhesions are thought to be an inflammatory response to surgical trauma. Local tissues and inflammatory cells produce and secrete pro-inflammatory cytokines which increase vascular permeability, inflammatory cell infiltration, cellular migration and proliferation, and the laying down of matrix between just-neighboring tissues. The accumulation of fibroblasts results in the accumulation of matrix and eventual adhesion of the two tissues. In theory, any agent that inhibits the inflammatory response and tissue remodeling would prevent the formation of surgical adhesions, particularly if these agents can be administered locally.

Thus, within one embodiment methods are provided for treating the aforementioned diseases associated with wounds/wound healing, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

10. Restenosis/Stenosis following Therapeutic Interventions in Vascular Disease: Angioplasty, Stent Insertion and Vascular Replacement/Grafts Vascular diseases such as atherosclerosis are a leading cause of death and disability in the developed world. Several therapeutic interventions have been developed to treat vascular diseases such as atherectomy, balloon angioplasty, insertion of stents, and insertion of arterial and venous grafts. For example, over 300,000 procedures of percutaneous transluminol coronary angioplasty are performed in the United States per year. Although these interventions are less costly and less invasive to the patient, there are a number of morphological changes and disease states produced in response to injury that are introduced by these new modes of therapy, namely restenosis.

Restenosis is characterized by thickening of the blood vessel wall in response to injury that progresses until full occlusion of the vessel. Despite the significant advance made in these therapies, chronic restenosis of the dilated lesions occur in 30 to 50% of the cases, remaining a serious and frequent problem. Furthermore, eventually stenosis occurs in virtually all grafted vessels. Restenosis has been suggested to represent an exaggerated healing response to local injury, in which smooth muscle cells in the media migrate to and proliferate in the intima. Local production of cytokines and growth factors by local cells and inflammatory cells results in abnormal matrix deposition and remodeling. There are number of underlying mechanisms which can play a role in the induction of this disease. An injury to the endothelial cell layer will expose blood vessel layers to serum components and platelets, initiating a wound healing process. Factors released locally lead to increased cell proliferation and increased expression of matrix metalloproteinases required for cell proliferation and migration. These cells accumulate in the intima and form lesions that eventually block the vessel. Utilizing the therapeutic compositions provided herein, blocking the activation of smooth muscle cells and inhibition of their migration and proliferation in response to injury can be utilized to therapeutically treat stenosis and restenosis.

Thus, within one embodiment methods are provided for inflammatory/proliferative diseases associated with surgical procedures or intervention (e.g., restonosis, stenosis, medical implants and the like), comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (SEQ ID NO:70), P-16 (SEQ ID NO:26); P-32 (SEQ ID NO:71); and GAHWQFNALTVR (SEQ ID NO:72); (b) an antibody which binds one of domains D1, D2, D3, D4, or D5 of RHAMM; (c) a peptide of less than 95 kDa or 73 kDa, comprising all or a portion of domains D1, D2, D3, D4, or D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally. In addition, within certain embodiments the compounds described herein may be administered by balloon catheter, or, delivered from a stent which is adapted to release the desired compound.

11. Atherosclerosis and Related Diseases: Myocardial Infarction and Stroke

Cardiovascular disease is a serious problem and accounts for 44% of the mortality in the USA. Atherosclerotic cardiovascular disease is generalized process that involves the brain, heart and peripheral arteries. Atherosclerosis is characterized by intimal thickening caused by the accumulation of cells, infiltration of inflammatory cells, lipids, and connective tissues that can lead to cardiac and cerebral infarction (such as heat attack and stroke). Although the role of injurious stimuli is not known, the responses of the endothelial cells and the adaptive changes within the intima are critical in vascular remodeling leading to atherosclerotic plaques. Endothelia cells, monocytes and smooth muscle cells express biologically active molecules such as adhesion molecules, cytokines, coagulation and fibrinolytic factors, metalloproteinases and vasoactive substances that contribute to atherogenesis and thrombosis. It is thought that atherosclerotic lesions develop by (1) invasion of artery wall by inflammatory cells, particularly monocytes; (2) smooth muscle cell migration, proliferation, and synthesis of matrix molecules; (3) intracellular lipoprotein uptake and lipid accumulation. Briefly, inflammatory cytokines induce the production of adhesion molecules resulting in inflammatory cell infiltration and responses. Activated smooth muscle cells migrate in response to local injury and produce large amounts of matrix and express lipoprotein scavenger receptors and can become involved in a generalized immune reaction. Occlusion of the artery leads to a series of clinical complications such as myocardial infarction and stroke. Prevention of inflammatory cell infiltration, production of matrix metalloproteinases, cell proliferation and migration will reduce smooth muscle cell and matrix accumulation, and inhibit vessel occlusion.

Thus, within one embodiment methods are provided for treating the above-noted atherosclerotic diseases, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

12. Tissue Transplantation

The increasing use of transplantation for bone marrow, renal, pulmonary, cardiovascular and hepatic disorders has generated a series of clinical complications. In addition, with recent advances in tissue engineering, there is considerable potential that skin, cartilage, bone and many other tissues-will be transplanted in the future. In many cases transplantation is the only form of treatment. For example, lung transplant is the only effective treatment of terminal lung diseases such as idiopathic pulmonary fibrosis, primary pulmonary hypertension, emphysema, and cystic fibrosis. The same is true for specific renal, hepatic and heart diseases. There are three major complications in the transplantation of organs: (1) host versus graft disease; (2) non-immunological damage; and (3) infection. Acute and chronic rejection is a significant problem where the host immune system invades the donor organ. This inflammatory response and mononuclear cell infiltrates are treated with immunosuppressive drugs with some success. However, these drugs can be very toxic and result in other clinical complications. The non-immunological damage from preservation injury results in inflammation and tissue damage. The role of infection can be treated with antibiotics. The disease processes involved in organ rejection are similar to other inflammatory diseases.

Disease intervention with devices has increased significantly over the past decade. These include the use of devices for hip and knee replacements, cardiovascular stents, esophageal stents, vascular wraps, bone grafts, venous and arterial grafts, many others. A common problem with the use of these devices is an inflammatory reaction to particles produced from the device or loosening of the device or injury caused by the local application of the device. It would seem likely that systemic or local application of the inflammatory response and local tissue reaction to the devices would inhibit this problem.

Thus, within one embodiment methods are provided for treating patients undergoing tissue or cell transplation, comprising administering to a patient a compound selected from the group consisting of (a) a polypeptide comprising the amino acid sequence BX7B (SEQ ID NO:28) which binds HA; phage display selected peptides that bind HA such such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

13. Cancer and Metastases

Cancer is a generic term representing a collection of diseases arising from mutations of key molecules that regulate cell proliferation, invasion, and metastasis. A representative cancer for which the key mutations are known is exemplified by colorectal cancer. This cancer originates as a benign growth as a result of a mutation in a gene termed APC. Mutation of three additional molecules are required for this benign growth to progress to a rapidly proliferating and invasive tumor. A plethora of mutations arises within the tumor as it progresses and these enhance the ability of the mutant tumor cells to attract normal endothelial cells to migrate into the growing tumor and form new blood vessels, a process known as angiogenesis. As angiogenesis proceeds and as mutations affecting the ability of tumors to respond to growth factors accumulate, subsets of tumor cells develop the capacity to invade blood vessels as well as lymphatics and to metastasize.

The ability of tumor cells to metastasize involves deregulation via overproduction or mutation of genes that allow cells to invade out of the tissue of origin, survive in a contact-independent manner, escape immune recognition, lodge at a distant site, then invade to a suitable place within the new tissue and grow there. The molecules that are commonly involved in tumor initiation, progression and metastasis include adhesion molecules, growth factor receptors, factors regulating the cytoskeleton, master switches regulating cell cycle, proliferation repressor genes, proteases and transcription factors.

Although our understanding of master switches, proliferation repressors, growth factors and proteases is quite well developed and pre-clinical and clinical approaches to targeting these molecules, particularly proteases have been developed, very little is known about the molecular characteristics of the invasive phenotype. The invasive tumor phenotype is predicted to be similar to the transitional phenotype noted for the above diseases and to be characterized by a propensity to form invadapodia or podosomes to release proteases and to express transition molecules that permit and prepare a cell to invade, move, and ultimately respond to growth factors and cytokines in a focal adhesion-dependent manner. It is likely that molecules required for generating this phenotype are also expressed transiently in tumor cells since they may be only temporarily required and permanent expression would not necessarily be advantageous. Thus, it is predicted that transitional molecules defining an invasive phenotype would appear in a subpopulation of tumor cells in a given tumor. A transient nature is likely one reason that markers of invasive phenotype have been so elusive to define. However, the ability of most tumors to kill is directly related to their capacity to invade and ultimately to metastasize. Therefore, identification of transient molecules is key for diagnosis, prognosis, adjuvant treatment or therapeutic treatment of a variety of cancers including: head and neck tumors (lip, oral cavity, auropharynx, nasopharynx, hypopharynx, larynx, glottis, supraglottis, subglottis, maxillary sinus, major salivary gland, lung, esophageal, gastric, colorectal cancer, anal, pancreatic liver, gall bladder, extrahepatic bile duct cancer, breast cancer, gynecologic cancers (cervix, endometrium, ovary, cancer of the uterine body, vaginal, vulvar, gestational trophoboblastic), testicular, urinary tract (renal, urinary bladder, penile, urethral, prostatic) neurologic, endocrine skin (basal cell and squamous cell melanoma) sarcomas, blood (leukemia, lymphoma) childhood neoplasm's (leukemia, lymphoma, neuroblastoma, Wilms' tumor rhabdomyosarcoma, Ewing's sarcoma, retinoblastoma) mediastinum, thymic germ cell, retroperitoneal, cardiovascular tumors, mastocytosis, carcinosarcomas, adenoid cystic carcinoma, dental tumors olfactory, neuroblastoma, paraganglioma.

With regard to transitional molecules involved in proliferative cancers, the present invention shows that RHAMM is highly overexpressed in subsets of cells in primary breast cancer tissue and this overexpression is prognostic of lymph node metastasis and poor outcome. Furthermore, RHAMM is shown to regulate ERK activation, a key player in AP-1 activation. ERK is also shown to regulate cell locomotion, a key behavior required for cell invasion into lymph nodes and is required for the invasion of tumor cells both in vitro and in transgenic models of breast cancer. Furthermore, CD44 is required for efficient signaling through her2/neu, an oncogene strongly implicated in regulating lymph node metastasis of breast cancer cells. Finally, HA promotes the expression of podosomes in invasive cancer cells and podosome formation is one important characteristic of the transitional phenotype. In addition, and consistent with this observation, HA promotes the invasion of these cells into collagen gels in vitro.

Thus, within one embodiment methods are provided for treating cancer and other metaseses, comprising administering to a patient a compound selected from the group consisting of (a) a polypeptide comprising the amino acid sequence BX7B (SEQ ID NO:28) which binds HA; phage display selected peptides that bind HA such as polypeptides comprising −15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

14. Chronic and Acute Respiratory Distress Syndrome:

Due to injury of the lung such as occurs in premature birth and consequent positive pressure breathing measures as well as in adults following accidents or chemotherapy, the lung is injured and macrophages and neutrophils accumulate within the lung eventually destroying type II aveolar cells that produce surfactant proteins required for maintenance of positive pressure following lung expansion. As a result, lungs are poorly functional and patients become cyanotic and breathe rapidly. This syndrome ends in death. Clinical indications characterized by lung inflammation include emphysema, asthma, cystic fibrosis, new-born lung disease involving chronic respiratory distress syndrome, and the acute respiratory distress syndrome that affects accident victims. Local inflammatory responses that recruit macrophages into the lung result in destruction of alveolar type II cells, which make the surfactant responsible for normal lung inflation. The infiltration of macrophages and abnormal local tissue responses result in further tissue destruction and disease. This pathological sequence results in improper lung expansion. As described in more detail herein, reagents that inhibit transitional proteins prevent massive accumulation of white cells that result in this syndrome and prevent the development of a surfactant deficit in the lung.

Thus, within one embodiment methods are provided for treating chronic and acute distress syndromes, comprising administering to a patient a compound selected from the group consisting of (a) a polypeptide comprising the amino acid sequence BX7B (SEQ ID NO:28) which binds HA; phage display selected peptides that bind HA such as polypeptides comprising −15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated.

The polypeptides, antibodies, or, vectors may be delivered to the patient by a variety of routes, including for example, systemically, intravenously, intramuscularly, and orally.

15. Diabetes Mellitus

Diabetes mellitus is a group of diseases characterized by high glucose resulting from defects in insulin secretion, insulin action, or both. Diabetes mellitus can be associated with serious complications such as heart disease, stroke, kidney disease, nervous system disease, blindness and complications in pregnancy.

Type I diabetes mellitus, also referred to as insulin dependent diabetes mellitus (IDDM), develops most often in children and young adults over a short period of time. About 30–40% of diabetic children eventually develop nephropathy. Type II diabetes mellitus usually develops in adults. Risk factors include obesity and family history of diabetes. The symptoms usually develop gradually and are not as noticeable as in Type I diabetes.

Type I diabetes mellitus is an autoimmune disorder, the onset of which results from a well characterized insulitis.

During this condition the inflammatory cells are apparently specifically directed against the insulin producing beta cells of the pancreatic islets. The destruction of pancreatic beta cells by invading leukocytes result in deterioration of the insulin-dependent homeostasis.

The inflammatory cascade is a complex process that involves triggering of the immunological response, release of chemokines, cytokines and a toxic agents by the activated cells, up-regulation of cell surface adhesion molecules and transendothelial cell migration. Although the triggering mechanism of IDDM remains elusive, it is clear that the entire process depends on the migration of inflammatory cells into the pancreatic islets and their interaction with matrix.

Within one embodiment methods are provided for treating or preventing diabetes mellitus, comprising administering to a patient a compound selected from the group consisting of (a) a polypeptide comprising the amino acid sequence BX7B (SEQ ID NO:28) which binds HA; phage display selected peptides that bind HA such as polypeptides comprising P-15 (Sequence ID No. 70), P-16 (Sequence ID No. 26); P-32 (Sequence ID no. 71); and GAHWQFNALTVR (Sequence ID No. 72); (b) an antibody which binds one of domains D1, D2, D3, D4, or D5 of RHAMM; (c) a peptide of less than 95 kD or 73 kd, comprising all or a portion of domains D1, D2, D3, D4, or, D5 of RHAMM; and (d) a gene delivery vector which expresses antisense RHAMM, or, delivers and expresses any one of (a), (b), or (c), such that the disease is treated. Within certain embodiments of the invention, the compounds described herein may be administered before, during, or subsequent to islet-cell transplantation. Within other related embodiments, the above-described compounds may be utilized to treat related diseases, including for example, obesity.

The polypeptides, antibodies, or, vectors may be delivered to the patient by a variety of routes, including for example, systemically, intravenously, intramuscularly, and orally.

Pharmaceutical Compositions

As noted above, the present invention also provides a variety of pharmaceutical compositions, comprising one of the above-described molecules with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as ethylenediamine tetraacetic acid (EDTA), gluthathione and other stabilizers and excipients. Neutral buffered saline or saline mixed with nonspecific serum albumin are exemplary appropriate diluents.

In addition, the pharmaceutical compositions of the present invention may be prepared for administration by a variety of different routes (e.g., systemically, orally, rectally, intravenously, intramuscularly, ocularly, or, topically). Further within other embodiments the compounds or compositions provided herein may be admixed with other carriers (e.g., polymers), and implanted on or contained within devices which are designed to release such compounds. Within further embodiments, the compounds may be delivered under radioscopic or other visual guidance to a desired site (e.g., outside the lumen of a desired vessel, or outside of an organ, or, tissue to be treated).

As should be readily evident, the compounds or compositions of the present invention should be administered sufficient to have the desired therapeutic outcome. As an example, it is generally desirable to administer between a total of 1 ng of the desired compound, and up to 80 mg/kg. Within certain embodiments, the dosage will be adjusted for the therapeutic regimen desired (e.g., from 1 ug/kg to 1 mg/kg). Within other embodiments the dosage for local administration may range from 1 to 100 ug/ml (2.5 ng/kg to 80 mg/kg), and for systemic administration from 1 ng/kg to 10 mg/kg. Further, the dosage can be adjusted based upon the desired route of treatment, e.g., a smaller dose may be given if applied locally or topically, whereas a larger dose may be given if the compound is administered systemically. Further, the dosage may vary with the desired regimen (e.g., daily, weekly, or monthly).

In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

The following examples are offered by way of illustration, and not by way of limitation.

EXAMPLES

Example 1

Figure 2:
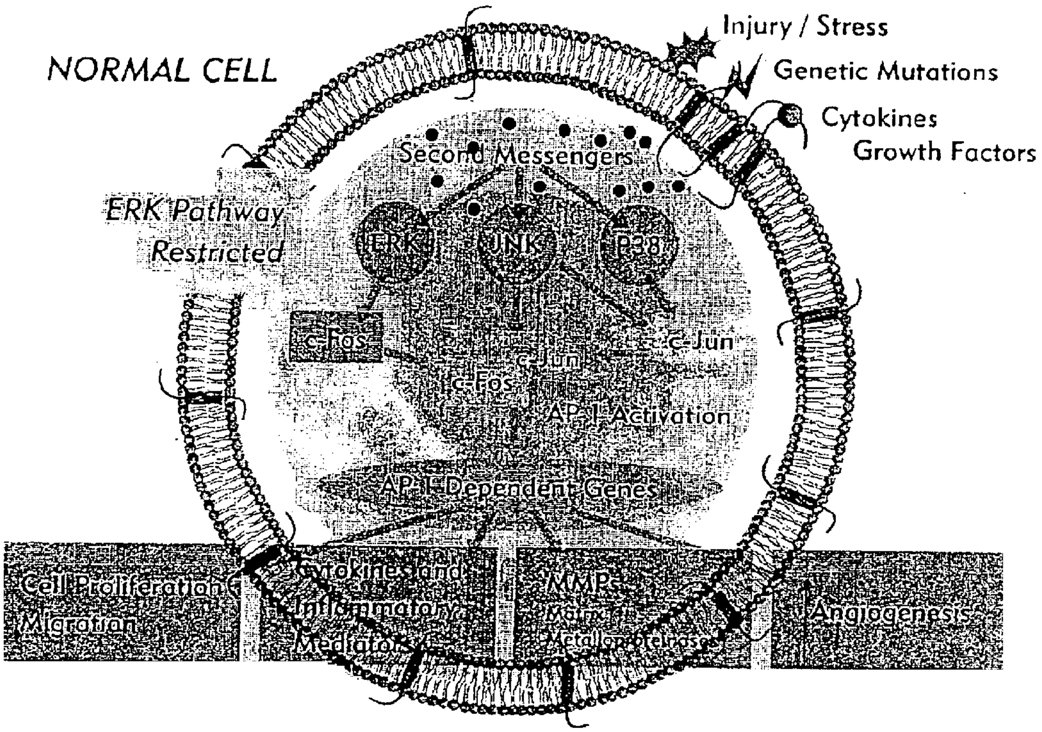
FIG. 2 is a schematic illustration of cell activation in response to a variety of factors, and this impact on disease pathways.
Figure 3:
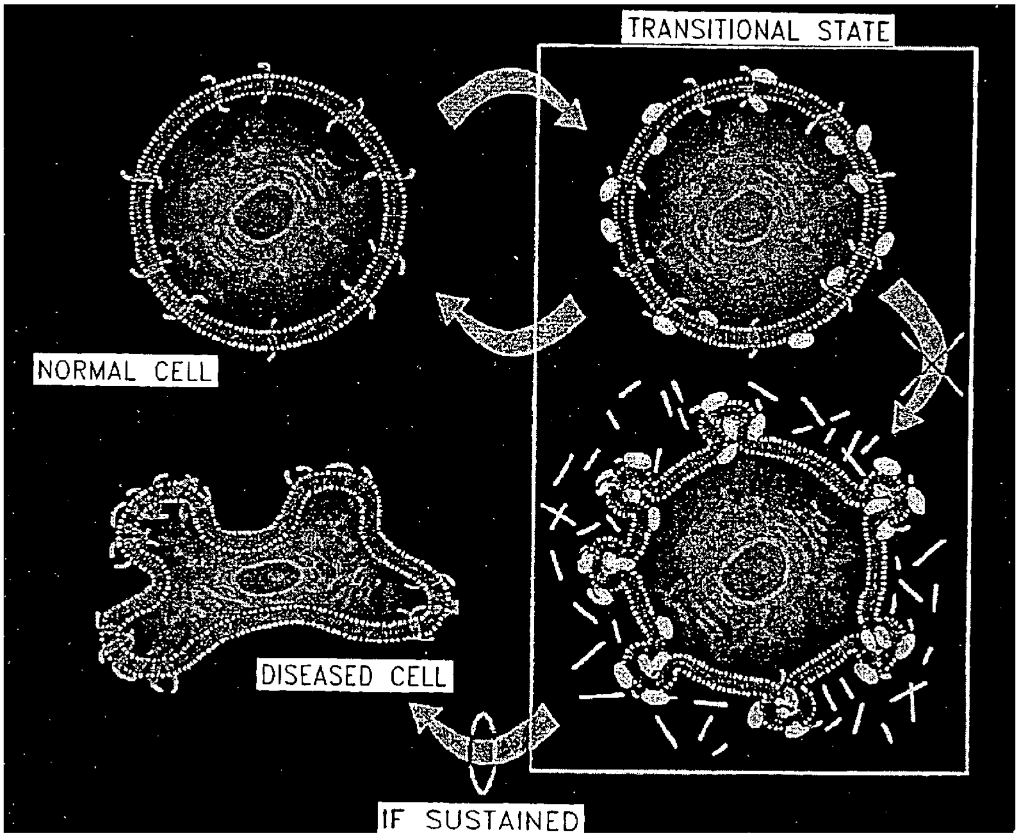
FIG. 3 depicts cells transition from a normal cell to a diseased cell.

Requirement for Focal Adhesions for Maximal Activation of Erk Kinase in Response to Growth Factors In disease or injury, mediators such as cytokines, growth factors and genetic mutations activate a myriad of responses leading in increased expression of AP-1 dependent genes (FIG. 1). These genes are required for cell proliferation, migration, inflammation, tissue destruction and abnormal tissue remodeling. The activation of the AP-1 pathway occurs through the activation of the mitogen-activated protein (MAP) kinase. The present invention discloses that in normal cells the activation of the AP-1 pathway by cytokines and other mediators is restricted and thus genes involved in disease cannot be induced significantly. Further, this restriction is a result of the lack of ERK-1 activation in normal cells, (FIG. 2). Normal cells must undergo a series of transitional stages to form a diseased state cell containing focal adhesions and is then responsive to inflammatory mediators. Transition stage cells provided by the present invention constitutively form podosomes and are unable to establish focal adhesions. Sustained formation of podosomes leads to the formation of focal adhesions and results in a diseased state (FIG. 3). The present invention further discloses a requirement for focal adhesions for maximal activation of erk kinase in response to growth factors and cytokines. Cellular response-to-injury processes including growth factor mediated responses which lead to cellular proliferation, migration, production of destructive enzymes and abnormal tissue remodeling are characterized by a maximal activation of the erk kinase signaling pathway. To demonstrate that this response requires the presence of focal adhesions, the response to IL-1 induction of erk kinase signaling was measured in cells grown under conditions permitting or preventing the formation of focal adhesions.

Cells were either plated without serum on culture dishes precoated at 4° C. overnight with 25 $\mu$g/ml fibronectin which permits formation of focal adhesions or with 100 $\mu$g/ml poly-l-Lysine which prevents formation of focal adhesions. Formation of focal contacts was detected by positive imnmunofluorescence of the marker protein, vinculin. Activation of erk kinase signaling in comparison to other MAP kinase signaling pathways regulated by growth factors was estimated by detection of proteins phsophoryalted by components of the differing signaling cascades. Phosphorylation of myelin basic protein (MBP) is an indicator of erk kinase signaling, phsophoryaltion of glutathione-S-transferase (GST)-c-jun is an indicator of jnk signaling, and phsophoryaltion of GST-ATF2 is an indicator of p38 kinase signaling cascade. Results of this analysis is shown in FIG. 4.

Figure 4A:
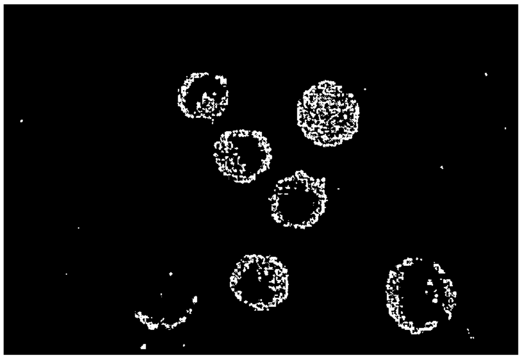
FIG. 4 shows immunofluorescence micrographs and phosphoprotein assays which indicate a requirement for cell adhesion for activation of the erk1 kinase signaling.
Figure 4B:
Figure 4C:
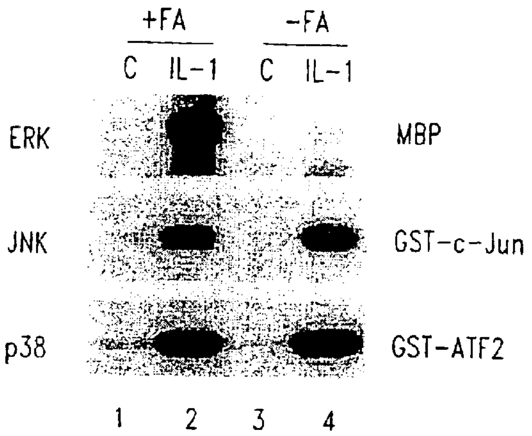

More specifically, FIG. 4B shows that cells plated onto fibronectin (FN) are able to form focal contacts as detected by positive immunofluorescence for the marker protein vinculin. Cells that are maintained on a non-physiological yet adhesive substratum poly-L-lysine (PL), attach but do not form focal contacts (4A). FIG. 4C shows that normal quiescent phase cells plated onto fibronectin substrata which make focal contacts are able to activate the erk kinase cascade as indicated by the phosphorylation of myelin basic protein (MBP) in response to the cytokine IL-1 (lane 2). These same cells plated onto poly-L-lysine do not make focal contacts and are unable to activate erk as detected by MBP phosphorylation (lane1). However, cells plated onto fibronectin ("FN") or in suspension are equally able to activate the other map kinases, jnk or p38 (lanes 1 and 2). FIG. 4C also shows, that normal cells in the absence of focal adhesions, when plated onto fibronectin or grown in suspension (SP), are restricted in their ability to activate erk in response to IL-1 in comparison to disease cells containing focal adhesions, but able to activate the other MAP kinases, jnk and p38 (lanes 3 and 4). These results indicate that responsiveness of the erk kinase cascade is restricted in transition stage cells but that the erk kinase cascade becomes maximally active when focal contacts are made as occurs upon entry of cells into a post-transitional stage that is fully responsive to growth factor stimulation, as indicated in FIG. 3.

Figure 4D:
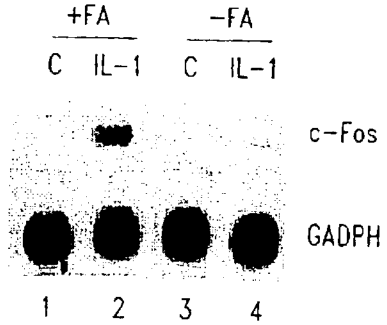

Northern analysis was used to further demonstrate IL-1 induction of the AP-1 transcriptional activator, c-fos, by cells able to form focal contacts. IL-1β was added to cells grown either on FN or PL, then RNA was isolated and analyzed by Northern blotting for levels of c-fos mRNA. FIG. 4D shows a Northern analyses of cells plated on fibronectin or PL and incubated with 20 ng/ml of IL-1β. 20 ng/ml IL-1β was able to induce c-fos expression in cells grown on FN (cells with focal adhesions) but not in cells grown on PL (in the absence of focal adhesions). Blots were first probed for c-fos mRNA expression, stripped, and then reprobed with control radiolabeled GAPDH cDNA to assess equality of RNA loading.

Figure 4E:
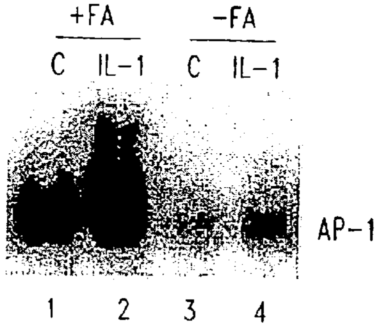

FIG. 4E shows that the level of AP-1 activated in response to IL-1 induction requires the ability to make focal adhesions (cells grown on PL which are unable to form focal adhesions have reduced levels of AP-1 induction relative to cells grown on fibronectin).

More specifically, to further demonstrate a requirement of focal adhesions for full IL-1 induction, the amount of the transcriptional factor AP-1 binding induced in response to IL-1 stimulation was analyzed. The level of DNA binding to an AP-1 oligonucleotide was measured in nuclear extracts from cells either grown on fibronectin or poly-l-Lysine coated dishes in medium without serum. Briefly, tissue culture dishes were precoated with 25 μg/ml fibronectin or 100 μg/ml poly-l-Lysine as before and washed twice with PBS before use. Cells were then incubated under starving condition for 6 h, media were removed and fresh serum-free medium containing IL-1 (20 ng/ml) was added to the cells for 4 h.

For the preparation of nuclear extracts, cells were washed twice with PBS (phosphate-buffered saline) and lysed with 1 ml buffer (10 mM Tris-Cl, pH 7.5, 10 mM NaCl, 3 mM $MgCl_2$, 0.5% Nonidet P-40, 0.5 mM phenylmethylsulfonyl fluoride (PMSF). Cells were scraped into an eppendorf tube and put on ice for 10 min. The nuclei were collected after centrifugation at 5000 rpm for 10 min. Nuclear proteins were prepared by resuspending the nuclei in buffer 2 (20 mM Hepes, pH7.9, 5 mM $MgCl_2$, 0.2 mM EDTA, 1 mM dithiothreitol (DTT), 300 mM NaCl, 20% glycerol, 0.5 mM PMSF), after centrifugation at 14,000 rpm for 10 min., supernatant was harvested. Double-stranded AP-1 oligonucleotide (Santa Cruz, Biotech, Inc.) was end-labeled with [γ-32P] ATP (DuPont NEN) using T4 polynucleotide kinase (Pharmacia). Labeled probe was separated from free nucleotide through a Sephadex G-50 mini-spin column (Pharmacia). DNA-protein binding was performed by mixing 10 μg of nuclear extract with $^{32}$P-labeled double-stranded AP-1 consensus oligonucleotide in a total volume of 20 μl containing mM Hepes, pH 7.9, 1 mM $MgCl_2$, 4% Ficoll, 0.5 mM DTT, 50 mM KCl, 1 mM EDTA, 2 μg poly(dIdC) and 1 mg/ml BSA for 45 min on ice. The DNA protein complex was separated on a 4% native polyacrylamide gel using 0.5× tris-borate-EDTA buffer at 150 V. Gels were then dried and autoradiographed.

Example 2

Figure 5:
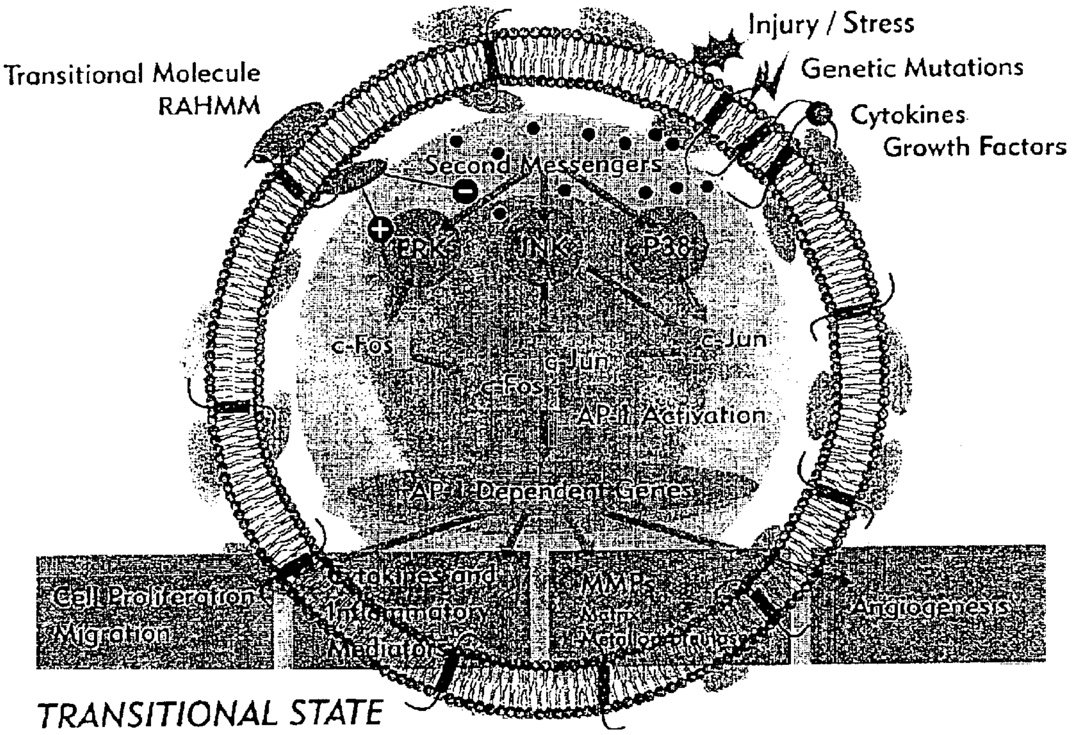
FIG. 5 schematically illustrates the involvement of RHAMM as a transitional molecule.

RHAMM Overexpression is Associated with Increased Erk Kinase Activation and AP-1 Activation As noted above, expression of transitional molecules such as RHAMM results in the initiation of cell transformation from a normal state to a diseased state. RHAMM is believed to play a role in the initial activation of ERK pathway, thus removing the ERK restriction found in normal cells. This activation leads to the expression of c-fos and c-jun resulting in the AP-1 activation and induction of AP-1 dependent genes involved in many of the disease processes associated with inflammatory, degenerative and proliferative diseases (FIG. 5).

Cells that overexpress a hyaladherin such as RHAMM in response to stress or during proliferation exhibit elevated activation of erk kinase signaling activity as shown in FIG. 6. Erk kinase activation is stimulated directly by overexpression of a hyaladherin such as RHAMM. Briefly, the cell line LP21 was constructed by transfecting normal quiescent parental 10T1/2 cells with a vector expressing a RHAMMv4 polypeptide. Cells that overexpress RHAMM show increased erk activation as indicated by phosphoryation of the MAP kinase activated myelin basic protein (MBP), p44 EkK1 and p42 ERK2, and by increased AP-1 binding activity.

Figure 6A:
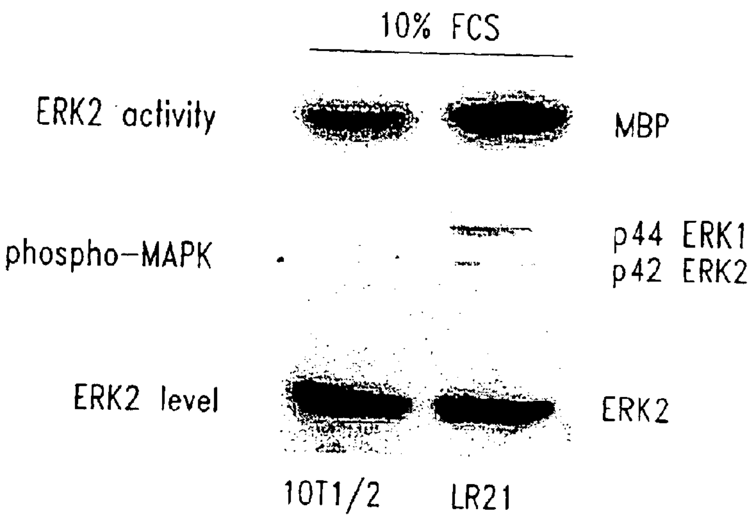
FIGS. 6A and 6B are two blots which show erk activity.

FIG. 6A illustrates that MAP kinase activity in quiescent 10T1/2 cells is reduced relative to the levels present in RHAMM transfected LR21 cells. Cells were growth in DMEM with 10% FBS, cell monolayers were washed three times with PBS and total cellular extracts were prepared in a buffer containing 25 mM Hepes, pH 7.7, 100 mM NaCl, 2 mM $MgCl_2$, 0.2 mM EDTA, 0.5% Triton X-100, 0.5 mM DTT, 20 mM β-glycerophosphate, 0.1 mM sodium orthovanadate, 0.5 μg/ml leupeptin, 100 μg/ml PMSF. Cellular lysates of 100 μg total protein were incubated with anti-ERK2 antibody conjugated agarose (ERK(C-14), Santa Cruz Biotech., Inc), immuno-complexes were washed twice with the above lysis buffer and twice with kinase buffer (20 mM Hepes, pH 7.7, 10 mM $MgCl_2$, 2 mM $MnCl_2$, 2 mM DTT and 25 $\mu$M ATP). ERK2 activity was determined by in vitro kinase assay using 2 [g substrate MBP and 1 $\mu$Ci [$\gamma$-$^{32}$P] ATP in 20 $\mu$l of kinase buffer. After incubation at 30° C. for 20 min, the reactions were terminated with Laemmli buffer, proteins were separated by SDS-PAGE and the gels were dried and autoradiographed.

The amount of ERK2 and phosphorylated MAPK was detected from the total extracts by western blot using an ECL chemiluminescence system. In brief, lysates of 25 $\mu$g total protein were resolved by 10% SDS-PAGE and transferred onto nitrocellulose membrane (BioBlot, Costar) using Trans-Blot® Semi-Dry Electrophoretic Transfer Cell (BioRad) with a transfer-blotting buffer containing 20 mM Tris, 150 mM glycine, 0.01% SDS and 20% methanol. The filters were blocked for non-fat skim milk in TBS-T (20 mM Tris, pH 7.5, 150 mM NaCl and 0.1% Tween 20) at 4° C. overnight. The membranes were then probed with phospho-specific anti-p44/p42 MAP kinase antibody (New England BioLabs, Inc.) by incubation at room temperature for 1.5 h. After washing three times with TBS-T for 30 min, blots were incubated with horseradish peroxidase conjugated anti-rabbit antibodies (NEB) for 1 h. The filters were washed three times for 30 min and visualized on X-ray film using the chemiluminescence detection method (NEB).

Figure 6B:

FIG. 6B illustrates that AP-1 DNA binding activity is stimulated in LR21 cells relative to parental 10T1/2 cell. Parental 10T1/2 cell and LR21 cells were grown in DMEM with 10% FBS. Cells were then starved in the medium without serum for 8 h. Cells were washed twice with PBS (phosphate-buffered saline) and lysed with 1 ml buffer 1 (10 mM Tris-Cl, pH7.5, 10 mM NaCl, 3 mM $MgCl_2$, 0.5% Nonidet P-40, 0.5 mM phenylmethylsulfonyl fluride [PMSF]). Cells were scraped into an eppendorf tube and put on ice for 10 min. The nuclei were collected after centrifugation at 5000 rpm for 10 min. Nuclear proteins were prepared by resuspending the nuclei in buffer 2 (20 mM Hepes, pH7.9, 5 mM $MgCl_2$, 0.2 mM EDTA, 1 mM DTT, 300 mM NaCl, 20% glycerol, 0.5 mM PMSF), after centrifugation at 14,000 rpm for 10 min the supernatant was harvested as nuclear extract. Double-stranded AP-1 oligonucleotide (Santa Cruz Biotech, Inc.) was end-labeled with [$\gamma$-$^{32}$P] ATP (DuPont NEN) using T4 polynucleotide kinase (Pharmacia). Labeled probe was separated from free nucleotide through a Sephadex G-50 mini-spin column (Pharmacia). DNA-protein binding was performed by mixing 10 $\mu$g of nuclear extract with $^{32}$P-labeled double-stranded AP-1 consensus oligonucleotide in a total volume of 20 $\mu$l containing 20 mM Hepes, pH 7.9, 1 mM $MgCl_2$, 4% Ficoll, 0.5 mM DTT, 50 mM KCl, 1 mM EDTA, 2 $\mu$g poly(dI•dC) and 1 mg/ml BSA for 45 min on ice. The DNA protein complex was separated on a 4% native polyacrylaminde gel using 0.5X Tris-borate-EDTA buffer at 150 V. Gels were then dried and autoradiographed.

Example 3

Overexpression of RHAMM Activates Expression of c-Fos and c-JUN, and Matrix Metlloproteinases Associated with Response-to-Injury Processes Expression of the transcription factors c-fos, c-jun, jun B are associated with response to injury processes in mammalian tissues. Northern analysis was used to show that of c-fos, c-jun, and jun B but not jun D expression are stimulated by overexpression of the transition stage hyaladherin, RHAMM.

Figure 7A:
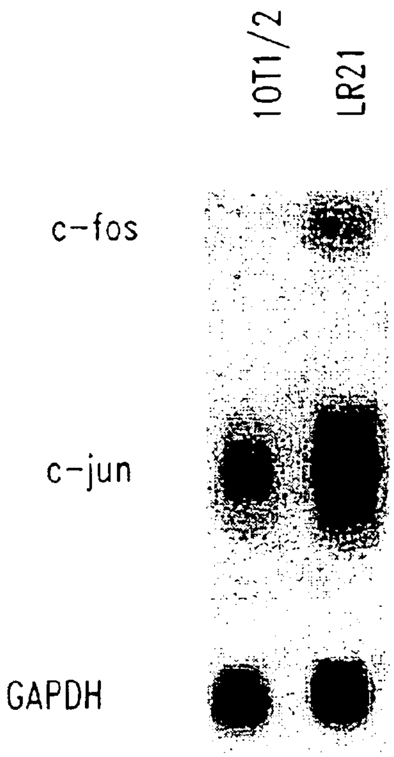
FIGS. 7A and 7B show the increased expression levels of e-fos, c-jun, junB genes by overexpression of RHAMM.
Figure 7B:
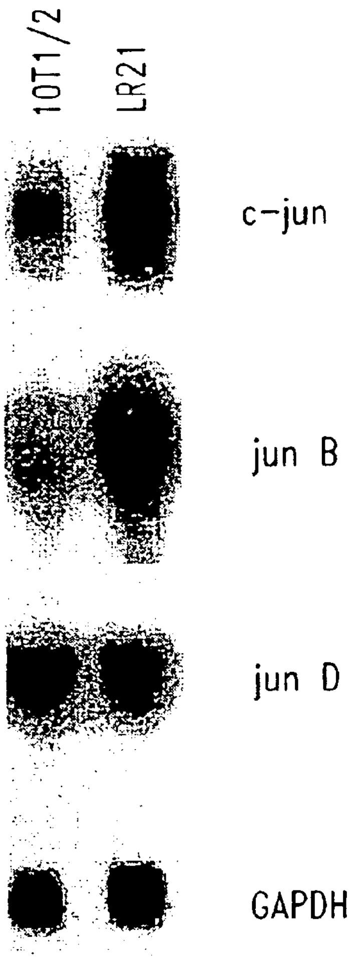

Briefly, cells were grown in DMEM with 10% FBS and were starved in the absence of serum for 6 h. Cells were washed twice with PBS and total RNA was isolated by guanidine isothiocyanate method. In concise, cells-were lysed in 4 ml solution D (5.3 M guanidine isothiocyanate, 30 mM sodium citrate, 0.7% N-laurylsarcosine, 0.72% 2-mercaptoethanol). To each sample, added 4 ml of acid phenol, 1 ml of chloroform and 0.45 ml of 2 M sodium acetate. The solution was mixed well and centrifuged at 7000 rpm for 30 min, the aqueous phase was collected and precipitated with an equal volume of 2-propanol. Pelleted RNA was dissolved in 50 ill diethyl pyrocarbonate (DEPC) treated water. The RNA was second extracted with 0.4 ml of TRizol reagent (GibcoBRL) with the addition of 0.1 ml chloroform. After vigorous mixing and centrifugation, the RNA supernatant was precipitated with 2-propanol and washed in 75% ethanol. Finally, the RNA was dissolved the DEPC-treated water. The expression level of c-fos, cjun, jun B and jun D were probed with a rat c-fos and a human c-jun probe, respectively. The blots were stripped and re-probed with rat GAPDH cDNA as internal standard. The results, as shown in FIG. 7, show that expression of c-fos, c-jun, jun B but not jun D is stimulated in LR21 cells that overexpress RHAMM. In addition, LR21 cells which overexpress RHAMM constitutively form podosomes and form few focal adhesions (data not shown).

Figure 8:
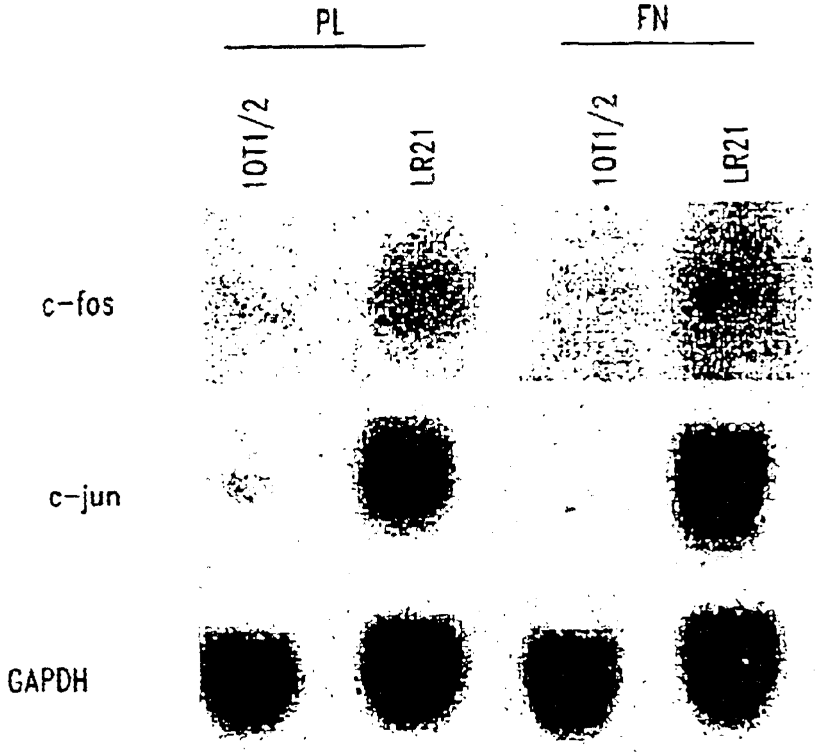
FIG. 8 shows the increased expression levels of c-fos and c-jun gene in cells overexpressing RHAMM regardless whether grown on poly L-lysine (PL) or fibronectin (FN).

C-fos and c-jun expression are stimulated in LR21 cells in comparison to parental 10T1/2 whether or not they are grown on fibronectin (FIG. 8). Briefly, cells were grown in DMEM with 10% FBS and cell monolayers were trypsinized. Cells were washed and plated on fibronectin and poly-l-Lysine coated dishes in the medium without serum. These tissue culture dishes were precoated with 25 $\mu$g/ml fibroiiectin or 100 $\mu$g/ml poly-l-Lysine at 4° C. for overnight and washed twice with PBS before use. Cells were then incubated under this starving condition for 6 hr, total RNAs were extracted and hybridized as previously described. The levels of c-fos and c-jun were determined by hybridization with a rat c-fos cDNA and a human c-jun cDNA. The blot was stripped and re-probed with rat GAPDH cDNA as internal control. These results, as shown in FIG. 8, further illustrate that a cell culture overexpressing a transition molecules such as RHAMM exhibits an activated signaling phenotype characteristics of transition stage cells.

Figure 9A:
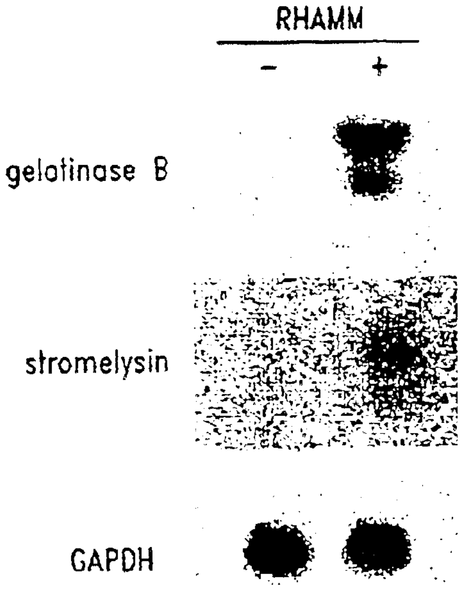
FIG. 9A and 9B are northern blots probed with gelatinase B, stromelysin, timp-1, and glyceraldehyde-3-phosphate dehydrogenase (GAPDH) complementary DNA (cDNA).
Figure 9B:
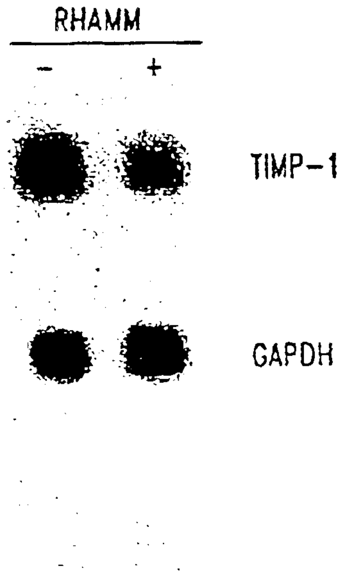

Another characteristic of transition cells is an increase in the expression of matrix metalloproteinases. This increase in metalloproteinases expression is exhibited in cells that over-express RHAMM and these cells show reduced expression of matrix metalloproteinase inhibitors. The association of increased RHAMM and metalloproteinases activity is demonstrated by Northern analysis of RHAMM and matrix metalloproteinase mRNA levels in 102T1/2 and LR21 cell lines as illustrated in FIG. 9.

Briefly, cells were grown in DMEM with 10% FBS and were starved for 6 hours in the medium without serum. Cells were washed twice with PBS and total RNA was isolated by guanidine isothiocyanate method. In concise, cells were lysed in 4 ml solution D (5.3 M guanidine isothiocyanate, 30 mM sodium citrate, 0.7% N-laurylsarcosine, 0.72% 2-mercaptoethanol). To each sample, added 4 ml of acid phenol, 1 ml of chloroform and 0.45 ml of 2 M sodium acetate. The solution was mixed well and centrifuged at 7000 rpm for 30 min, the aqueous phase was collected and precipitated with an equal volume of 2-propanol. Pelleted RNA was dissolved in 50 $\mu$l diethyl pyrocarbonate (DEPC) treated water. The RNA was second extracted with 0.4 ml of TRizol reagent (GibcoBRL) with the addition of 0.1 ml chloroform. After vigorous mixing and centrifugation, the RNA supernatant was precipitated with 2-propanol and washed in 75% ethanol. Finally, the RNA was dissolved the DEPC-treated water.

Denatured RNA samples of 20 μg were separated in 1% agarose gel containing 2.2 M formaldehyde, transferred to a Zeta probe membrane (BioRad), cross-linked with an ultraviolet cross-linker (Strategene). The membrane was prehybridized in 0.35 M phosphate buffer containing 1% BSA, 7% SDS and 30% formamide for 5–6 h at 55° C. The expression level of RHAMM, gelatinase B, and stromelysin were detected by. hybridizing the membrane with a $^{32}$P-labeled cDNA of a mouse full length RHAMMv2. After washing the membrane in 0.5×SSC and 0.5% SDS at 55° C. for 1.5 h, the membrane was autoradiographed. The blot was subsequent stripped and re-probed with a mouse gelatinase B cDNA, a human stromelysin cDNA, or a rat GAPDH cDNA as internal standard.

In addition to showing increased expression of metalloproteinases, cells that overexpress RHAMM also show decreased expression of inhibitors of metalloproteinase such as timp-I. Northern analysis of tissue inhibitor of matrix metalloproteinase (timp-I) expression in LR21 cell shows a reduced level in comparison to normal quiescent cells as illustrated in FIG. 9. LR21 cells which overexpress RHAMMv4 show decreased expression of timp-I, which normally blocks activity of metalloproteinases.

Example 4

Overexpression of RHAMM Restricts the Extent to Which Cytokines and Growth Factors Activate Erk Signaling Pathways As previously mentioned, the overexpression of RHAMM produces a transition cell phenotype that only partially activates erk signaling pathways. This is further illustrated in FIGS. 10 and 11 which show that signaling molecules ordinarily fully activated by growth factor induction are restricted, or partially activated by overexpression of RHAMM.

Figure 10:
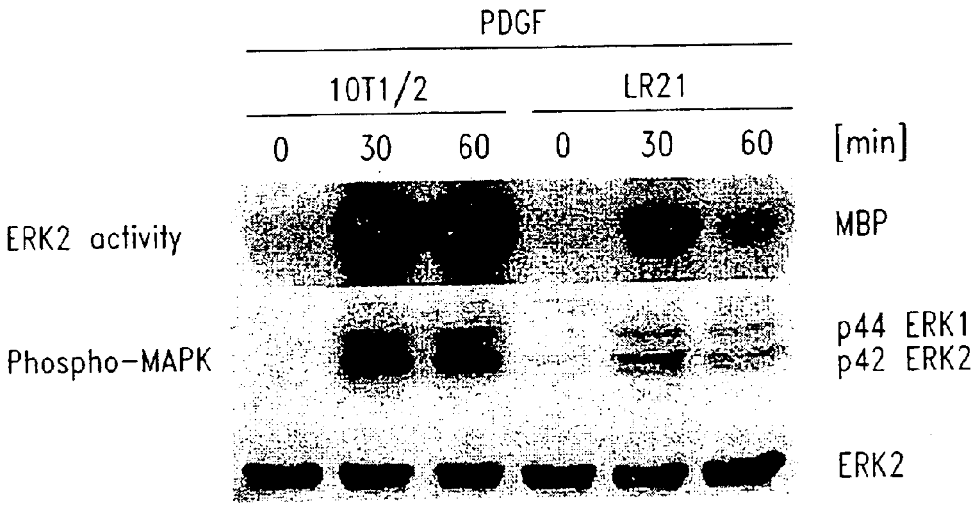
FIG. 10 is a blot which shows that LR21 cells overexpressing RHAMMv4 are restricted in the extent to which proinflammatory cytokines can activate erk kinase.

FIG. 10 shows a phosphoprotein activity analysis that directly illustrates that cells that overexpress RHAMM have elevated erk activation of MAP kinases but that this activation is restricted relative to the level of activity observed in normal cells induced by a growth factor (PDGF). The Figure shows both phosphoylation of erk molecules and erk2 dependent phosphorylation of MBP molecules.

Briefly, cells were grown in DMEM with 10% FBS, and cells were starved for 6 h in the medium without serum. Cells were then stimulated with PDGF (25 ng/ml) for 30 and 60 min. Cell monolayers were washed three times with PBS and total cellular extracts were prepared in a buffer containing 25 mM Hepes, pH 7.7, 100 mM NaCl, 2 mM $MgCl_2$, 0.2 mM EDTA, 0.5% Triton X-100, 0.5 mM DTT, 20 mM β-glycerophosphate, 0.1 mM sodium orthovanadate, 0.5 μg/ml leupeptin, 100 μg/ml PMSF. Cellular lysates of 100 μg total protein were incubated with anti-ERK2 antibody conjugated agarose (ERK(C-14), Santa Cruz Biotech., Inc.), immuno-complexes were washed twice with the above lysis buffer and twice by kinase buffer (20 mM Hepes, pH 7.7, 10 mM $MgCl_2$, 2 mM $MnCl_2$, 2 mM DTT and 25 μM ATP). ERK2 activity was determined by in vitro kinase assay using 2 μg substrate MBP and 1 μCi [γ-$^{32}$P] ATP in 20 μl of kinase buffer. After incubation at 30° C. for 20 min, the reactions were terminated with Laemmli buffer, and proteins were separated by SDS-PAGE, gels were dried and autoradiography.

The amount of ERK2 and phosphorylated MAPK were detected from the total extracts by western blot analysis and ECL chemiluminescence system. Lysates of 25 μg total protein were resolved by 10% sodium dodecylsulfate_polyacrylamide gel electrophoresis (SDS_PAGE) and transferred onto nitrocellulose membrane (BioBlot, Costar) using Trans-Blot® Semi-Dry Electrophoretic Transfer Cell (BioRad) with a transfer-blotting buffer containing 20 mM Tris, 150 mM glycine, 0.01% SDS and 20% methanol. The filters were blocked for non-fat skim milk in TBS-T (20 mM Tris, pH 7.5, 150 mM NaCl and 0.1% Tween 20) at 4° C. overnight. The membranes were then probed with phospho-specific anti-p44/p42 MAP kinase antibody (New England BioLabs, Inc) by incubation at room temperature for 1.5 h. After washing three times with TBS-T for 30 min, blots were incubated with horseradish peroxidase conjugated anti-rabbit antibodies (NEB) for 1 h. The filters were washed three times for 30 min and visualized on X-ray film with chemiluminescence detection method (NEB).

As shown in FIG. 10, the results of this analysis shows that LR21 cells overexpressing RHAMMv4 are restricted in the extent to which proinflammatory cytokines/growth factors (e.g. PDGF) can activate erk kinase.

Figure 11A:
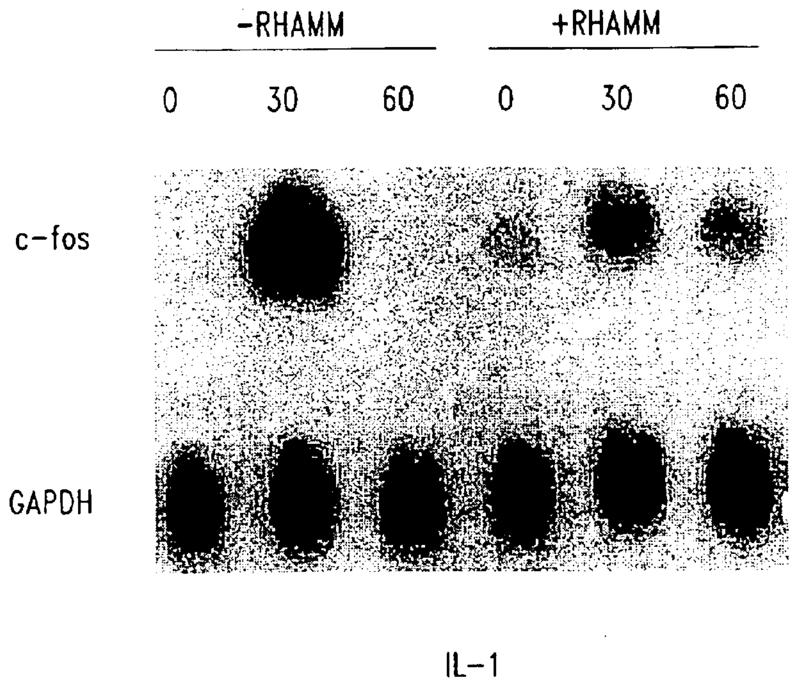
FIGS. 11A and 11B are northern analysis of interleukin-1 (IL-1) and tumor necrosis factor (TNF) alpha induction of c-fos.

FIG. 11A shows a Northern analysis of IL-1 induction of c-fos expression in 10T1/2 and LR21 cell lines. Cells were grown in DMEM with 10% FBS and starved for 6 hours in the medium without serum. Cells were then stimulated with IL-1 (20 ng/ml) for 30 min and 60 min. Total RNAs were extracted and hybridized as described above. The level of c-fos was measured by hybridization with a rat c-fos cDNA. The blot was stripped and re-probed with rat GAPDH cDNA as internal control. The results show that expression of c-fos in response to IL-1 and TNF is restricted in LR21 cells.

Figure 11B:
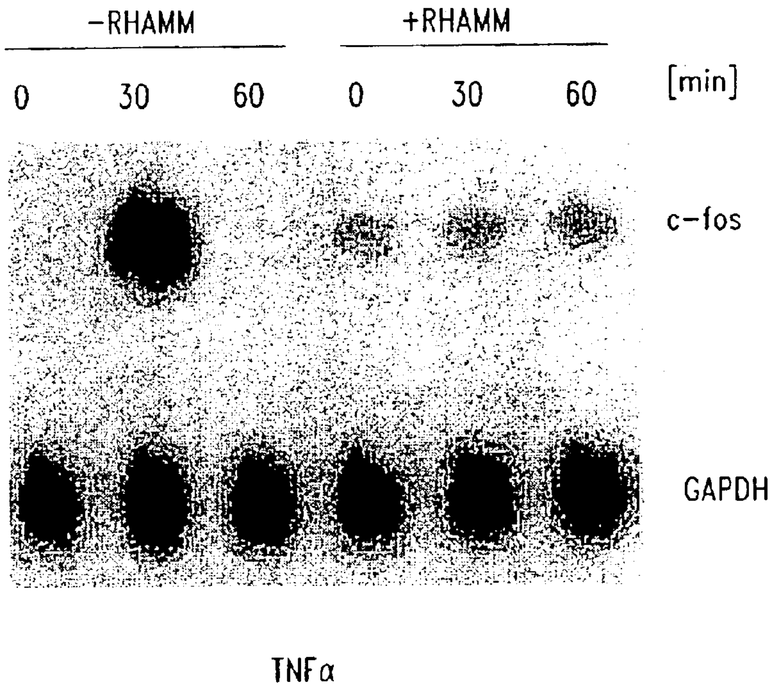

FIG. 11B shows a Northern analysis of TNF-α induction of c-fos expression in 10T1/2 and LR2] cell lines. Cells were grown in DMEM with 10% FBS and starved for 6 h in the medium without serum. Cells were then stimulated with TNF-α (30 ng/ml) for 30 min and 60 min. Total RNAs were extracted and hybridized as described above. The level of c-fos was measured by hybridization with a rat c-fos cDNA. Again it can be seen that the expression of c-fos in response to a injury response growth factor i.e., TNF-α, is restricted in LR21 cells.

Example 5

Figures 12A, 12B:
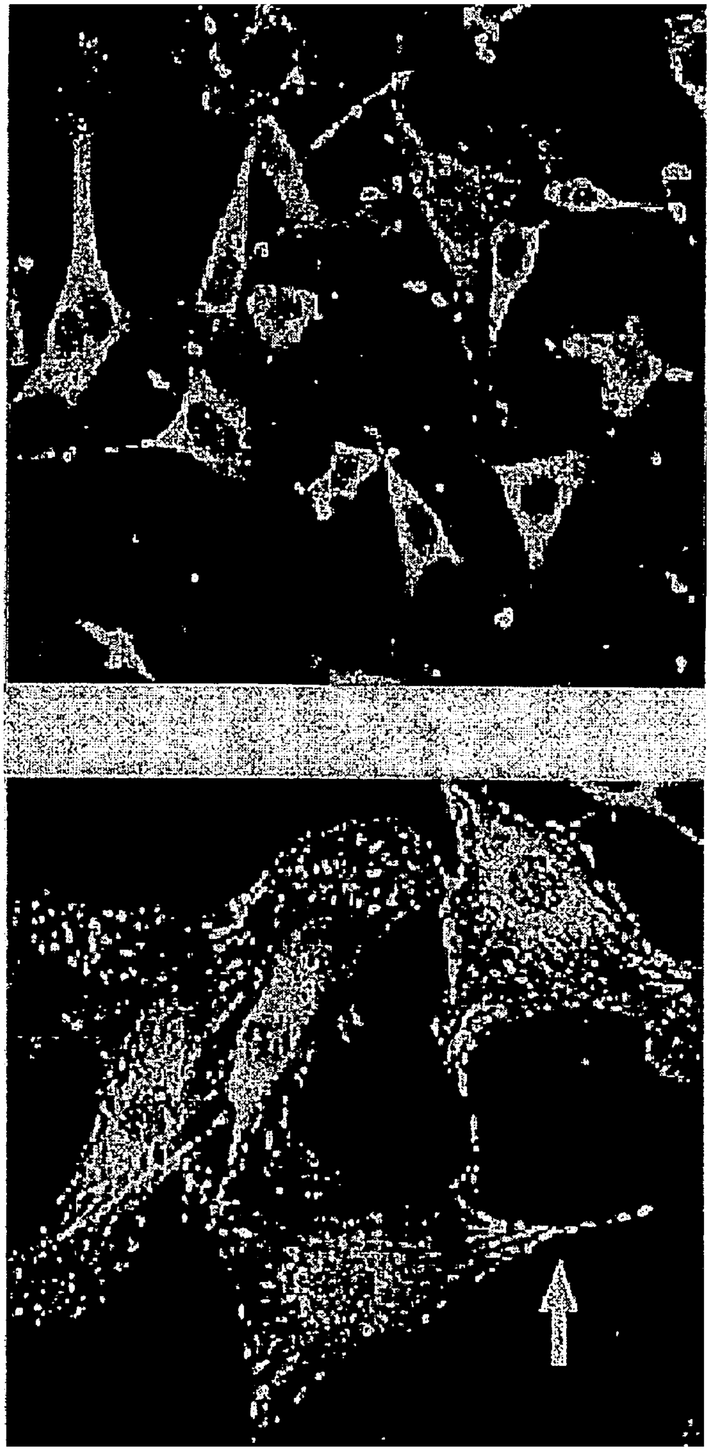
FIGS. 12A and 12B are photographs of LR21 cells, showing, in 12A, the formation of discrete focal adhesions.

RHAMM Overexpression Prevents Focal Adhesion Formation and Induces Constitutive Podosome Production A key feature of cells over-expressing RHAMM, LR21, prepared as described above is that they do not form focal adhesions. FIG. 12A shows that the parent cell line, 10T1/2, form very discreet focal adhesions, as demonstrated with anti-vinculin staining. In contrast LR21 cells do not form focal adhesions (FIG. 12B). This inhibition of focal adhesion formation may be responsible for the lack of response of these cells to cytokines such as IL-1 and TNF. It would appear that as long as cells are expressing RHAMM they do not form focal adhesions and remain unresponsive to cytokines.

Figure 13A:
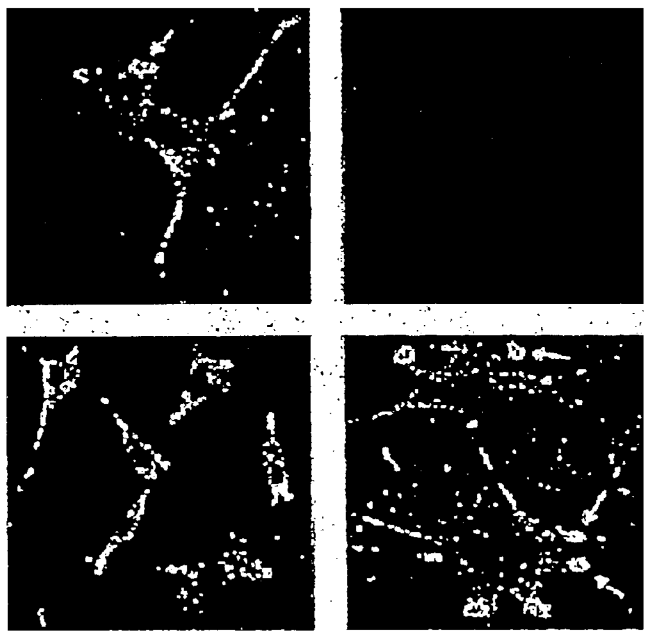
FIGS. 13A and 13B are photos, and graphs (respectively), which show that overexpression of RHAMM results in podosome formation.
Figure 13B:
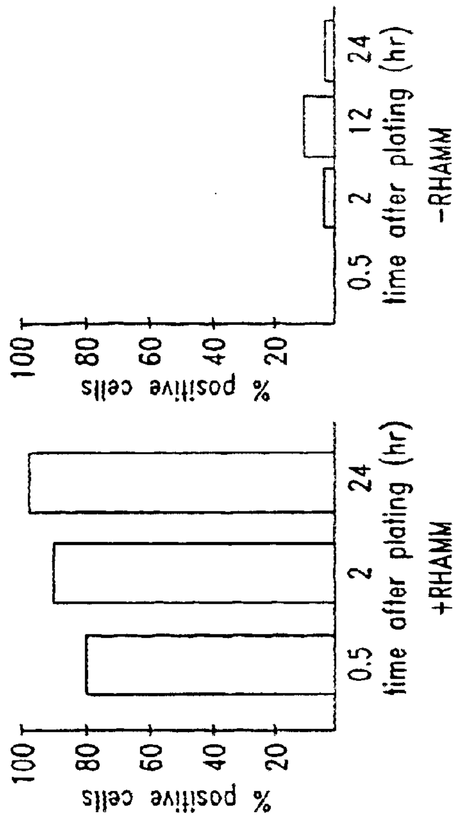

In addition, 10T1/2 cells, the parent cell line when plated form small numbers of podosomes immediately following plating as shown in FIG. 13. By 12 to 24 hours, there is little formation of podosomes and there is now the formation of focal adhesions in these cells. In contrast to 10T1/2 cells, LR21 cells that over-express RHAMM form podosomes constitutively. The level of podosome formation is higher and continuous in cells over-expressing RHAMM. These data indicate that RHAMM overexpression is required for podosome formation in cells immediately following injury or sustained disease conditions.

Example 6

Figure 14A:
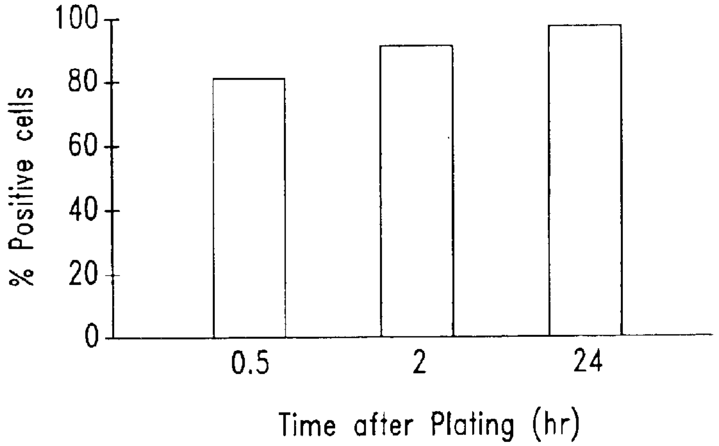
FIG. 14A, 14B, and 14C are graphs which illustrate the relationship of RHAMM, erk activity and podosome formation.
Figure 14B:
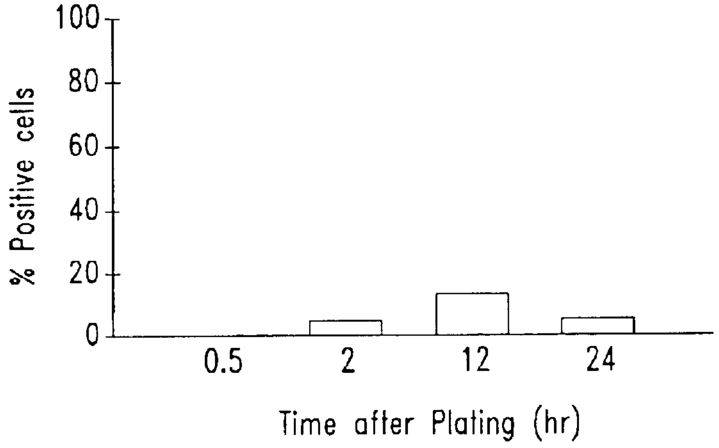
Figure 14C:
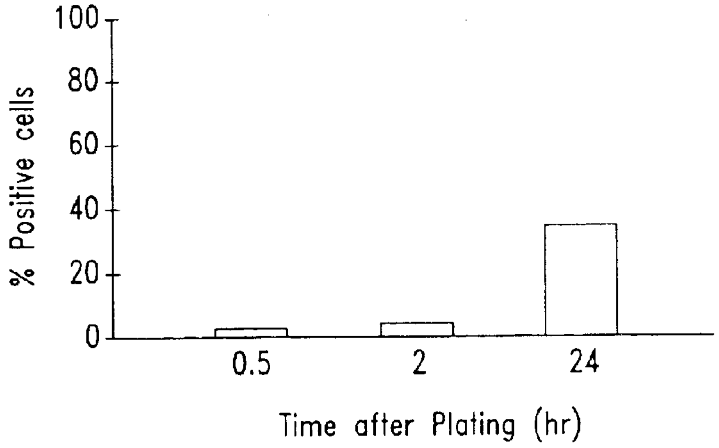

Blockage of Erk Activity Inhibits the Formation of Podosomes and Migration of Cells Toward Wounds Promoted by Overexpression RHAMM To further illustrate the relationship between RHAMM, erk activity and podosome formation in transient stage cells, podosome formation is shown to be inhibited by inhibitors of erk activity. FIG. 14 shows that enhanced podosome formation resulting from RHAMMv4 overexpression, is blocked by inhibitors of erk kinase which also blocks cell migration into wound sites. Overexpression of RHAMMv4 results in a sustained high production of podosomes, detected by the marker protein cortactin (A). Inhibition of erk kinase by PD09058 reduces the number of podosomes (B) as does mutation of intracellular RHAMMv4 (C) so that erk does not bind to RHAMM. Overexpression of RHAMMv4 enhances cell migration into wounds (D) compared to the parent 10T1/2 fibroblast line that produces little RHAMMv4 (E). The addition of PD09058 blocks wound repair of RHAMMv4 overexpressing cells (F).

Example 7

RHAMM is Transiently Detected on the Surface of Cells and is required for Podosome Formation and Cell Motility Method of Detecting transient Cells Exon 3 and 4 of RHAMM provide peptides and antibodies thereto which are useful for detecting RHAMM expression and demonstrating that RHAMM is associated with podosomes. FIG. 15A shows a comparison of the expression of RHAMM at the cell surface using anti-exon 4 RHAMM antibody or antibody "R3.8" raised against a whole RHAMM polypeptide. The chart summarizes the results of FACS analysis of in vitro growth of invasive MDA231 cells in comparison to MCF-7 human breast cancer cells which are non invasive cells. The results show that cell surface RHAMM is present in larger amounts on MDA-231 cells than on MCF-7 cells.

FIG. 15B shows the amino acid sequences of murine and human RHAMM peptides including: a peptide from murine exon 3 (SEQ. ID NO: 14); a smaller peptide used to raise anti-exon 3 antibodies (SEQ. ID NO: 15); a peptide from murine exon 4 (SEQ. ID NO: 16); a smaller peptide used to raise anti-exon 4 antibodies (SEQ. ID NO: 17), a human RHAMM peptide from exon 5 (SEQ. ID NO: 18); a human RHAMM peptide homologous to murine exon 3 (SEQ. ID NO: 19); and a murine RHAMM peptide homologous to human exon 5 (SEQ. ID NO: 20). The human exon 4 homologue is identical to the murine sequence used to raise anti-exon 4 antibodies. The C residues shown in parenthesis were added during synthesis of the peptides.

Figures 16A, 16B:
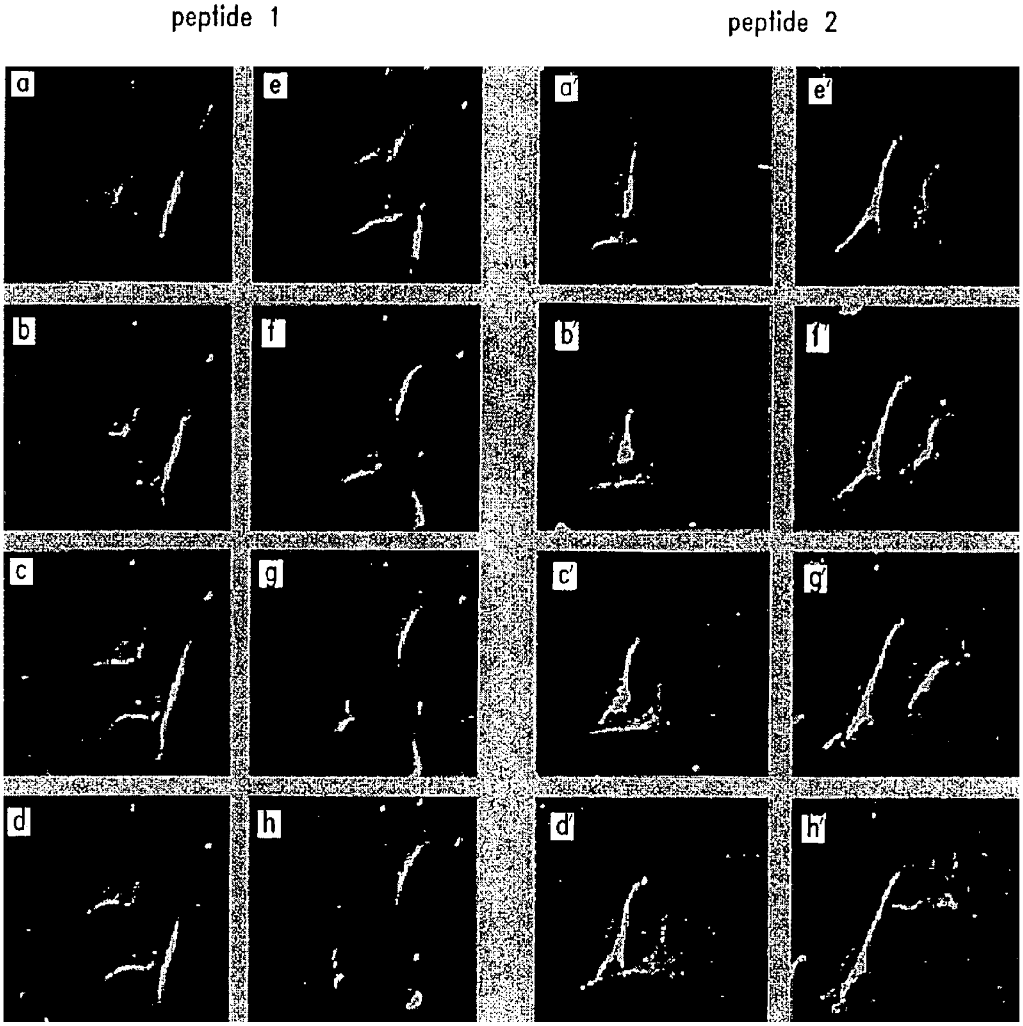
FIGS. 16A and 16B are photographs showing cells treated with peptides.
Figure 16C:
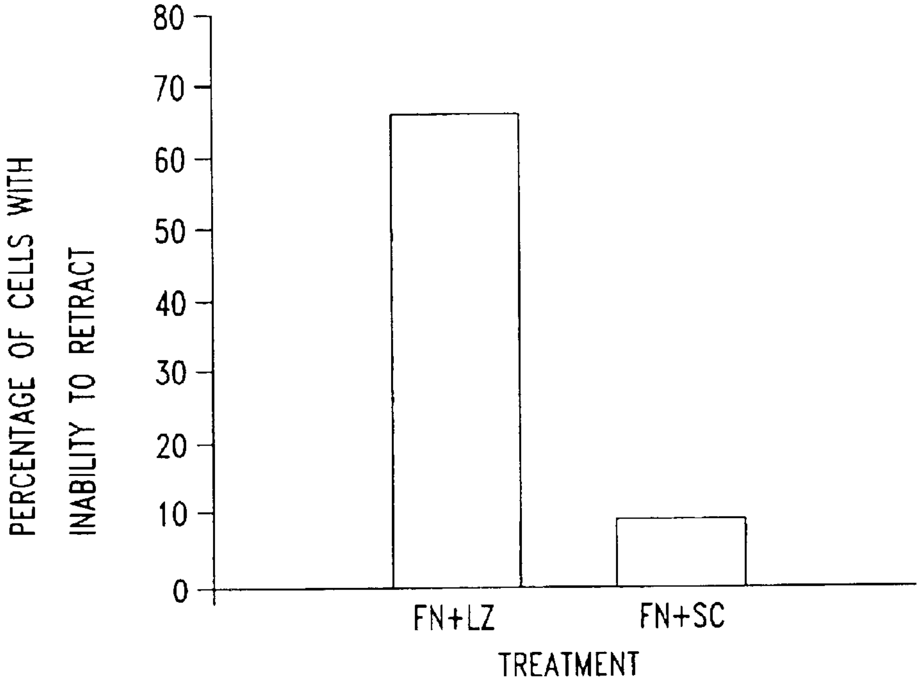
FIGS. 16C and 16D are bar graphs quantifying the effect.
Figure 16D:
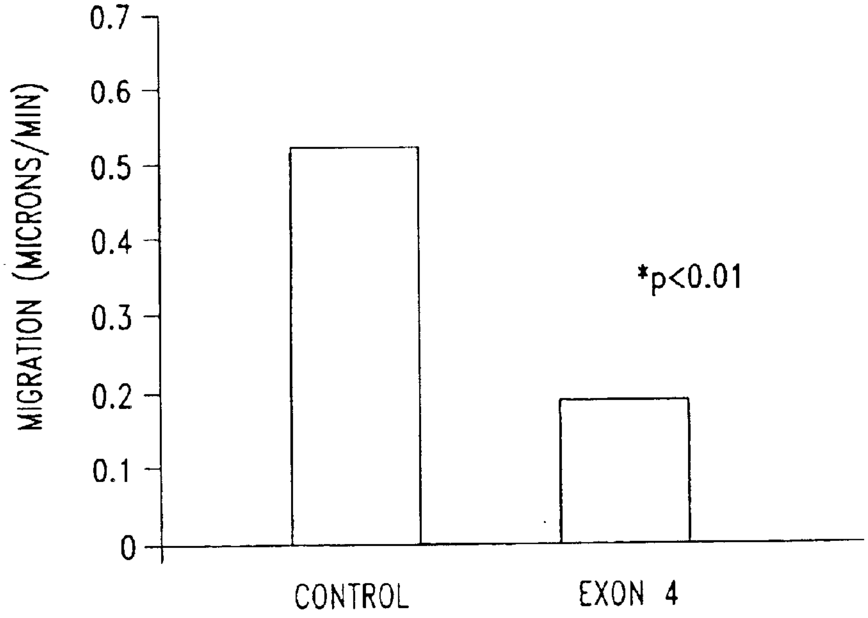

FIG. 16 shows that cells treated by administering peptides mimicking exon 3, i.e., SEQ. ID NO: 15 (peptide 1, panel A) block the motility of invasive cells relative to a scrambled peptide (peptide 2, panel B). This effect is quantified in the graph shown in 16C and is highly significant ($P<0.001$, student's T test). FIG. 16D shows that administration of antibodies against peptides mimicking exon 4 (i.e., antibodies to SEQ. ID NO: 16) also inhibit the motility of invasive cells.

Figure 17A:
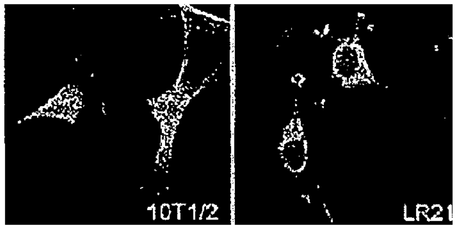
FIGS. 17A and 17B are photographs showing podosome formation under various conditions.
Figure 17B:
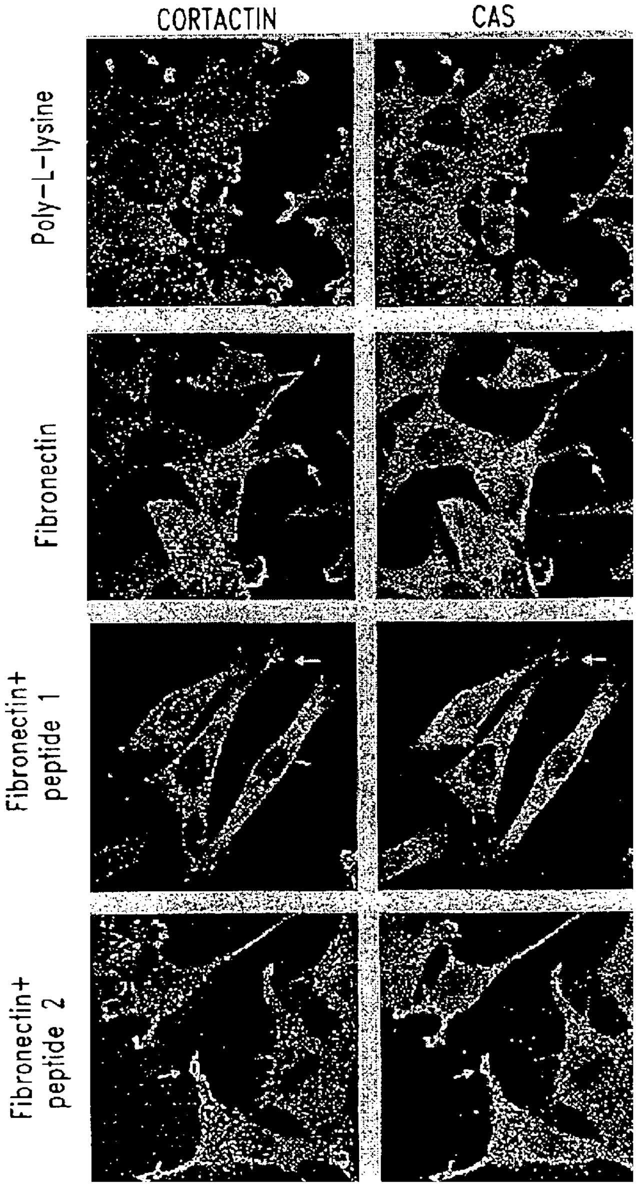

FIG. 17, panel A are micrographs that show that podosome formation is enhanced on the perimeter of LR21 cells that overexpress RHAMM in comparison to control 10T1/2 cells. Panel B shows that administration of exon 4, i.e., peptide SEQ. ID NO: 16 (peptide 1) blocks the formation of podosomes while scrambled exon 4 peptide (peptide 2) does not. Podsomome formation was visualized using either fluorescent cortactin or CAS, the latter being a particularly useful marker for podosomes as illustrated by the micrographs in FIG. 17B.

Figure 18:
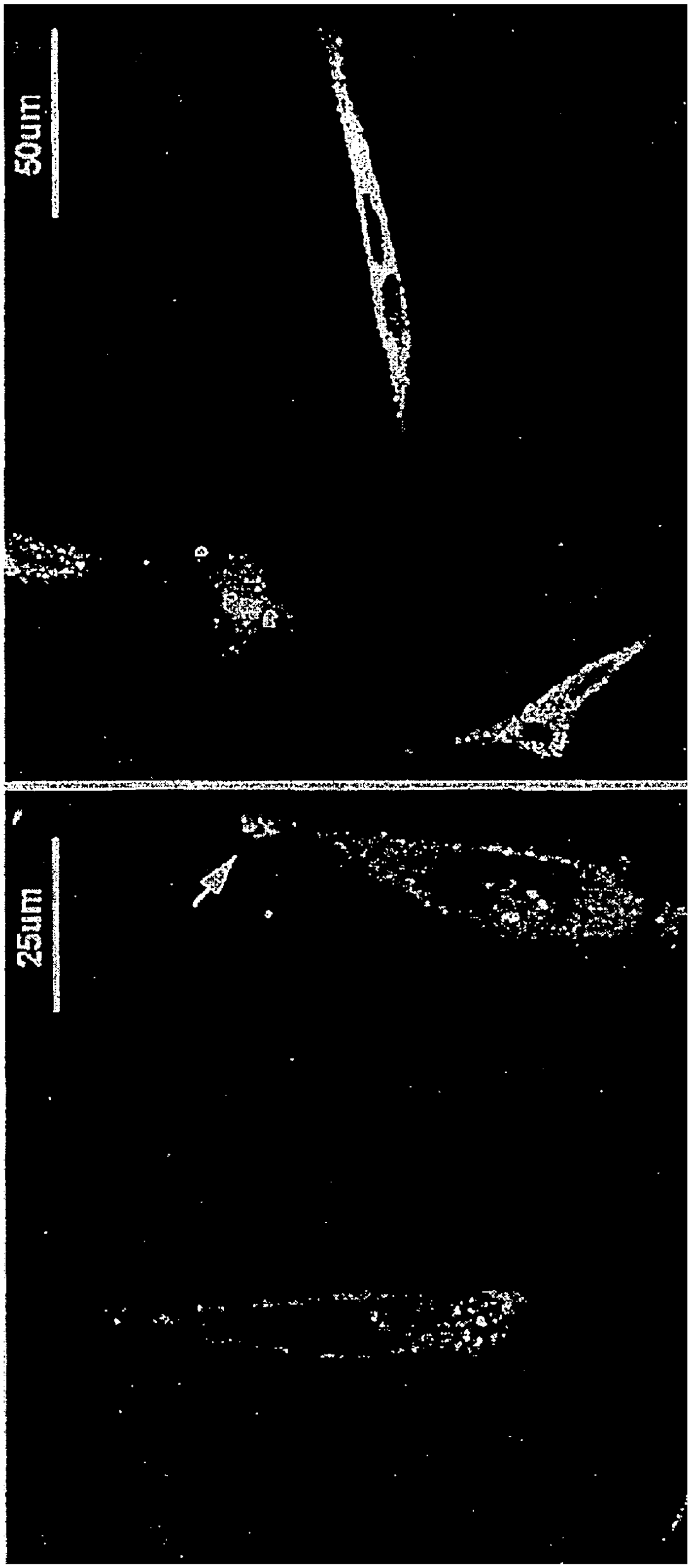
FIG. 18 is two photographs showing MDA-231 cells trated with hyaluronan together with anti-RHAMM antibody.

In FIG. 18, MDA-231 cells were treated with hyaluronan together with anti-RHAMM antibody (exon 4 antibody). The antibody blocked the formation of podosomes as detected by cortactin staining.

Figure 19:
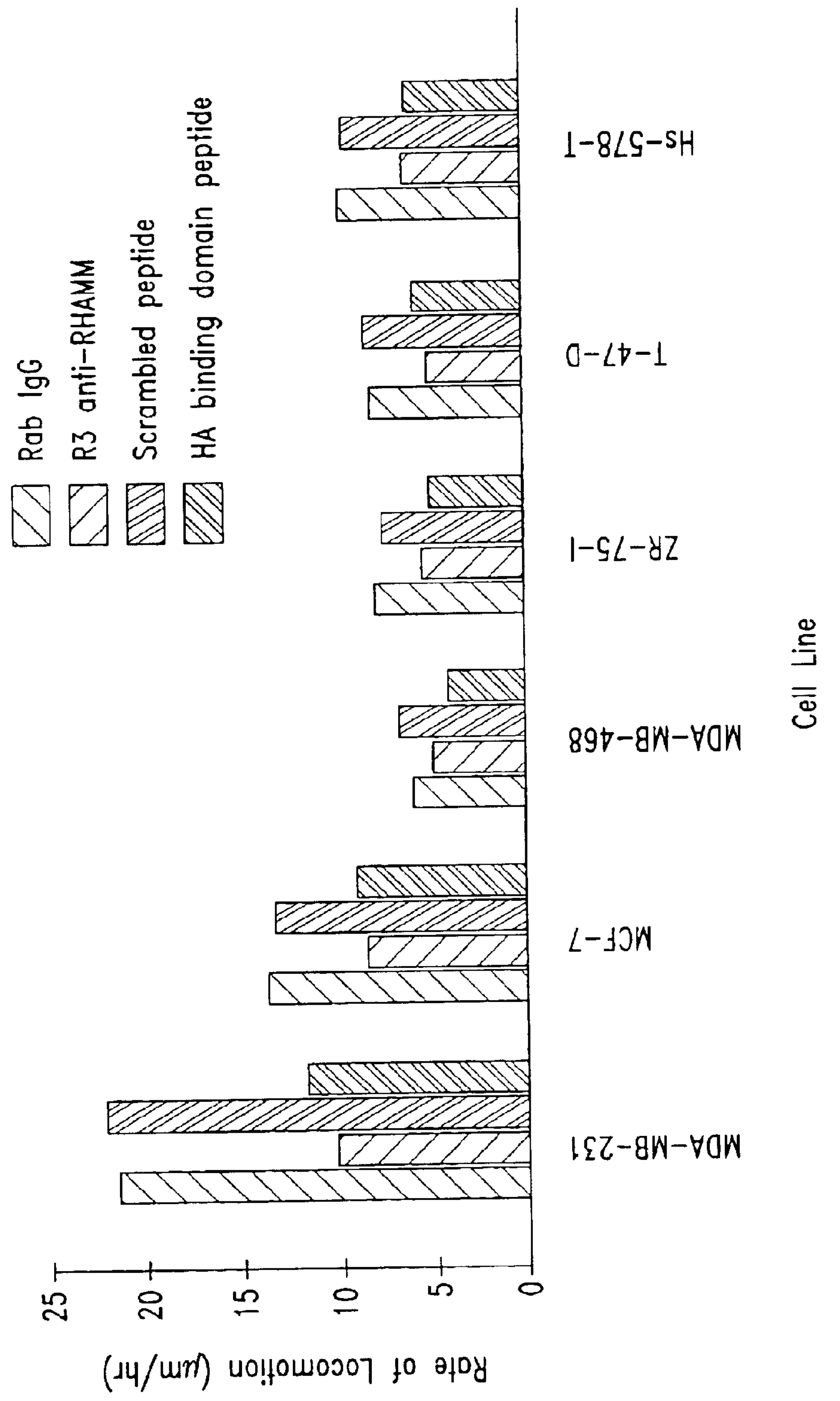
FIG. 19 is a chart that compares rate of locomotion for various cell lines and various substrates.

FIG. 19 is a chart that quantitatively shows that anti-RHAMM antibodies block the rapid motility characteristic of MDA231 human breast cancer cells but have only a small effect on the less rapid motility of cells of the benign MCF human breast cancer cell line.

Figure 20A:
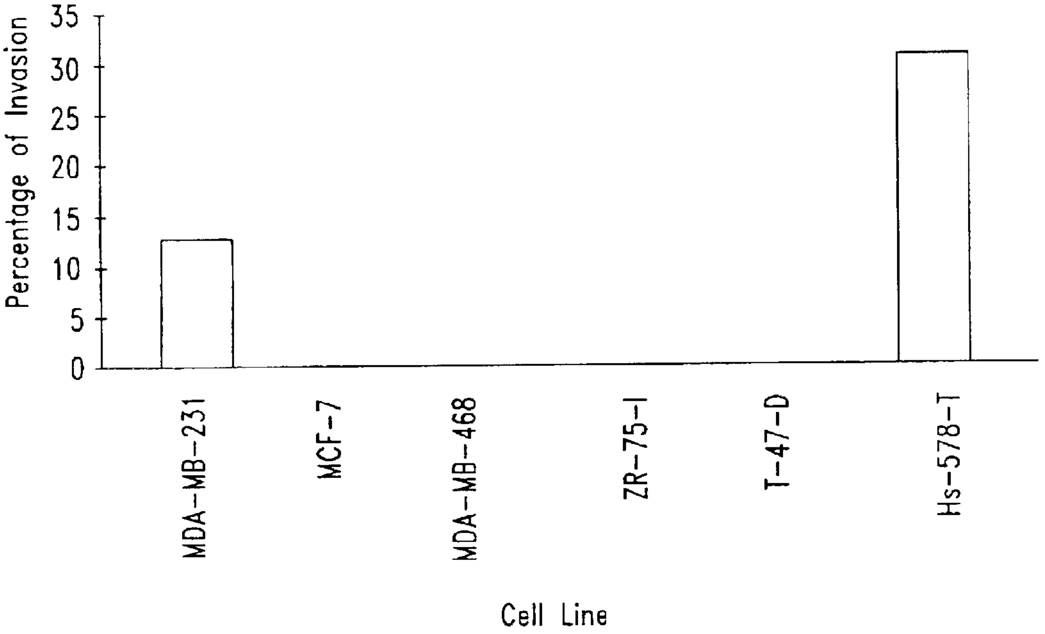
FIGS. 20A and 20B show that anti-RHAMM antibodies inhibit the ability of MDA231 cells to invade in vitro.
Figure 20B:
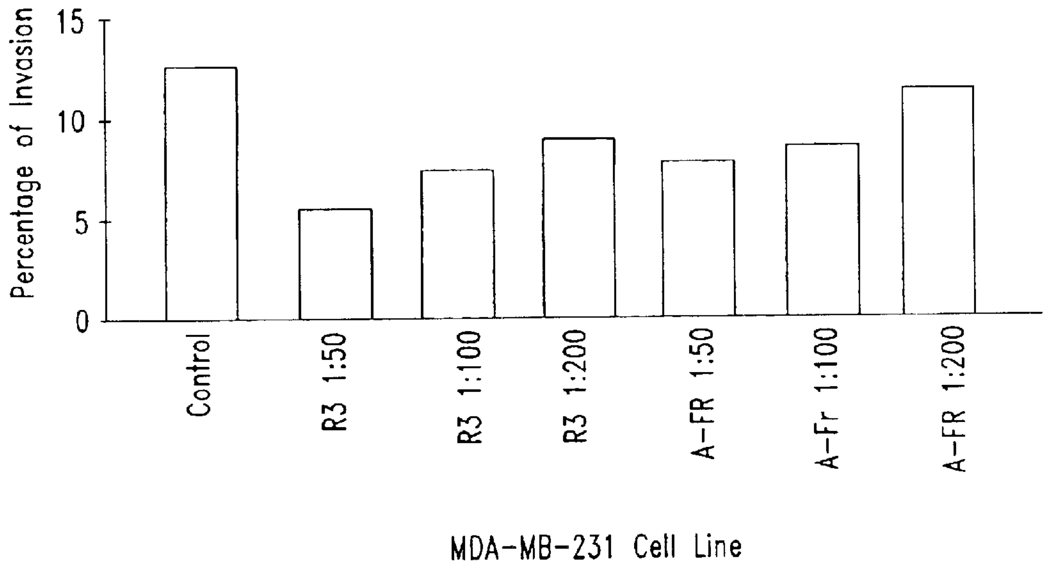

FIG. 20 further shows that anti-RHAMM antibodies inhibit the ability of MDA231 cells to invade in vitro. The chart in 20A illustrates the invasiveness of a variety of cell lines while 20B shows the ability of a variety of RHAMM antibodies to reduce invasiveness of MDA231 cells.

Figure 21A:
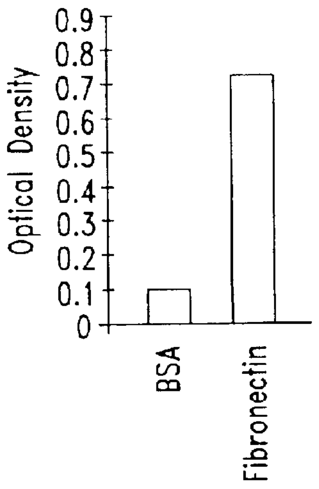
FIGS. 21A, 21B and 21C show RHAMM binding to fibronectin being blocked by selected antibodies.
Figure 21B:
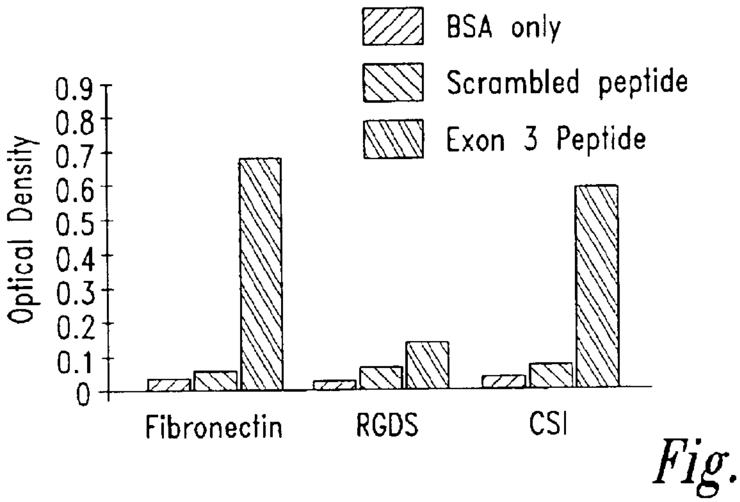
Figure 21C:
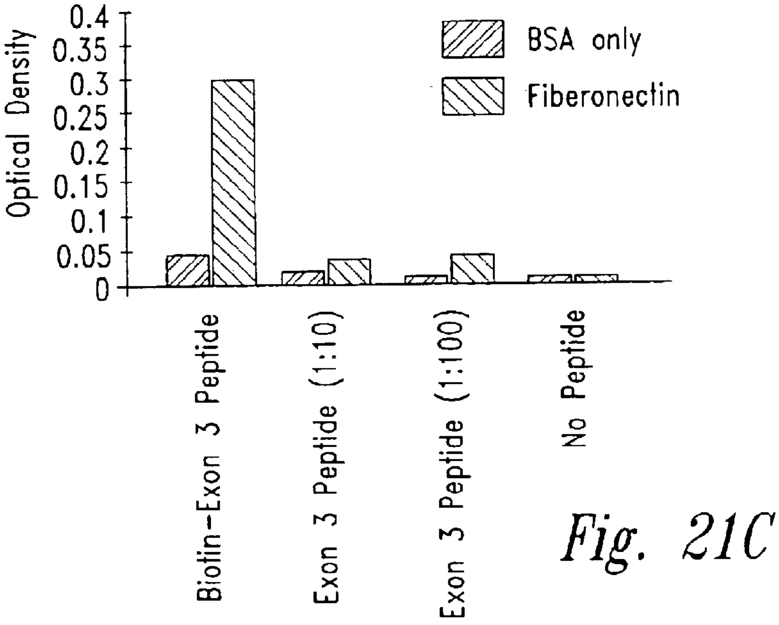

FIG. 21 shows that RHAMM binds to fibronectin but is blocked by antibody to exon 3 indicating that exon 3 contains a fibronectin binding domain. FIG. 21 further illustrates that RHAMM binds to the CS-1 fragment of fibornectin and not to the RGDS sequence which was previously considered to be a critical sequence for fibronectin signaling of matrix protein degradation. Panel A shows that RHAMM binds to fibronectin as detected by an ELISA. Panel B shows that exon 3 of RHAMM binds to fibronectin but not through the RGDS region but rather through the CS-1 region. Panel C shows that peptides mimicking exon 3 are able to block the binding of intact RHAMM to fibronectin, providing a rationale for why peptides block cell locomotion and podosome formation.

Example 8

Erk Kinase Involved in Cellular Motility

Elevated erk activity is associated with, and required for, rapid cell motility characteristic of proliferative or invasive cells such as the breast cancer cell line MDA231 which express high levels of RHAMM.

Figure 22:
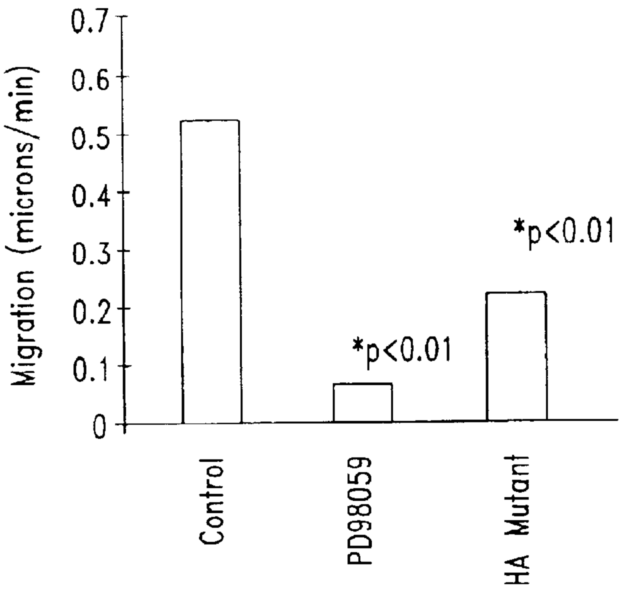
FIG. 22 is a bar graph which shows that MDA231 cells expressing RHAMM have a high degree of motility.

The relationship between erk activation and cell motility is illustrated in FIG. 22 which shows that when cells overexpress RHAMM such as in the case of MDA231 cells, the level of cell motility is high. When erk kinase activity is inhibited by treatment with a MEK inhibitor (PD09058), that inhibition strongly reduces cellular locomotion and blocks cell invasion. FIG. 22 further shows that MDA231 cells expressing a mutant version of RHAMM (HA mutant) have reduced mobility. The relationship between RHAMM expression and cell motility is further established by treating MDA231 cells with anti RHAMM antibodies, resulting in reduced cell mobility.

Example 9

Overexpression of RHAMM Promotes Podosome Formation

Podosomes are transient structures at lamellae tips that are required for the efficient release of the MMPs. Together with other proteinases, MMPs initiate extracellular matrix remodeling. This initial remodeling of matrix attracts white cells to the site of injury, providing additional source of pro-inflammatory cytokines and growth factors that are responsible for the amplification of the response-to-injury. This experiment shows that transient RHAMM overexpression will alter podosome formation in transfected 10T1/2 cells.

Briefly, RHAMMv4 cDNA was tagged with HA and transfected into 10T1/2 cells. 10T1/2 cells were cultured to 40–50% confluence and transfected with 10 μg of RHAMMv4 CDNA tagged with HA in 60 μl of superFect reagent. After five hours of incubation, monolayers were washed twice with PBS and the transfected cells were cultured an additional 48 hours with growth medium supplemented with 10% FBS. The cells were harvested in RIPA buffer and RHAMM expression was detected by Western analysis. Only the transfectants that expressed similar level of (2–3 fold higher than parenthal cells) were used for assays. HAv4tag cells were selected and used in this experiment. For the experimental purposes transfected cells were plated on the fibronectin (FN) substrate at the 50% density. To visualize the presence of Hav4tag cDNA cells were stained at different time points: ½ h, 2 h, 6 h, and 24 h respectively with monoclonal antibody against HA. Additionally, cells were stained with the monoclonal Ab against HA (dil.1:50) 1 h at room temperature. Cells were then washed with 1% BSA in PBS and incubated with x4 antibody. X4 antibody was detected by Texas-red (1:100). Cells were incubated 1 h at room temperature in Texas red. Some cells were plated onto RITC-labeled fibronectin in order to detect the ability of cells to digest this extracellular matrix protein providing an assessment of the functional capability of the podosomes. A clearing of fluorescence indicates that cells have released collagenases that are able to digest fibronectin.

In both experimental paradigms, results were examined under the confocal microscope.

Figure 23A:
FIGS. 23A and 23B are micrographs which show podosome formation in various cells.
Figure 23B:
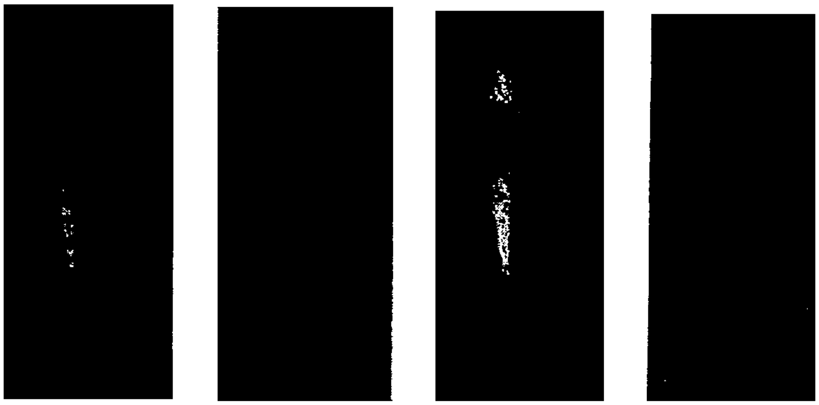

As shown on FIG. 23A, at the 2 h point 100% of plated cells formed podosomes. Additionally, v4 tagged RHAMM cDNA was found in perinuclear region as well as in the podosomes. Evidence that podosomes made by RHAMM transfected cells are releasing proteases is provided in FIG. 23B which shows the clearing of FITC-fibronectin underneath the plated cells. The dark area indicates that fibronectin has been proteolyzed and released from the cell substratum. Based upon this experiment it is evident that overexpression of RHAMM promotes podosome formation in 10T1/2 cells.

Example 10

Antibodies Against TAM Domains and Leucine Zipper Inhibit Podosome Formation The objective of this experiment was to investigate whether RHAMM induces podosome formation in a system where RHAMM surface sites were blocked with a exon4 (TAM) A antibody. Leucine zipper peptide (LZP) was also tested for its capability to compete for RHAMM surface sites with fibronectin, since this is the binding site for fibronectin.

Briefly, LR21 cells were plated in DMEM with 10% serum at 70–80% density and allow to grow for 8 h. Cells were then washed twice with PBS. After being washed cells were incubated in cell dissociation medium to detach from the plates. Cell dissociation medium was harvested and centrifuged at 1000 rpm's for 3.5 min. Then, cells were plated at fibronectin-coated coverslips at 50% density in DMEM supplemented with 10% FBS. Cells were allowed to grow for up to 9 h. Plates were then divided into 4 groups and treated in the following manner: control group was treated with 50 μg/ml of BSA in DMEM supplemented with 10% FBS; second group was treated with 50 μg/ml of v4 antibody; third group was treated with 100 mg/ml of LZP and the fourth group was treated with combination of v4 antidoby and LZP at the same concentrations as they were used in separate treatments. Cells were kept with the proteins for 30 min and they were fixed with 3% paraformaldehyde. Cells were stained with cortactin (dil. 1:100) for 1 h. Subsequently, cells were washed with 1% bovine serum albumin (BSA) in phosphate buffered saline (BS) and stained with Texas-red mouse IgG (dil. 1:100). Staining of the cells was examined by confocal microscope.

LR21 cells were plated onto fibronectin substrata as outlined above for 8–12 hrs in serum free medium in the presence of IgG alone or anti-TAM antibody ("exon 4"). The supernatant culture medium was collected at that time and concentrated on an amicon filter that retains proteins of over 20 kDa. The retentate was suspended in loading buffer without mercaptoethanol or SDS-PAGE and run on a polyacrylamide gel impregnanted with gelatin. The gel was then incubated in PBS containing Mg++ and Ca++ buffer to permit collagenase activity at 37C for several hours. The gel was washed and stained with Coomassie Blue. Cleared areas indicate that collagenases released into the supernatant medium by LR21 cells is active.

Figure 24A:
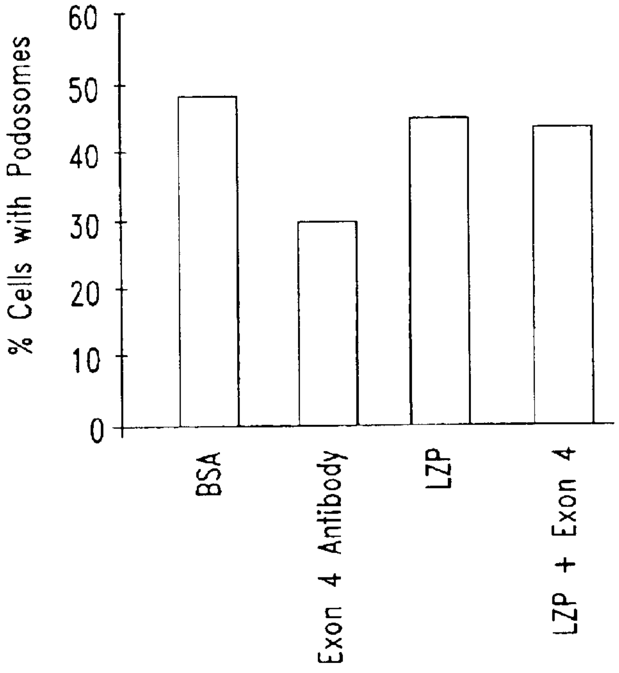
FIGS. 24A and 24B are a graph, and a blot, respectively, which show the effects of exon 4 antibody and leucine zipper neotide (LZP) on the formation of podosomes.

As shown on FIG. 24A, v4 antibody added to the medium competed for the RHAMM binding sites with fibronectin which resulted in reduced podosome formation by those cells up to 25% compared to the BSA-treated control. LZP and combination of LZP and v4 antibody didn't result in any changes in podosome number. The reason for this result could be the fairly high concentration of LZ peptide used in this experiment.

Figure 24B:
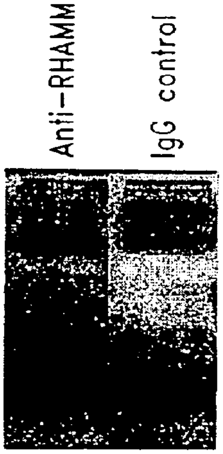
Figure 25A:
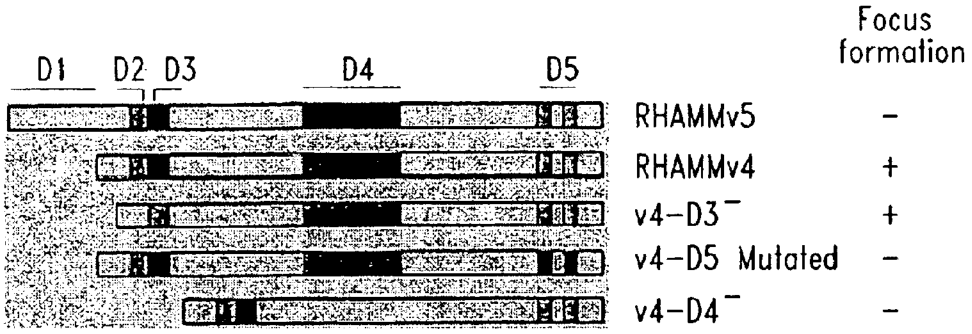
FIGS. 25A–D show that both v4 and v5 forms of RHAMM associated with erk1 in vivo and in vitro, but that only the short form stongly activates the erk kinase cascade.
Figure 25B:
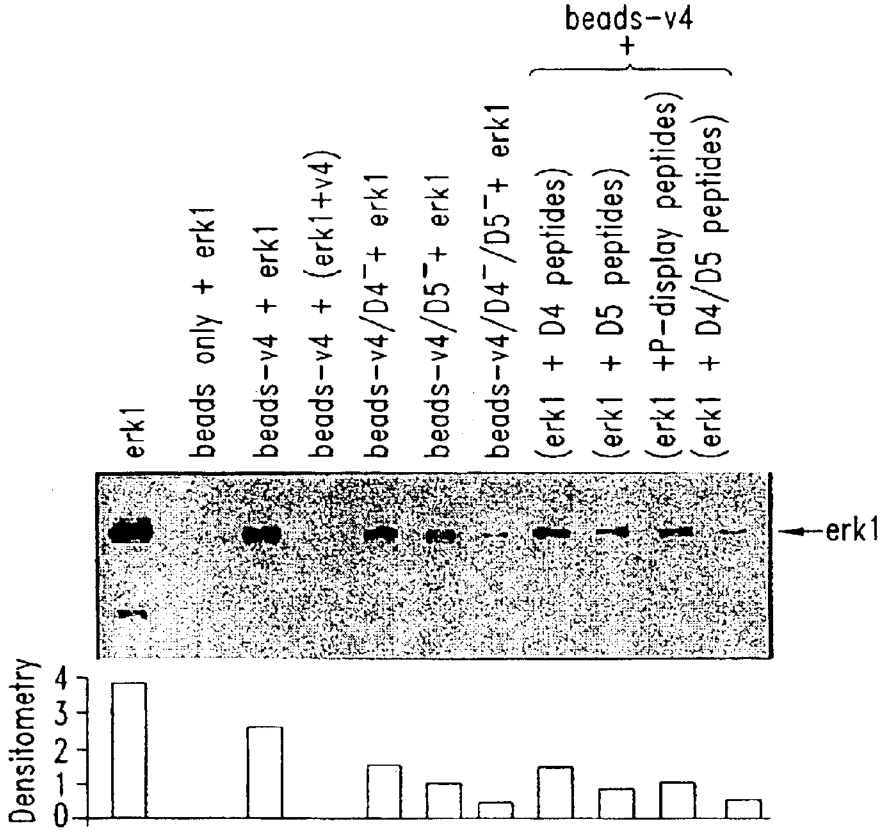
Figure 25C:
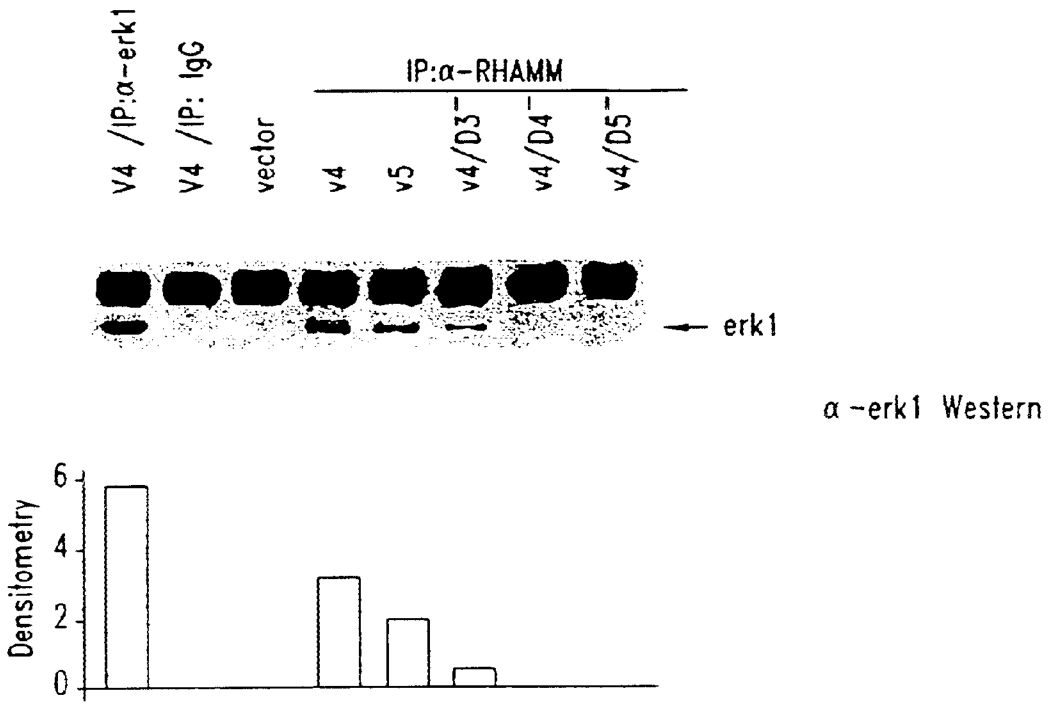
Figure 25D:
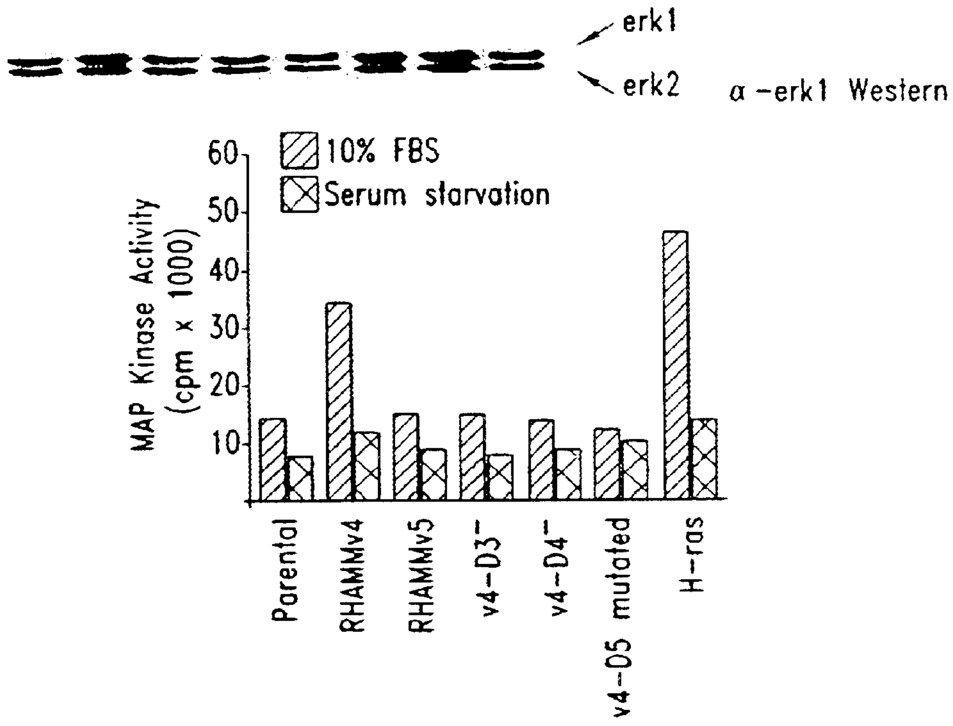

Based upon these results it is evident that RHAMM on the cell surface is required for the efficient podosome formation. Addition of v4 antibodies competed with fibronectin for the RHAMM binding sites which resulted in lower podosome formation by LR21 cells. The antibody also blocked release of collagenase (FIG. 24B), consistent with its blocking podosome formation.

Example 11

RHAMM V4 and Full Length RHAMMV5 Interact with Erk 1 Kinase

The most common murine RHAMM RNA transcript encodes a 95 kDa protein (referred to as "v5"). In addition, a shorter form of RHAMM may exist encoding a 73 kDa protein (v4), which lacks 163 N-terminal amino acids found in the longer RHAMM form. The objective of this experiment was to determine which form of RHAMM associates with erk and which particular domain of RHAMM is responsible for this interaction.

A. In vitro Binding Competition Assays.

Purified GST-RHAMM proteins were released from GST with trombin and RHAMM was coupled to Amino Link plus coupling gel (Pierce). After several washes with PBS, RHAMM-coupled beads were incubated with purified erk1 His-6tagged fusion proteins in binding buffer for 1 h at 4° C. on Nutator rotor. After several washes with cold binding buffer, the beads were boiled for 2 min in cold loading buffer, then proteins were separated on SDS-PAGE and transfer to nitrocellulose blots for western analysis. Anti-erk1 antibody (K23) was used to detect this kinase on western blots. For competition assays, 1 μg of purified erk1 His-6 fusion protein was incubated with 10 μg of soluble RHAMM protein for 1 h at room temperature, then incubated with beads-RHAMM for an additional 1 h. For peptide competition assays, 1 μg of erk1 His6 fusion protein was incubated with beads-RHAMM for another 1 h on a Rotator. Three different peptides were used in competition binding assay, D4: QEKYNDTAQSLRDVTAQLESV (SEQ ID NO:50), D5: KQKIKHVVKLKDENSQLKSEVSKLR-SQLVKRK (SEQ ID NO:51), and P-16 peptide: CST-MMSRSHKTRSHHV (SEQ ID NO:26).

B. Immunoprecipitation.

Parental 10T1/2 cells and transfected cell lines were plated at 50% confluence for 6–24 h and washed two times with cold PBS and lysed in a lysis buffer, containing leupeptin (1 mg/ml), aprotinin (0.2 TIU/ml) and dichloroisocoumarin (200 )uM). The lysates were centrifuged and equal amounts of protein (300–400 μg) from each sample were added to 2 μg of anti-RHAMM antibody (R3.2), and anti-erk-1 (K23) antibody. After 1 h of incubation at 4° C. on a Nutator rotor, 50 μg of a 50% solution of protein G Sepharose was added and incubated at 4° C. for an additional 1 h, then washed four times with lysis buffer.

C. Western Analysis.

Cells were plated at 50% confluence and grown for 6–24 h. Then, monolayers were washed with cold PBS, lysed in RIPA buffer and subjected to SDS-PAGE. Separated proteins were transferred onto nitrocellulose membranes (BioRad) using a Transfer buffer. Non-specific binding sites were blocked with 5% defatted milk in Tris buffer. RHAMMv4 antibody was prepared against following sequence: VSIEKEKIDEK (SEQ ID NO:50). RHAMMv5 antibody was prepared against following sequence: QERGTQD-KRIQDME (SEQ ID NO:21). Membranes were washed three times with TBST, then incubated with horseradish peroxidase-conjugated goat anti-rabbit IgG (1;10000) for 30 min at room temperature. Bound antibody was visualized by chemiluminescence (ECL). The densitometry was performed with a Multi-Analyst program (Bio-Rad). To determine antibody specificity, anti-RHAMM antibodies were incubated with beads-linked with RHAMM protein (1 μg antibody/20 μl beads) for 1 h at 4° C. on a Rotator, and then centrifuged for 5 min. The supernatant was used to probe membranes.

Results are shown in FIG. 25. Briefly, FIG. 25B shows erk1 binding to v4 and v5 obtained in vitro, whereas FIG. 25C shows similar results in vivo. The Bottom Western blot represents total cellular erk kinase and densitometery was calculated as the ratio of total cellular erk versus erk associated with RHAMM. Both RHAMMv5 and v4 associated with erk1 kinase. RHAMMv4 more strongly activates erk kinase than RHAMMv5 (FIG. 25D), which contains all of the domains of v4 but in addition N-terminal sequence that negatively regulates the functions of the activating D2–5 domains (FIG. 25B). The presence of mutations in both D5 or D4 domains or in competition assays the presence of both D4 and D5 peptides, reduced erk1 binding to v4 by 90% (FIG. 25C), suggesting key roles of those domains in binding.

Thus, in summary both forms of RHAMM (v4 and v5) associate with erk1 in vivo and in vitro but only the short form strongly activates the erk kinase cascade. The hyaluronan binding domains (See FIGS. 25A, D5) and a repeated sequence (D4) are required for binding of erk1 to RHAMM. However, both D3 (encoding the TAM domain) and D2 (encoding the leucine zipper) are required for activation of erk kinase although they are not involved in the binding of erk1 to RHAMM.

Example 12

HA Binding Domains of RHAMM Peptides and Antibodies Thereto for Affecting a Response-to-Injury Process FIG. 26 illustrates that HA binding peptides including artificial mimics of hyalauronan binding domains of RHAMM are able to block cell motility in podosome forming cells while scrambled peptides do not. FIG. 26A provides the sequence of several artificial HA binding peptides of the formula BX7B (SEQ ID NO:28) discussed above. Panel B shows that each of these peptides are able to block cell motility when administered to cells. Panel C shows that an HA binding peptide according to one of the general structures provided in SEQ ID NOs: 1–5, and more particularly having one of the structures provided in SEQ ID NOs: 6–10 is even more effective in blocking cell motility and that a scrambled version of this peptide is not.

Example 13

HA-Binding Peptide Mometic (P-16) and RHAMM Sequence Peptide (423–432 AA) Inhibit Migration of Human Fibroblast Wound healing is the response to injury. By day three after the wounding, fibroblasts appear in the fibronectin—fibrin framework and initiate collagen synthesis. Fibroblast proliferate in response to growth factors present on the wound site and this complex series of cellular and inflammatory processes resulting in deposition of connective tissues and its remodeling into the scar tissue. The fibroproliferative response is accompanied with wound contraction and fibrosis due to the presence of myofibroblasts and to the enhanced production of collagen. In adult humans, the extracellular matrix is remodeled to sustain and direct the cellular changes and to restore the tissue integrity. Such exuberant healing responses often lead to tissue fibrosis and contraction commonly referred to us as scarring. Fibrosis of adult human tissue is a serious clinical problem that results in malfunction of tissue due to, for example: formation of intraabdominal adhesions, cirrhosis of liver, failure of anastomoses as well as adhesions following injury.

In animal models of skin wounding, expression of an active (73 kDa) RHAMM form is transiently increased early after injury and this elevated expression occurs in most cell types present in the wound site. A specific domain within RHAMM (D5) that is responsible for interactions of hyalauronan with cell surface RHAMM and erk1 binding to intracellular RHAMM was identified and utilized to develop a peptide mimetic reagent (p-16), which blocks function of cell surface RHAMM. Another RHAMM sequence consisted of 9 amino acid residues (423–432) which was also tested in the following experiment.

The objectives of following experiment were to test the abilities of two RHAMM synthetic peptides to inhibit migration of human fibroblasts. One experimental model tested a 16 amino acid RHAMM peptide mimetic (P-peptide) to inhibit migration of Human Foreskin Fibroblast (HFF) through the wound gap. Another peptide consisted of 9 amino acids (RHAMM sequence, aa. 423–432 was also tested in regards of cell locomotion of human fibroblasts.

Experiment A.

Human fibroblasts were seeded at $5\times10^5$ cells/well in 6 well plates using α-MEM supplemented with glucose and 10% fetal bovine serum (FBS). After being 6 hours in the culture (80–90% confluency), cells were injured with the single edge cell scraper (one injury/dish). Cells were washed twice with PBS and treated with two different concentrations of P-peptide (10 $\mu$g and 100 $\mu$g) for 15 h. Untreated cells served as control. Following 15 hours of incubation, images were taken using a 5× modulation objective (Zeis, Germany) attached to the Zeiss Axiovert 100 inverted microscope equipped with Hoffman Modulation contrast optical filters (Greenvale, N.Y.). The number of migrated cells in each image was counted choosing the ~70% of the middle of each injury. Statistically significant ($P<0.05$) differences between means were assessed by the unpaired Student's t-test method, using Microsoft Excel '97 software.

Experiment B.

To quantify the effect of RHAMM sequence (aa. 423–432) to alter velocity of cell locomotion human fibroblasts were seeded on T-12.5 fibronectin coated flasks using α-MEM supplemented with glucose and 10% FBS. $2.5\times10^4$ cells were seeded and cells incubated for 4 hrs at 37° C. After incubation time cells were treated with increasing concentrations of RHAMM sequence peptide aa. 423–432, 0.1, 1.0, 5.0, 10 and 50 ng/ml) and cell locomotion was monitored over the period of 16 hrs on 37° C. using 10× modulation objective (Zeiss, Germany) attached to a Zeiss Axiovert 100 inverted microscope equipped with Hoffman Modulation contrast optical filters (Greenvale, N.Y.). Cell images were captured with a charge coupled device (CCD) video camera module attached to a Hamamatsu CCD camera controller. Motility was assessed using Northern Exposure 2.9 image analysis software (Empix Imaging, Mississauga, Ontario). Nuclear displacement of 7–10 cells was measured and data were subjected to statistical analysis. Statistically significant ($P<0.05$) differences between means were assessed by the unpaired Student's T-test method, performed using Microsoft Excel "97 software.

Figure 27:
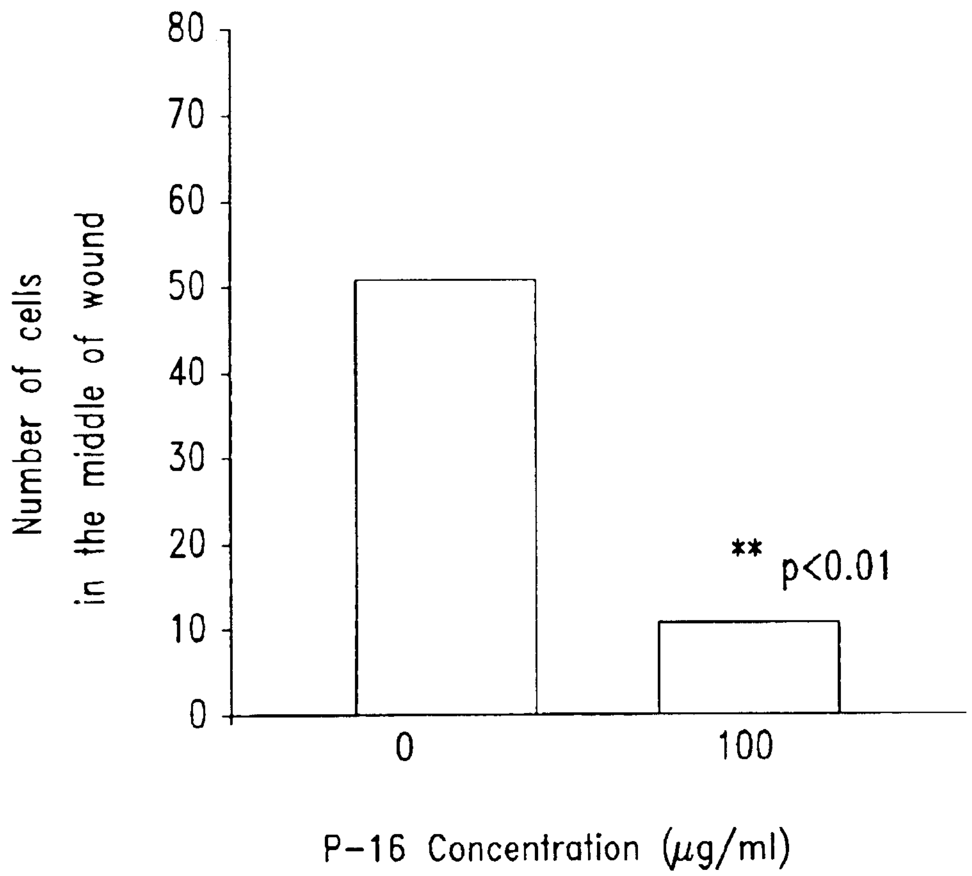
FIG. 27 is a bar graph which shows that treatment of injured cells with P-peptide (CSTMMSRSHKTRSHHV—SEQ ID NO:26 inhibits migration of human foreskin fibroblast (HFF) cells.
Figure 28:
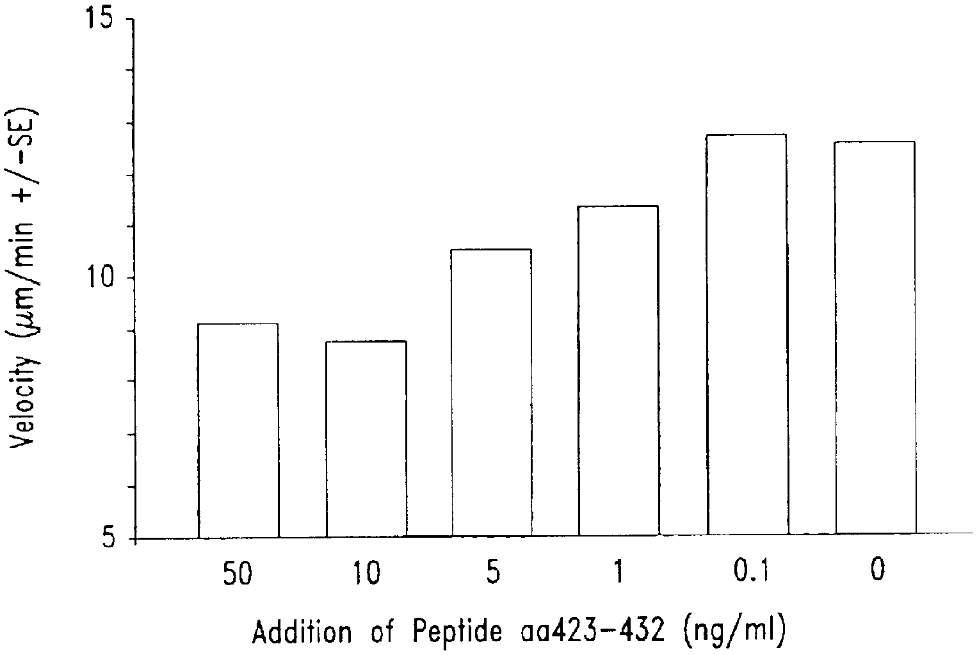
FIG. 28 is a bar graph which shows velocity of cells after addition of peptide amino acid residues 423–432 (SEQ ID NO: 24).

Results are shown in FIGS. 27 and 28. Briefly, FIG. 27 shows that treatment of injured cells with 100 $\mu$g/ml of P-peptide inhibited migration of HFF cells approximately 4 fold compared to control cells ($P<0.01$). Lower concentration (10 $\mu$g/ml) of P-peptide didn't have any effect. As shown in FIG. 28, different concentrations of RHAMM sequence (aa. 423–432) progressively inhibited migration of human fibroblasts up to 40%.

Both treatments were successful in inhibition of cell migration in vitro. These important data suggests potential implementation of the both P-peptide and RHAMM sequence aa. 423–432 peptide in prevention of tissue contraction and fibrosis and ultimately prevention of abnormal tissue remodeling and scaring.

Example 14

Fibroblasts from RHAMM Knockout Mouse Produce Two Times Less MMP's Than Wild Type MMP expression is involved in a wide variety of inflammatory diseases and cancers. This experiment investigates whether fibroblasts which are obtained from RHAMM knockout mice have altered MMP production.

Briefly, embryonic stem cells (ES) were transfected with antisense cDNA that recombined with the RHAMM gene, resulting in recombination and a genetic deletion of the RHAMM gene. The ES cells were injected into mouse blastocysts, and placed into pseudo-pregnant mice. Mice from the resultant litters were crossed and examined for the presence of a genetic deletion, in order to determine germ line transmission. Founders were identified and homozygotes obtained.

Embryos from normal and knockout mice were taken out at the $13^{th}$ day of their intrauterine development. Tissue was cut and tripsinized in the incubator at 37° C. for 10 min. Cell suspension was pipeted up and down several times in order to release fibroblasts from the tissue. Then, fibroblasts were plated on the Petri dishes (one embryo per one Petri dish). Cells were grown for 2 days before first passage was done. Five passages were done before actual experiment was performed.

For experimental purposes, fibroblasts were plated on 6-well dishes, normal ones and fibronectin coated, both at the 70% confluency. Cells were grown in DMEM medium for 2 h. After 2 h, medium was changed to DMEM without serum and cells kept in starvation medium for 24 h. Then, medium was taken out and the amount of gelatinase released into medium measured by zymografic analysis. Briefly, DMEM medium taken out from plates was run on overnight in a cold room (+4° C.) on 10% acrylamide gel containing 1 mg/ml of gelatin. Then, gel was washed in TritonX-100 for 1 h and subsequently incubated in a buffer on 37° C. for 24 h in order to develop zymogram. Then, gel was stained with commassi blue whereas areas with MMPs were left unstained. Intensities of unstained bands were measured and presented as relative numbers.

Figure 29:
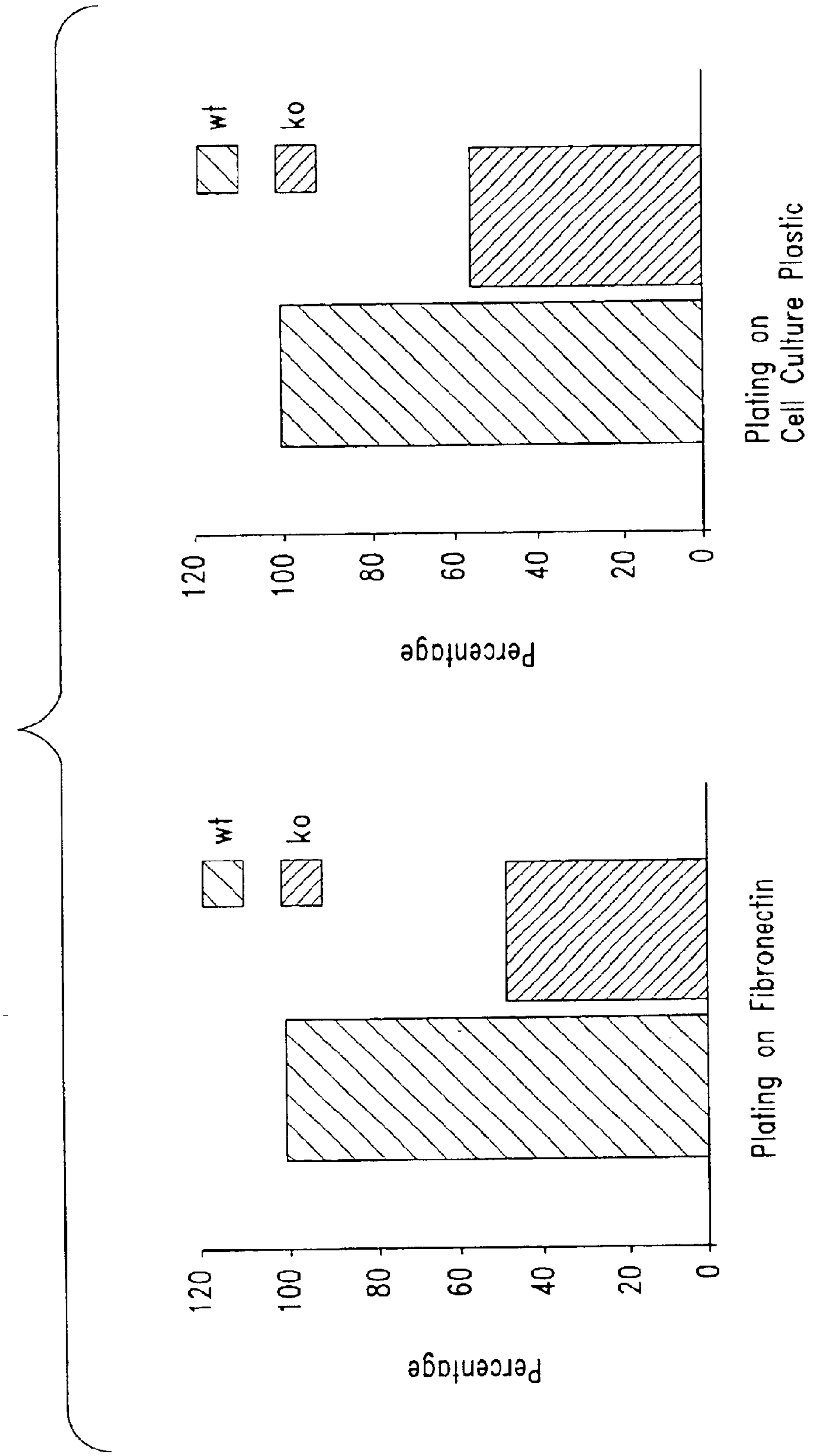
FIG. 29 is two bar graphs which, show MMP release from knockout fibroblasts compared to normal ones (on fibronectin vs. cell culture plastic).

Results are shown in FIG. 29. Briefly, MMP release from knockout fibroblasts is approximately 2.5 times lower compared to normal ones.

Thus, it is evident that RHAMM expression regulates production of MMPs. Absence of RHAMM in knockout fibroblasts resulted in marked decrease in MMP production.

Example 15

RHAMM Influences Erk Phosphorylation upon PDGF Treatment in Mouse Primary Fibroblasts The purpose of this experiment was to investigate if erk phosphorylation is decreased in primary fibroblasts of the RHAMM knockout mouse.

Briefly, mouse normal and RHAMM knockout fibroblasts are plated in DMEM medium and starved overnight. Medium was changed and two different concentrations of PDGF added. After 10 min cells were lysed in RIPA (RIPA comprises 150 mM Nacl, 1.0% Igepa1CA-630, 0.5% sodium deoxycholate, 0.1% SDS, 50 mM Tris, pH 8.0) buffer. Western blot analysis was done and proteins separated by SDS-PAGE. Bands were visualized by phospho-specific erk antibody. Subsequently, blot was stripped and reprobed with erk antibody.

Figure 30:
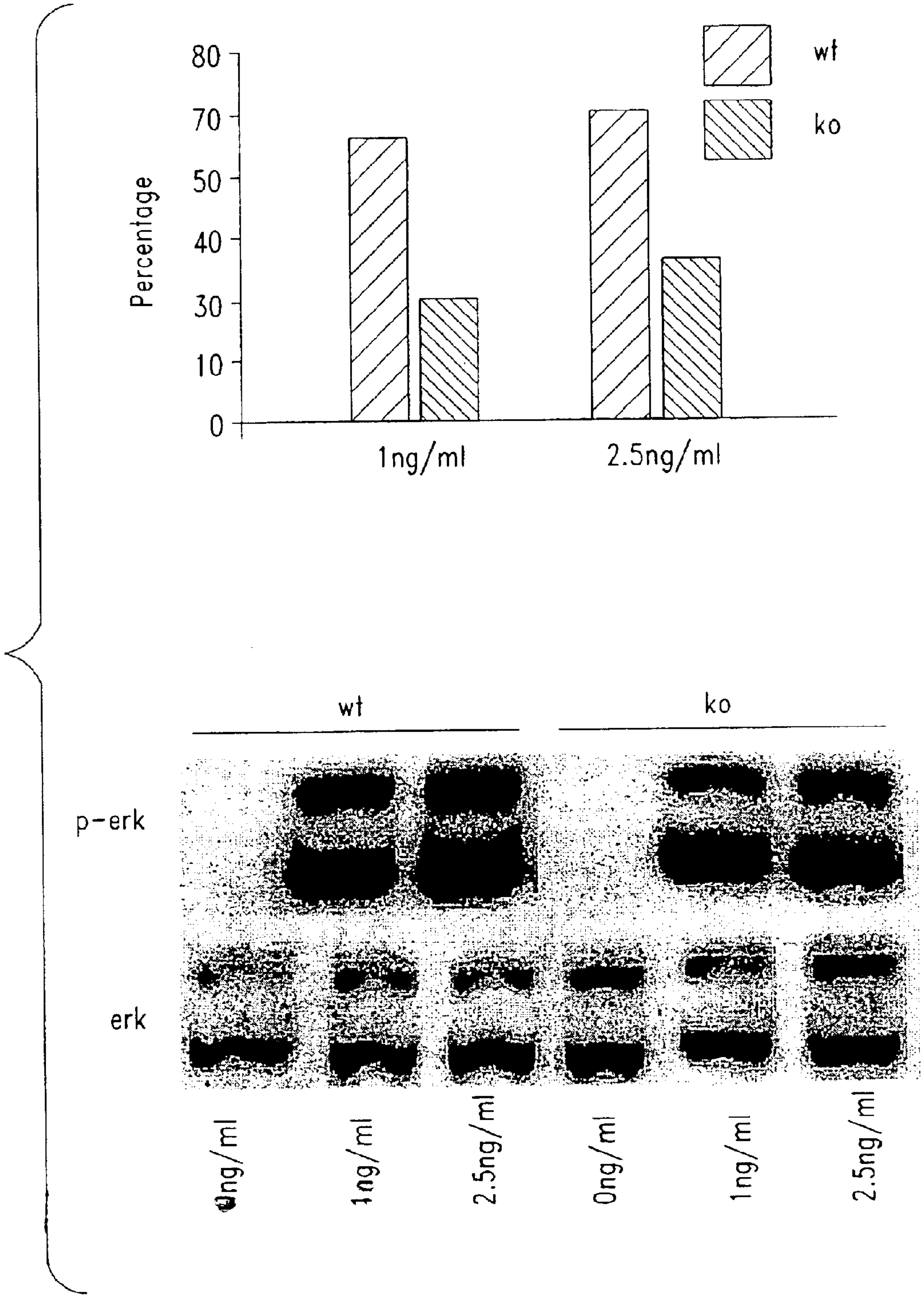
FIG. 30 is a bar graph and blots which show that erk phosphorylation is influenced by RHAMM expression.

Results are shown in FIG. 30. Briefly, erk phosphorylation is influenced by RHAMM expression: knockout mice exhibited at least two folds lower phosphorylation of erk1 isoform compared to wild type. PDGF concentration of 1 ng/ml produced the largest decrease (2.3 fold) in erk phosphorylation (FIG. 30). Thus, deficiency in RHAMM expression in knockout fibroblasts down regulates the capability of PDGF to activate erk pathway.

Example 16

Fibroblasts Isolated from RHAMM Knockout Mouse Locate at Significantly Lower Rate than Wild Type Fibroblasts This experiment investigates the impact of lacking RHAMM expression on cell migration in mouse knockout fibroblasts.

Briefly, knockout and wild type mouse fibroblasts were plated in 100 mm Petry dishes (normal or gelatin and fibronectin coated) and grown in normal DMEM medium. Cells were plated sparsely and left for 2 h to attach, spread and start to migrate. Two hours after plating, cells were checked for migration and pictures were taken from the same spot every 15 min. The images were overlaid and cell migration analyzed by measurement of the migration distance.

Figure 31:
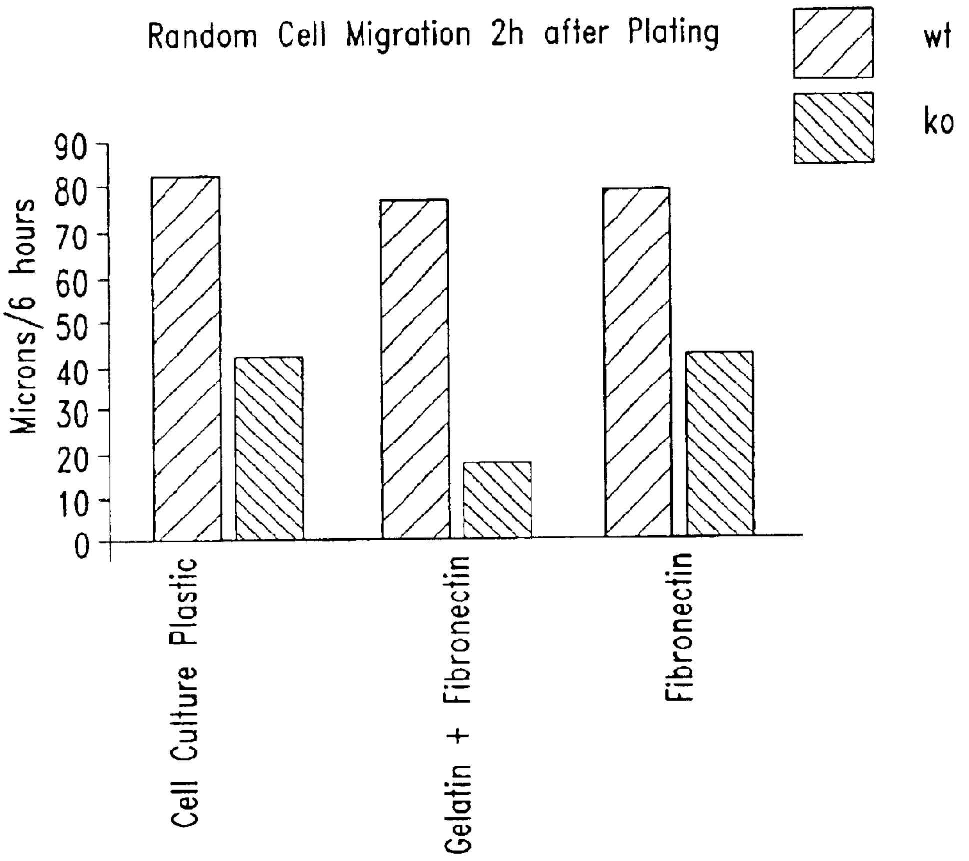
FIG. 31 is a bar graph which shows knockout fibroblasts have decreased motility compared to wild-type fibroblasts.

Results are shown in FIG. 31. Briefly, knockout fibroblasts have decreased cell motility compared to wild type by two folds. Combination of gelatin and fibronectin coating seem to potentiate slower migration of mouse RHAMM knockout fibroblasts. Thus, it is evident that mouse RHAMM knockout fibroblasts migrate at the slower rate compared to wild type cells. Attenuation of cell migration is between 2 to 4 fold.

Example 17

Administration of RHAMM Peptides or Antibodies Inhibit Response-to-Injury Processes Associated with Macrophages in Injured Lung Tissue Clinical diseases characterized by lung inflammation include emphysema, asthma, cystic fibrosis, new-born lung disease involving chronic respiratory distress syndrome, and the acute respiratory distress syndrome that affects accident victims. Local inflammatory responses that recruit macrophages into the lung result in destruction of alveolar type II cells, which make the surfactant responsible for normal lung inflation. The infiltration of macrophages and abnormal local tissue responses result in further tissue destruction and disease. This pathological sequence results in improper lung expansion. A common response to injury in mammalian tissue is increased motility of macrophages and macrophage accumulation near a wound site.

Figure 32:
FIGS. 32*a*, 32*b*, 32*c* and 32*d* are photographs of bleomycin-induced lung fibrosis.

As described in more detail below, the RHAMM peptide mimetics prevent these pathological events, particularly recruitment and activation of macrophages, from occurring following bleomycin-induced lung fibrosis (FIG. 32). In particular, the infiltration of inflammatory cells and local responses such as fibrosis is completely absent with treatment. Yet, no toxicity was observed in the animals even at very high concentrations. Therefore, these reagents should be effective for treating lung diseases that involve recruiting macrophages and inflammatory cells, as well as fibrosis.

Figure 33:
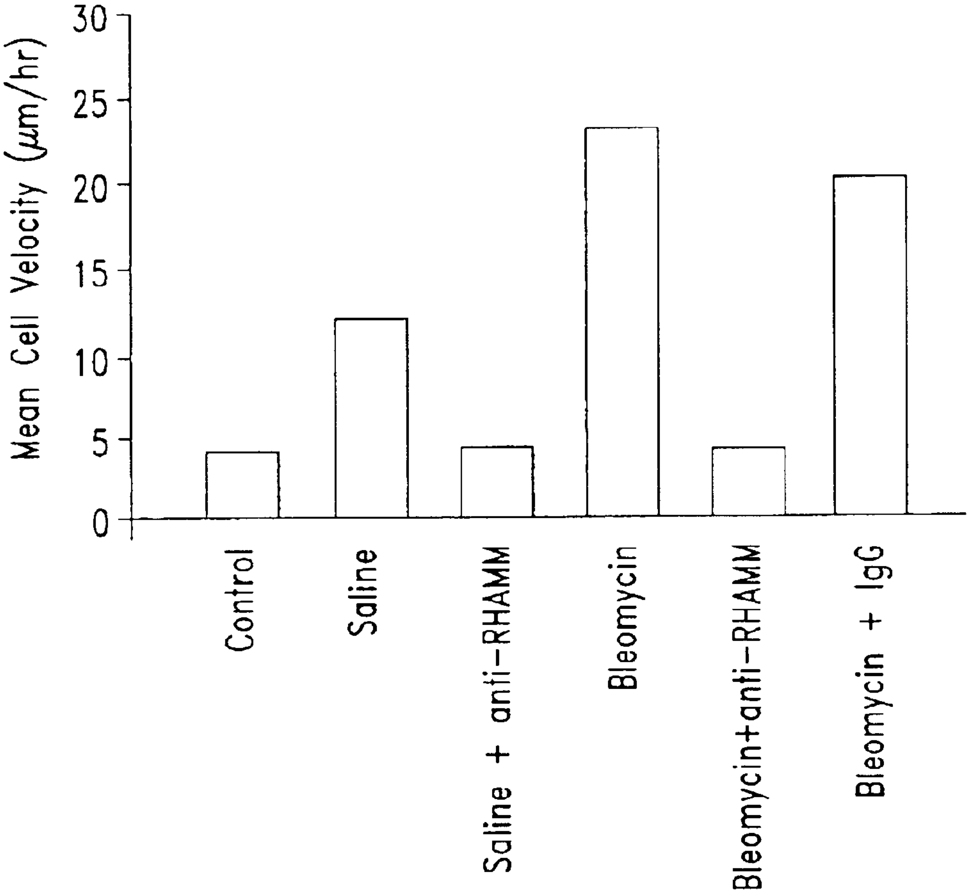
FIG. 33 is a bar graph which illustrates that a significant increase in motility of macrophages from both bleomycin and salinie-treated animals.

This experiment shows that macrophage responses are inhibited by administration of antisera to RHAMM peptides. More specifically, FIG. 33 illustrates that a significant increase occurs in the motility of macrophages from both bleomycin and saline-treated animals at four days after intratracheal instillation (*$p<0.01$ versus control; $p<0.01$ versus saline and control). Normal rabbit IgG had no effect on macrophage motility, but anti-RHAMM peptide aa antiserum inhibited macrophage motility from both saline—(#$p<0.01$ versus saline) and bleomycin-treated ($p<0.01$ versus bleomycin, saline and bleomycin+normal IgG) animals to levels observed in macrophages from untreated healthy control animals. Values represent mean and standard errors of five animals studied for each condition with mean velocities calculated.

Figure 34:
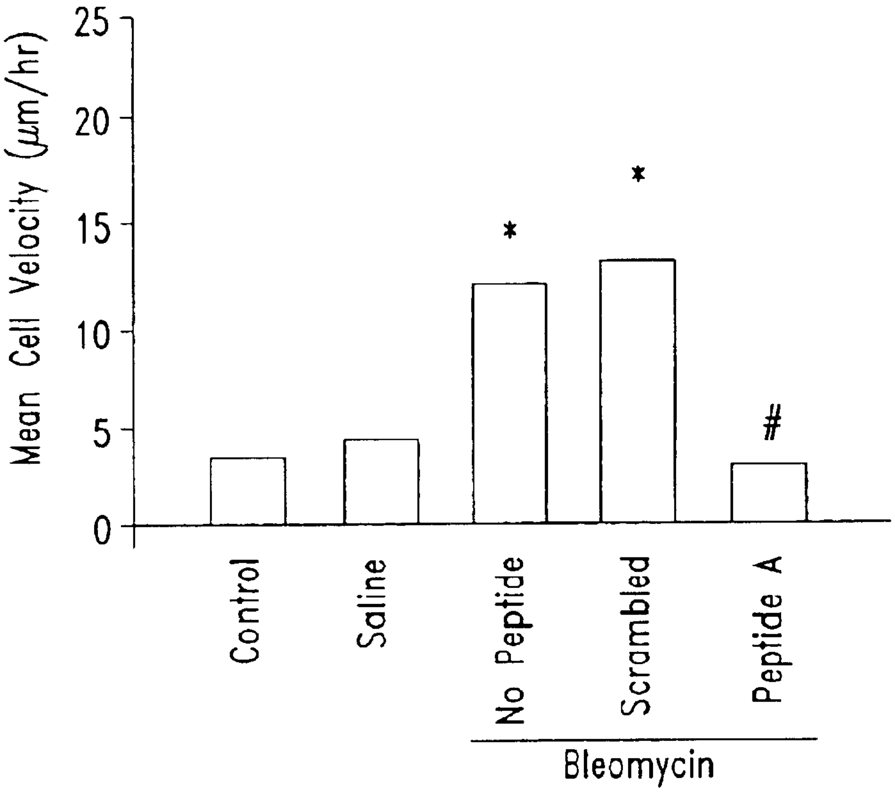
FIG. 34 is a bar graph which illustrates the motility of bronchoalveolar lavage (BAL) cells four days after injury in response to administration of RHAMM peptides.

FIG. 34 illustrates motility of BAL cells four days after injury in response to administration of RHAMM peptides. Macrophages from bleomycin-treated animals showed increased motilities as compared to those from control and saline animals (*$p<0.001$). Animals pretreated with Scrambled Peptide A showed the same motility as macrophages obtained from animals injured with bleomycin. However, macrophages from animals treated with Peptide A prior to bleomycin-induced injury showed significantly lower cell locomotion than either bleomycin-injured or scrambled peptide treated controls (#$p<0.001$). Values represent mean and standard error with three animals studied for each condition and at least 20 cells tracked per animal studied.

Based on these findings, peptide mimetic and antibody formulations can be utilized in the treatment of a variety of "response to injury" indications, including for example, emphysema, asthma and the chronic respiratory distress syndrome associated with newborn lung disease.

Example 18

Figure 35A:
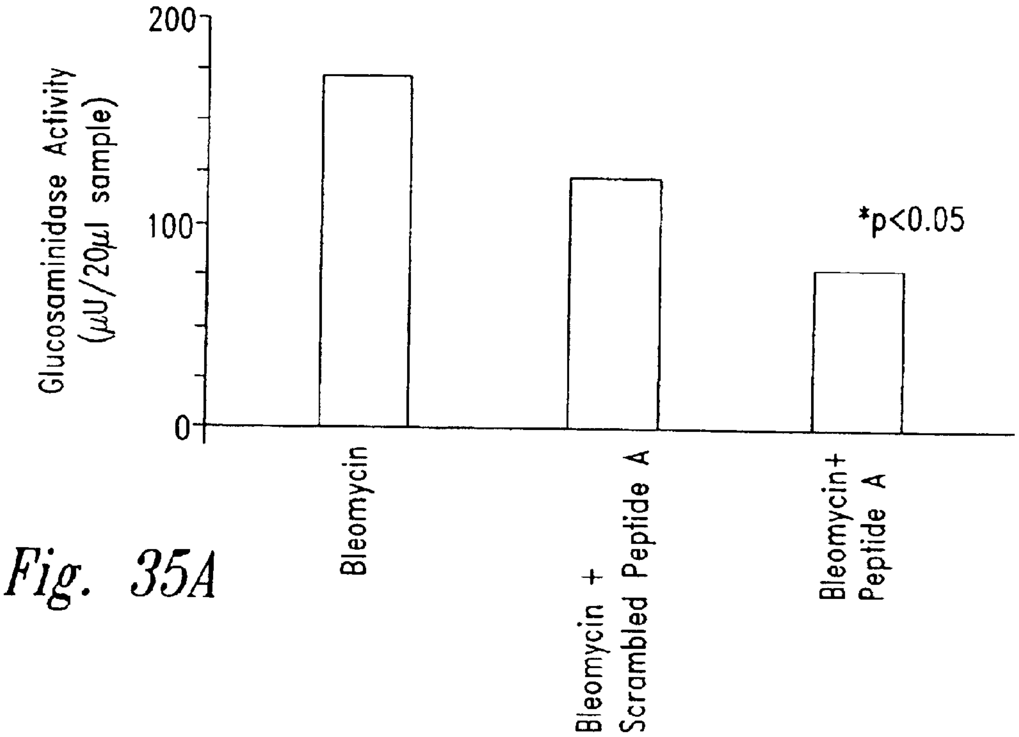
FIG. 35 is a bargraph, and a blot which shows the ability of HA binding peptides to inhibit firbosis.

Administration of HA Binding Peptides Inhibit Response-to-Injury Processes Associated with Fibroses in Injured Lung Tissue Increased N-acetyl-β-glucosaminidase activity is a known marker for fibrosis in lung tissue. FIG. 35A shows in vivo effects of a HA-binding (Peptide A) on N-acetyl-β-glucosaminidase activity of BAL cells obtained 7 days after injury.

Briefly, bleomycin injury results in an increased glucosaminidase activity (*$p<0.01$ versus controls and saline animals). Scrambled Peptide A had no effect on the glucosaminidase activity whereas Peptide A significantly decreased glucosaminidase activity (#$p<0.05$ versus bleomycin alone and bleomycin+scrambled peptide A). Values represent mean and standard error with five animals studied for each condition.

Figure 35B:
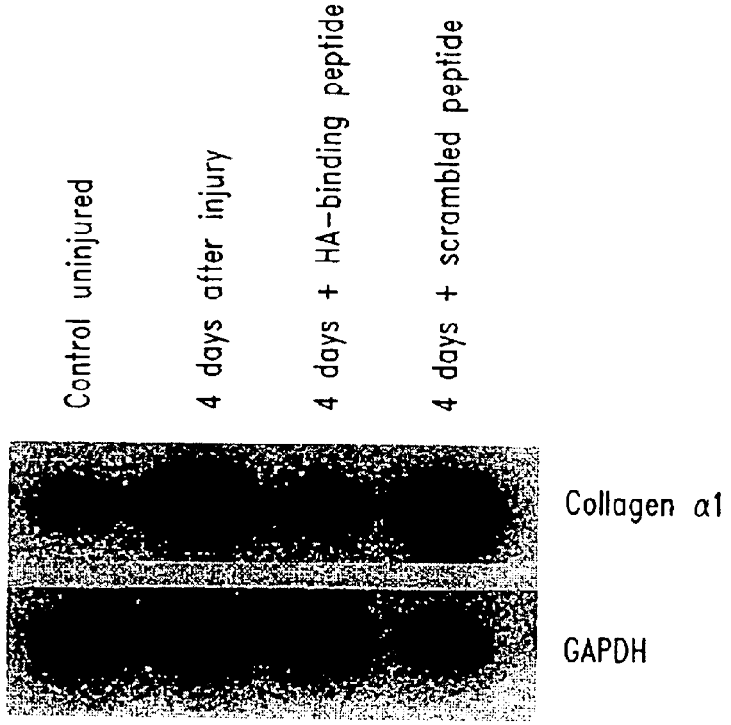

FIG. 35B illustrates that mRNA of collagen type 1a in lungs harvested 4 days after injury is reduced in response to administration of HA binding Peptide A. Collagen type 1a is common indicator of fibrosis in lung tissue injury models as used throughout this invention. An increase in collagen type 1a mRNA was observed by 4 days after injury in control tissue, however, this increase was completely inhibited by administration of HA binding Peptide A, whereas scrambled Peptide A had no effect on the mRNA expression levels for this collagen. The data shown are representative of three independent experiments.

Figure 36:
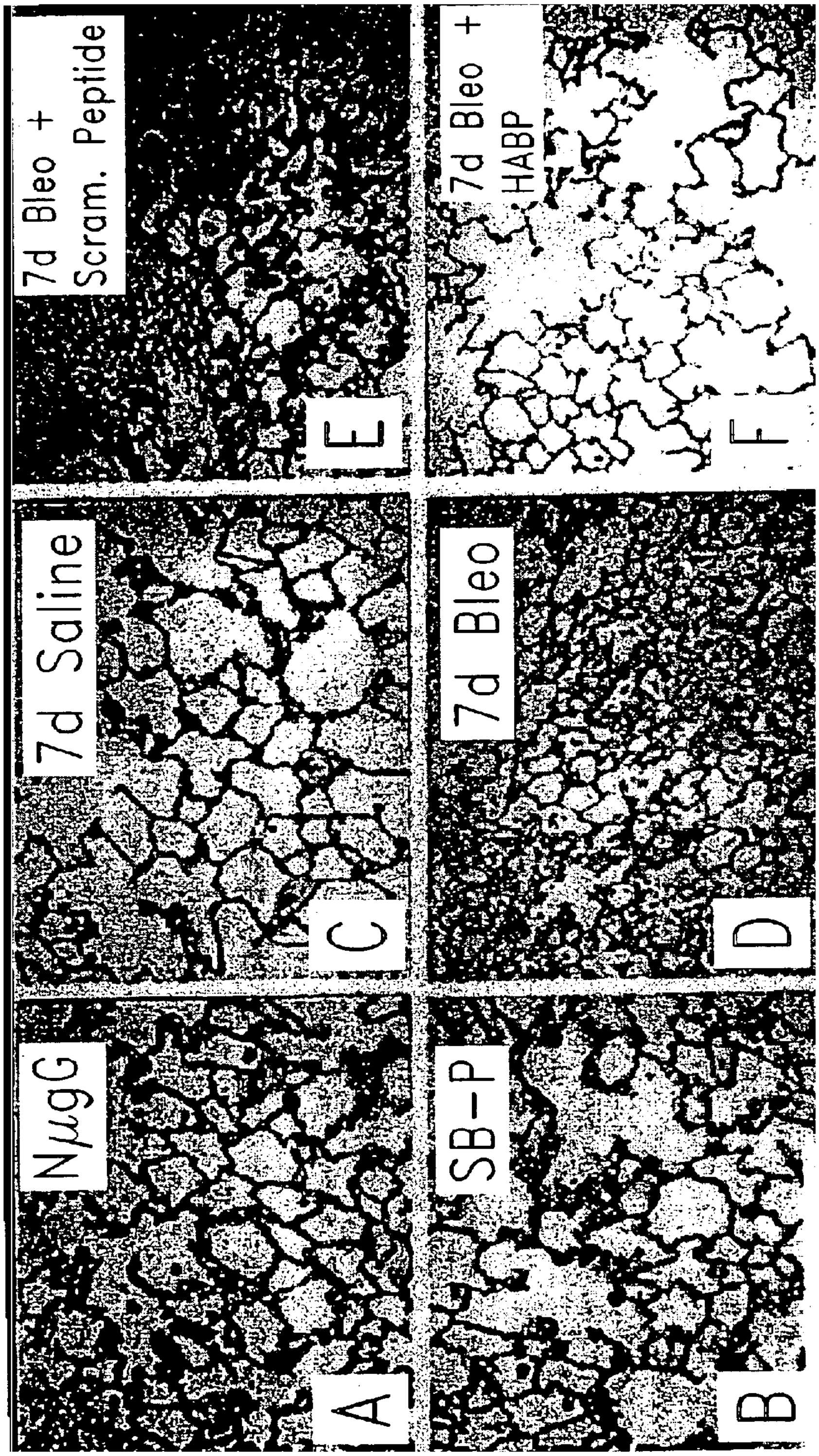
FIGS. 36*a–f* are a series of photographs from a histological analysis of lung tissue.

The ability of HA binding peptides to inhibit fibrosis is further illustrated by histological analysis. FIG. 36 are micrographs from a histological analysis of lung tissue treated with and without HA binding Peptide A after bleomycin injury. Panels (a–c) show tissue after treatment with saline alone, and panels (d–f) show tissues injured by bleomycin treatment. Panel (d) shows a fibrotic morphology in the presence of bleomycin alone while panel (e) shows the morphology in the presence of bleomycin and scrambled RHAMM peptide. In contrast, panel (f) shows that injection of bleomycin-treated animals with the sense RHAMM HA binding Peptide A results in a normal lung architecture despite the injury caused by bleomycin.

Example 19

Expression of RHAMM in Different Cells Present in Synovial Fluids Isolated from RA Patients This experiment determines which cell type from synovial fluids of rheumatoid arthritis (RA) patients express RHAMM isoforms.

Briefly, samples of synovial fluids from different RA patients were centrifuged at 1600 rpm's for 10 min and pellets resuspended in 2–5 ml of Blocking buffer (BB, 1% human serum albumin in Hank's buffered salt solution (HBSS). After counting, $10^6$ to $2.5\times10^6$ cells per ml, were taken into each tube. Cells were washed once with 1 ml of BB and the pellets resuspended in 100 $\mu$l of BB. First antibody was added (dil. 1:100) and samples incubated for 30 min on ice. Along with the first antibody 20 $\mu$l of specific markers for certain cell type present in the synovial fluid were added, as well. Rabbit IgG was used as a control. Samples were washed twice with 1 ml of BB. After washing, secondary antibody was added (fluorescein isothiocyanate (FITC), dil. 5:100) and cells kept 30 min on ice. Again, samples were washed twice, each time with 1 ml of BB and fixed with 0.3 ml of 0.5% paraformaldehyde. Immunofluorescence was determined by flowcytometer.

Results are shown on FIG. 37. Briefly, the majority of cells present in synovial fluid are neutrophils. Macrophage/monocyte cells are present as 5–10% of cells and T cells are also present as a minority. Macrophage/monocyte cells exhibited the highest RHAMM expression. In some cases the number of exon4-positive cells was as high as 99.8%. A similar pattern was observed in neutrophil populations but the percentage of positively labeled cells was between 54.6% and 99.3%. T cells also express RHAMM isoforms, although to a lesser extent compared to the other two cell types.

In summary, all tested RA patients expressed RHAMM on the surface of cells present in synovial fluid. The most abundant cell type is neutrophils. In all tested patients more than 50% of neutrophil cell population was X4-positive. Significant number of macrophages expressing x4 was uncovered: in all tested RA patients more than 75% of macrophage/monocyte population was labeled x4 positive.

Example 20

RHAMM x4 and RHAMM R3.8 are Present in the Synovium Tissue Sections from RA Patients Rheumatoid arthritis is the most prevalent type of inflammatory arthritis, affecting 1.5% of the human population. RA is characterized by synovial hyperplasia, destruction of articular cartilage and bone and macrophage infiltration into synovial joints. Cytokines like IL-1 are present in increased levels and they play a major role in production of MMPs, such as collagenase and gelatinase.

In order to investigate if there is any RHAMM expressed in the synovium tissue of RA patients, immunohistochemistry was done. Briefly, pannus formed from synovium tissue was isolated and embedded in wax. Three microns tissue sections were obtained and slides were heated on 58° C. for 30 min. To deparafinized slides the following procedure was done: tissue sections were washed in xylene three times each four minutes. After washing in hylene, slides were washed in 100% ethanol two times each three minutes. Additionally sections were washed in 96% ethanol the same amount of time. Slides were then incubated in $dH_2O$ two times each three minutes and once in PBS. Tissue on the slides was then marked with barrier-pen. The activity of endogenous peroxidase was blocked with 0.3% of hydrogen peroxide for 10 min. Slides were washed with dH20 two times each 3 minutes and with PBS two times each 5 minutes. Unspecific binding was blocked with 1% bovine serum albumin (BSA) in PBS at 37° C. for 30 minutes. Different dilutions of RHAMMv4 and RHAMM R3.8 antibodies were made: 1:100, 1:50, 1:25) in 1% BSA-PBS and incubated with tissue samples overnight at +4° C. Two tissue sections served as controls and they were incubated with either rabbit IgG (at the same dilution as the antibodies) or with vehicle which was 1% BSA PBS, without primary antibody. After incubation with primary antibodies, slides were washed with PBS three times, minutes each. Consequently, biotinylated antirabbit IgG was added and slides kept at room temperature for 1 hour (dil.1:200 in BSA-PBS). Slides were again washed with PBS three times each 10 minutes. Additionally, Avidin-biotin avidin peroxidase conjugate (ABC) reagent was premixed and incubated with slides at room temperature for one hour. Slides were washed with PBS three times each 5 minutes. After washing, diaminobenzidine (DAB) solution was premixed and incubated with slides for 5 minutes at room temperature. Samples were washed with $dH_2O$ three times each time 5 minutes and counterstained with hematoxylene for 1–2 minutes. Samples were washed with regular water and dehydrated. For dehydration similar procedure was done as for deparafinization only this time steps were done backwards. Slides were mounted and left to dry overnight.

Figure 38:
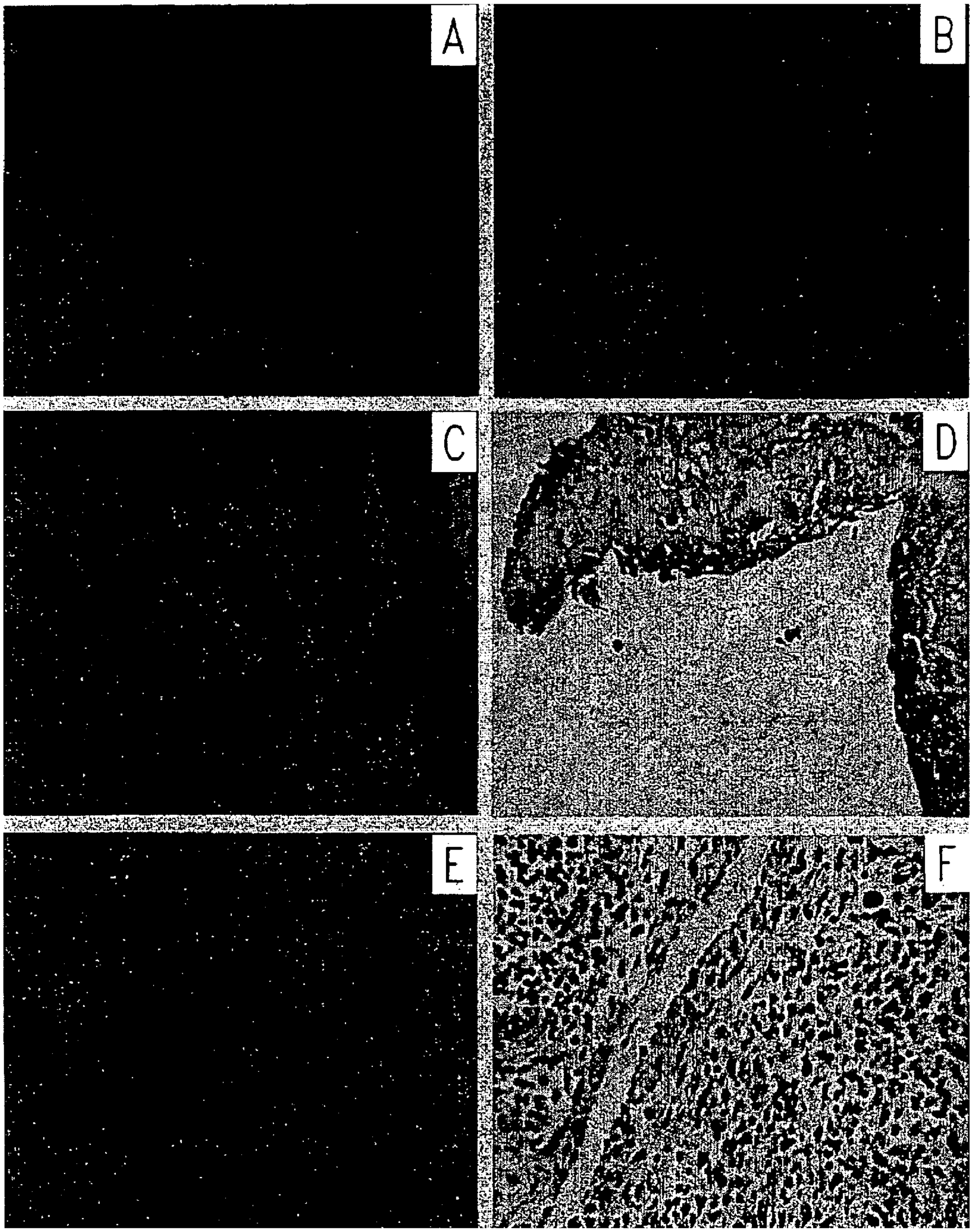
FIGS. 38A–F are a series of photographs of stained RA tissue.

Results are shown in FIG. 38. Briefly, synovium tissue isolated from joints of RA patient was positively stained (brawn staining) with RHAMM exon4 (pictures A and B) and RHAMM R3.8 (pictures C and D). Areas of synovial lining cells are enriched in RHAMM staining which are most likely macrophage cell type, although other cell types in the RA synovium also express RHAMM (pictures A, B, C and D). Controls BSA (picture E) and rabbit IgG (picture F) are unstained.

Hence, it is evident that RHAMM is present in high levels in human arthritic joints.

Example 21

RHAMM Peptide Mimetic Inhibits Progression in Existing Multiple Sclerosis (MS) Model Multiple sclerosis (MS) is a major human neurological disease in North America and Western Europe. Although the mechanism by which demyelination takes place in MS is not fully understood, it appears that the persistence of high levels of improperly assembled myelin which is prone to destruction is a leading cause for on set of the disease. Creation of ND 4 model of transgenic mice (Mastronardi et. al. J. Neurosci Res (93) Vol. 36 pp. 315–324) provides useful tool for investigation of the possible mechanism involving destabilization of the myelin membranes and appearance of distinctive features of MS disease.

The purpose of this experiment was to attenuate clinical signs of demyelination in MS by inhibition of function of the cells involved in pathological processes.

Briefly, transgenic mice (ND 4) bearing 70 copies of the transgene for DM20, a myelin proteolipid protein, were utilized for assignment of scores based upon clinical signs of demyelination. Clinical signs which were assessed included general shaking, seizures, head jerk, hind-limb and tail shiver, unsteadiness, wobbly gait and limp tail. Within each sign score between 0–4 was given: where zero score means absent and score 4 means constant and uncontrollable appearance of the sign of the disease. Experimental groups of mice were divided into 4; each group contained 5 animals: one normal, one ND 4 mouse untreated and three ND 4 mice treated with RHAMM mimetic—P-peptide. Animals were treated three times per week with 10 mg/kg of P-peptide intraperitoncaly. Peptide was resuspended in 300 $\mu$l of PBS.

Figure 39:
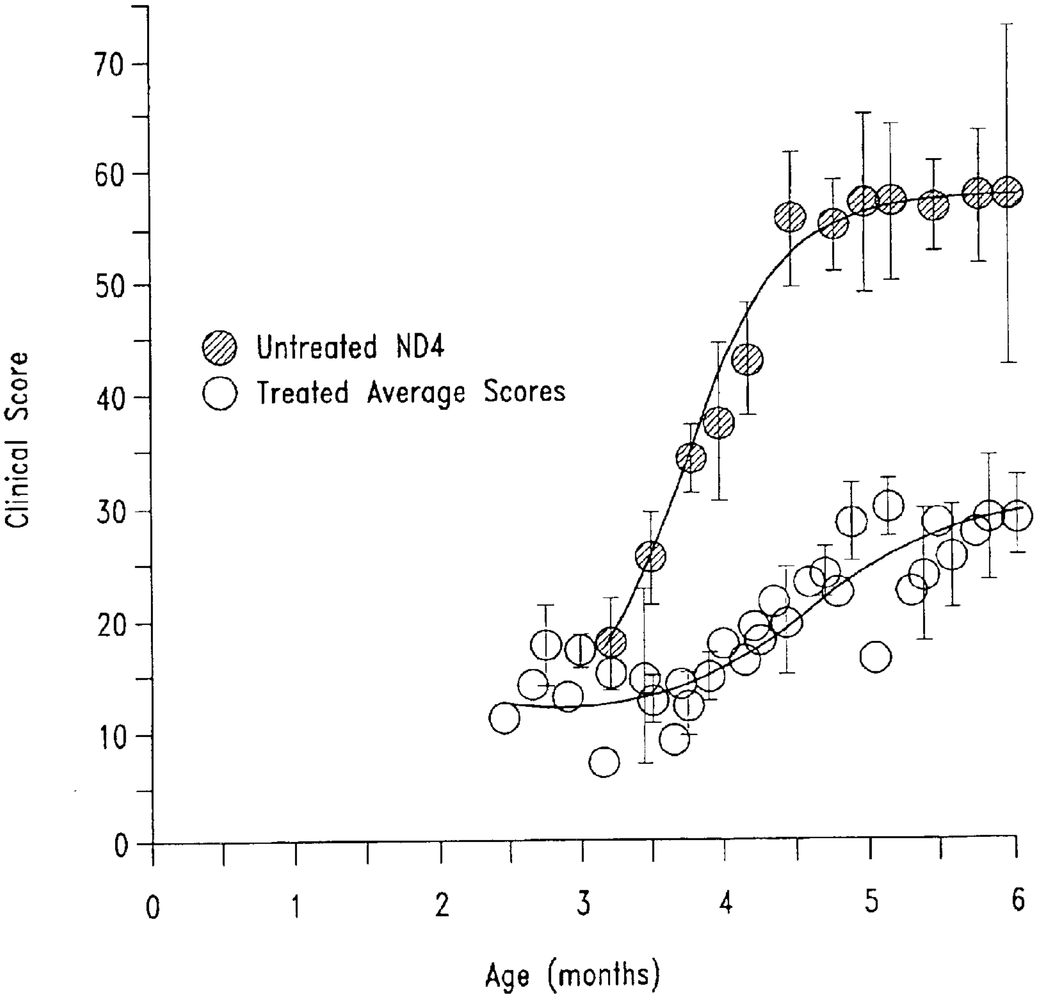
FIG. 39 is a graph which shows attenuation of clinical signs of MS after treatment.

Results are shown in FIG. 39. Briefly, treatment of ND 4 mice with P-peptide showed significant attenuation of clinical signs of MS symptoms from 3 to 6 months of age (FIG.

39). Applied in a fairly high dosage (10 mg/kg), the peptide exhibited 2 fold inhibition of disease symptoms, without observing toxicological or lethal effects on animals.

Example 22

Scar Reduction: P-Peptide Reduces Collagen I and III Expression in Excisional Model of Rat Skin Wound-healing responses to injury involve a complex series of cellular and inflammatory processes resulting in deposition of connective tissues and its remodeling into the scar tissue. The fibroproliferative response is accompanied by wound contraction and fibrosis due to the presence of myofibroblasts and to the enhanced production of collagen. In adult humans, the extracellular matrix is remodeled to sustain and direct the cellular changes and to restore tissue integrity. Such exuberant healing responses often lead to tissue fibrosis and contraction, commonly referred to as scarring. Fibrosis of adult human tissue is a serious clinical problem that results in malfunction of tissue due to intraabdominal adhesions, cirrhosis of liver, failure of anastomoses as well as adhesions following surgery.

A fibrotic wound response contrasts with repair of fetal skin wound wounds which exhibit reduced leukocyte infiltration, reduced fibroplasia and altered extracellular matrix remodeling resulting in a non-scared appearance of the healed wound. Additionally, hyaluronan accumulation is sustained in fetal skin while its accumulation is only transient in wounded adult skin.

This experiment tests the ability of 16 amino acid RHAMM peptide mimetic (P-peptide) to reduce tissue fibrosis in a rat punch biopsy model of skin repair.

A. Animal Model.

Three-month old female Sprague-Dawley (200–250 g) rats were anesthetized with Somnitol (1 ml/kg) and subjected to 4 mm full-thickness dorsal punch biopsies. Series of the P-peptide concentrations (1 ng–20 mg) were mixed into a diluted bovine/1% collagen (type I) suspension and applied once only per biopsy punch at the time of wounding. A 50 μl of the peptide/collagen solution was applied to the punch biopsy wound and allowed to polymerize over several hours. Collagen was used as vehicle to stimulate inflammation and fibrosis as rat skin normally shows minimal fibrosis. Collagen alone (control wounds) does not influence the rate of healing when compared to phosphate buffer saline. A twenty four hours after dorsal punch biopsies, animals were anesthetized with Isofluorane inhalant with oxygen and nitrous oxide and the experimental and control wounds (collagen alone) were excised. Samples were flash frozen in liquid nitrogen for RNA extraction.

B. RNA Extraction.

Frozen wounds were homogenized in 1 ml of Trizol (Gibco, BRL) until completely homogenous. After being homogenized, samples were incubated at room temperature for 5 min and 200 μl of chloroform was added. Tubes were tightly capped and shaken vigorously for 15 sec. Then, samples were incubated at room temperature for 2–3 min. After incubation, samples were centrifuged at 11200 rpm's for 15 min, at 2–8° C. Upper aqueous phase was transferred to another tube, carefully not to disturb interphase or organic phase of extract solution. After transfer, 10 μg of T-RNA was added into the tube along with 0.5 ml of isopropyl alcohol. Samples were incubated at room temperature for 10 min. Subsequently, they were centrifuged in picofuge at 11200 rpm's for 10 min at 4–8° C. After being centrifuged, supernatant was removed and pellet washed once in 75% ethanol. Samples were vortexed for 15 sec and spun in picofuge for 5 minutes on 8800 rpm's at 4–8° C. Remaining ethanol solution was carefully removed and RNA pellet allowed to air dry. Pellet was dissolved in DEPC $H_2O$ (Diethylpyrocarbonate). Concentration of RNA was determined by spectrophotometer. RNA was aliquoted into 20 μg portions and stored in −70° C. freezer until required.

C. Reverse Transcriptase Polymerase Chain Reactor Analysis (RT-PCR)

Frozen wound samples (50–100 mg tissue) were homogenized in 1 ml of Trizol reagent and RNA was isolated according to standard Trizol Reagent Protocol. For the synthesis of oligo-dT-primed cDNA, 2 μg of total RNA, 1 μg of oligo(dT) primers and Moloney Murine Leukemia Virus Reverse Transcriptase (Gibco Brl# 28025–013) were used. Following 1 h incubation at 37° C., the reaction was stopped by heating samples at 95° C. for 5 min and 2 μl of RT reaction mixture was used for PCRF PCR amplification was performed with platinum Taq DNA polymerase (Gibco BRL#10966-018) and specific primers for collagen I and III were used: 5' CGA TGT CGC TAT CCA GCT GA (SEQ ID NO:52) for collagent I and the following primer 5' ATC AGT CAG CCA TCT ACC ACC (SEQ ID NO:53) was used for collagen type III. Thermal cycles for collagen type I and III were as follows: denaturation at 94° C., annealing at 60° C. and polymerization at 72° C. for 20 cycles. In addition, a set of primers of a common housekeeping gene B-actin, were run in parallel on 1.5% agarose gel as a loading standard.

Figure 40A:
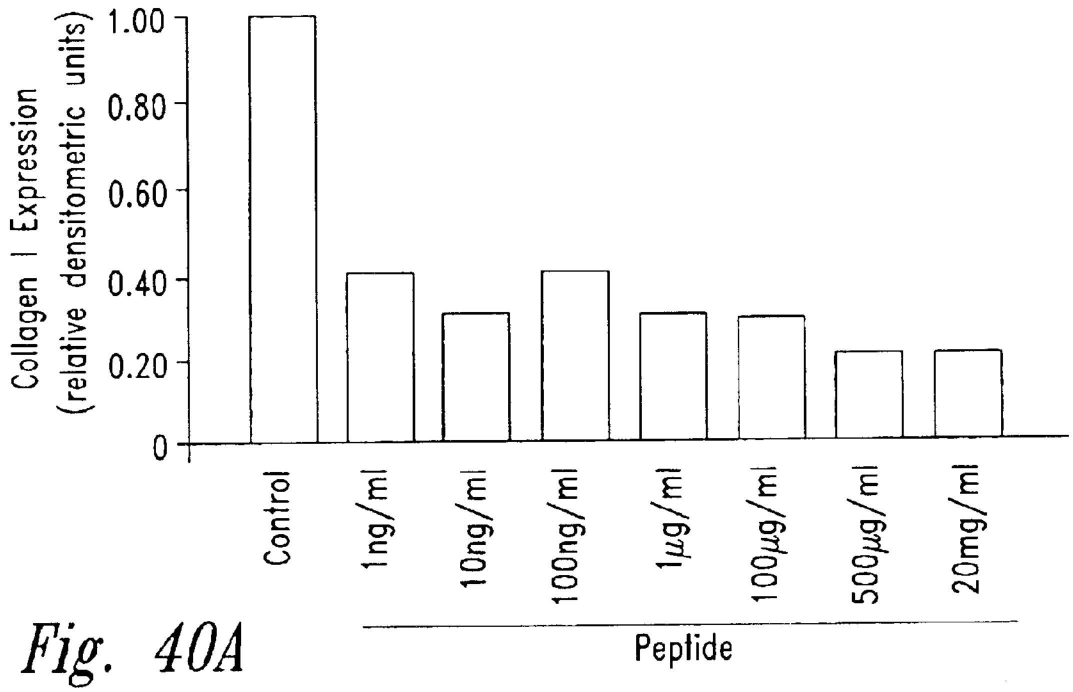
FIGS. 40A and 40B are bar graphs which show that collagen production following treatment with P-peptide.
Figure 40B:
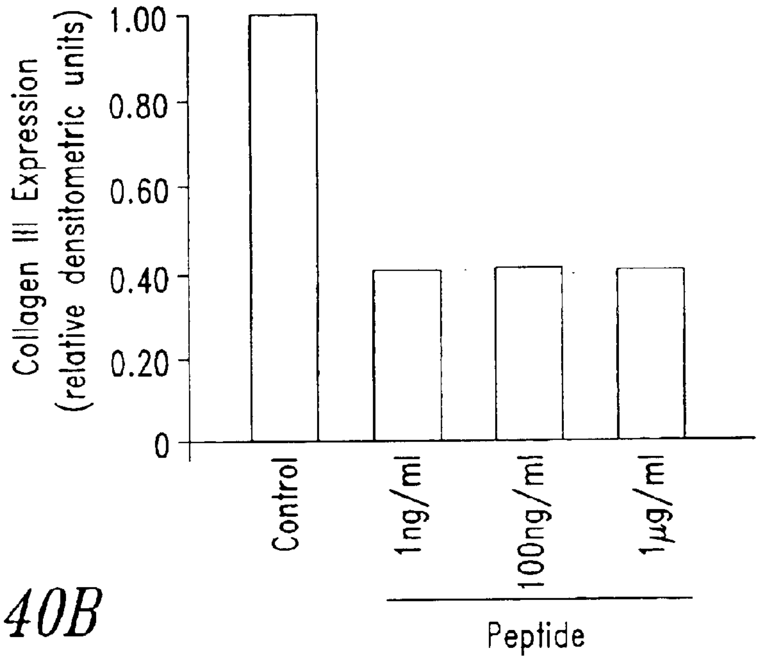

Results are shown in FIG. 40. Briefly, collagen production, which is a marker for fibrosis, was assessed by semiquantitative RT-PCR analysis of collagen type I and III mRNA within the wound site. Levels of collagen type I and III mRNA following P-peptide (1 ng/ml–20 mg/ml) application are shown in FIG. 40. Treatment of wound sites with P-peptide reduced levels of collagen type I and III measured at 24 h post wounding.

Example 23

Scar Reduction: ED-1 Expression is reduced by P-Peptide Treatment in Excisional Model of Rat Skin Fibrosis of adult human tissues is a serious clinical problem that results in malfunction of tissue due to keloids, hypertrophic scars, anatomonic strictures, intraabdominal adhesions, cirrhosis of the liver, neurologic deficits following injury to the spinal cord, valvular heart disease, burned-injured joints as well as failure of anastomoses and adhesions following surgery.

The P-peptide was assessed for its effect on the course of wound repair by measuring macrophage infiltration into the wound through the measurement of ED-1 expression, a marker for macrophages and fibroblasts.

A. Animal Model.

Three-month old female Sprague-Dawley (200–250 g) rats were anesthetized with Somnitol (1 ml/kg) and subjected to 4 mm full-thickness dorsal punch biopsies. Series of the P-peptide concentrations (1 ng–20 mg) were mixed into a diluted bovine/1% collagen (type I) suspension and applied once only per biopsy punch at the time of wounding. A 50 μl of the peptide/collagen solution was applied to the punch biopsy wound and allowed to polymerize over several hours. Collagen was used as vehicle to stimulate inflammation and fibrosis as rat skin normally shows minimal fibrosis. Seven days after dorsal punch biopsies, animals were anesthetized with Isofluorane inhalant with oxygen and nitrous oxide and the experimental and control wounds (collagen alone) were excised. Samples were flash frozen in liquid nitrogen for RNA extraction.

B. RNA Extraction.

Frozen wounds were homogenized in 1 ml of Trizol (Gibco, BRL) until completely homogenous. After homogenization, samples were incubated at room temperature for 5 min and 200 μl of chloroform was added. Tubes were tightly capped and shaken vigorously for 15 seconds. Then, samples were incubated at room temperature for 2–3 min. After incubation, samples were centrifuged at 11200 rpm's for 15 min, at 2–8° C. Upper aqueous phase was transferred to another RNAse free tube, carefully not disturbing interphase or organic phase of extract solution. After transfer, 10 μg of T-RNA was added into the tube together with 0.5 ml of isopropyl alcohol. Samples were incubated at room temperature for 10 min. Subsequently, they were centrifuged in picofuge at 11200 rpm's for 10 min at 4–8° C. After being centrifuged, supernatant was removed and pellet washed once in 75% ethanol. Samples were vortexed for 15 sec and spun in picofuge for 5 minutes on 8800 rpm's between 4–8° C. Remaining ethanol solution was carefully removed and RNA pellet allowed to air dry. Pellet was dissolved in $DEPCH_2O$). Concentration of RNA was determined by spectrophotometer. RNA was aliquoted into 20 μg portions and stored in −70° C. freezer until required.

C. RT-PCR Analysis

Frozen wound samples (50–100 mg tissue) were homogenized in 1 ml of Trizol reagent and RNA was isolated. For the synthesis of oligo-dT-primed cDNA, 2 μg of total RNA, 1 μg of oligo(dT) primers and Moloney Murine Leukemia Virus Reverse Transcriptase (Gibco Brl #28025-013) were used. Following 1 h incubation at 37° C., the reaction was stopped by heating samples at 95° C. for 5 min and 2 μl of R reverse transcriptase (RT) reaction mixture was used for PCR. PCR amplification was performed with platinum Taq DNA polymerase (Gibco BRL #10966-018) and specific primers that used for ED-1 is: for ED-1—5' C.GA TGG CAG GAC AGT AGT CGC (SEQ ID NO:54) and/or 5' AAG GCT GCT GTF GAA AGG ACG (SEQ ID NO:55).

Thermal cycles for ED-1 was as follows: denaturation at 94° C., annealing at 59° C. and polymerization at 72° C. for 28 and 29 cycles. In addition, a set of primers of a common housekeeping gene B-actin, were run in parallel on 1.5% agarose gel as a loading standard.

Figure 41:
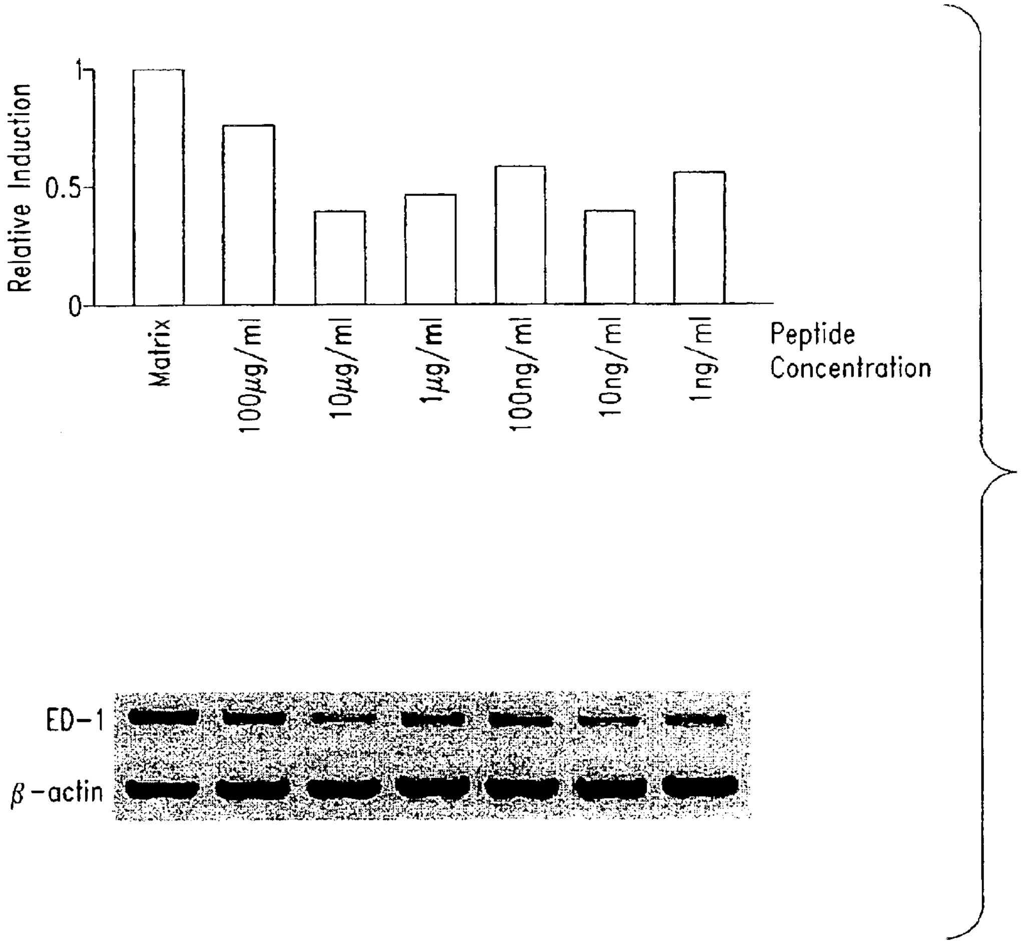
FIG. 41 shows that P-peptide reduces infiltration of macrophages into the site of a wound.

Results are shown in FIG. 41. Briefly, RT-PCR analysis of mRNA isolated from the wound site treated with P-peptide (1 ng/ml to 100 ug/ml) showed down regulation of ED-1 expression at 7 days after injury in comparison to the untreated wounds.

Thus, P-peptide reduces infiltration of macrophages into the site of the wound.

Example 24

RHAMM HA Binding Peptides Inhibit Macrophage Infiltration Following Skin Wounding Several key processes are involved in excisional wounding healing and scarring. These include local inflammation and infiltration of macrophages and neutrophils. The objective of this study was to determine whether different HA binding peptides inhibit macrophage infiltration.

The excisional wound healing rat model used and the method of local application of peptides was similar to that described in example 23. Tissue biopsies were removed and assayed for Glucosiminidase activity, a biological marker for macrophages.

Figure 42:
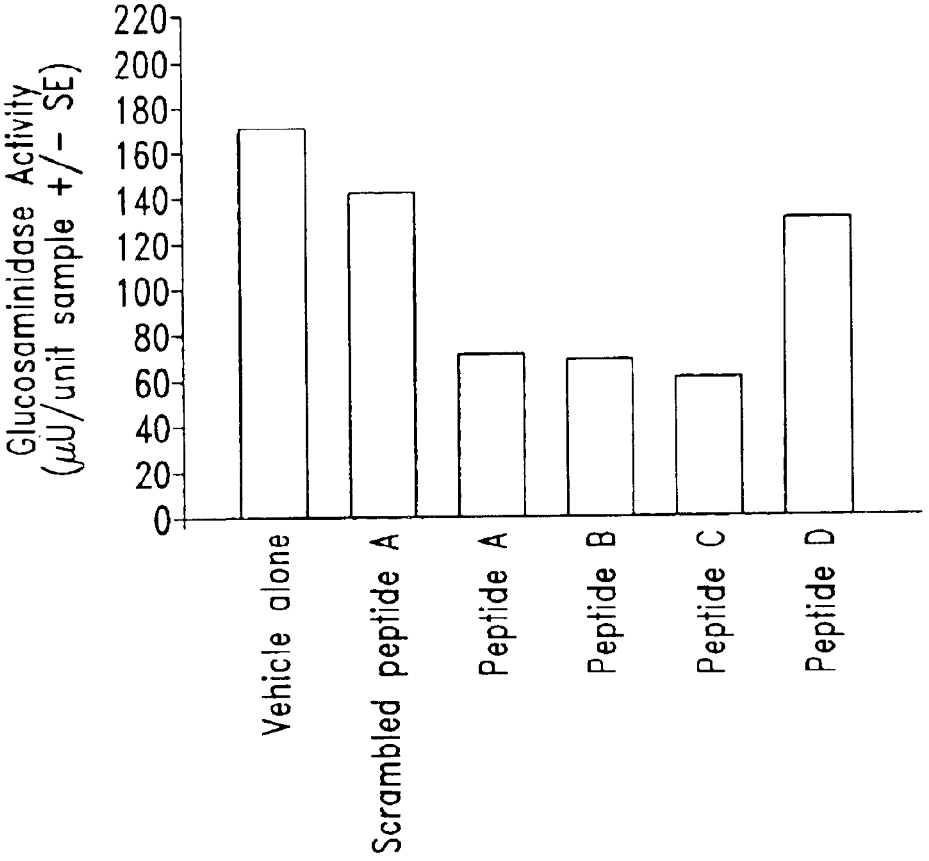
FIG. 42 is a bar graph which compares glucosamine activity after treament of various peptides.

As shown in FIG. 42, the data demonstrate that HA-binding peptides A (RGGGRGRRR; SEQ ID NO:27), B (RGGGRGGRR; SEQ ID NO:56), C (RGGGRGGGR; SEQ ID NO:57) inhibited the infiltration of macrophages in wounded biopsies, whereas peptide D (RGGGGGGGR; SEQ ID NO:58) which has a similar sequence but does not bind HA does not inhibit macrophage infiltration in wounding. In addition the scrambled peptide A did not have any effect on macrophage levels.

In conclusion these data demonstrate that HA-binding peptides inhibit macrophage motility and infiltration in wounding, and thus have potential to promote wound healing and reduce scarring.

Example 25

RHAMM Regulates Prostate Cancer Progression

This experiment investigates whether functional expression of the HA receptor RHAMM is required for enhancement of prostate cancer cells (CaP) cell motility and invasion in vitro.

Briefly, Dunning CaP cell lines (AT-1, MatLyLu) were grown in Delbeco's modified Eagle's medium (DMEM) medium supplemented with 10% FBS at 37° C. in a humidified atmosphere containing 5% $CO_2$. All cell lines were passaged every 3–4 days upon reaching confluency.

A. Immunofluorescence.

Cells were seeded sparsely on glass coverslip and incubated in growth media for 24 h. cells were then fixed with 3% paraformaldehyde and permeabilized with 0.2% triton X-100. RHAMM was visualized by indirect immunofluorescence using a polyclonal antibody to the C-terminus (Zram 2.3, 1:100) and Texas red conjugated donkey anti-rabbit antibody (1:100). Images are obtained using a Zeiss laser scanning confocal microscope.

B. Western Blotting.

Cells were also grown to 50–60% confluency were lysed using RIPA buffer. Equal amounts of total cell protein were loaded onto a 10% SDS-PAGE gel. RHAMM was probed using a polyclonal antibody to the C-terminus (Zram, 1:1000) and horseradish peroxidase (HRP-conjugated goat anti-rabbit antibody (1:5000). RHAMM was visualized by chemiluminescence.

C. Cell Motility.

Cell were seeded sparsely and-grown in 25 $cm^2$ flasks overnight. Serum-free medium was used for the experiments. Random cell motility of cells untreated, or treated with either RHAMM polyclonal antibody (Re4) or peptide mimicking the HA-binding domain over two hours was visualized by videomicroscopy. Cell motility tracks were analyzed using a Northern Exposure software. Statistical analysis was performed on 100 cells per field and statistical significance was determined using unpaired Student t-test.

D. Cell Invasion.

Cell were grown to confluency in growth media, detached, and equal number of cells were seeded in 24-well Matrigel invasion chambers. Cells were left untreated with RHAMM peptide and allowed to invade for 24 h. For statistical analysis, 5 high-power fields (400×) were counted for the number of cells that invaded through the membrane. Statistical significance was determined using unpaired Student t-test.

E. Matrix Metaloproteases (MMP) Activity.

Cells were grown to confluency in growth media, detached and equal number of cells were seeded in 6-well plates uncoated or coated with 50% Matrigel in media. Cells were allowed to adhere for 1 h to the substrate, and then treated with the peptide mimicking the HA-binding domain of RHAMM (100 μg/ml) for 24 h in serum-free media The activity of MMP secreted into the media was determined by zymography using 8% SDS-PAGE.

Figure 43A:
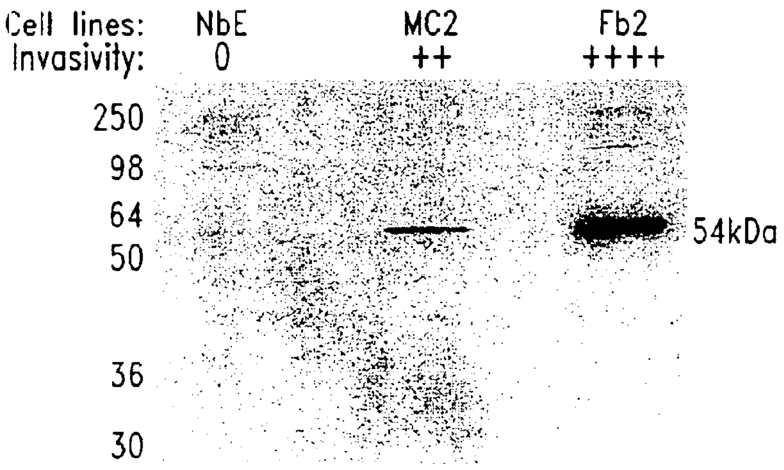
FIGS. 43A and 43B illustrate expression of RHAMM isoforms from various cell lines.
Figure 43B:
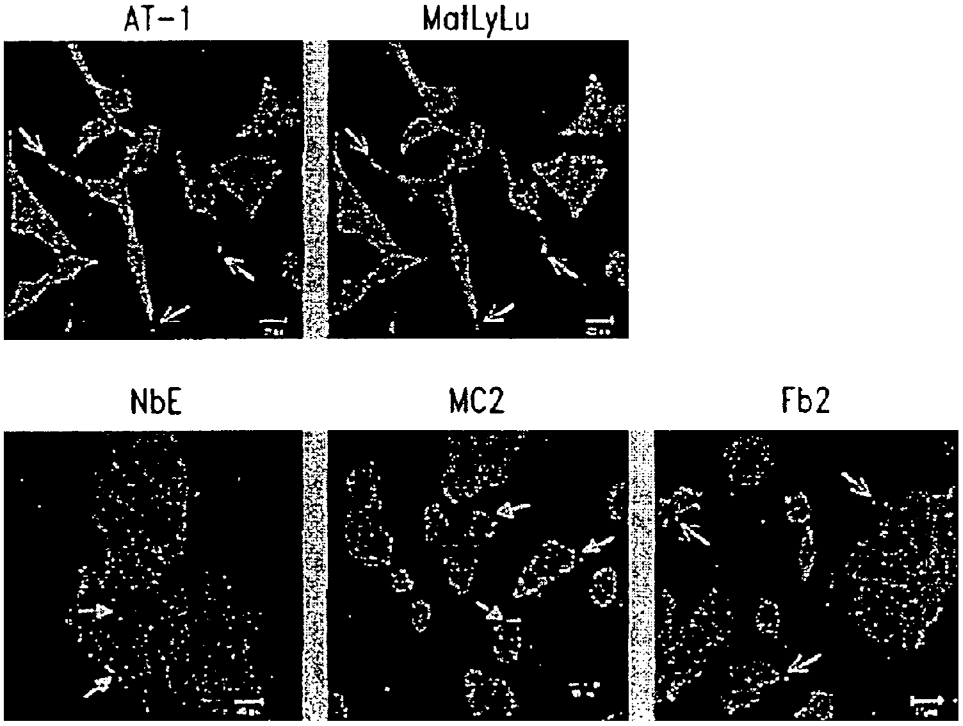
Figure 44A:
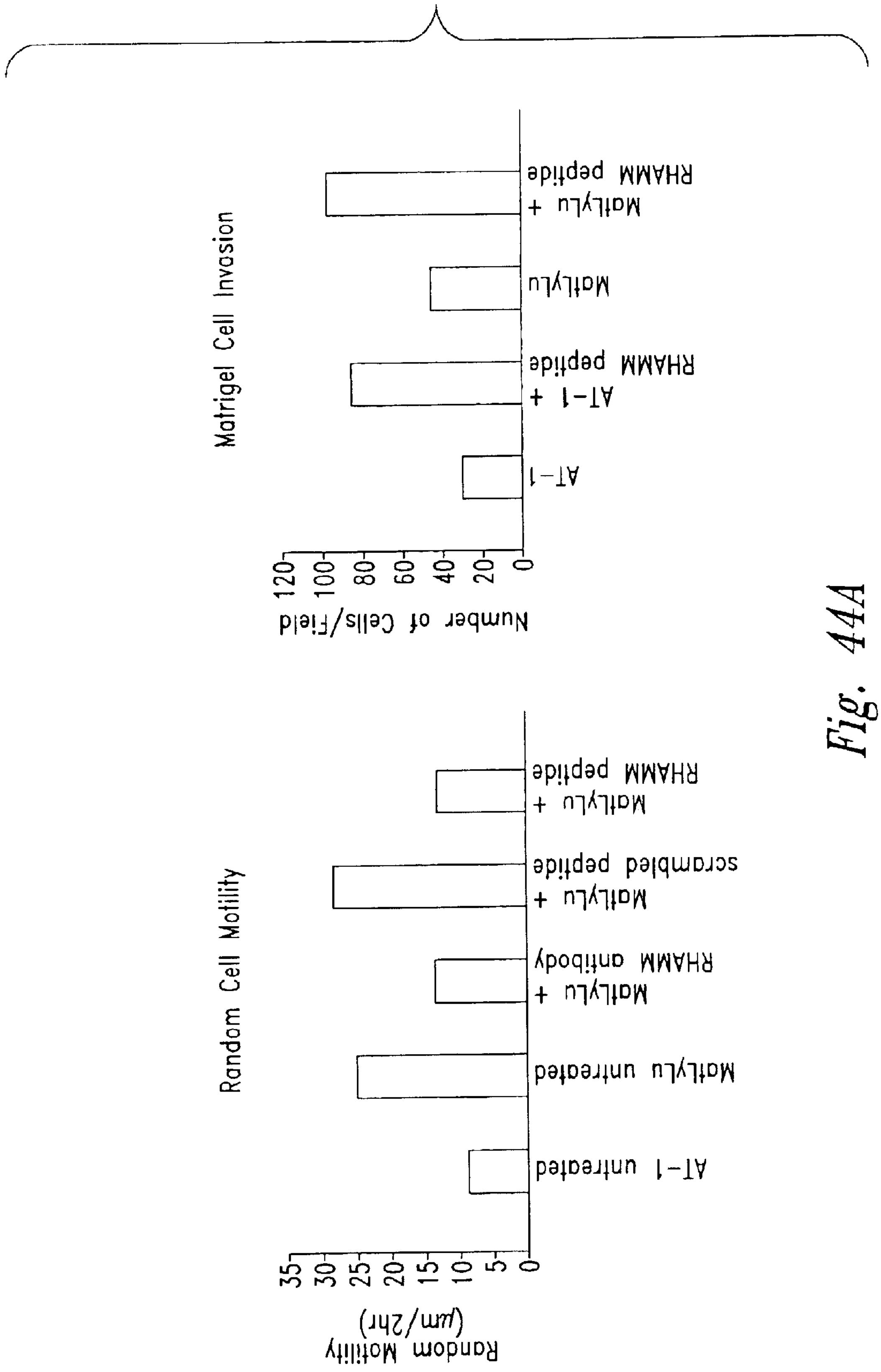
FIGS. 44A (bar graphs) and 44B (a blot) illustrate random cell motility and matrigel cell invasion utilizing various peptides.
Figure 44B:
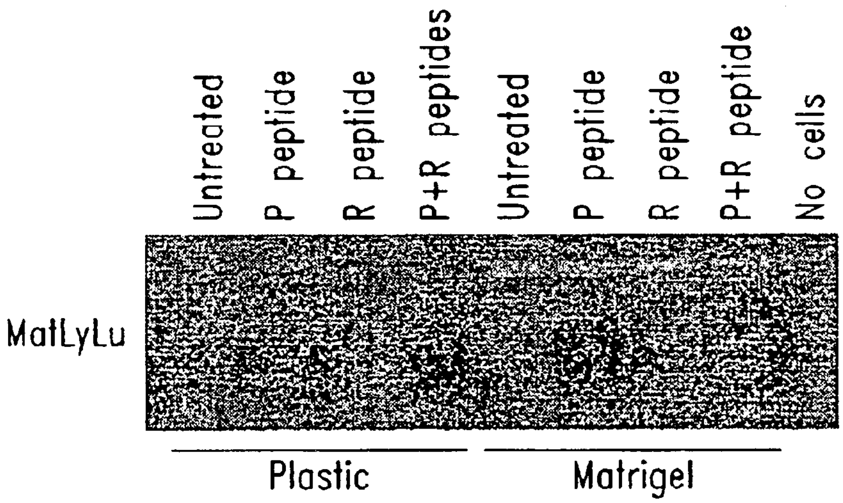

Results are shown in FIG. 43. Briefly, FIG. 43A shows the Western blot analysis using a RHAMM polyclonal antibody detecting progressively increasing expression of 54 kDa RHAMM isoform in proportion to motility/invasivity: the highly motile/invasive subline, Fb2> the weakly motile/invasive parental line, MC2> the nontumotigenic parental NbE epithelial line. FIG. 43B shows RHAMM localization to a sites of cell extension and to podosomes of invasive CaP cells. Open arrows point to sites of cell protrusion, whereas closed arrows point to circular structures known as podosomes or invadopodia. Left panel FIG. 44A shows that RHAMM regulates Dunning CaP cell line motility and invasion, whereas right panel of FIG. 44A showed that MaTLyLu cells treated with a RHAMM peptide showed a significant reduction ($p<0.025$) of about 20% in invasive potential as determined using Matrigel in vitro invasion chambers. However no effect of peptide was observed upon treatment of the AT-1 cells. FIG. 44B shows that secretion of MMP was higher in AT-1 cells compared to MatLyLu cells when grown on plastic. Matrigel did not reduce MMP activity in AT-1 in MatLyLu. When RHAMM blocking peptide was added, MMP activity was suppressed.

Thus, RHAMM is preferentially expressed in more motile/invasive and metastatic CaP cells. Blocking RHAMM function significantly and preferentially reduces motility, invasion, and MMP activity in highly metastatic CaP cells.

Example 26

Influence of RHAMM Peptide Mimetic on Weight Gain in Murine Model of SLE

F1 (NZB/W) mice, hybrids of New Zealand Black (NZB) and New Zealand White (NZW) mice, are a murine model of SLE (Systemic Lupus Erythematosus). These mice develop spontaneously autoantibodies to DNA and other cell components. Female mice develop a more rapid disease course than males, with death from renal failure occurring by 8–10 months of age in females and 18–20 months of age in males. Females of 8 weeks of age are free of overt symptoms of disease, with gradual development of autoantibodies, glomerulonephritis, proteinuria, renal failure and death. The renal disease is likely secondary to the immune dysfunction.

In addition to progressive renal inflammatory disease, these mice show increase in body weight of 20%–30%, which is manifested by increased accumulation of body fat. These lupus mice also have elevated triglycerides, similar to that seen in human SLE patients. A number of studies in murine SLE model have shown that dietary manipulations and restrictions have an effect on the development on this life shortening autoimmune disease. Several lines of evidence have supported a link between adipose tissue and immunocompetent cells. For example, in obesity, excess adiposity is linked to impaired immune function. Studies in rodents with genetic abnormality of leptin and leptin receptors, which result in obesity, revealed obesity-related changes in macrophage phagocytosis and the production of proinflammatory cytokines. These data identify an important link between obesity and regulation of inflammatory and immune responses.

This experiment assesses the effect of the P-peptide on body fat accumulation in murine SLE model.

Briefly, female NZB/WF1 were obtained from Jackson Laboratories at 6 weeks of age and housed locally for 2 weeks prior to initiation of the studies. The study design comprised of four groups of 10 female NZB/WF1 mice; one control and three experimental groups. The control group of mice were not treated with 16 amino acid RHAMM peptide mimetic (P-peptide). First group of mice were given P-peptide (5 mg/kg), three times a week via the IP route. The treatment started at 8 weeks of age and continued up to 28 weeks of age. The animals in the other two experimental groups were started on the P-peptide (5 mg/kg) at 16 and 24 weeks of age to determine whether interference with P-peptide can arrest or reverse active weight gain. The treatment in these animals also continued up to 28 weeks. The animals were assessed for weight gain during the development of the disease at weekly intervals.

Figure 45:
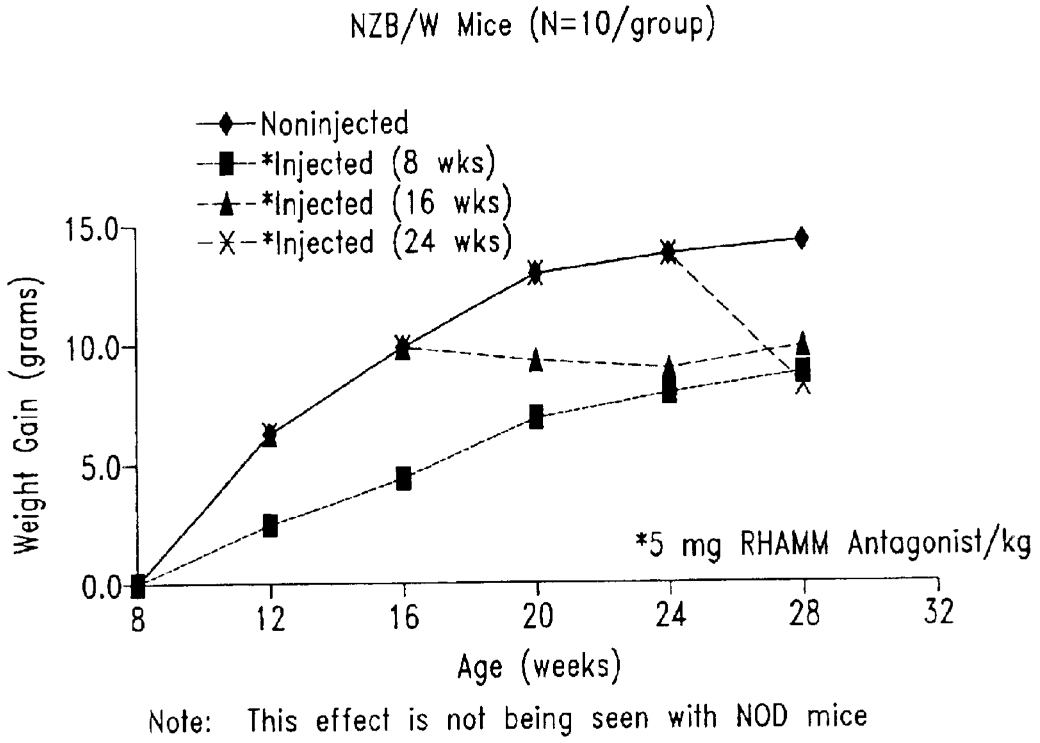
FIG. 45 is a graph which shows weight change in transgenic mice.

Results are shown in FIG. 45. Briefly, the control group of mice showed a trend of increase in body weight of approximately 5 g per month. The total average increase after 20 weeks was 13 g. The group of mice that was treated from 8 weeks of age showed significant reduction in weight gain in comparison with the control group. The average increase of body weight in this group was 2 g per month, whereas total accumulation of weight was 6 g after 20 weeks. Weight gain in mice in the other two experimental groups was identical to the control group until the initiation of treatment. The body weigh in these mice showed decrease within the first week of the treatment, with the trend of further decrease toward the levels observed in animals that were treated at early stage of the disease (FIG. 45). The treatment with P-peptide did not effect the weight gain in NOD mice, which served as a control for this experiment.

In summary, the weight gain in mice that were treated at the early stage of disease (8 weeks) was similar to the weight gain in normal mice. Mice that were treated at later stages of disease showed not only arrest but reverse of weight gain that was similar to early stage treated mice. Thus, the P-peptide can be utilized as a therapeutic agent in the treatment of obesity and obesity related diseases (e.g., diabetes and cardiovascular disease), as well as for diseases such as kidney fibrosis and lupus (SLE).

Example 27

Correlation Between RHAMM Levels and Cancer Cell Invasiveness

This experiment assesses the relationship between RHAMM expression and aggressiveness of cancer cell lines. RT-PCR was conducted as described in the attached Wang et al., (*Clinical Cancer Research*, 4:567–576, 1998). Western blot analyses was conducted as described above.

Figure 46A:
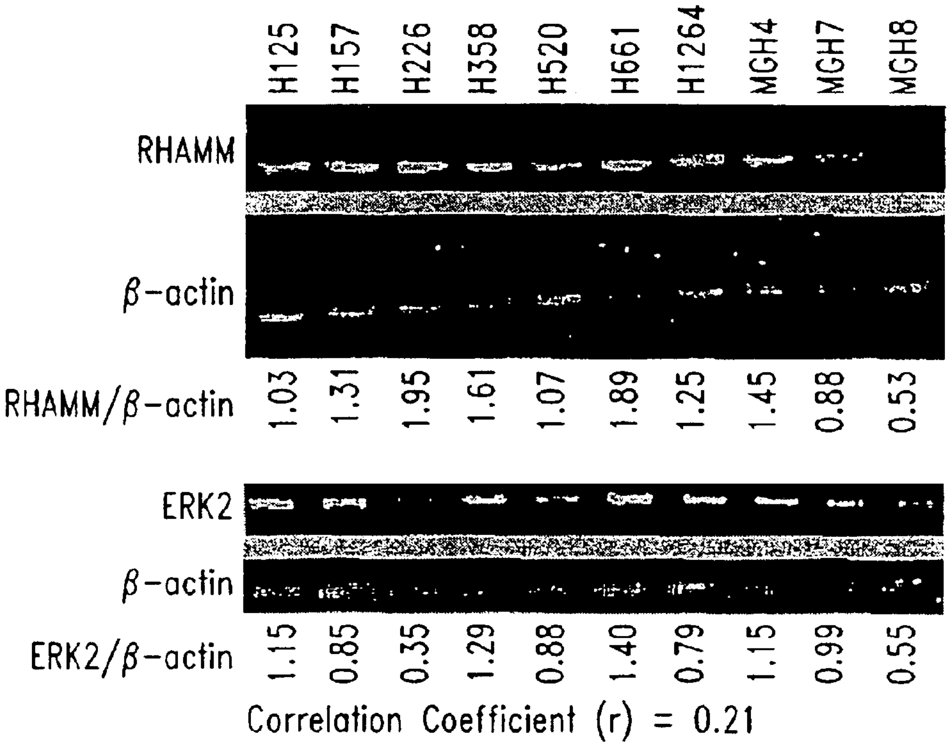
FIGS. 46A and 46B show that RHAMM is most highly expressed in the most invasive lung cancer cell lines.
Figure 46B:
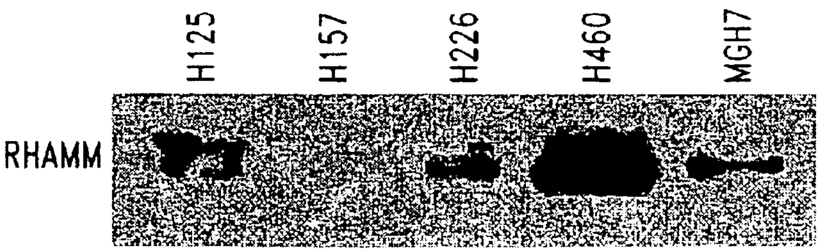

Results of these experiments are shown in FIG. 46. Briefly, the levels of erk kinase correlated significantly with the levels of RHAMM expression ($r=0.21$, $p<0.007$, Students "t" test). The cell lines H125, H157 and H226 are less invasive and aggressive than the H460 and MGH 7. As shown in the Figures, RHAMM expression is highest in the latter two cell lines. Of the two cell lines, the H460 is more invasive in matrigel assays than the MGH7 cell lines.

Based upon this experiment it is evident that the highest level of RHAMM expression is observed in the most invasive lung cancer cell lines.

Example 28

Correlation Between Astrocytoma Cell Metastases and RHAMM Expression

Figure 47A:
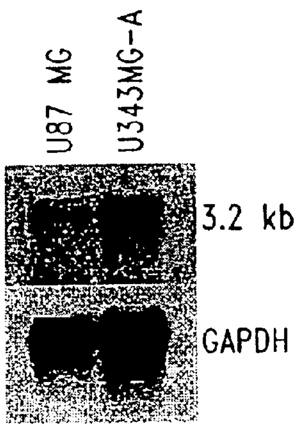
FIGS. 47A and 47B show that RHAMM is most highly expressed in high grade or invasive astnocytomas.
Figure 47B:
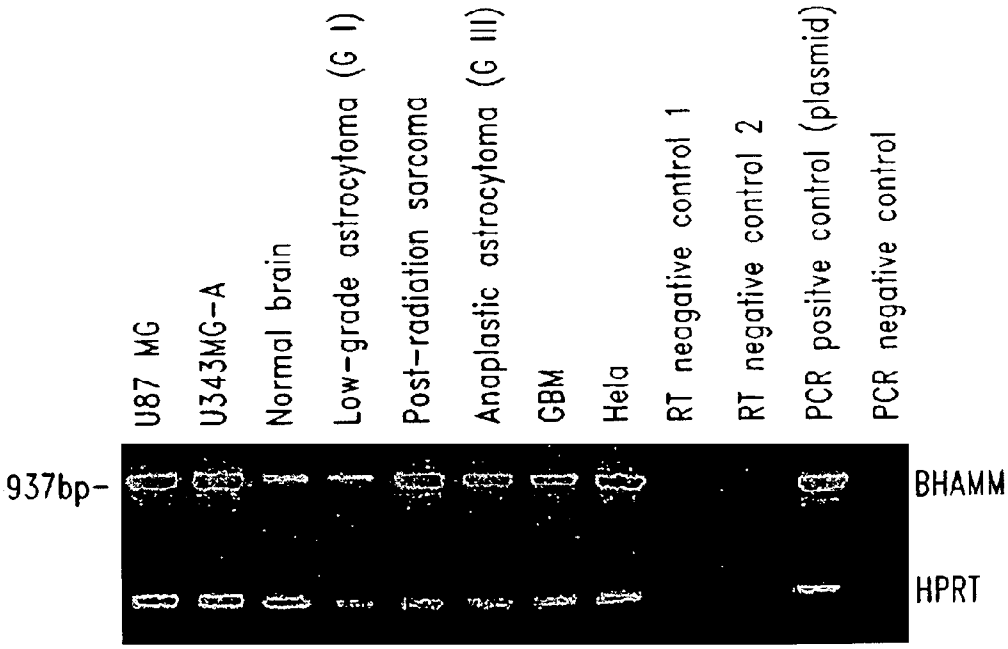

Invasive astrocytoma cell lines (U87MG and U343MG-A), astrocytoma biopsies from patients, cervical tumor cell lines (HeLa) were extracted for mRNA and analyzed for the presence of RHAMM using northern blots and RT-PCR as described by Sambrook et al. Results are shown in FIG. 47. Briefly, astrocytoma cell lines express approximately equal amounts of RHAMM, as detected by Northern blot analysis. RT-PCR analysis show that RHAMM is most highly expressed in high grade or invasive astrocytomas (FIG. 47B)

These results support that RHAMM is involved in the tumor invasion step of neoplastic progression and this is consistent with its ability to regulate podosome formation, structures that permit release of collagenases that are required for cell invasion.

Example 29

Screening for Proteins that Regulate HA Transport in a Transitional Cell

A RHAMM induced cDNA expression library is obtained from mRNA populations extracted from RHAMM transfected cells maintained in serum free medium for 24 h. These culture conditions allow uptake of HA into the cell cytoplasm but will not allow HA uptake into the cytoplasm of non-transfected cells unless a HA transport protein is expressed. The cDNA library is used to infect COS or CHO cells which are then exposed to Texas red-labeled HA in the presence of cytochalasin D which inhibits endocytic uptake of HA. Under these conditions cells would not ordinarily take up HA into the cytoplasm, hence, HA uptake will depend on the expression of a HA transporter. Infected cells are briefly exposed to streptomyces hyaluronidase to remove any Texas red labeled HA coating the outside of the cell and then cells are sorted for positive fluorescence with FACS.

Cells that are positive are cloned and rescreened for HA uptake. Transfected genes encoding an HA transporter are then retrieved by RT-PCR of mRNA and sequenced. These genes are then transfected into 10T1/2 cells which do not take up HA into the cytoplasm unless they are exposed to phorbol ester to activate protein kinase C. These cells are in turn assessed for uptake of Texas red-labeled HA into the cytoplasm and scored for altered growth factor sensitivity by techniques previously described herein.

The cDNA encoding a HA transporter is then cloned into an appropriate expression vector that will permit expression and isolation of the transporter protein. Appropriate vectors and expression systems are well known in the art. Antibodies are then be prepared against this protein. In addition, peptide regions instrumental in taking up HA (i.e., an HA binding domains) are identified and peptides that mimic these sites are prepared for assessment of the ability to compete with HA transport or otherwise impact signaling pathways, podosome formation and/cell motility which characterize transition stage cells.

Example 30

Figure 48A:
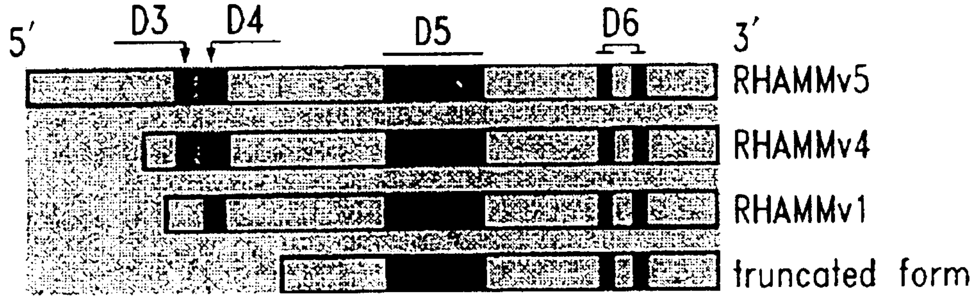
FIG. 48A is a schemata showing domains of various RHAMM polypeptides required for podosome formation and activation of erk kinase signaling and FIG. 48B is a protein gel showing that intracellular RHAMMv4 binds to extracellular signal-regulated kinase (ERK).
Figure 48B:
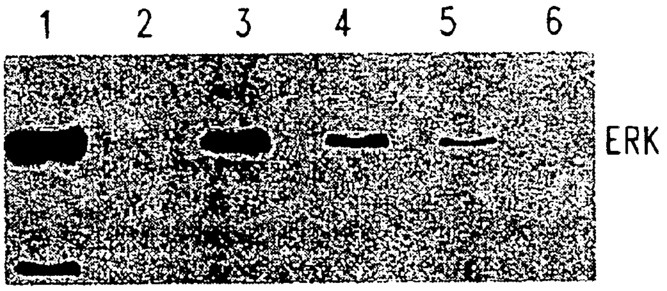

Identification of RHAMM Binding Proteins or Other Transition Stage Molecules by use of RHAMM Overexpression Cells Cultures To identify proteins that are transiently regulated with RHAMM to control cell activation, cDNA expression libraries obtained from the "CHIP" differential screen described above are used to establish libraries expressing transition molecules that is capable of binding to a hyaladherin or other transition stage molecule. Several techniques are known in the art for identifying an expressed binding partner. These include a two hybrid phage display system and a two hybrid yeast expression system. The two hybrid expression system is used to screen for peptides or polypeptides that bind to RHAMM or other transition molecule, and the ability to actually bind the transition molecule is further characterized using a far Western assay system. Specific binding regions of the RHAMM binding partners can be further identified using the functional regions of RHAMM exons and the regions of RHAMM known to be involved in the transient phenotype through the ability to activate erk kinases as provided for example, in FIG. 48. Antibodies may be made to the identified binding protein and assessed for the ability to affect cell motility or erk signaling cascades according as previously described.

Figure 49B:
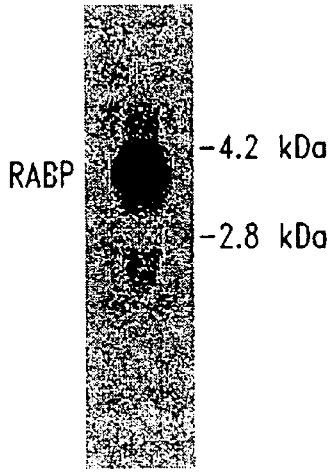
FIG. 49 shows (A) a partial amino acid (SEQ ID NO:46) and nucleotide sequence (SEQ ID NO:45) of a RHAMM binding protein (RABP) isolated using a phage two hybrid system; (B) a Northern blot of RABP expression in transition cells; (C) a Western blot of transitional cell lysate indicating that RABP is a 60 kDa protein; and (D) a fluorescence-activated cell sorting (FACS) analysis illustrating that RABP is present on the cell surface.
Figure 49C:
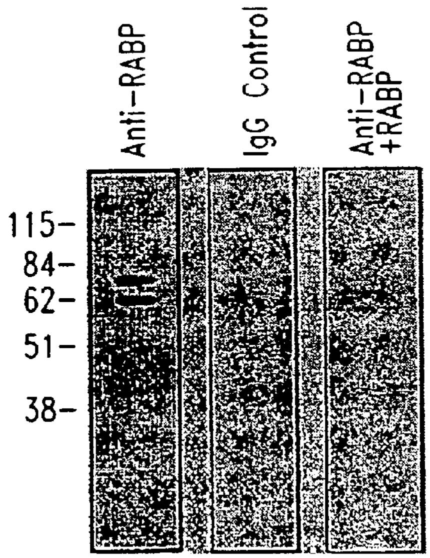
Figure 49D:
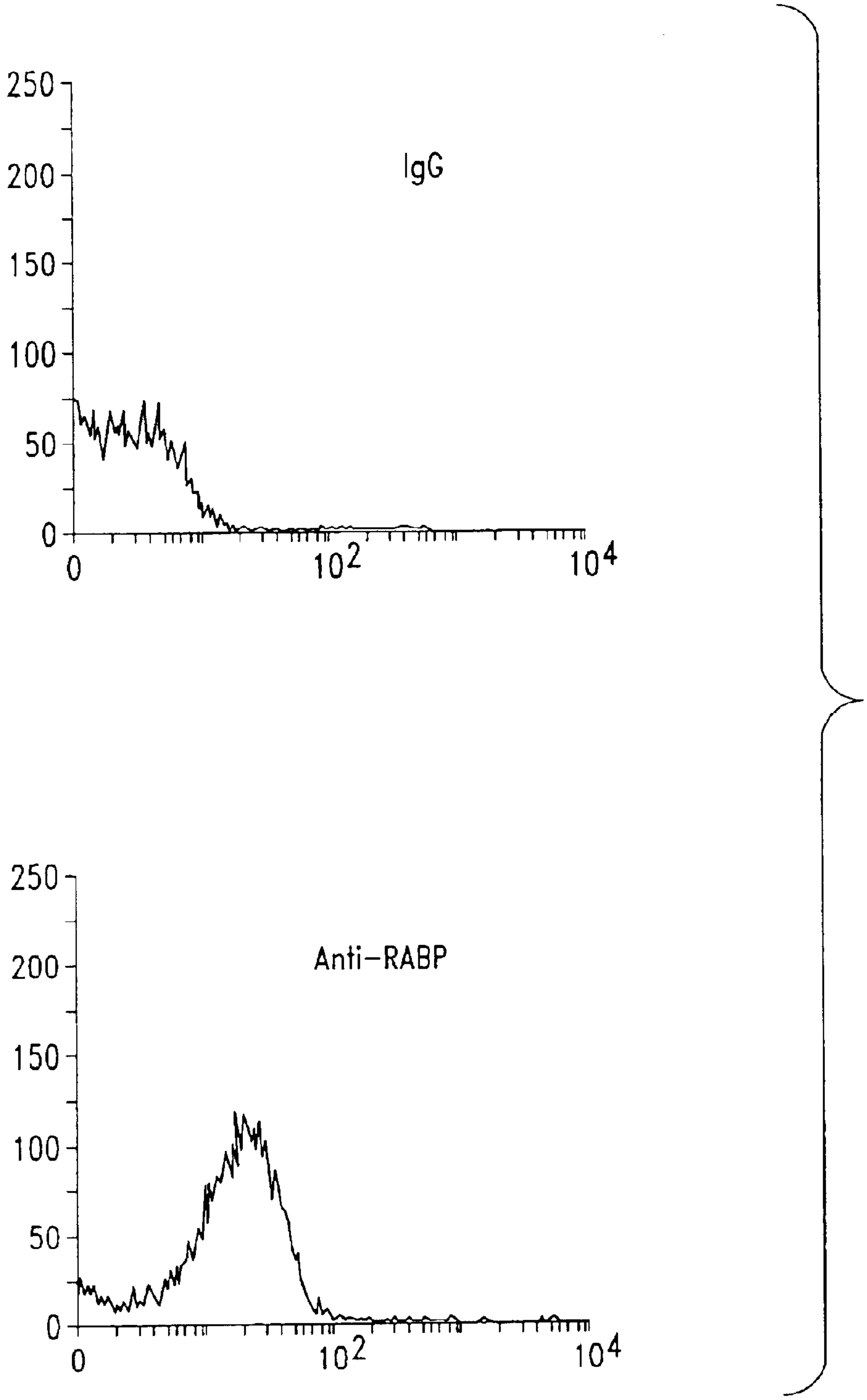

One such protein herein designated as RABP for RHAMM Associated Binding Protein has been identified using this method by using a phage display library mentioned above to bind to the peptide regions of exon 4 described as SEQ. ID NO: 17. A partial polypeptide and nucleic acid sequence for RABP is provided as SEQ. ID NO: 47 and 46. Antibody against this protein has been prepared and shown to be effective in inhibiting RHAMM activated podosome formation and signaling in RHAMM overexpressing cells. FIG. 49 shows the sequence for this novel RHAMM binding protein which was determined to be a 60 kDa protein that binds to exon 4 of RHAMM, and which is transiently present on the cell surface. Panel A shows the partial sequence of RABP isolated by a two hybrid screen using exon 4 of RHAMM. Panel B shows a Northern blot of RABP in transitional cells. Panel C shows a Western blot of transitional cell lysate indicating that RABP occurs within a 60 kDa protein. Panel D is a FACS analysis showing that RABP is present on the cell surface.

Other proteins regulating transition stage cells can be identified using cell cultures characterized by the transition stage phenotypes described for LR21 cells provided herein. Briefly, transitional cell cultures that overexpress RHAMM at precisely the levels required for enhancing podosome formation are grown to subconfluence (50–60%) in 10% FBS then released from their substratum using a 0.15 median, PBS, non-enzymatic disassociation medium. These cells are maintained in suspension in defined medium for 30 minutes and then plated for 24 hrs, at 5×15 cells/ml on plasma fibronectin coated dishes which promotes podosome positive, transitional phenotype. PolyA mRNA is isolated from the transitional cells and a differential screen is conducted using a cell line that is plated onto plastic dishes so that podosomes are not produced. RNA is placed into CHIPS for differential screening and genes associated with the transition phenotype are identified using CHIP protein technology. Positive cDNA's are sequenced, cDNA libraries are screened and RACE technology is used to obtain a full length cDNA.

The CHIP will contain cDNA's encoding proteins involved in the transition stage phenotype that do not necessarily bind to HA but are nevertheless involved in regulating this stage. Hence, this method for obtaining transitional mRNA is useful for identifying other important dominant acting proteins involved with the transitional stage of response to injury processes. The CHIP screen can be used for proteins that bind to important podosome proteins such as CAS and cortactin, and full length sequences of these can be obtained. The function of such sequences may be analyzed for their effect on podosome formation by transient transfection. The entire differentially screened mRNA can be used to transiently transfect cells to determine whether they can induce podosome formation, using CAS or cortactin to detect podosomes as described above. Particular sequences are identified by increasingly restricting the number of mRNAs included in a transfection group until ultimately restricting the size of the group to single mRNAs encoding single genes affecting the transition stage phenotype.

Example 31

Identification of Hyaladherins by Searching Databases for Hyaluronan Binding Motifs In addition to specific peptides such as those described in SEQ ID NOs: 1–10 that represent hyaladherins which bind to hyalauronic acid, a variant of additional polypeptides may be identified, generated and tested for use within the methods described herein. All such binding motifs are characterized by the presence of general amino acid motifs including staggered basic residues. These motifs can be more generally described as BX7B (SEQ ID NO:28) where B is any basic amino acid and X7 is any amino acid sequence of about seven residues but usually including at least one hydrophobic amino acids or an additional basic amino acid. Most importantly however, none of the intervening X amino acids should be acidic, as acidic amino acids appear to interfere with binding to hyalauronan, a negatively charged polymer. Peptides which are specifically excluded from this motif include: BBXXBBBXXBB, KQKIKHVVKLK, KLKSQLVKRK, RYPISRPRKR, KNGRYSISR, RDGTRYVQKGEYR, RRRCGQKKK, RGTRSGSTR, RRRKKIQGRSKR, RKSYGKYQGR, KVGKSPPVR, KTFGKMKPR, RIKWSRVSK, KRTMRPTRR, KVGKSPPVR, or HREARSGKYK (SEQ ID NOs: 29–44 respectively). These excluded peptides do not bind HA with the same high affinity as peptides of the present invention which require are peptides that form an alpha helix. All motifs that bind to hyalauronan also preferably form strong alpha helices as predicted in secondary structure protein analysis programs which further show that hyalauronan binding motifs contain at least two basic amino acids aggregating along one plane of the helix.

Using this information, a search of the data bases for previously undetected hyaladherins can be made, searching first for the aforementioned motif then coupling this with analysis of the structural requirements again using protein prediction programs such as for example are available on the internet (e.g., GCG). Additional sequence candidates can be found by searching appropriate databases of the technical literature such as Medline, Biosis, Chemical Abstracts and the like. Searches can then be made to determine which of the newly identified hyaladherins have previously been associated with disease and with the expression of podosomes. Those that are present at the cell surface can then be screened for their potential therapeutic use.

Example 32

Screening for Inhibitors of Podosome Formation

The present invention provides for novel cell lines that overexpress RHAMM and that produce enhanced formation of podosomes. These cell lines may be utilized to screen for inhibitors of podosome formation. Concomitant with the formation of podosomes and development of a transient phenotype, cells release proteases that result in degradation of fibronectin, revealing a previously sequestered CS-1 sequence. Antibodies to this CS-1 sequence have been prepared. The presently provided RHAMM overexpressing cell lines are coated on microsphere beads in conjunction with plasma fibronectin to form an assay mixture which is incubated at 37° C. for 2–3 h. The aforementioned CS antibody conjugated to a fluorochrome is added to this mixture causing a fluorescence response indicative of fibronectin degradation which is in turn indicative of the formation of functional podosomes. Candidate inhibitors of podosome formation are identified by the ability to reduce fluorescence in this assay and these candidates may be screened using any of several high through-put screening systems known in the art.

Inhibitors to be screened include, but are not limited to antibodies, HA binding peptides/polypeptides and RHAMM binding peptides/polypeptides associated with regulation of the novel transitional stage cells as provided in this invention. In addition, upon identification of functional portions of newly discovered transitional proteins using the methods described herein, candidate inhibitors comprised of small chemicals or peptide mimics of these functional portions can be synthesized according to methods known in the art. One set of peptide mimics includes for example, HA binding mimics.

Example 33

Humanized Antibodies that Inhibit Transitional Molecule Function

Humanized antibodies raised against transitional molecules identified above (e.g., hyaladherins, RHAMM binding partners, transitional proteins) can be screened for their inhibition of specific cell signaling pathways involved in cell transition (inhibition of erk kinase activity, AP-1 activity, MMP expression or specific transition states of the cell (e.g., podosome formation, cell migration, cell proliferation) in fluorescent screening assays. Cell lines over expressing specific transition molecules will activate ERK kinases, c-fos expression, AP-1 activity, MMP expression, and increased transitional states of the cell such as podosome formation resulting increased cell migration and proliferation.

Humanized antibodies to identified transition molecules such as RHAMM can be screened for inhibition of the aforementioned cell signaling pathways, gene expression, podosome formation, and/or cell motility and proliferation. These studies will identify potent antibodies which inhibit the transition of normal cells to diseased cells which can be utilized clinically in humans for the treatment and diagnosis of disease.

Example 34

Complimentary Peptides and Peptide Mimics that Interfere with Transition Molecule Function A variety of candidate peptides affecting transition state cells can be detected and/or screened using the methods provided by the present invention. Candidate peptides include peptides generated from transition molecules provided in the present disclosure (such as the RHAMM peptides), peptides of the transition stage which may further be identified using the aforementioned methods, peptides that bind strongly to active regions of transition molecules, or peptides that compete with binding of transition molecules of specific ligands generated by standard synthetic processes. Each of these can also be screened for effects on the particular features of transition cells disclosed herein including effects on specific signaling pathways (e.g., ERK activity, AP-1 activity,) gene expression (e.g., c-fos and MMP expression), podosome formation, cell motility and proliferation.

The structure of peptides effective in inhibiting transition molecule-induced processes can be determined by several methods including standard structure function analyses of a proteins shown to inhibit podosome formation and/or by using the above screening methods for analyzing peptide sequences encoded by a gene shown to be involved in podosome formation. Complementary peptides and peptide mimics can be designed based upon functional peptide motifs, particularly when an inhibitory peptide motiff is small (e.g., 10 amino acids or less). Such peptides and their mimics would be candidate molecules for therapeutic treatment of a variety of disease states dependent upon entry and passage of cells through the transition stage phenotype taught by the present invention. Candidate molecules would be tested for efficacy by assay in animal models of disease or using cultured cells expressing a transitional stage cells.

Similar studies may be performed to screen small molecules for their inhibition of transition molecule function and the progression of cells from the normal to diseased state as described in the present invention.

Example 35

Diagnostics Method for Detecting HA, Hyaladherins and Injured Cells

1. Detection of Intracellular and Plasma HA

Serum and tissue levels of HA are valuable diagnostic markers of arthritis and neoplasia. Thus, levels of HA in the serum are currently used to follow the course of osteoarthritis response to steroid therapy. Further, HA accumulation within colorectal and breast cancers is prognostic of a poor outcome. Because HA levels are enhanced following most forms of tissue injury, other conditions including restenosis, MS, Alzheimer's, stroke, myocardial infarction, sports injuries, burns and other inflammatory diseases would benefit from methods of detecting HA. In addition, HA increase in plasma is associated with a variety of other diseases, particularly rheumatoid arthritis and in tumors such as mesetheliomas and Wilm's tumors. Therefore testing of HA levels in serum or in biopsy tissue will be useful, alone or in combination with other disease markers for determination of a variety of disease conditions.

Currently, HA is routinely detected using fragments of HA binding proteins such as the 60 kDa fragment of aggrecan or link protein. The procedures for purifying these proteins is laborious and results are inconsistent making it difficult to routinely assess HA as a diagnostic parameter. The sensitivity of this technique is 5 $\mu$g HA in serum using ELISA assays.

The present invention provides a method of similar sensitivity but which is cheaper and more reliable. The method is based on using HA binding partners discovered using the techniques described above for detecting RHAMM binding partners. Using a phage display library to bind to biotinylated HA permitted identification of five particular species of HA binding motifs described in SEQ. ID NOS: 6–10. This was accomplished by isolating phage that attached to HA which were further isolated, rescreened twice and recloned. The clones were then bound to biotinylated HA-sepharose beads and only those phage that could be released with unlabeled HA were retrieved, recloned and sequenced. Five clones comprising the sequences identified above were detected. These sequences all bind to HA and are useful for detecting HA in serum and tissues in an assay described below.

An assay was developed based upon HA binding to these newly discovered peptide sequences. Synthetic peptides comprising these sequences were synthesized with a linker arm of glycine-glycine-cysteine to which KLH was covalently linked using EDAC. One to 200 $\mu$g of any one of these peptides were coated onto the surface of ELISA plates in phosphate buffered saline for 1 h at room temperature. Plates were washed in PBS and then coated with 1 $\mu$g/ml of HA and washed with PBS and 0.1% triton. Texas red labeled peptide was then applied to the coated plate for 1 h. Serum samples and HA standard solutions were then applied to the plates and left on a mixer for 2 h. The plates were then washed and read in a fluorescent ELISA plate reader at 545 um. The amount of HA in the samples was determined by comparison to the HA standards.

This assay has a similar sensitivity to previously described assays using aggrecan but is more reproducible due to the standardization possible using peptide synthesis. This contrast to the more variable results obtained using assays based on preparation of purified aggrecan for which a reproducible reagent capable of binding to HA is difficult to make.

These newly discovered peptides are also useful for detecting HA present in tissue (e.g., biopsy tissue). In one example, frozen or paraffin embedded tissue sections are incubated with biotinylated peptides for 1 h in sections that have been either exposed to hyaluronidase, used as a control, or to buffer alone. Sections are washed then developed with horseradish peroxidase labeled streptavidin and sections are then examined for a positive reaction indicated by brown staining. This procedure can be readily adapted for use in a kit as can the ELISA assay for detecting HA in plasma.

2. Development of an Assay for Detection of Soluble Hyaladherins

The above mentioned HA binding peptides are also useful in an assay for soluble hyaladherins. In this regard, an important aspect of the present disclosure is that the transition phenotype plays a heretofore undisclosed role in many disease processes such as inflammatory diseases, cancers, degenerative diseases and wound healing. In each case HA will be shed during the podosome stage of a cell that typifies the transitional phenotype. Therefore, the presence of a transitional phenotype during the early stages of disease establishment may be detected by assaying for the presence of hyalauronan or hyaladherins present in serum.

An assay for hyaladherins can be provided using the small peptides that bind to HA as described herein before. In one example, these peptides can be synthesized with an additional cysteine at the carboxy terminus. The peptides are then covalently linked to sepharose as per standard procedures. The sepharose beads are incubated with biotinylated HA for one hour, then washed. The beads containing biotinylated HA are then incubated for 1–2 hours at room temperature with an aliquot of sample serum. Hyaladherins that are present within the serum will compete with the peptide bound to sepharose for the biotinylated HA and therefore the amount of biotin label remaining with the sepharose beads will be inversely proportional to the amount of hyaladherins present in the serum sample.

An alternative to the general hyaladherins assay mentioned above is a specific hyaladherins assay for selected hyaladherins observed to increase during a particular disease or cellular response as may be detected using the screening methods provided in the foregoing Examples. In this specific assay, monoclonal antibodies are prepared against the selected hyaladherins observed to increase during disease as detected by these screening methods. The monoclonal antibodies are used in a standard ELISA assay where antibodies are coated onto the ELISA well, serum is added to this coating, washed and a second layer of anti-hyaladherin will be layered on top. The top layer of antibody is detected using a fluorochrome labeled secondary antibody and the amount of label quantified in an ELISA plate reader.

The presently described assays based upon use of HA binding peptides hyaladherins and antibodies thereto are readily adaptable for detecting other components associated with the transitional state such as HA transporters or other proteins which may be detected using the aforementioned screening systems.

Example 36

RHAMM Regulates Prostate Cancer Progression

This experiment investigates whether functional expression of the HA receptor RHAMM is required for enhancement of Cap cell motility and invasion in vitro.

Briefly, Dunning CaP cell lines (AT-1, MatLyLu) were grown in DMEM medium supplemented with 10% FBS at 37° C. in a humidified atmosphere containing 5% $CO_2$. All cell lines were passaged every 3–4 days upon reaching confluency.

A. Immunofluorescence.

Cells were seeded sparsely on glass coverslip and incubated in growth media for 24 h. cells were then fixed with 3% paraformaldehyde and permeabilized with 0.2% triton X-100. RHAMM was visualized by indirect immunofluorescence using a polyclonal antibody to the C-terminus (Zram 2.3, 1:100) and Texas red conjugated donkey anti-rabbit antibody (1:100). Images are obtained using a Zeiss laser scanning confocal microscope.

B. Western Blotting.

Cells were also grown to 50–60% confluency were lysed using RIPA buffer. Equal amounts of total cell protein were loaded onto a 10% SDS-PAGE gel. RHAMM was probed using a polyclonal antibody to the C-terminus (Zram, 1:1000) and HRP-conjugated goat anti-rabbit antibody (1:5000). RHAMM was visualized by chemiluminescence.

C. Cell Motility.

Cell were seeded sparsely and grown in 25 $cm^2$ flasks overnight. Serum-free medium was used for the experiments. Random cell motility of cells untreated, or treated with either RHAMM polyclonal antibody (Re4) or peptide mimicking the HA-binding domain over two hours was visualized by videomicroscopy. Cell motility tracks were analyzed using a Northern Exposure software. Statistical analysis was performed on 100 cells per field and statistical significance was determined using unpaired Student t-test.

D. Cell Invasion.

Cell were grown to confluency in growth media, detached, and equal number of cells were seeded in 24-well Matrigel invasion chambers. Cells were left untreated with RHAMM peptide and allowed to invade for 24 h. For statistical analysis, 5 high-power fields (400×) were counted for the number of cells that invaded through the membrane. Statistical significance was determined using unpaired Student t-test.

E. MMP Activity,

Cells were grown to confluency in growth media, detached and equal number of cells were seeded in 6-well plates uncoated or coated with 50% Matrigel in media. Cells were allowed to adhere for 1 h to the substrate, and then treated with the peptide mimicking the HA-binding domain of RHAMM (100 $\mu$g/ml) for 24 h in serum-free media. The activity of MMP secreted into the media was determined by zymography using 8% SDS-PAGE.

Thus, RHAMM is preferentially expressed in more motile/invasive and metastatic CaP cells. Blocking RHAMM function significantly and preferentially reduces motility, invasion, and MMP activity in highly metastatic CaP cells.

Example 37

Treatment and/or Prevention of Diabetes Mellitus

The purpose of these experiments was to evaluate the RHAMM (P-16) peptide on the treatment of diabetes in the non-obese diabetic (NOD) mouse model. NOD mouse is a model of human type I diabetes mellitus, which is characterized by a cell-mediated autoimmune process resulting in spontaneous diabetes (see, e.g., Zaho et al., Lithium (1991), 2(4), 227–34; see also, The Jackson Laboratory). Studies have shown that the major populations of cells infiltrating the islets of Langerhans in the early stage of insulitis in NOD mice are T cells and macrophages.

There are different colonies of NOD mice and there can be some variability between the colonies. The colony used develops the disease between 15–20 weeks of age and there is a 70–80% incidence of diabetes mellitus. The mice treated were divided into two groups of 10 animals; the first group being treated with P-16 peptide and the other group comprising of the control group, which was treated with saline. Once the NOD mice were 5 weeks old, the P-16 peptide was injected three times a week interperitoneally at a dose of 5 mg/kg for 23 weeks. The untreated mice and five mice from the treated group were sacrificed at 28 weeks of age. The remaining five mice from the treated group were taken off the peptide treatment at 28 weeks of age and were assessed for the disease after 16 weeks.

Figure 51:
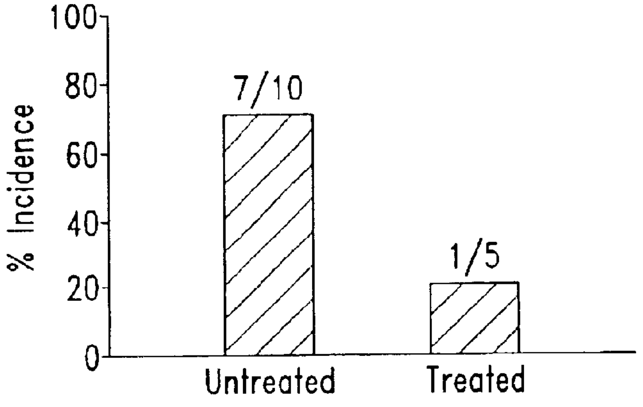
FIG. 51 is a bar graph that depicts the incidence of abnormal blood glucose levels in NOD mice.
Figure 52:
FIG. 52 is a bar graph that depicts the incidence of abnormal urine glucose level in NOD mice.
Figure 53:
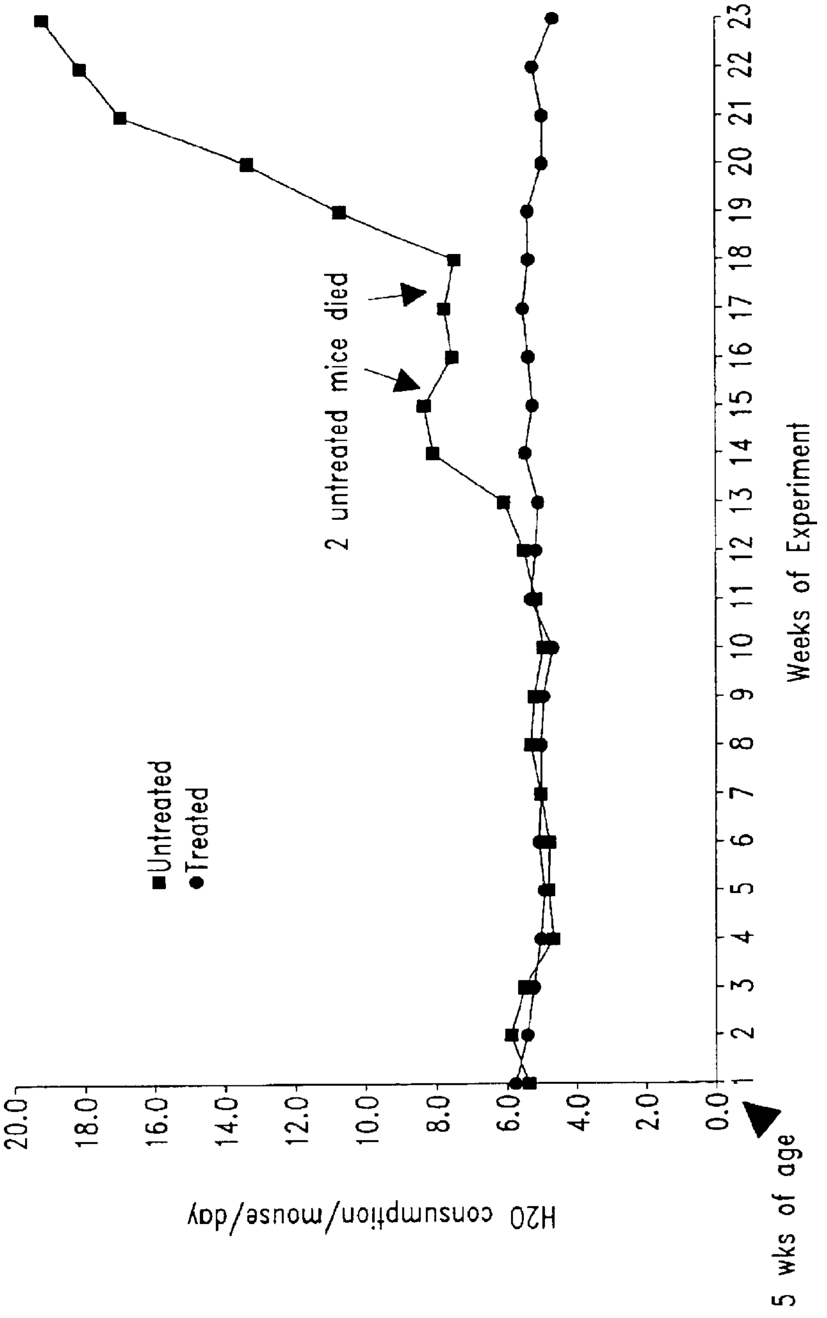
FIG. 53 is a graph that indicates the effect of P-16 peptide on water consumption in NOD mice.

As shown in FIG. 51, the incidence of diabetes measured by blood glucose level in untreated NOD mice was 70% whereas the incidence in the treated mice was 20%. The untreated mice also had a higher incidence of abnormal urine glucose level, 80%, compared to 0% in the treated mice (FIG. 52). Further, when examining water consumption associated with diabetes, water consumption increased significantly in untreated animals with the onset of diabetes around week 12 to 13 (FIG. 53). In contrast, the water consumption did not change in animals treated with P-16. These data clearly demonstrate that P-16 peptide inhibited the incidence of diabetes.

The treated mice that had the treatment stopped at 28 weeks have not developed any signs of the disease after 16 weeks. They looked healthy and did not show presence of polydipsia or urinary glucose.

Figure 54:
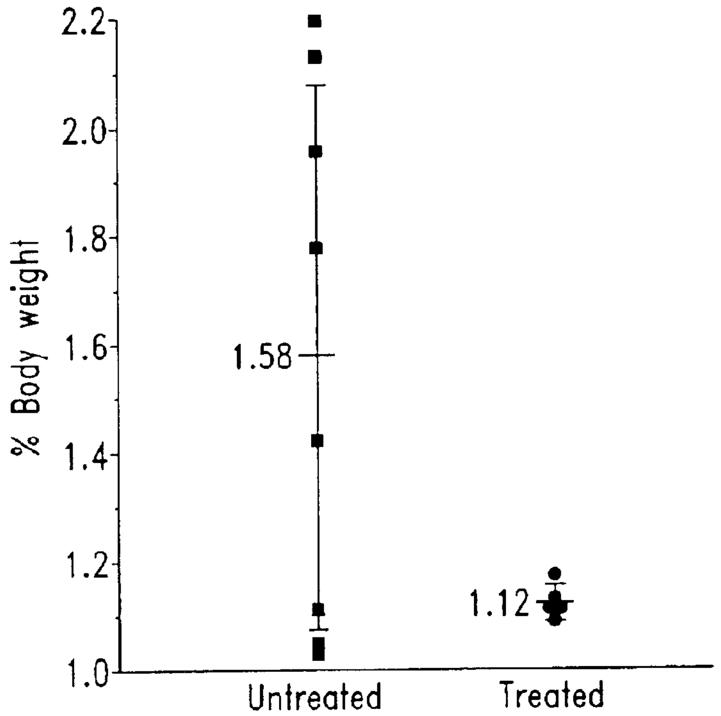
FIG. 54 is a graph that indicates the effect of P-16 peptide on kidney weight in NOD mice.

In NOD mice, there was an increase in kidney weight due to renal hypertrophy that is associated with the onset and progression of diabetic symptoms. As shown in FIG. 54, treatment with the P-16 completely inhibited the increase in kidney weight, presumably by inhibiting glomerulosclerosis.

The histological analysis of pancreatic tissue showed that treated mice had more intact pancreatic islets than the untreated animals and significantly smaller inflammation of the islets with inflammatory cells.

Presented results clearly show that RHAMM (P-16) peptide administration potently prevents the development of diabetes and associated complications in the NOD model of Type I diabetes mellitus in the absence of any toxicity. The diabetes-sparing effect is probably due to the inhibition of the destruction of beta cells in the pancreatic islets. The effectiveness of RHAMM (P-16) peptide-administration to induce long-term inhibition of disease was demonstrated by the negative results of urinary glucose and polydipsia of 16 weeks post-peptide treatment NOD mice.

These results indicate that RHAMM and its major ligand HA associate functionally with autoimmune insulitis leading to insulin dependent diabetes mellitus (IDDM) and that by using specific RHAMM peptides they can serve as potential therapeutic targets.

These findings also show that the RHAMM peptides, peptide mimetics, antibodies and potential HA binding peptides can be used as an effective method for preventing and/or treating diabetes mellitus by interfering with the penetration of the inflammatory cells into the islets and destructive invasion of the islets.

From the foregoing, it will be appreciated that, although specific embodiments of the invention have been described herein for purposes of illustration, various modifications may be made without deviating from the spirit and scope of the invention.

We claim:

1. An isolated polypeptide of less than 60 amino acid residues comprising at least one amino acid sequence BX7B motif consisting of amino acid sequence of SEQ ID NO:28 which binds hyaluronic acid, wherein said amino acid sequence is selected from the group consisting of SEQ ID NO: 26, SEQ ID NO: 27, SEQ ID NO: 51, SEQ ID NO: 56, SEQ ID NO: 57, SEQ ID NO: 58, SEQ ID NO: 64, SEQ ID NO: 66, SEQ ID NO: 69 and SEQ ID NO: 71.

2. A composition comprising at least one polypeptide according to claim 1.

3. The polypeptide of claim 1 which is less than 50 amino acid residues.

4. The polypeptide of claim 1 which is less than 40 amino acid residues.

5. The polypeptide of claim 1 which is less than 30 amino acid residues.

6. The polypeptide of claim 1 which is less than 20 amino acid residues.

7. The polypeptide of claim 1 which is an amino acid sequence selected from the group consisting of SEQ ID NO: 26, SEQ ID NO: 27, SEQ ID NO: 51, SEQ ID NO: 56, SEQ ID NO: 57, SEQ ID NO: 58, SEQ ID NO: 64, SEQ ID NO: 66, SEQ ID NO: 69 and SEQ ID NO: 71.

8. The composition of claim 2 which comprises a pharmaceutically or physiologically acceptable carrier, excipient or diluent.

9. The composition of claim 2 which is formulated for administration by a route selected from the group consisting of systemic, oral, rectal, intravenous, intramuscular, subcutaneous, ocular and topical.

10. The composition of claim 2 wherein the polypeptide is delivered at a dose ranging from 1 ng/kg to 80 mg/kg.

11. A method of treating a condition selected from the group consisting of tissue disorders associated with a response-to-injury process, proliferative disorders and diseases and inflammatory disorders and diseases comprising administering to a subject in need thereof at least one polypeptide according to any of claims 1 or 3–7.

12. A method of treating a condition selected from the group consisting of tissue disorders associated with a response-to-injury process, proliferative disorders and diseases and inflammatory disorders and diseases comprising administering to a subject in need thereof at least one composition according to any of claims 2 or 8–10.

13. The method of claim 11 wherein the condition is selected from the group consisting of multiple sclerosis, diabetes, obesity, wounds and restenosis.

14. The method of claim 12 wherein the condition is selected from the group consisting of multiple sclerosis, diabetes, obesity, wounds and restenosis.

* * * * *